United States Patent
Bagal et al.

(10) Patent No.: US 9,328,096 B2
(45) Date of Patent: May 3, 2016

(54) TROPOMYOSIN-RELATED KINASE INHIBITORS

(71) Applicant: PFIZER INC, New York, NY (US)

(72) Inventors: Sharanjeet Kaur Bagal, Great Abington (GB); Jingrong Jean Cui, San Diego, CA (US); Samantha Elizabeth Greasley, San Diego, CA (US); Elizabeth Ann Lunney, San Diego, CA (US); Indrawan James McAlpine, San Diego, CA (US); Asako Nagata, San Diego, CA (US); Sacha Ninkovic, La Jolla, CA (US); Kiyoyuki Omoto, Great Abington (GB); Sarah Elizabeth Skerratt, Great Abington (GB); Robert Ian Storer, Great Abington (GB); Joseph Scott Warmus, Ledyard, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/705,272

(22) Filed: May 6, 2015

(65) Prior Publication Data
US 2015/0322043 A1    Nov. 12, 2015

Related U.S. Application Data

(60) Provisional application No. 61/989,615, filed on May 7, 2014.

(51) Int. Cl.
| | |
|---|---|
| *A61P 35/00* | (2006.01) |
| *C07D 413/14* | (2006.01) |
| *A61P 29/00* | (2006.01) |
| *C07D 405/14* | (2006.01) |
| *A61K 31/4439* | (2006.01) |
| *C07D 401/12* | (2006.01) |
| *C07D 401/14* | (2006.01) |

(52) U.S. Cl.
CPC ............ *C07D 401/14* (2013.01); *C07D 401/12* (2013.01); *C07D 405/14* (2013.01); *C07D 413/14* (2013.01)

(58) Field of Classification Search
CPC .. C07D 401/14; C07D 401/12; C07D 405/14; C07D 413/14
USPC ......................................................... 514/171
See application file for complete search history.

(56) References Cited

U.S. PATENT DOCUMENTS

| | | | |
|---|---|---|---|
| 5,556,873 A | 9/1996 | Huang et al. | |
| 6,407,256 B1 | 6/2002 | Pinto | |
| 6,548,525 B2 | 4/2003 | Galemmo et al. | |
| 7,132,546 B2 | 11/2006 | Kato et al. | |
| 7,312,227 B2 | 12/2007 | Ledeboer et al. | |
| 7,396,935 B2 * | 7/2008 | Dyckman ............ | C07D 231/12 546/275.4 |
| 7,417,152 B2 * | 8/2008 | Tung ..................... | C07D 231/16 548/312.4 |
| 7,504,401 B2 | 3/2009 | Kelly et al. | |
| 7,605,273 B2 | 10/2009 | Dyckman et al. | |
| 7,855,198 B2 | 12/2010 | Kuramochi et al. | |
| 7,888,364 B2 | 2/2011 | Gunzner et al. | |
| 7,919,617 B2 | 4/2011 | Boman et al. | |
| 8,153,793 B2 | 4/2012 | Kugimiya et al. | |
| 8,163,756 B2 | 4/2012 | Flynn et al. | |
| 8,198,308 B2 | 6/2012 | Steurer et al. | |
| 8,247,401 B2 | 8/2012 | Burgey et al. | |
| 8,362,017 B2 | 1/2013 | Cheng et al. | |
| 8,481,738 B2 | 7/2013 | Beaton et al. | |
| 8,501,933 B2 | 8/2013 | Chen et al. | |
| 8,575,204 B2 | 11/2013 | Aston et al. | |
| 8,846,698 B2 * | 9/2014 | Andrews ............... | A61K 31/519 514/265.1 |
| 8,846,727 B2 | 9/2014 | Rossignol et al. | |
| 8,940,927 B2 | 1/2015 | Tian et al. | |
| 9,163,021 B2 * | 10/2015 | Andrews ............... | C07D 471/04 |
| 2006/0281733 A1 | 12/2006 | Tung et al. | |

(Continued)

FOREIGN PATENT DOCUMENTS

| | | |
|---|---|---|
| EP | 1633348 | 10/2008 |
| EP | 2385036 | 11/2011 |

(Continued)

OTHER PUBLICATIONS

Narayanan; PLoS ONE 2013, 8, e83380.*
International Search Report and Written Opinion, mailed Jun. 30, 2015, to corresponding International Patent Application No. PCT/IB2015/052414, filed Apr. 1, 2015, 9 pages.
Darren, D., et al., "Preparation and Optimization of a Series of 3-Carboxamido-5-phenacylaminopyrazole Bradykinin B1 Receptor Antagonists", Journal of Medicinal Chemistry, Sep. 19, 2007, pp. 5161-5167, 50(21).

(Continued)

*Primary Examiner* — Janet L Anders
*Assistant Examiner* — Daniel Carcanague
(74) *Attorney, Agent, or Firm* — Richard V. Zanzalari

(57) ABSTRACT

The present invention relates to compounds of Formula I

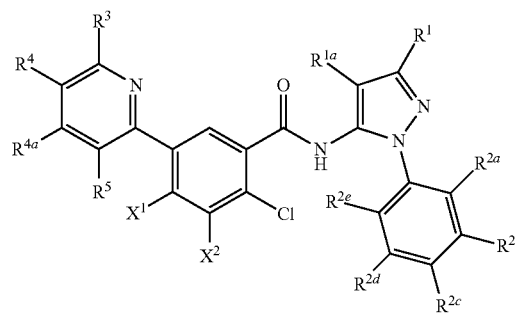

and their pharmaceutically acceptable salts, wherein the substituents are as described herein, and their use in medicine, in particular as TrkA antagonists.

21 Claims, No Drawings

(56) References Cited

U.S. PATENT DOCUMENTS

| | | | |
|---|---|---|---|
| 2007/0287719 A1* | 12/2007 | Boyden | A61K 9/1652 514/265.1 |
| 2008/0280891 A1 | 11/2008 | Kelly et al. | |
| 2009/0069288 A1 | 3/2009 | Breinlinger et al. | |
| 2010/0016320 A1* | 1/2010 | Dyckman | C07D 231/12 514/236.5 |
| 2010/0240657 A1 | 9/2010 | Sapountzis et al. | |
| 2010/0292274 A1 | 11/2010 | Rossignol et al. | |
| 2011/0065681 A1 | 3/2011 | Wei et al. | |
| 2011/0294758 A1 | 12/2011 | Tian et al. | |
| 2012/0022067 A1 | 1/2012 | Chen | |
| 2012/0094980 A1 | 4/2012 | Gunzner et al. | |
| 2012/0232112 A1 | 9/2012 | Ruf et al. | |
| 2012/0270858 A1 | 10/2012 | Tao et al. | |
| 2013/0022629 A1 | 1/2013 | Sharpe et al. | |
| 2013/0303492 A1 | 11/2013 | Raaum et al. | |
| 2014/0005245 A1 | 1/2014 | Jung et al. | |
| 2014/0031547 A1 | 1/2014 | Sheridan et al. | |
| 2014/0113012 A1 | 4/2014 | Schultz et al. | |
| 2014/0193906 A1 | 7/2014 | Androphy et al. | |
| 2014/0228367 A1* | 8/2014 | Flynn | C07D 403/12 514/248 |

FOREIGN PATENT DOCUMENTS

| | | |
|---|---|---|
| WO | 03/068747 | 8/2003 |
| WO | 2004022536 A1 | 3/2004 |
| WO | 2004/041789 | 5/2004 |
| WO | 2004/098528 | 11/2004 |
| WO | 2004098589 | 11/2004 |
| WO | 2004/110986 | 12/2004 |
| WO | 2007011760 A2 | 1/2007 |
| WO | 2008071664 A1 | 6/2008 |
| WO | 2008071665 A1 | 6/2008 |
| WO | 2008/124610 | 10/2008 |
| WO | 2009/011850 | 1/2009 |
| WO | 2009034390 A1 | 3/2009 |
| WO | 2009/110985 | 9/2009 |
| WO | 2010048149 A2 | 4/2010 |
| WO | 2010144586 A1 | 12/2010 |
| WO | 2012/066065 | 5/2012 |
| WO | 2012066065 A1 | 5/2012 |
| WO | 2012129562 A2 | 9/2012 |
| WO | 2013038390 A1 | 3/2013 |
| WO | WO2013100672 * | 7/2013 |
| WO | 2013/138617 | 9/2013 |
| WO | 2014012050 A2 | 1/2014 |
| WO | 2014058691 A1 | 4/2014 |
| WO | 2014181287 A1 | 11/2014 |
| WO | 2015143653 | 10/2015 |
| WO | 2015148350 | 10/2015 |
| WO | 2015159175 | 10/2015 |

OTHER PUBLICATIONS

Wang, T. et al., Trk kinase inhibitors as new treatments for cancer and pain, Expert Opinion Ther, Patents, 2009, pp. 305-319, 19(3).
PCT International Search Report and Written Opinion of the International Searching Authority, PCT/IB2015/053060, dated Jul. 31, 2015.
Compound No. 1. Chemical Abstracts Services (CAS): American Chemical Society, Columbus, Ohio, Aug. 9, 2012. Registry No. 1388749-18-5. N-[3-methyl-1-[5-(trifluoromethyl)-2-pyridinyl]-1H-pyrazol-5-yl]-3-(1H-tetrazol-1-yl)-Benzamide.
Compound No. 2. Chemical Abstracts Services (CAS): American Chemical Society, Columbus, Ohio, Aug. 31, 2011. Registry No. 1326096-65-4. N-[1-(3,5-dimethylphenyl)-3-methyl-1H-pyrazol-5-yl]-3-(1H-tetrazol-1-yl)-Benzamide.
Compound No. 3. Chemical Abstracts Services (CAS): American Chemical Society, Columbus, Ohio, Aug. 24, 2011. Registry No. 1322589-14-9. N-[3-(1,1-dimethylethyl)-1-(2-pyrimidinyl)-1H-pyrazol-5-yl]-3-[2-(methylthio)-1H-imidazol-1-yl]-Benzamide.
Compound No. 4. Chemical Abstracts Services (CAS): American Chemical Society, Columbus, Ohio, Aug. 23, 2011. Registry No. 1322119-17-4. N[3-methyl-1-(4-nitrophenyl)-1H-pyrazol-5-yl]-3-[2-(methylthio)-1H-imidazol-1-yl]-Benzamide.
Compound No. 5. Chemical Abstracts Services (CAS): American Chemical Society, Columbus, Ohio, Aug. 18, 2011. Registry No. 1319340-01-6. N-[3-(1,1-dimethylethyl)-1-(2-pyrimidinyl)-1H-pyrazol-5-yl]-3-[2-(methylthio)-1H-imidazol-1-yl]-Benzamide.
Compound No. 6. Chemical Abstracts Services (CAS): American Chemical Society, Columbus, Ohio, Aug. 15, 2011. Registry No. 1318184-07-4. N-[1-(4,6-dimethyl-2-pyrimidinyl)-3-methyl-1H-pyrazol-5-yl]-3-[2-(methylthio)-1H-imidazol-1-yl]-Benzamide.
Compound No. 7. Chemical Abstracts Services (CAS): American Chemical Society, Columbus, Ohio, May 30, 2011. Registry No. 1302592-24-0. N-[1-(2-fluorophenyl)-3-methyl-1H-pyrazol-5-yl]-3-(1H-tetrazol-1-yl)-Benzamide.
Compound No. 8. Chemical Abstracts Services (CAS): American Chemical Society, Columbus, Ohio, May 24, 2011. Registry No. 1299365-66-4. N-[1-(4,6-dimethyl-2-pyrimidinyl)-3-methyl-1H-pyrazol-5-yl]-3-(1H-tetrazol-1-yl)-Benzamide.
Compound No. 9. Chemical Abstracts Services (CAS): American Chemical Society, Columbus, Ohio, May 15, 2011. Registry No. 1294659-55-4. N-[1-(4,6-dimethyl-2-pyrimidinyl)-3-methyl-1H-pyrazol-5-yl]-3-(5-phenyl-1H-pyrazol-1-yl)-Benzamide.
Compound No. 10. Chemical Abstracts Services (CAS): American Chemical Society, Columbus, Ohio, May 12, 2011. Registry No. 1293547-70-2. N-[1-(2-fluorophenyl)-3-methyl-1H-pyrazol-5-yl]-3-[2-(methylthio)-1H-imidazol-1-yl]-Benzamide.
Compound No. 11. Chemical Abstracts Services (CAS): American Chemical Society, Columbus, Ohio, Sep. 26, 2014. Registry No. 1626919-60-5. 3-(3,6-dihydro-3,6-dioxo-1(2H)-pyridazinyl)-N-[3-(3-furanyl)-1-phenyl-1H-pyrazol-5-yl]-Benzamide.
Compound No. 12. Chemical Abstracts Services (CAS): American Chemical Society, Columbus, Ohio, Sep. 26, 2014. Registry No. 1626919-28-5. 3-(3,6-dihydro-3,6-dioxo-1(2H)-pyridazinyl)-N-[3-methyl-1-(4-nitrophenyl)-1H-pyrazol-5-y1]-Benzamide.
Compound No. 13. Chemical Abstracts Services (CAS): American Chemical Society, Columbus, Ohio, Sep. 26, 2014. Registry No. 1626692-38-3. N-[3-cyclopropyl-1-(2-pyrimidinyl)-1H-pyrazol-5-yl]-3-(3,6-dihydro-3,6-dioxo-1(2H)-pyridazinyl)-Benzamide.
Compound No. 14. Chemical Abstracts Services (CAS): American Chemical Society, Columbus, Ohio, Sep. 26, 2014. Registry No. 1626589-87-4. 3-(3,6-dihydro-3,6-dioxo-1(2H)-pyridazinyl)-N-[3-(1,1-dimethylethyl)-4-methyl-1-phenyl-1H-pyrazol-5-yl]-Benzamide.
Compound No. 15. Chemical Abstracts Services (CAS): American Chemical Society, Columbus, Ohio, Sep. 24, 2014. Registry No. 1625476-16-5. 3-(3,6-dihydro-3,6-dioxo-1(2H)-pyridazinyl)-N-[3-(1,1-dimethylethyl)-1-(2- pyridinyl)-1H-pyrazol-5-yl]-Benzamide.
Compound No. 16. Chemical Abstracts Services (CAS): American Chemical Society, Columbus, Ohio, Sep. 24, 2014. Registry No. 1625067-90-4. N-[3-cyclopropy1-1-(2-pyrimidiny1)-1H-pyrazol-5-yl]-3-[2-(methylthio)-1H-imidazol-1-yl]-Benzamide.
Compound No. 17. Chemical Abstracts Services (CAS): American Chemical Society, Columbus, Ohio, Sep. 23, 2014. Registry No. 1624537-55-8. 3-(3,6-dihydro-3,6-dioxo-1(2H)-pyridazinyl)-N-[1-(2-fluorophenyl)-3-methyl-1Hpyrazol-5-yl]-Benzamide.
Compound No. 18. Chemical Abstracts Services (CAS): American Chemical Society, Columbus, Ohio, Sep. 22, 2014. Registry No. 1624065-96-8. N-(3-cyclopentyl-1-phenyl-1H-pyrazol-5-yl)-3-(1H-tetrazol-1-yl)-Benzamide.
English abstract of CN103664878 from http://patbase.com/, Jul. 14, 2015.
English abstract of WO13100672 from http://patbase.com, Jul. 14, 2015.

* cited by examiner

TROPOMYOSIN-RELATED KINASE INHIBITORS

CROSS-REFERENCE

This application claims the benefit of priority to U.S. Provisional Patent Application Ser. No. 61/989,615 filed May 7, 2014, the disclosure of which is hereby incorporated by reference in its entirety.

The invention described herein relates to certain heterocyclic compounds and the pharmaceutically acceptable salts of such compounds. The invention also relates to the processes for the preparation of the compounds, compositions containing the compounds, and the uses of such compounds and salts in treating diseases or conditions associated with tropomyosin-related kinase (Trk) activity. More specifically the invention relates to the compounds and their salts useful as inhibitors of Trk, especially TrkA, more especially selective TrkA inhibitors.

BACKGROUND

Tropomyosin-related kinases (Trks) are a family of receptor tyrosine kinases activated by neurotrophins. Trks play important roles in pain sensation as well as tumour cell growth and survival signaling. Thus, inhibitors of Trk receptor kinases might provide targeted treatments for conditions such as pain and cancer. Recent developments in this field have been reviewed by Wang et al in Expert Opin. Ther. Patents (2009) 19(3): 305-319 and an extract is reproduced below.

1.1 Trk Receptors

As one of the largest family of proteins encoded by the human genome, protein kinases are the central regulators of signal transduction as well as control of various complex cell processes. Receptor tyrosine kinases (RTKs) are a subfamily of protein kinases (up to 100 members) bound to the cell membrane that specifically act on the tyrosine residues of proteins. One small group within this subfamily is the Trk kinases, with three highly homologous isoforms: TrkA, TrkB, and TrkC. All three isoforms are activated by high affinity growth factors named neurotrophins (NT): i) nerve growth factor (NGF), which activates TrkA; ii) brain-derived neurotrophic factor (BDNF) and NT-4/5, which activate TrkB; and iii) NT-3, which activates TrkC. The binding of neurotrophins to the extracellular domain of Trks causes the Trk kinase to autophosphorylate at several intracellular tyrosine sites and triggers downstream signal transduction pathways. Trks and neurotrophins are well known for their effects on neuronal growth and survival.

1.2 Trks and Cancer

Originally isolated from neuronal tissues, Trks were thought to mainly affect the maintenance and survival of neuronal cells. However, in the past 20 years, increasing evidence has suggested that Trks play key roles in malignant transformation, chemotaxis, metastasis, and survival signaling in human tumors. The association between Trks and cancer focused on prostate cancer in earlier years and the topic has been reviewed. For example, it was reported that malignant prostate epithelial cells secrete a series of neurotrophins and at least one Trks. In pancreatic cancer, it was proposed that paracrine and/or autocrine neurotrophin-Trk interactions may influence the invasive behavior of the cancer. TrkB was also reported to be overexpressed in metastatic human pancreatic cancer cells. Recently, there have been a number of new findings in other cancer settings. For example, a translocation leads to expression of a fusion protein derived from the N-terminus of the ETV6 transcription factor and the C-terminal kinase domain of TrkC. The resulting ETV6-TrkC fusions are oncogenic in vitro and appear causative in secretory breast carcinoma and some acute myelogenous leukemias (AML). Constitutively active TrkA fusions occurred in a subset of papillary thyroid cancers and colon carcinomas. In neuroblastoma, TrkB expression was reported to be a strong predictor of aggressive tumor growth and poor prognosis, and TrkB overexpression was also associated with increased resistance to chemotherapy in neuroblastoma tumor cells in vitro. One report showed that a novel splice variant of TrkA called TrkAIII signaled in the absence of neurotrophins through the inositol phosphate-AKT pathway in a subset of neuroblastoma. Also, mutational analysis of the tyrosine kinome revealed that Trk mutations occurred in colorectal and lung cancers. In summary, Trks have been linked to a variety of human cancers, and discovering a Trk inhibitor and testing it clinically might provide further insight to the biological and medical hypothesis of treating cancer with targeted therapies.

1.3 Trks and Pain

Besides the newly developed association with cancer, Trks are also being recognized as an important mediator of pain sensation. Congenital insensitivity to pain with anhidrosis (CIPA) is a disorder of the peripheral nerves (and normally innervated sweat glands) that prevents the patient from either being able to adequately perceive painful stimuli or to sweat. TrkA defects have been shown to cause CIPA in various ethnic groups.

Currently, non-steroidal anti-inflammatory drugs (NSAIDs) and opiates have low efficacy and/or side effects (e.g., gastrointestinal/renal and psychotropic side effects, respectively) against neuropathic pain and therefore development of novel pain treatments is highly desired. It has been recognized that NGF levels are elevated in response to chronic pain, injury and inflammation and the administration of exogenous NGF increases pain hypersensitivity. In addition, inhibition of NGF function with either anti-NGF antibodies or non-selective small molecule Trk inhibitors has been shown to have effects on pain in animal models. It appears that a selective Trk inhibitor (inhibiting at least NGF's target, the TrkA receptor) might provide clinical benefit for the treatment of pain. Excellent earlier reviews have covered targeting NGF/BDNF for the treatment of pain so this review will only focus on small molecule Trk kinase inhibitors claimed against cancer and pain. However, it is notable that the NGF antibody tanezumab was very recently reported to show good efficacy in a Phase II trial against osteoarthritic knee pain."

Further trk-mediated conditions which have been investigated and show promise for treatment with a trk inhibitor include atopic dermatitis, psoriasis, eczema and prurigo nodularis, acute and chronic itch, pruritis, atopic dermatitis, inflammation, cancer, restenosis, atherosclerosis, psoriasis, thrombosis, pruritus, lower urinary tract disorder, inflammatory lung diseases such as asthma, allergic rhinitis, lung cancer, psoriatic arthritis, rheumatoid arthritis, inflammatory bowel diseases such as ulcerative colitis, Crohn's disease, fibrosis, neurodegenerative disease, diseases disorders and conditions related to dysmyelination or demyelination, certain infectious diseases such as *Trypanosoma cruzi* infection (Chagas disease), cancer related pain, chronic pain, neuroblastoma, ovarian cancer, colorectal cancer, melanoma, head and neck cancer, gastric carcimoma, lung carcinoma, breast cancer, glioblastoma, medulloblastoma, secratory breast cancer, salivary gland cancer, papillary thyroid carcinoma, adult myeloid leukaemia, tumour growth and metastasis and interstitial cystitis (C. Potenzieri and B. J. Undem, *Clinical & Experimental Allergy,* 2012 (42) 8-19; Yamaguchi J, Aihara M, Kobayashi Y, Kambara T, Ikezawa Z, J Dermatol Sci. 2009; 53:48-54; Dou Y C, Hagstromer L, Emtestam L, Johansson O., Arch Dermatol Res. 2006; 298:31-37; Johansson O, Liang Y, Emtestam L., Arch Dermatol Res. 2002; 293:614-619; Grewe M, Vogelsang K, Ruzicka T, Stege H, Krutmann J., J Invest Dermatol. 2000; 114:1108-1112; Urashima R, Mihara M. Virchows Arch. 1998; 432:363-370; Kinkelin I, Motzing S, Koltenzenburg M, Brocker E B., Cell Tissue Res. 2000; 302:31-37; Tong Liu & Ru-Rong Ji, Pflugers Arch—Eur J Physiol, DOI 10.1007/s00424-013-1284-2, published online 1 May 2013); International Patent Application publication numbers WO2012/158413, WO2013/088256, WO2013/088257 and WO2013/161919, (Brodeur, G. M., Nat. Rev. Cancer 2003, 3, 203-216), (Davidson. B., et al., Clin. Cancer Res. 2003, 9, 2248-2259), (Bardelli, A., Science 2003, 300, 949), (Truzzi, F., et al., Dermato-Endocrinology 2008, 3 (I), pp. 32-36), Yilmaz, T., et al., Cancer Biology and Therapy 2010, 10 (6), pp. 644-653), (Du, J. et al., World Journal of Gastroenterology 2003, 9 (7), pp. 1431-1434), (Ricci A., et al., American Journal of Respiratory Cell and Molecular Biology 25 (4), pp. 439-446), (Jin, W., et al., Carcinogenesis 2010, 31 (11), pp. 1939-1947), (Wadhwa, S., et al., Journal of Biosciences 2003, 28 (2), pp. 181-188), (Gruber-Olipitz, M., et al., Journal of Proteome Research 2008, 7 (5), pp. 1932-1944), (Euthus, D. M. et al., Cancer Cell 2002, 2 (5), pp. 347-348), (Li, Y.-G., et al., Chinese Journal of Cancer Prevention and Treatment 2009, 16 (6), pp. 428-430), (Greco, A., et al., Molecular and Cellular Endocrinology 2010, 321 (I), pp. 44-49), (Eguchi, M., et al., Blood 1999, 93 (4), pp. 1355-1363), (Nakagawara, A. (2001) Cancer Letters 169:107-114; Meyer, J. et al. (2007) Leukemia, 1-10; Pierottia, M. A. and Greco A., (2006) Cancer Letters 232:90-98; Eric Adriaenssens, E., et al. Cancer Res (2008) 68:(2) 346-351), (Freund-Michel, V; Frossard, N., Pharmacology ck Therapeutics (2008) 117(1), 52-76), (Hu Vivian Y; et. al. The Journal of Urology (2005), 173(3), 1016-21), (Di Mola, F. F, et. al. Gut (2000) 46(5), 670-678) (Dou, Y.-C., et. al. Archives of Dermatological Research (2006) 298(1), 31-37), (Raychaudhuri, S. P., et al., J. Investigative Dermatology (2004) 122(3), 812-819) and (de Melo-Jorge, M. et al., Cell Host ck Microbe (2007) 1(4), 251-261).

International Patent Application publication number WO2009/012283 refers to various fluorophenyl compounds as Trk inhibitors; International Patent Application publication numbers WO2009/152087, WO2008/080015 and WO2008/08001 and WO2009/152083 refer to various fused pyrroles as kinase modulators; International Patent Application publication numbers WO2009/143024 and WO2009/143018 refer to various pyrrolo[2,3-d]pyrimidines substituted as Trk inhibitors; International Patent Application publication numbers WO2004/056830 and WO2005/116035 describe various 4-amino-pyrrolo[2,3-d]pyrimidines as Trk inhibitors. International Patent Application publication number WO2011/133637 describes various pyrrolo[2,3-d]pyrimidines and pyrrolo[2,3-b]pyridines as inhibitors of various kinases. International Patent Application publication number WO2005/099709 describes bicyclic heterocycles as serine protease inhibitors. International Patent Application publication number WO2007/047207 describes bicyclic heterocycles as FLAP modulators. International Patent Application publication number WO2012/158413 describes pyrrolidinyl urea and pyrrolidinyl thiourea compounds as trkA kinase inhibitors. International Patent Application publication number WO2010/077680 describes compounds with a bicyclic core as trkA kinase inhibitors.

Thus Trk inhibitors have a wide variety of potential medical uses. There is a need to provide new Trk inhibitors that are good drug candidates. In particular, compounds should preferably bind potently to the Trk receptors in a selective manner compared to other receptors, whilst showing little affinity for other receptors, including other kinase and/or GPC receptors, and show functional activity as Trk receptor antagonists. They should be non-toxic and demonstrate few side-effects. Furthermore, the ideal drug candidate will exist in a physical form that is stable, non-hygroscopic and easily formulated. They should preferably be e.g. well absorbed from the gastrointestinal tract, and/or be injectable directly into the bloodstream, muscle, or subcutaneously, and/or be metabolically stable and possess favourable pharmacokinetic properties.

Among the aims of this invention are to provide orally-active, efficacious, compounds and salts which can be used as active drug substances, particularly Trk antagonists, i.e. that block the intracellular kinase activity of the Trk, e.g. TrkA (NGF) receptor. Other desirable features include selectivity for TrkA vs other Trk receptors (e.g. B and/or C), good HLM/hepatocyte stability, oral bioavailability, metabolic stability, absorption, selectivity over other types of kinase, dofetilide selectivity. Preferable compounds and salts will show a lack of CYP inhibition/induction, and be CNS-sparing.

SUMMARY

The present invention provides compounds of Formula I

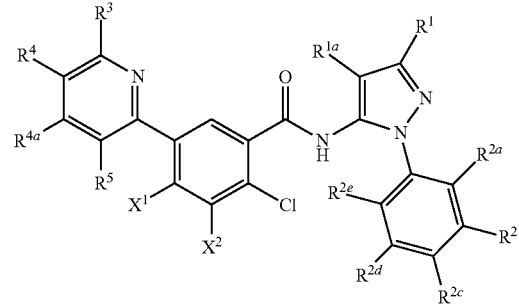

and prodrugs thereof, and pharmaceutically acceptable salts thereof, wherein $R^1$ is CN, $CO_2R^x$, CO—(NHet), $CONR^{x1}$—($C_{3-8}$ cycloalkyl, Ar, Het or $R^{x2}$),
$CONR^{x1}(CR^xR^y)_m$(NHet, $NR^{x1}R^{x2}$, $C_{3-8}$ cycloalkyl, Ar, Het or $R^{x2}$),
$CONR^{x1}(CR^YR^X)_m$CO(NHet, $NR^{x1}R^{x2}$, $C_{3-8}$ cycloalkyl, Ar, Het or $R^{x2}$),
$CONR^{x1}(CR^YR^X)_m NR^{x1}$CO(NHet, $NR^{x1}R^{x2}$, $C_{3-8}$ cycloalkyl, Ar, Het or $R^{x2}$),
$CONR^{x1}$CO(NHet, $NR^{x1}R^{x2}$, $C_{3-8}$ cycloalkyl, Ar, Het or $R^{x2}$),
$CONR^{x1}$CO—($CR^xR^y)_m$(NHet, $NR^{x1}R^{x2}$, $C_{3-8}$ cycloalkyl, Ar, Het or $R^{x2}$), $CONR^{x1}(CR^xR^y)_m CONR^{x1}$—(NHet, $NR^{x1}R^{x2}$, $C_{3-8}$ cycloalkyl, Ar, Het or $R^{x2}$), $R^{x1}$ and $R^{x2}$ are each independently H, $C_{1-6}$ alkyl optionally substituted by up to 3 substituents independently selected from
halogen,
OH,
$NH_2$,
$NH(C_{1-6}$ alkyl),
$N(C_{1-6}$ alkyl)$_2$, CN,
(C$_{1-6}$ alkoxy optionally substituted by up to 3 substituents independently selected from halogen, OH, NH$_2$, NH(C$_{1-6}$ alkyl optionally substituted by up to 3 substituents independently selected from halogen, OH, NH$_2$), N(C$_{1-6}$ alkyl optionally substituted by up to 3 substituents independently selected from halogen, OH, NH$_2$)$_2$, and C$_{1-6}$ alkoxy)
and (C$_{1-6}$ alkyl optionally substituted by up to 3 substituents independently selected from halogen, NH$_2$, NH(C$_{1-6}$ alkyl), N(C$_{1-6}$ alkyl)$_2$, and C$_{1-6}$ alkoxy),
or, together with the nitrogen atom to which they are attached, R$^{x1}$ and R$^{x2}$ form a 4- to 8-membered saturated or unsaturated heterocyclic ring with a ring N atom directly linked to the linked moiety, having from 0 to 2 further hetero ring atoms independently selected from N, O and S,
NHet is a 4- to 8-membered saturated or unsaturated heterocyclic ring with a ring N atom directly linked to the linked moiety, having from 0 to 2 further hetero ring atoms independently selected from N, O and S,
Het is a 4- to 8-membered saturated or unsaturated heterocyclic ring having at least 1, and up to 3, hetero ring atoms independently selected from N, O and S, the C$_{3-8}$ cycloalkyl, NHet and Het groups may be monocyclic, bicyclic, bridged or spirocyclic if the number of ring atoms allows,
Ar is phenyl,
wherein each of C$_{3-8}$ cycloalkyl, Ar, NHet and Het are optionally substituted, where valency allows, by up to 5 substituents independently selected from
  C$_{1-6}$ alkyl optionally substituted by up to 3 substituents independently selected from halogen, OH, CN, NR$^{x1}$R$^{x2}$, NHCOR$^{x1}$, NHCO(CR$^{x}$R$^{y}$)$_m$NR$^{x1}$R$^{x2}$, CONR$^{x1}$R$^{x2}$, C$_{1-6}$ alkoxy, C$_{1-6}$ alkoxy-C(O)—, CONR$^{x1}$R$^{x2}$, C$_{1-6}$ alkylthio, hydroxy-C$_{1-6}$ alkyl, C$_{1-6}$ alkyl-SO$_2$—, CO$_2$R$^x$ and C$_{1-3}$ alkoxy-C$_{1-3}$ alkyl-O—C(O)—,
  halogen, CN, C$_{1-6}$ alkoxy, C$_{1-6}$ alkoxy-C(O)—, CONR$^{x1}$R$^{x2}$, C$_{1-6}$ alkylthio, hydroxy-C$_{1-6}$ alkyl, C$_{1-6}$ alkyl-SO$_2$—, CO$_2$R$^x$, C$_{1-3}$ alkoxy-C$_{1-3}$ alkyl-O—C(O)—, OH, =O, O(C$_{1-6}$ alkyl optionally substituted by one or more F), C(O)(C$_{1-6}$ alkyl optionally substituted by one or more F), C$_{1-6}$ alkyl optionally substituted by one or more F, C$_{1-6}$ alkyl substituted by CN, C$_{1-6}$ alkyl substituted by up to 3 OH, C$_{1-6}$ alkyl substituted by CO$_2$(C$_{1-4}$ alkyl), C$_{1-6}$ alkyl substituted by one or more C$_{1-3}$ alkoxy, SO$_2$(C$_{1-6}$ alkyl optionally substituted by one or more F), CO$_2$(C$_{1-6}$ alkyl), C$_{3-6}$ cycloalkyl, C(O)(C$_{3-6}$ cycloalkyl), N(H or C$_{1-3}$ alkyl)CO(C$_{1-3}$ alkyl), and N(H or C$_{1-3}$ alkyl)(H or C$_{1-3}$ alkyl),
m is an integer from 1 to 4,
R$^{2a}$, R$^2$, R$^{2c}$, R$^{2d}$ and R$^{2e}$ are each independently selected from H, OH, halogen, NH$_2$, or methyl optionally substituted by up to 3 F,
X$^1$, X$^2$, R$^{1a}$, R$^4$, R$^{4a}$ and R$^5$ are each independently selected from H; C$_{3-6}$ cycloalkyl; and C$_{0-6}$ alkyl optionally substituted by up to 3 substituents independently selected from halogen, CN, CO$_2$H, OH, (C$_{1-6}$ alkoxy optionally substituted by up to 3 F), S(O)$_p$(C$_{1-6}$ alkyl optionally substituted by up to 3 F), C(O)(C$_{1-6}$ alkoxy optionally substituted by up to 3 F or by C$_{1-3}$ alkoxy), C(O)NR$^{x1}$R$^{x2}$, NR$^{x1}$R$^{x2}$, O(C$_{3-6}$ cycloalkyl), Ar, Het, CO$_2$(C$_{1-6}$ alkyl optionally substituted by up to 3 F), NR$^{x1}$C(O)(C$_{1-6}$ alkyl optionally substituted by up to 3 F), NR$^{x1}$C(O)NR$^{x2}$(C$_{1-6}$ alkyl optionally substituted by up to 3 F), OC(O)(C$_{1-6}$ alkyl optionally substituted by up to 3 F), and OC(O)NR$^{x1}$R$^{x2}$,
p is 0, 1 or 2,
R$^3$ is H,
C$_{0-3}$ alkyl optionally substituted by
  CN
  N(H or C$_{1-3}$ alkyl optionally substituted by one or more F)(C$_{1-3}$ alkyl optionally substituted by one or more F)
  Het
  OH
  SH
  Ar
  OAr
  One or more halogen
  CONR$^X$R$^Y$
  CO$_2$CR$^X$R$^Y$
  CONR$^X$R$^Y$
  S(C$_{1-3}$ alkyl optionally substituted by one or more F),
  S—(CR$^X$R$^Y$)$_{0-2}$Het
  S—(CR$^X$R$^Y$)$_{0-2}$Ar
  S—(CR$^X$R$^Y$)$_{0-2}$(C$_{3-6}$ cycloalkyl),
  SONR$^X$R$^Y$
  SO$_2$CR$^X$R$^Y$
  O(CR$^X$R$^Y$)$_m$(CO)NR$^X$R$^Y$
  NHSO$_2$(C$_{1-3}$ alkyl optionally substituted by one or more F, or by Ar or Het or (C$_{3-6}$ cycloalkyl))
  NHSO$_2$NR$^X$R$^Y$
  CONHSO$_2$CR$^X$R$^Y$
  C$_{2-6}$ alkyne
  C$_{2-6}$ alkene
  C$_{3-6}$ cycloalkyl optionally substituted by one or more F, or by
  O(C$_{1-3}$ alkyl optionally substituted by one or more F),
or R$^3$ is
NH(C$_{1-3}$ alkyl optionally substituted by one or more F), NH(C$_{3-6}$ cycloalkyl), NH-Het, NHCO(C$_{1-4}$ alkyl optionally substituted by one or more F), NHCOCR$^X$R$^Y$Het, NHCOCR$^X$R$^Y$Ar, NHSO$_2$—(C$_{1-6}$ alkyl), NHCONH—(H or C$_{1-6}$ alkyl), NHCONH—(C$_{3-6}$ cycloalkyl), NHSO$_2$—(C$_{3-6}$ cycloalkyl), CR$^X$R$^Y$O(C$_{1-3}$ alkyl optionally substituted by one or more F, Het, Aryl or C$_{3-6}$ cycloalkyl), CH$_2$O-Het, CH$_2$O—(C$_{3-6}$ cycloalkyl), O(C$_{1-3}$ alkyl optionally substituted by one or more F), O(C$_{3-6}$ cycloalkyl), O-Het, NHCO(C$_{3-6}$ cycloalkyl, Ar or Het), C$_{3-6}$ cycloalkyl, Het, C(O)N(H or C$_{1-3}$ alkyl optionally substituted by one or more F)(H or C$_{1-3}$ alkyl optionally substituted by one or more F), or NH(C$_{2-3}$ alkyl optionally substituted by one or more F, or C$_{1-3}$ alkyl)NHCO(C$_{1-6}$ alkyl optionally substituted by one or more F),
and R$^x$ and R$^y$ are each independently H, C$_{1-3}$ alkyl (optionally substituted by up to 3 substituents independently selected from F, OH and OCH$_3$), or together with the C to which they are attached are C$_{3-6}$ cycloalkyl.

The invention also comprises pharmaceutical compositions comprising a therapeutically effective amount of a compound of formula I as defined herein, or a pharmaceutically acceptable salt thereof, and a pharmaceutically acceptable carrier.

The invention is also directed to a method of treating a disease or condition indicated for treatment with a Trk antagonist, in a subject, by administering to a subject in need thereof a therapeutically effective amount of one or more of the compounds herein, or a pharmaceutically acceptable salt thereof.

Other aspects of the invention will be apparent from the remaining description and claims.

Preferably, the compounds of the present invention are potent antagonists at TrkA receptors, and have a suitable PK profile to enable once daily dosing.

The compounds of the present invention are potentially useful in the treatment of a range of disorders where a TrkA antagonist is indicated, particularly pain indications.

Depending on the disease and condition of the patient, the term "treatment" as used herein may include one or more of curative, palliative and prophylactic treatment.

Disorders for which a trkA inhibitor may be indicated include pain. Pain may be either acute or chronic and additionally may be of central and/or peripheral origin. Pain may be of a neuropathic and/or nociceptive and/or inflammatory nature, such as pain affecting either the somatic or visceral systems, as well as dysfunctional pain affecting multiple systems.

Physiological pain is an important protective mechanism designed to warn of danger from potentially injurious stimuli from the external environment. The system operates through a specific set of primary sensory neurones and is activated by noxious stimuli via peripheral transducing mechanisms (see Meyer et al., 2006, Wall and Melzack's Textbook of Pain ($5^{th}$ Ed), Chapter 1). These sensory fibres are known as nociceptors, and are characteristically small diameter axons with slow conduction velocities, of which there are two main types, A-delta fibres (myelinated) and C fibres (non-myelinated). Nociceptors encode the intensity, duration and quality of noxious stimulus and by virtue of their topographically organised projection to the spinal cord, the location of the stimulus. The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually, although not always, associated with a specific cause such as a defined injury, is often sharp and severe and can result from numerous origins such as surgery, dental work, a strain or a sprain. Acute pain does not generally result in any persistent psychological response. When a substantial injury occurs to body tissue, via disease or trauma, the characteristics of nociceptor activation may be altered such that there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury or alteration which can be associated with maladaptation and aberrant activity (Woolf & Salter, 2000, Science, 288, 1765-1768). As such, chronic pain is long-term pain, typically persisting for more than three months and leading to significant psychological and emotional problems. Common examples of chronic pain are neuropathic pain (e.g. painful diabetic neuropathy or postherpetic neuralgia), carpal tunnel syndrome, back pain, headache, cancer pain, arthritic pain and chronic post-surgical pain, but may include any chronic painful condition affecting any system, such as those described by the International Association for the Study of Pain (Classification of Chronic Pain, a publication freely available for download at http://www.iasp-pain.org).

The clinical manifestation of pain is present when discomfort and abnormal sensitivity feature among the patient's symptoms. Patients tend to be quite heterogeneous and may present with various pain symptoms. Such symptoms can include: 1) spontaneous pain which may be dull, burning, or stabbing; 2) exaggerated pain responses to noxious stimuli (hyperalgesia); and 3) pain produced by normally innocuous stimuli (allodynia) (Meyer et al., 2006, Wall and Melzack's Textbook of Pain ($5^{th}$ Ed), Chapter 1). Although patients suffering from various forms of acute and chronic pain may have similar symptoms, the underlying mechanisms may be different and may, therefore, require different treatment strategies. Apart from acute or chronic, pain can also be broadly categorized into: nociceptive pain, affecting either the somatic or visceral systems, which can be inflammatory in nature (associated with tissue damage and the infiltration of immune cells); or neuropathic pain.

Nociceptive pain can be defined as the process by which intense thermal, mechanical, or chemical stimuli are detected by a subpopulation of peripheral nerve fibers, called nociceptors, and can be induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 2006, Wall and Melzack's Textbook of Pain ($5^{th}$ Ed), Chapter 1). Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from strains/sprains, burns, myocardial infarction and acute pancreatitis, post-operative pain (pain following any type of surgical procedure), posttraumatic pain, pain associated with gout, cancer pain and back pain. Cancer pain may be chronic pain such as tumour related pain (e.g. bone pain, headache, facial pain or visceral pain) or pain associated with cancer therapy (e.g. in response to chemotherapy, immunotherapy, hormonal therapy or radiotherapy). Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Nociceptive pain can also be related to inflammatory states. The inflammatory process is a complex series of biochemical and cellular events, activated in response to tissue injury or the presence of foreign substances, which results in swelling and pain (McMahon et al., 2006, Wall and Melzack's Textbook of Pain ($5^{th}$ Ed), Chapter 3). A common inflammatory condition associated with pain is arthritis. It has been estimated that almost 27 million Americans have symptomatic osteoarthritis (OA) or degenerative joint disease (Lawrence et al., 2008, Arthritis Rheum, 58, 15-35); most patients with osteoarthritis seek medical attention because of the associated pain. Arthritis has a significant impact on psychosocial and physical function and is known to be the leading cause of disability in later life. Rheumatoid arthritis is an immune-mediated, chronic, inflammatory polyarthritis disease, mainly affecting peripheral synovial joints. It is one of the commonest chronic inflammatory conditions in developed countries and is a major cause of pain.

In regard to nociceptive pain of visceral origin, visceral pain results from the activation of nociceptors of the thoracic, pelvic, or abdominal organs (Bielefeldt and Gebhart, 2006, Wall and Melzack's Textbook of Pain ($5^{th}$ Ed), Chapter 48). This includes the reproductive organs, spleen, liver, gastrointestinal and urinary tracts, airway structures, cardiovascular system and other organs contained within the abdominal cavity. As such visceral pain refers to pain associated with conditions of such organs, such as painful bladder syndrome, interstitial cystitis, prostatitis, ulcerative colitis, Crohn's disease, renal colic, irritable bowl syndrome, endometriosis and dysmenorrheal (Classification of Chronic Pain, available at http://www.iasp-pain.org). Currently the potential for a neuropathic contribution (either through central changes or nerve injury/damage) to visceral pain states is poorly understood but may play a role in certain conditions (Aziz et al., 2009, Dig Dis 27, Suppl 1, 31-41)

Neuropathic pain is currently defined as pain arising as a direct consequence of a lesion or disease affecting the somatosensory system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Dworkin, 2009, Am J Med, 122, S1-S2; Geber et al., 2009, Am J Med, 122, S3-S12; Haanpaa et al., 2009, Am J Med, 122, S13-S21). The symptoms of neuropathic pain are difficult to treat, as they are often heterogeneous even between patients with the same disease (Dworkin, 2009, Am J Med, 122, S1-S2; Geber et al., 2009, Am J Med, 122, S3-S12; Haanpaa et al., 2009, Am J Med, 122, S13-S21). They include spontaneous pain, which can be continuous, and paroxysmal or abnormal evoked pain, such as hyperalgesia (increased sensitivity to a noxious stimulus) and allodynia (sensitivity to a normally innocuous stimulus).

It should be noted that some types of pain have multiple aetiologies and thus can be classified in more than one area, e.g. back pain, cancer pain and even migaine headaches may include both nociceptive and neuropathic components.

Similarly other types of chronic pain, perhaps less well understood, are not easily defined by the simplistic definitions of nociceptive or neuropathic. Such conditions include in particular fibromyalgia and chronic regional pain syndrome, which are often described as dysfunctional pain states e.g. fibromyalgia or complex regional pain syndrome (Woolf, 2010, J Clin Invest, 120, 3742-3744), but which are included in classifications of chronic pain states (Classification of Chronic Pain, available at http://www.iasp-pain.org).

As well as pain, and as noted in the background, trk inhibitors such as trkA inhibitors may be useful in treating a wide variety of other conditions and diseases.

DETAILED DESCRIPTION

Embodiment 1 is a compound of Formula I

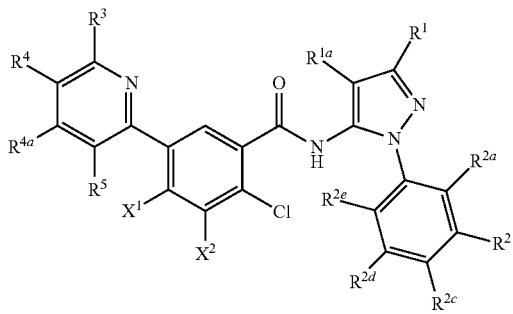

I or a prodrug thereof, or a pharmaceutically acceptable salt thereof, wherein $R^1$ is CN, $CO_2R^x$, CO—(NHet), $CONR^{x1}$—($C_{3-8}$ cycloalkyl, Ar, Het or $R^{x2}$), $CONR^{x1}(CR^xR^y)_m$(NHet, $NR^{x1}R^{x2}$, $C_{3-8}$ cycloalkyl, Ar, Het or $R^{x2}$), $CONR^{x1}(CR^YR^X)_m$CO(NHet, $NR^{x1}R^{x2}$, $C_{3-8}$ cycloalkyl, Ar, Het or $R^{x2}$), $CONR^{x1}(CR^YR^X)_m NR^{x1}$CO(NHet, $NR^{x1}R^{x2}$, $C_{3-8}$ cycloalkyl, Ar, Het or $R^{x2}$), $CONR^{x1}$CO(NHet, $NR^{x1}R^{x2}$, $C_{3-8}$ cycloalkyl, Ar, Het or $R^{x2}$), $CONR^{x1}$CO—($CR^xR^y)_m$(NHet, $NR^{x1}R^{x2}$, $C_{3-8}$ cycloalkyl, Ar, Het or $R^{x2}$), $CONR^{x1}(CR^xR^y)_m CONR^{x1}$—(NHet, $NR^{x1}R^{x2}$, $C_{3-8}$ cycloalkyl, Ar, Het or $R^{x2}$), $R^{x1}$ and $R^{x2}$ are each independently H, $C_{1-6}$ alkyl optionally substituted by up to 3 substituents independently selected from
  halogen,
  OH,
  $NH_2$,
  $NH(C_{1-6}$ alkyl),
  $N(C_{1-6}$ alkyl)$_2$,
  CN,
  ($C_{1-6}$ alkoxy optionally substituted by up to 3 substituents independently selected from halogen, OH, $NH_2$, $NH(C_{1-6}$ alkyl optionally substituted by up to 3 substituents independently selected from halogen, OH, $NH_2$), $N(C_{1-6}$ alkyl optionally substituted by up to 3 substituents independently selected from halogen, OH, $NH_2$)$_2$, and $C_{1-6}$ alkoxy)
  and ($C_{1-6}$ alkyl optionally substituted by up to 3 substituents independently selected from halogen, $NH_2$, $NH(C_{1-6}$ alkyl), $N(C_{1-6}$ alkyl)$_2$, and $C_{1-6}$ alkoxy), or, together with the nitrogen atom to which they are attached, $R^{x1}$ and $R^{x2}$ form a 4- to 8-membered saturated or unsaturated heterocyclic ring with a ring N atom directly linked to the linked moiety, having from 0 to 2 further hetero ring atoms independently selected from N, O and S, NHet is a 4- to 8-membered saturated or unsaturated heterocyclic ring with a ring N atom directly linked to the linked moiety, having from 0 to 2 further hetero ring atoms independently selected from N, O and S, Het is a 4- to 8-membered saturated or unsaturated heterocyclic ring having at least 1, and up to 3, hetero ring atoms independently selected from N, O and S, the $C_{3-8}$ cycloalkyl, NHet and Het groups may be monocyclic, bicyclic, bridged or spirocyclic if the number of ring atoms allows, Ar is phenyl, wherein each of $C_{3-8}$ cycloalkyl, Ar, NHet and Het are optionally substituted, where valency allows, by up to 5 substituents independently selected from
  $C_{1-6}$ alkyl optionally substituted by up to 3 substituents independently selected from halogen, OH, CN, $NR^{x1}R^{x2}$, $NHCOR^{x1}$, $NHCO(CR^xR^y)_m NR^{x1}R^{x2}$, $CONR^{x1}R^{x2}$, $C_{1-6}$ alkoxy, $C_{1-6}$ alkoxy-C(O)—, $CONR^{x1}R^{x2}$, $C_{1-6}$ alkylthio, hydroxy-$C_{1-6}$ alkyl, $C_{1-6}$ alkyl-$SO_2$—, $CO_2R^x$ and $C_{1-3}$ alkoxy-$C_{1-3}$ alkyl-O—C(O)—,
  halogen, CN, $C_{1-6}$ alkoxy, $C_{1-6}$ alkoxy-C(O)—, $CONR^{x1}R^{x2}$, $C_{1-6}$ alkylthio, hydroxy-$C_{1-6}$ alkyl, $C_{1-6}$ alkyl-$SO_2$—, $CO_2R^x$, $C_{1-3}$ alkoxy-$C_{1-3}$ alkyl-O—C(O)—, OH, =O, O($C_{1-6}$ alkyl optionally substituted by one or more F), C(O)($C_{1-6}$ alkyl optionally substituted by one or more F), $C_{1-6}$ alkyl optionally substituted by one or more F, $C_{1-6}$ alkyl substituted by CN, $C_{1-6}$ alkyl substituted by up to 3 OH, $C_{1-6}$ alkyl substituted by $CO_2(C_{1-4}$ alkyl), $C_{1-6}$ alkyl substituted by one or more $C_{1-3}$ alkoxy, $SO_2(C_{1-6}$ alkyl optionally substituted by one or more F), CO$_2$(C$_{1-6}$ alkyl), C$_{3-6}$ cycloalkyl, C(O)(C$_{3-6}$ cycloalkyl), N(H or C$_{1-3}$ alkyl)CO(C$_{1-3}$ alkyl), and N(H or C$_{1-3}$ alkyl)(H or C$_{1-3}$ alkyl), m is an integer from 1 to 4, R$^{2a}$, R$^2$, R$^{2c}$, R$^{2d}$ and R$^{2e}$ are each independently selected from H, OH, halogen, NH$_2$, or methyl optionally substituted by up to 3 F, X$^1$, X$^2$, R$^{1a}$, R$^4$, R$^{4a}$ and R$^5$ are each independently selected from H; C$_{3-6}$ cycloalkyl; and C$_{0-6}$ alkyl optionally substituted by up to 3 substituents independently selected from halogen, CN, CO$_2$H, OH, (C$_{1-6}$ alkoxy optionally substituted by up to 3 F), S(O)$_p$(C$_{1-6}$ alkyl optionally substituted by up to 3 F), C(O)(C$_{1-6}$ alkoxy optionally substituted by up to 3 F or by C$_{1-3}$ alkoxy), C(O)NR$^{x1}$R$^{x2}$, NR$^{x1}$R$^{x2}$, O(C$_{3-6}$ cycloalkyl), Ar, Het, CO$_2$(C$_{1-6}$ alkyl optionally substituted by up to 3 F), NR$^{x1}$C(O)(C$_{1-6}$ alkyl optionally substituted by up to 3 F), NR$^{x1}$C(O)NR$^{x2}$(C$_{1-6}$ alkyl optionally substituted by up to 3 F), OC(O)(C$_{1-6}$ alkyl optionally substituted by up to 3 F), and OC(O)NR$^{x1}$R$^{x2}$, p is 0, 1 or 2, R$^3$ is H, C$_{0-3}$ alkyl optionally substituted by
  CN
  N(H or C$_{1-3}$ alkyl optionally substituted by one or more F)(C$_{1-3}$ alkyl optionally substituted by one or more F
  Het
  OH
  SH
  Ar
  OAr
  One or more halogen
  CONR$^X$R$^Y$
  CO$_2$CR$^X$R$^Y$
  CONR$^X$R$^Y$
  S(C$_{1-3}$ alkyl optionally substituted by one or more F),
  S—(CR$^X$R$^Y$)$_{0-2}$Het
  S—(CR$^X$R$^Y$)$_{0-2}$Ar
  S—(CR$^X$R$^Y$)$_{0-2}$ (C$_{3-6}$ cycloalkyl),
  SONR$^X$R$^Y$
  SO$_2$CR$^X$R$^Y$
  O(CR$^X$R$^Y$)$_m$(CO)NR$^X$R$^Y$
  NHSO$_2$(C$_{1-3}$ alkyl optionally substituted by one or more F, or by Ar or Het or (C$_{3-6}$ cycloalkyl))
  NHSO$_2$NR$^X$R$^Y$
  CONHSO$_2$CR$^X$R$^Y$
  C$_{2-6}$ alkyne
  C$_{2-6}$ alkene
  C$_{3-6}$ cycloalkyl optionally substituted by one or more F, or by
  O(C$_{1-3}$ alkyl optionally substituted by one or more F), or R$^3$ is NH(C$_{1-3}$ alkyl optionally substituted by one or more F), NH(C$_{3-6}$ cycloalkyl), NH-Het, NHCO(C$_{1-4}$ alkyl optionally substituted by one or more F), NHCOCR$^x$R$^y$Het, NHCOCR$^x$R$^y$Ar, NHSO$_2$—(C$_{1-6}$ alkyl), NHCONH—(H or C$_{1-6}$ alkyl), NHCONH—(C$_{3-6}$ cycloalkyl), NHSO$_2$—(C$_{3-6}$ cycloalkyl), CR$^x$R$^y$O(C$_{1-3}$ alkyl optionally substituted by one or more F, Het, Aryl or C$_{3-6}$ cycloalkyl), CH$_2$O-Het, CH$_2$O—(C$_{3-6}$ cycloalkyl), O(C$_{1-3}$ alkyl optionally substituted by one or more F), O(C$_{3-6}$ cycloalkyl), O-Het, NHCO(C$_{3-6}$ cycloalkyl, Ar or Het), C$_{3-6}$ cycloalkyl, Het, C(O)N(H or C$_{1-3}$ alkyl optionally substituted by one or more F)(H or C$_{1-3}$ alkyl optionally substituted by one or more F), or NH(C$_{2-3}$ alkyl optionally substituted by one or more F, or C$_{1-3}$ alkyl)NHCO(C$_{1-6}$ alkyl optionally substituted by one or more F), and R$^x$ and R$^y$ are each independently H, C$_{1-3}$ alkyl (optionally substituted by up to 3 substituents independently selected from F, OH and OCH$_3$), or together with the C to which they are attached are C$_{3-6}$ cycloalkyl.

Embodiment 2 is a compound, prodrug, or salt according to embodiment 1 wherein R$^{1a}$ is H.

Embodiment 3 is a compound, prodrug, or salt according to embodiment 1 or 2 wherein R$^{4a}$ is H.

Embodiment 4 is a compound, prodrug, or salt according to embodiment 1, 2 or 3 wherein R$^{2a}$, R$^2$, R$^{2c}$, R$^{2d}$ and R$^{2e}$ are each independently selected from H, F and OH.

Embodiment 5 is a compound, prodrug, or salt according to embodiment 1, 2, 3 or 4 wherein R$^{2a}$, R$^{2c}$, R$^{2d}$ and R$^{2e}$ are H.

Embodiment 6 is a compound, prodrug, or salt according to embodiment 1, 2, 3, 4 or 5 wherein R$^2$ is H or OH.

Embodiment 7 is a compound of formula I',

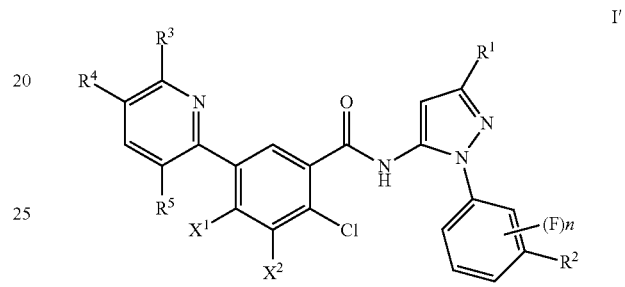

or a prodrug thereof, or a pharmaceutically acceptable salt thereof, according to embodiment 1, wherein n is an integer from 0 to 4, R$^1$ is CN, CO$_2$R$^x$,
CO—(NHet),
CONR$^{x1}$—(C$_{3-8}$ cycloalkyl, Ar, Het or R$^{x2}$),
CONR$^{x1}$(CR$^x$R$^y$)$_m$(NHet, NR$^{x1}$R$^{x2}$, C$_{3-8}$ cycloalkyl, Ar, Het or R$^{x2}$),
CONR$^{x1}$(CR$^Y$R$^X$)$_m$CO(NHet, NR$^{x1}$R$^{x2}$, C$_{3-8}$ cycloalkyl, Ar, Het or R$^{x2}$),
CONR$^{x1}$(CR$^Y$R$^X$)$_m$NR$^{x1}$CO(NHet, NR$^{x1}$R$^{x2}$, C$_{3-8}$ cycloalkyl, Ar, Het or R$^{x2}$),
CONR$^{x1}$CO(NHet, NR$^{x1}$R$^{x2}$, C$_{3-8}$ cycloalkyl, Ar, Het or R$^{x2}$),
CONR$^{x1}$CO—(CR$^x$R$^y$)$_m$(NHet, NR$^{x1}$R$^{x2}$, C$_{3-8}$ cycloalkyl, Ar, Het or R$^{x2}$),
CONR$^{x1}$(CR$^x$R$^y$)$_m$CONR$^{x1}$—(NHet, NR$^{x1}$R$^{x2}$, C$_{3-8}$ cycloalkyl, Ar, Het or R$^{x2}$), NHet is a 4- to 8-membered saturated or unsaturated heterocyclic ring with a ring N atom directly linked to the linked moiety, having from 0 to 2 further hetero ring atoms independently selected from N, O and S, Het is a 4- to 8-membered saturated or unsaturated heterocyclic ring having at least 1, and up to 3, hetero ring atoms independently selected from N, O and S, the C$_{3-8}$ cycloalkyl, NHet and Het groups may be monocyclic, bicyclic, bridged or spirocyclic if the number of ring atoms allows, Ar is phenyl, R$^{x1}$ and R$^{x2}$ are each independently H, C$_{1-6}$ alkyl optionally substituted by up to 3 substituents independently selected from
  halogen,
  OH,
  NH$_2$,
  NH(C$_{1-6}$ alkyl),
  N(C$_{1-6}$ alkyl)$_2$,
  CN, ($C_{1-6}$ alkoxy optionally substituted by up to 3 substituents independently selected from halogen, OH, $NH_2$, NH($C_{1-6}$ alkyl optionally substituted by up to 3 substituents independently selected from halogen, OH, $NH_2$), N($C_{1-6}$ alkyl optionally substituted by up to 3 substituents independently selected from halogen, OH, $NH_2$)$_2$, and $C_{1-6}$ alkoxy)

and ($C_{1-6}$ alkyl optionally substituted by up to 3 substituents independently selected from halogen, $NH_2$, NH($C_{1-6}$ alkyl), N($C_{1-6}$ alkyl)$_2$, and $C_{1-6}$ alkoxy), or, together with the nitrogen atom to which they are attached, $R^{x1}$ and $R^{x2}$ form a 4- to 8-membered saturated or unsaturated heterocyclic ring with a ring N atom directly linked to the linked moiety, having from 0 to 2 further hetero ring atoms independently selected from N, O and S, wherein each of $C_{3-8}$ cycloalkyl, Ar, NHet and Het are optionally substituted, where valency allows, by up to 5 substituents independently selected from $C_{1-6}$ alkyl optionally substituted by up to 3 substituents independently selected from halogen, OH, CN, $NR^{x1}R^{x2}$, $NHCOR^{x1}$, $NHCO(CR^xR^y)_m NR^{x1}R^{x2}$, $CONR^{x1}R^{x2}$, $C_{1-6}$ alkoxy, $C_{1-6}$ alkoxy-C(O)—, $CONR^{x1}R^{x2}$, $C_{1-6}$ alkylthio, hydroxy-$C_{1-6}$ alkyl, $C_{1-6}$ alkyl-$SO_2$—, $CO_2R^x$ and $C_{1-3}$ alkoxy-$C_{1-3}$ alkyl-O—C(O)—, halogen, CN, $C_{1-6}$ alkoxy, $C_{1-6}$ alkoxy-C(O)—, $CONR^{x1}R^{x2}$, $C_{1-6}$ alkylthio, hydroxy-$C_{1-6}$ alkyl, $C_{1-6}$ alkyl-$SO_2$—, $CO_2R^x$ and $C_{1-3}$ alkoxy-$C_{1-3}$ alkyl-O—C(O)—, OH, =O, O($C_{1-6}$ alkyl optionally substituted by one or more F), C(O)($C_{1-6}$ alkyl optionally substituted by one or more F), $C_{1-6}$ alkyl optionally substituted by one or more F, $C_{1-6}$ alkyl substituted by CN, $C_{1-6}$ alkyl substituted by up to 3 OH, $C_{1-6}$ alkyl substituted by $CO_2$($C_{1-4}$ alkyl), $C_{1-6}$ alkyl substituted by one or more $C_{1-3}$ alkoxy, $SO_2$($C_{1-6}$ alkyl optionally substituted by one or more F), $CO_2$($C_{1-6}$ alkyl), $C_{3-6}$ cycloalkyl, C(O)($C_{3-6}$ cycloalkyl), N(H or $C_{1-3}$ alkyl)CO($C_{1-3}$ alkyl), and N(H or $C_{1-3}$ alkyl)(H or $C_{1-3}$ alkyl), m is an integer from 1 to 4, $R^2$ is H, OH, halogen, $NH_2$ or methyl optionally substituted by up to 3 F, $R^3$ is H, $C_{0-3}$ alkyl optionally substituted by
CN,
N(H or $C_{1-3}$ alkyl optionally substituted by one or more F)(H or $C_{1-3}$ alkyl optionally substituted by one or more F)
one or more F
Het
$C_{3-6}$ cycloalkyl optionally substituted by one or more F, or by
O($C_{1-3}$ alkyl optionally substituted by one or more F),
or $R^3$ is
NH($C_{1-3}$ alkyl optionally substituted by one or more F),
NH($C_{3-6}$ cycloalkyl),
NH-Het,
NHCO($C_{1-4}$ alkyl optionally substituted by one or more F),
$NHCOCR^xR^y$Het,
$NHCOCR^xR^y$Ar,
$NHSO_2$—($C_{1-6}$ alkyl),
NHCONH—(H or $C_{1-6}$ alkyl),
NHCONH—($C_{3-6}$ cycloalkyl),
$NHSO_2$—($C_{3-6}$ cycloalkyl),
$CR^xR^yO$($C_{1-3}$ alkyl optionally substituted by one or more F, Het, Aryl or $C_{3-6}$ cycloalkyl)
$CH_2O$-Het,
$CH_2O$—($C_{3-6}$ cycloalkyl),
O($C_{1-3}$ alkyl optionally substituted by one or more F),
O($C_{1-6}$ cycloalkyl),
O-Het,
NHCO($C_{3-6}$ cycloalkyl, Ar or Het),
$C_{3-6}$ cycloalkyl,
Het,
C(O)N(H or $C_{1-3}$ alkyl optionally substituted by one or more F)(H or $C_{1-3}$ alkyl optionally substituted by one or more F), or
NH($C_{2-3}$ alkyl optionally substituted by one or more F, or $C_{1-3}$ alkyl)NHCO($C_{1-6}$ alkyl optionally substituted by one or more F), $X^1$ is H, Cl, F, CN, $C_{1-3}$ alkyl optionally substituted by one or more F, $C_{1-3}$ alkoxy optionally substituted by one or more F, or cyclopropyl, $X^2$ is H, Cl, F, CN, $C_{1-3}$ alkyl optionally substituted by one or more F, $C_{1-3}$ alkoxy optionally substituted by one or more F, or cyclopropyl, $R^4$ is H, F, Cl, CN, $C_{1-3}$ alkyl optionally substituted by one or more F, $C_{1-3}$ alkoxy optionally substituted by one or more F, or cyclopropyl, $R^5$ is H, Cl, F, CN, $C_{1-3}$ alkyl optionally substituted by one or more F, $C_{1-3}$ alkoxy optionally substituted by one or more F, or cyclopropyl, and $R^x$ and $R^y$ are each independently H or $C_{1-3}$ alkyl or together with the C to which they are attached are $C_{3-6}$ cycloalkyl.

Embodiment 8 is a compound, prodrug or salt according to embodiment 1, 2, 3, 4, 5, 6 or 7 wherein $R^1$ is selected from:
CON(H or $C_{1-4}$ alkyl optionally substituted by 1 or 2 substituents independently selected from F, OH and OMe)(H or $C_{1-4}$ alkyl optionally substituted by 1, 2 or 3 substituents independently selected from F, $NH_2$, OH and OMe),
CONH($C_{3-6}$ cycloalkyl optionally substituted by 1, 2 or 3 substituents independently selected from OH, $NH_2$, $CH_3$ and $CH_2OH$),
CONH-Het,
and $C(O)NH(CR^YR^X)_m$-Het.

Embodiment 9 is a compound, prodrug or salt according to embodiment 1, 2, 3, 4, 5, 6, 7 or 8 wherein $R^1$ is selected from:
CONH(H, $CH_3$ or $C_{2-4}$ alkyl optionally substituted by F, $NH_2$, OH or OMe),
CONH($C_{3-6}$ cycloalkyl optionally substituted by 1, 2 or 3 substituents independently selected from OH, $CH_3$ and $CH_2OH$),
CON H-Het,
and $C(O)NH(CR^YR^X)_m$-$Het^1$,
where $Het^1$ is a 5- or 6-membered unsaturated heterocyclic ring having from 1 to 3 N ring atoms, and which ring is optionally substituted by up to 3 substituents independently selected from $C_{1-6}$ alkyl optionally substituted by one or more F.

Embodiment 10 is a compound, prodrug or salt according to embodiment 1, 2, 3, 4, 5, 6, 7, 8 or 9 wherein $R^1$ is selected from:
CONH(H, $CH_3$ or $C_{2-4}$ alkyl optionally substituted by OH),
CONH-Het,
And $C(O)NHCH_2$-$Het^1$,
where $Het^1$ is a 5- or 6-membered unsaturated heterocyclic ring having from 1 to 3 N ring atoms, and which ring is optionally substituted by up to 3 substituents independently selected from $C_{1-6}$ alkyl optionally substituted by one or more F.

Embodiment 11 is a compound, prodrug or salt according to embodiment 1, 2, 3, 4, 5, 6, 7, 8, 9 or 10 wherein $R^1$ is selected from $CONHCH_2$-(pyrazolyl or 1,2,3-triazolyl optionally substituted by 1 or 2 methyl groups); CONH (pyrazolyl or 1,2,3-triazolyl optionally substituted by 1 or 2 methyl groups; and CONH($C_{2-4}$ alkyl substituted by OH).

Embodiment 12 is a compound, prodrug or salt according to any previous embodiment wherein $R^1$ is selected from:

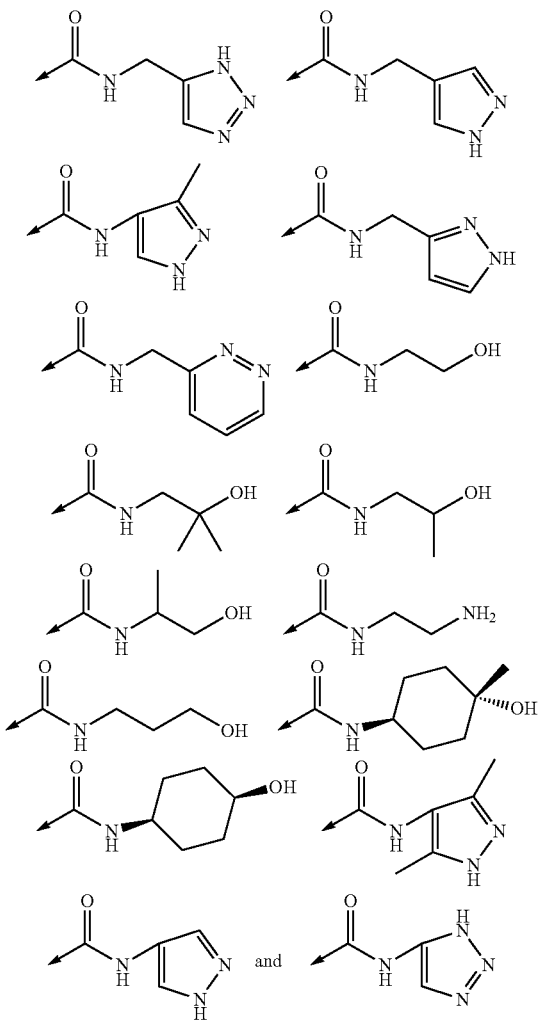

Embodiment 13 is a compound, prodrug or salt according to embodiment 1, 2, 3, 4, 5, 6 or 7 wherein $R^1$ is selected from the $R^1$ groups present in the compounds of the Examples herein.

Embodiment 14 is a compound, prodrug or salt according to embodiment 1 or 7 wherein $R^1$, $R^2$, n, $X^1$, $X^2$, $R^4$ and $R^5$ are selected from the relevant groups in the compounds of the Examples herein.

Embodiment 15 is a compound, prodrug or salt according to embodiment 1 or 7 wherein $R^1$ is selected from the $R^1$ groups present in the compounds of Examples 1, 11, 28, 29, 30, 34, 35, 36, 39, 40, 42, 43, 45, 46, 47, 55, 59, 60, 61, 68, 71, 87, 134, 135, 136 and 137.

Embodiment 16 is a compound, prodrug or salt according to any one of embodiments 7 to 15 wherein n is 0.

Embodiment 17 is a compound, prodrug or salt according to any one of embodiments 7 to 16 10 wherein $X^1$ is H, F or Cl.

Embodiment 18 is a compound, prodrug or salt according to any one of embodiments 7 to 17 wherein $X^2$ is H.

Embodiment 19 is a compound, prodrug or salt according to any one of embodiments 7 to 18 wherein $R^4$ is H, F, Cl, $CH_3$, CN or $OCH_3$.

Embodiment 20 is a compound, prodrug or salt according to any one of embodiments 7 to 19 wherein $R^5$ is H, F, Cl, $CH_3$, CN or $OCH_3$.

Embodiment 21 is a compound, prodrug or salt according to any one of embodiments 7 to 20 wherein $R^2$ is H.

Embodiment 22 is a compound, prodrug or salt according to any one of embodiments 7 to 21 wherein $R^3$ is H, ($C_{1-3}$ alkyl optionally substituted by CN, or by N(H or $C_{1-3}$ alkyl optionally substituted by one or more F)(H or $C_{1-3}$ alkyl optionally substituted by one or more F), or by one or more F, or by O($C_{1-3}$ alkyl optionally substituted by one or more F)),
or $R^3$ is
NH($C_{1-3}$ alkyl optionally substituted by one or more F), NHCO($C_{1-4}$ alkyl optionally substituted by one or more F), O($C_{1-3}$ alkyl optionally substituted by one or more F), or C(O)N(H or $C_{1-3}$ alkyl optionally substituted by one or more F)(H or $C_{1-3}$ alkyl optionally substituted by one or more F).

Embodiment 23 is a compound, prodrug or salt according to any one of embodiments 7 to 22 wherein $R^3$ is H, ($C_{1-3}$ alkyl optionally substituted by CN, or by N(H or $C_{1-3}$ alkyl optionally substituted by from 1-3 F)(H or $C_{1-3}$ alkyl optionally substituted by from 1-3 F), or by from 1-3 F, or by O($C_{1-3}$ alkyl optionally substituted by from 1-3 F)),
or $R^3$ is
NH($C_{1-3}$ alkyl optionally substituted by from 1-3 F), NHCO($C_{1-4}$ alkyl optionally substituted by from 1-3 F), O($C_{1-3}$ alkyl optionally substituted by from 1-3 F), or C(O)N(H or $C_{1-3}$ alkyl optionally substituted by from 1-3 F)(H or $C_{1-3}$ alkyl optionally substituted by from 1-3 F).

Embodiment 24 is a compound, prodrug or salt according to any one of embodiments 7 to 23 wherein $R^3$ is H, NHCO($C_{1-4}$ alkyl), $C_{1-3}$ alkyl optionally substituted by from 1-3 F, $CH_2CN$, $CH_2OCH_3$, $CH(CH_3)OCH_3$, $CONH_2$, O($C_{1-3}$ alkyl optionally substituted by from 1-3 F), NH($C_{1-3}$ alkyl), or $CH_2N$(H or $C_{1-3}$ alkyl optionally substituted by from 1-3 F)(H or $C_{1-3}$ alkyl optionally substituted by from 1-3 F).

Embodiment 25 is a compound, prodrug or salt according to any one of embodiments 7 to 24 wherein $R^3$ is H, $NHCOCH_3$, $NHCO(C(CH_3)_3)$, $CH_3$, $CH_2F$, $CHF_2$, $CF_3$, $CF_2CH_3$, $CH_2CHF_2$, $CH_2OCH_3$, $OCH_3$, $CH_2CN$, O (methyl optionally substituted by 1-3 F), $CH_2NHCH_3$, $CH(CH_3)OCH_3$, $CONH_2$, or $NHCH3$.

Embodiment 26 is a compound, prodrug or salt of embodiment 7 wherein
n is zero,
$R^2$ is H or OH,
$X^1$ is H, Cl, F, $CH_3$ or $OCH_3$,
$X^2$ is H, Cl or F,
$R^3$ is H,
$R^4$ is H or F,
$R^5$ is H, F, Cl or CN,
and $R^1$ is selected from:

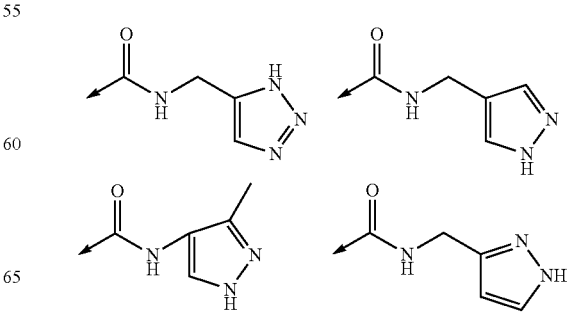

-continued

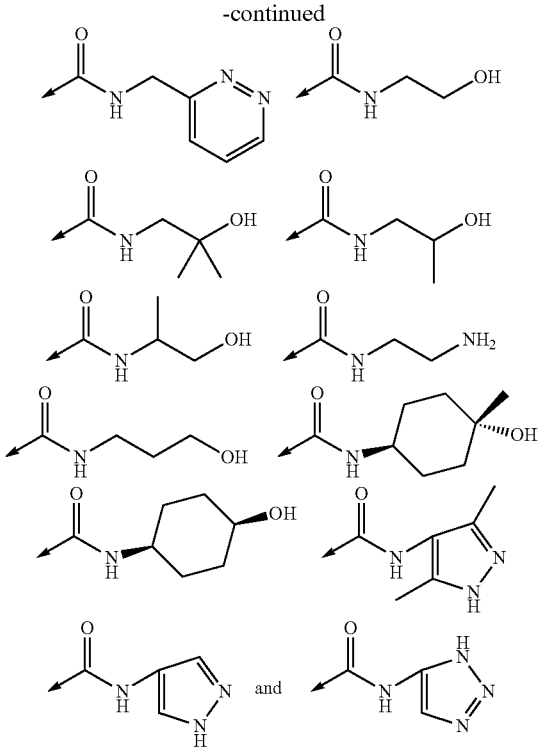

or a pharmaceutically acceptable salt thereof.

Embodiment 27 is a prodrug of any previous embodiment, such as a phosphate prodrug.

Embodiment 28 is a compound of any one of embodiments 1 to 26.

Embodiment 29 is a pharmaceutically acceptable salt of any one of embodiments 1 to 26.

Embodiment 30 is a compound selected from any of the Examples herein, or a prodrug thereof, or a pharmaceutically acceptable salt thereof.

Embodiment 31 is a compound selected from the compounds of Examples 1, 11, 28, 29, 30, 34, 35, 36, 39, 40, 42, 43, 45, 46, 47, 55, 59, 60, 61, 68, 71 87, 134, 135, 136, 137 or 138, or a prodrug thereof, or a pharmaceutically acceptable salt thereof.

Embodiment 32 is a compound of Formula I

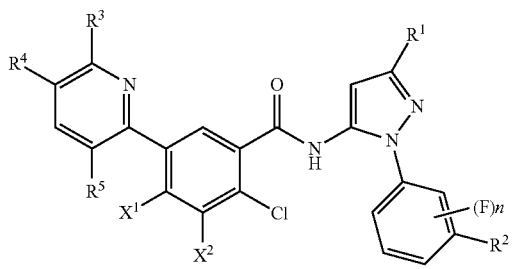

or a pharmaceutically acceptable salt thereof, according to embodiment 1, wherein
n is an integer from 0 to 4,
$R^1$ is
$CON(H$ or $C_{1-4}$ alkyl optionally substituted by 1 or 2 substituents independently selected from F, OH and $OCH_3)(H$ or $C_{1-4}$ alkyl optionally substituted by 1, 2 or 3 substituents independently selected from F, $NH_2$, OH and $OCH_3)$,
$CONH(C_{3-6}$ cycloalkyl optionally substituted by 1, 2 or 3 substituents independently selected from OH, $NH_2$, $CH_3$ and $CH_2OH$),
$CONH(CR^YR^X)_m(C_{3-6}$ cycloalkyl optionally substituted by 1, 2 or 3 substituents independently selected from OH, $NH_2$, $CH_3$ and $CH_2OH$),
$CONH(CR^YR^X)_m$—$CON(H$ or $C_{1-4}$ alkyl optionally substituted by 1 or 2 substituents independently selected from F, OH and $OCH_3)(H$ or $C_{1-4}$ alkyl optionally substituted by 1, 2 or 3 substituents independently selected from F, OH and $OCH_3)$,
$CONH(CR^YR^X)_m$—$N(H$ or $C_{1-4}$ alkyl optionally substituted by 1 or 2 substituents independently selected from F, OH and $OCH_3)(H$ or $C_{1-4}$ alkyl optionally substituted by 1, 2 or 3 substituents independently selected from F, OH and $OCH_3)$,
$CONH(CR^YR^X)_mN(H$ or $C_{1-4}$ alkyl optionally substituted by 1 or 2 substituents independently selected from F, OH and $OCH_3)CO(C_{1-4}$ alkyl optionally substituted by 1, 2 or 3 substituents independently selected from F, OH and $OCH_3)$,
$CONHC(O)$-Het,
$CONH(CR^YR^X)_m$-Het,
$CONH$—Ar,
$CONH$-Het,
CN,
$CO_2H$, or
$CO_2(C_{1-4}$ alkyl optionally substituted by 1 or 2 substituents independently selected from F, OH and $OCH_3)$,
m is an integer from 1 to 3,
Ar is phenyl optionally substituted by 1, 2 or 3 groups independently selected from $C_{1-6}$ alkyl, halogen, CN, $CF_3$, $CF_3O$, $C_{1-6}$ alkoxy, $C_{1-6}$ alkoxy-C(O)—, $CONH_2$, $C_{1-6}$ alkylthio, hydroxy-$C_{1-6}$ alkyl, $C_{1-6}$ alkyl-$SO_2$—, $CO_2H$ and $C_{1-3}$ alkoxy-$C_{1-3}$ alkyl-O—C(O)—,
Het is a 4-7-membered saturated or unsaturated heterocyclic ring having at least 1, and up to 3, hetero ring atoms independently selected from N, O and S, and which ring is optionally substituted by 1, 2 or 3 substituents independently selected from halogen,
OH,
=O,
CN,
$CONH_2$,
$O(C_{1-6}$ alkyl optionally substituted by one or more F),
$C(O)(C_{1-6}$ alkyl optionally substituted by one or more F),
$C_{1-6}$ alkyl optionally substituted by one or more F,
$C_{1-6}$ alkyl substituted by CN,
$C_{1-6}$ alkyl substituted by up to 3 OH,
$C_{1-6}$ alkyl substituted by $CO_2(C_{1-4}$ alkyl),
$C_{1-6}$ alkyl substituted by one or more $C_{1-3}$ alkoxy,
$SO_2(C_{1-6}$ alkyl optionally substituted by one or more F),
$CO_2(C_{1-6}$ alkyl),
$C_{3-6}$ cycloalkyl,
$C(O)(C_{3-6}$ cycloalkyl), and
$N(H$ or $C_{1-3}$ alkyl)$CO(C_{1-3}$ alkyl),
$R^2$ is H or OH,
$R^3$ is
H,
$C_{1-3}$ alkyl optionally substituted by
CN,
or by $N(H$ or $C_{1-3}$ alkyl optionally substituted by one or more F)(H or $C_{1-3}$ alkyl optionally substituted by one or more F),
or by one or more F,
or by Het,
or by $C_{3-6}$ cycloalkyl optionally substituted by one or more F,
or by $O(C_{1-3}$ alkyl optionally substituted by one or more F), or R³ is
NH(C$_{1-3}$ alkyl optionally substituted by one or more F),
NH(C$_{3-6}$ cycloalkyl),
NH-Het,
NHCO(C$_{1-4}$ alkyl optionally substituted by one or more F),
NHCOCR$_x$R$_y$Het,
NHCOCR$^x$R$^y$Ar,
NHSO$_2$—(C$_{1-6}$ alkyl),
NHCONH—(H or C$_{1-6}$ alkyl),
NHCONH—(C$_{3-6}$ cycloalkyl),
NHSO$_2$—(C$_{3-6}$ cycloalkyl),
CR$^x$R$^y$O(C$_{1-3}$ alkyl optionally substituted by one or more F, Het, Aryl or C$_{3-6}$ cycloalkyl)
CH$_2$O-Het,
CH$_2$O—(C$_{3-6}$ cycloalkyl),
O(C$_{1-3}$ alkyl optionally substituted by one or more F),
O(C$_{3-6}$ cycloalkyl),
O-Het,
NHCO(C$_{3-6}$ cycloalkyl, Ar or Het),
C$_{3-6}$ cycloalkyl,
Het,
C(O)N(H or C$_{1-3}$ alkyl optionally substituted by one or more F)(H or C$_{1-3}$ alkyl optionally substituted by one or more F), or NH(C$_{2-3}$ alkyl optionally substituted by one or more F, or C$_{1-3}$ alkyl)NHCO(C$_{1-6}$ alkyl optionally substituted by one or more F),
X$^1$ is H, Cl, F, CN, C$_{1-3}$ alkyl optionally substituted by one or more F, C$_{1-3}$ alkoxy optionally substituted by one or more F, or cyclopropyl,
X$^2$ is H, Cl, F, CN, C$_{1-3}$ alkyl optionally substituted by one or more F, C$_{1-3}$ alkoxy optionally substituted by one or more F, or cyclopropyl,
R$^4$ is H, F, Cl, CN, C$_{1-3}$ alkyl optionally substituted by one or more F, C$_{1-3}$ alkoxy optionally substituted by one or more F, or cyclopropyl,
R$^5$ is H, Cl, F, CN, C$_{1-3}$ alkyl optionally substituted by one or more F, C$_{1-3}$ alkoxy optionally substituted by one or more F, or cyclopropyl, and R$^x$ and R$^y$ are each independently H or C$_{1-3}$ alkyl.

Embodiment 33 is compound or salt according to embodiment 32 wherein R$^1$ is selected from
CON(H or C$_{1-4}$ alkyl optionally substituted by 1 or 2 substituents independently selected from F, OH and OMe)(H or C$_{1-4}$ alkyl optionally substituted by 1, 2 or 3 substituents independently selected from F, NH$_2$, OH and OMe),
CONH(C$_{3-6}$ cycloalkyl optionally substituted by 1, 2 or 3 substituents independently selected from OH, NH$_2$, CH$_3$ and CH$_2$OH),
CON H-Het,
and C(O)NH(CR$^y$R$^x$)$_m$-Het.

Embodiment 34 is a compound or salt according to embodiment 32 or 33 wherein R$^1$ is selected from
CONH(H, CH$_3$ or C$_{2-4}$ alkyl optionally substituted by F, NH$_2$, OH or OMe),
CONH(C$_{3-6}$ cycloalkyl optionally substituted by 1, 2 or 3 substituents independently selected from OH, CH$_3$ and CH$_2$OH),
CONH-Het,
and C(O)NH(CR$^y$R$^x$)$_m$-Het$^1$,
where Het$^1$ is a 5- or 6-membered unsaturated heterocyclic ring having from 1 to 3 N ring atoms, and which ring is optionally substituted by up to 3 substituents independently selected from C$_{1-6}$ alkyl optionally substituted by one or more F.

Embodiment 35 is compound or salt according to embodiment 32, 33 or 34 wherein R$^1$ is selected from
CONH(H, CH$_3$ or C$_{2-4}$ alkyl optionally substituted by OH),
CONH-Het$^1$,
And C(O)NHCH$_2$-Het$^1$.

Embodiment 36 is a compound or salt according to embodiment 32, 33, 34 or 35 wherein R$^1$ is selected from CONH (pyrazolyl or 1,2,3-triazolyl optionally substituted by 1 or 2 methyl groups); 2-methyl-2-hydroxypropyl or 2-hydroxyethyl); CONHCH$_2$(pyrazolyl or 1,2,3-triazolyl optionally substituted by 1 or 2 methyl groups); and CONH(C$_{2-3}$ alkyl substituted by OH).

Embodiment 37 is a compound or salt according to embodiment 32, 33, 34 or 35 wherein R$^1$ is selected from:

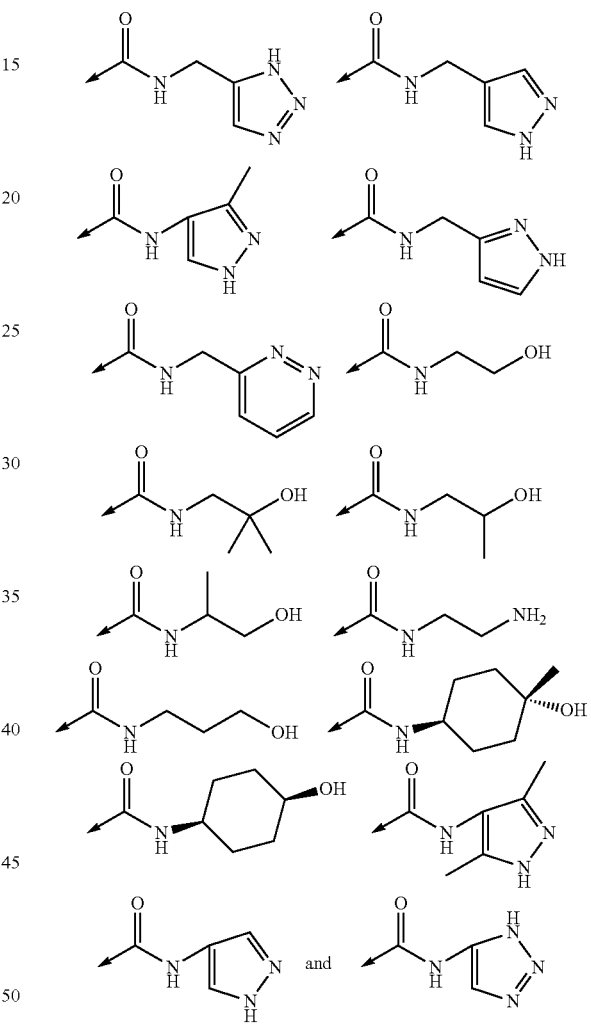

Embodiment 38 is a compound or salt according to embodiment 32, 33, 34, 35, 36 or 37 wherein n is 0.
Embodiment 39 is a compound or salt according to 32, 33, 34, 35, 36, 37 or 38 wherein X$^1$ is H, F or Cl.
Embodiment 40 is a compound or salt according to embodiment 32, 33, 34, 35, 36, 37, 38 or 39 wherein X$^2$ is H.
Embodiment 41 is a compound or salt according to embodiment 32, 33, 34, 35, 36, 37, 38, 39 or 40 wherein R$^4$ is H, F, Cl, CH$_3$, CN or OCH$_3$.
Embodiment 42 is a compound or salt according to embodiment 32, 33, 34, 35, 36, 37, 38, 39, 40 or 41 wherein R$^5$ is H, F, Cl, CH$_3$, CN or OCH$_3$.
Embodiment 43 is a compound or salt according to embodiment 32, 33, 34, 35, 36, 37, 38, 39, 40, 41 or 42 wherein R$^2$ is H.

Embodiment 44 is a compound or salt according to embodiment 32, 33, 34, 35, 36, 37, 38, 39, 40, 41, 42 or 43 wherein $R^3$ is H, ($C_{1-3}$ alkyl optionally substituted by CN, or by N(H or $C_{1-3}$ alkyl optionally substituted by one or more F)(H or $C_{1-3}$ alkyl optionally substituted by one or more F), or by one or more F, or by O($C_{1-3}$ alkyl optionally substituted by one or more F)), or $R^3$ is NH($C_{1-3}$ alkyl optionally substituted by one or more F), NHCO($C_{1-4}$ alkyl optionally substituted by one or more F), O($C_{1-3}$ alkyl optionally substituted by one or more F), or C(O)N(H or $C_{1-3}$ alkyl optionally substituted by one or more F)(H or $C_{1-3}$ alkyl optionally substituted by one or more F).

Embodiment 45 is a compound or salt according to embodiment 32, 33, 34, 35, 36, 37, 38, 39, 40, 41, 42, 43 or 44 wherein $R^3$ is H, ($C_{1-3}$ alkyl optionally substituted by CN, or by N(H or $C_{1-3}$ alkyl optionally substituted by from 1-3 F)(H or $C_{1-3}$ alkyl optionally substituted by from 1-3 F), or by from 1-3 F, or by O($C_{1-3}$ alkyl optionally substituted by from 1-3 F)), or $R^3$ is NH($C_{1-3}$ alkyl optionally substituted by from 1-3 F), NHCO($C_{1-4}$ alkyl optionally substituted by from 1-3 F), O($C_{1-3}$ alkyl optionally substituted by from 1-3 F), or C(O)N(H or $C_{1-3}$ alkyl optionally substituted by from 1-3 F)(H or $C_{1-3}$ alkyl optionally substituted by from 1-3 F).

Embodiment 46 is a compound or salt according to embodiment 32, 33, 34, 35, 36, 37, 38, 39, 40, 41, 42, 43, 44 or 45 wherein $R^3$ is H, NHCO($C_{1-4}$ alkyl), $C_{1-3}$ alkyl optionally substituted by from 1-3 F, $CH_2CN$, $CH_2OCH_3$, $CH(CH_3)OCH_3$, $CONH_2$, O($C_{1-3}$ alkyl optionally substituted by 1-3 F), NH($C_{1-3}$ alkyl), or $CH_2N$(H or $C_{1-3}$ alkyl optionally substituted by from 1-3 F)(H or $C_{1-3}$ alkyl optionally substituted by from 1-3 F).

Embodiment 47 is a compound or salt according to embodiment 32, 33, 34, 35, 36, 37, 38, 39, 40, 41, 42, 43, 44, 45 or 46 wherein $R^3$ is H, $NHCOCH_3$, $NHCO(C(CH_3)_3)$, $CH_3$, $CH_2F$, $CHF_2$, $CF_3$, $CF_2CH_3$, $CH_2CHF_2$, $CH_2OCH_3$, $CH_2CN$, O (methyl optionally substituted by 1-3 F), $CH_2NHCH_3$, $CH(CH_3)OCH_3$, $CONH_2$, or $NHCH3$.

Embodiment 48 is a compound of formula I" according to embodiment 32 wherein n is 0,
$R^2$ is H or OH,
$X^1$ is H, Cl, F, $CH_3$ or $OCH_3$,
$X^2$ is H, Cl or F,
$R^3$ is H,
$R^4$ is H or F,
$R^5$ is H, F, Cl or CN,
and $R^1$ is selected from:

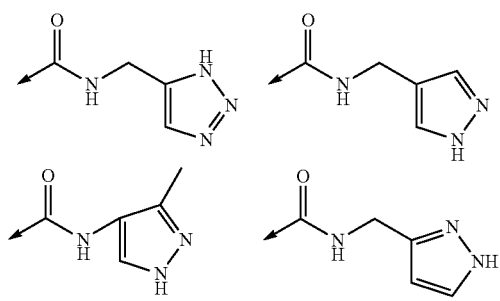

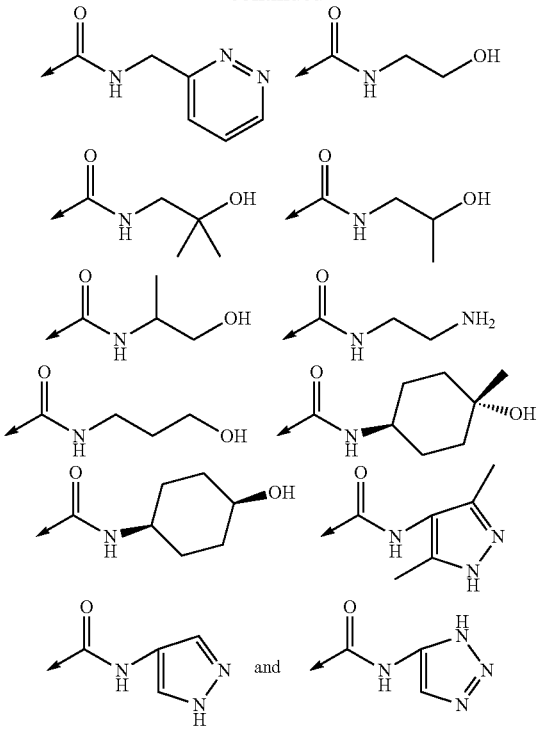

or a pharmaceutically acceptable salt thereof.

Embodiment 49 is a pharmaceutical composition comprising a compound of the formula I or I' or 1" as appropriate, a prodrug or a pharmaceutically acceptable salt thereof, as defined in any one of the preceding embodiments 1 to 48, and a pharmaceutically acceptable carrier.

Embodiment 50 is a compound of the formula I or I' or I" as appropriate, a prodrug or a pharmaceutically acceptable salt thereof, as defined in any one of embodiments 1 to 48, for use as a medicament.

Embodiment 51 is a compound of formula I or I' or I" as appropriate, a prodrug or a pharmaceutically acceptable salt thereof, as defined in any one of embodiments 1 to 48 for use in the treatment of a disease for which a TrkA receptor antagonist is indicated.

Embodiment 52 is a compound of formula I or I' or I" as appropriate, a prodrug or a pharmaceutically acceptable salt thereof, as defined in any one of embodiments 1 to 48 for use in the treatment of pain or cancer.

Embodiment 53 is the use of a compound of the formula I or I' or I" as appropriate, a prodrug or a pharmaceutically acceptable salt or composition thereof, as defined in any one of embodiments 1 to 48, for the manufacture of a medicament to treat a disease for which a TrkA receptor antagonist is indicated.

Embodiment 54 is the use of a compound of the formula I or I' or I" as appropriate, a prodrug or a pharmaceutically acceptable salt or composition thereof, as defined in any one of embodiments 1 to 48, for the manufacture of a medicament to treat pain or cancer.

Embodiment 55 is a method of treatment of a mammal, to treat a disease for which a TrkA receptor antagonist is indicated, comprising treating said mammal with an effective amount of a compound of the formula I or I' or I" as appropriate, a prodrug or a pharmaceutically acceptable salt thereof, as defined in any one of embodiments 1 to 48.

Embodiment 56 is a method of treatment of pain or cancer in a mammal, comprising treating said mammal with an effective amount of a compound of the formula I or I' or I" as appropriate, a prodrug or a pharmaceutically acceptable salt thereof, as defined in any one of embodiments 1 to 48.

Embodiment 57 is a compound, prodrug or salt according to any one of embodiments 1 to 48 for use in a medical treatment in combination with a further drug substance.

Further embodiments include:
Any novel genus of intermediates described in the Schemes below;
Any novel specific intermediate described in the Preparations below;
Any novel process described herein;
Any other novel material disclosed herein.

"Halogen" means a fluoro, chloro, bromo or iodo group.

"Alkyl" groups, containing the requisite number of carbon atoms, can be unbranched or branched. Examples of alkyl include methyl, ethyl, n-propyl, i-propyl, n-butyl, i-butyl, sec-butyl and t-butyl.

"Het is a 4-7-membered saturated or unsaturated heterocyclic ring" includes fully saturated, partially unsaturated and fully unsaturated rings. Typical, but non-limiting, ring moieties include the following: oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazapanyl, 1,4-diazepinyl, 3,4-dihydro-2H-pyranyl, 5,6-dihydro-2H-pyranyl, 2H-pyranyl, 1,2,3,4-tetrahydropyridinyl, 1,2,5,6-tetrahydropyridinyl, pyrrolyl, furanyl, thiophenyl, pyrazolyl, imidazolyl, isoxazolyl, oxazolyl, isothiazolyl, thiazolyl, 1,2,3-trazolyl, 1,3,4-trazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, pyridinyl, pyridazinyl, pyrimidinyl, pyrazinyl, etc.

"Substituted by" means that substituents are present only if valency allows.

"Pharmaceutically acceptable salts" of the compounds of formula I include the acid addition and base addition salts (including disalts, hemisalts, etc.) thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base addition salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic or enzymatic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl)phosphate prodrugs.

Further examples of replacement groups in accordance with the foregoing examples and examples of other prodrug types may be found in the aforementioned references. Specific prodrug groups envisaged for, and included in the definition of, the invention include: phosphate esters of alcohols "ROH", e.g. RO—P(=O)(OH)$_2$ or salts thereof; and amino acid esters of alcohols "ROH", e.g. RO—C(=O)—C*—NH$_2$ wherein NH2-C*—CO2H is an amino acid such as histidine, alanine, isoleucine, leucine, lysine, methionine, phenylalanine, threonine, tryptophan, valine, arginine, asparagine, aspartic acid, cysteine, glutamic acid, glutamine, glycine, ornithine, proline, selenocysteine, tyrosine; Or derivative thereof such as dimethylglycine, and the like.

The compounds of the invention include compounds of formula I and salts thereof as hereinbefore defined, polymorphs, and isomers thereof (including optical, geometric and tautomeric isomers) as hereinafter defined and isotopically-labelled compounds of formula I.

Unless otherwise specified, compounds of formula (I) containing one or more asymmetric carbon atoms can exist as two or more stereoisomers. Where a compound of formula (I) contains for example, a keto or guanidine group or an aromatic moiety, tautomeric isomerism ('tautomerism') can occur. It follows that a single compound may exhibit more than one type of isomerism.

Included within the scope of the claimed compounds of the present invention are all stereoisomers, geometric isomers and tautomeric forms of the compounds of formula (I), including compounds exhibiting more than one type of isomerism, and mixtures of one or more thereof. Also included are acid addition or base addition salts wherein the counterion is optically active, for example, D-lactate or L-lysine, or racemic, for example, DL-tartrate or DL-arginine.

Examples of types of potential tautomerisms shown by the compounds of the invention include hydroxypyridine ⇔ pyridone; amide ⇔ hydroxyl-imine and keto ⇔ enol tautomersims:

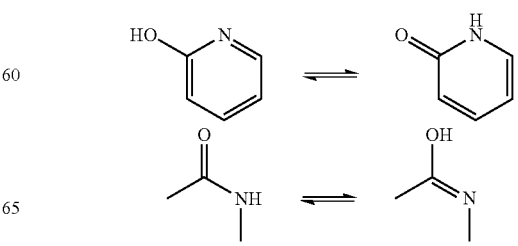

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or other derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed. The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

All of the derivatives of formula (I) can be prepared by the procedures described in the general methods presented below or by routine modifications thereof. The present invention also encompasses any one or more of these processes for preparing the derivatives of formula (I), in addition to any novel intermediates used therein. The person skilled in the art will appreciate that the following reactions may be heated thermally or under microwave irradiation.

It will be further appreciated that it may be necessary or desirable to carry out the transformations in a different order from that described in the schemes, or to modify one or more of the transformations, to provide the desired compound of the invention.

The routes below, including those mentioned in the Examples and Preparations, illustrate methods of synthesising compounds of formula I. The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example: "Comprehensive Organic Transformations" by R C Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and D M Smith, Longman (1982); "Protective Groups in Organic Synthesis" by T W Greene and P G M Wuts, John Wiley and Sons, Inc. (1999); and "Protecting Groups" by P J, Kocienski, Georg Thieme Verlag (1994); and any updated versions of said standard works.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

In the general synthetic methods below, unless otherwise specified, the substituents are as defined above with reference to the compounds of formula (I) above.

Where ratios of solvents are given, the ratios are by volume.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I).

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

All of the derivatives of formula (I) can be prepared by the procedures described in the general methods presented below or by routine modifications thereof. The present invention also encompasses any one or more of these processes for preparing the derivatives of formula (I), in addition to any novel intermediates used therein. The person skilled in the art will appreciate that the following reactions may be heated thermally or under microwave irradiation.

It will be further appreciated that it may be necessary or desirable to carry out the transformations in a different order from that described in the schemes, or to modify one or more of the transformations, to provide the desired compound of the invention.

The general routes below are also applicable to the analogous compounds of formula (I') and (I'').

According to a first process, compounds of formula I as appropriate (I: IA; $R^1$ is an amide), (IB; $R^1$ is $CO_2H$) and (IC; $R^1$ is an ester) may be prepared from compounds of formulae (VI) and (IV), as illustrated by Scheme 1.

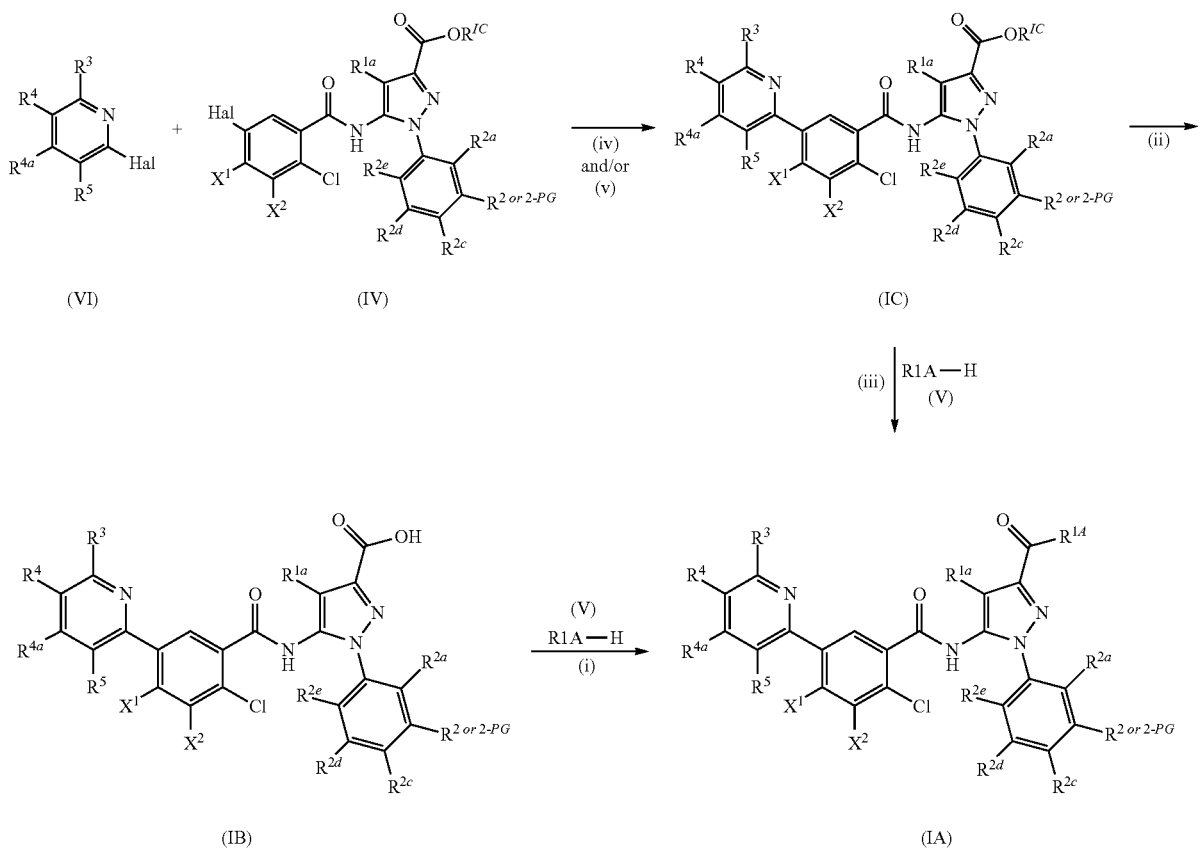

Scheme 1 wherein $CO_2R^{1C}$ corresponds to the ester groups of $R^1$ as defined herein, or a protected version thereof; $COR^{1A}$ corresponds to the amide groups of $R^1$ as defined herein, or a protected version thereof; $R^{2-PG}$ represents a protected hydroxyl group such as benzyloxy; Hal is chloro, bromo or iodo.

Compounds of formulae (V) and (VI) are commercially available or may be synthesized by those skilled in the art according to the literature or preparations described herein. Wherein compounds of formulae (IA) contain a protecting group such as trimethylsilylethoxymethyl, or tertbutoxycarbonyl, a deprotection step may be employed to obtain compounds of formula (I). Preferred conditions comprise TFA or 4M HCl in dioxane or DCM at room temperature. Wherein compounds of formulae (IA), (IB) or (IC) include a protecting group such as tert-butoxycarbonyl or tert-butyl, an acid mediated deprotection step may be employed at any stage in Scheme 1. Preferred conditions comprise aqueous HCl or TFA in dioxane or DCM at room temperature. Alternatively the protecting group may be removed in situ during steps (i)-(iv).

Wherein compounds of formula (IA), (IB) or (IC) include $R^{2-PG}$ such as benzyl, deprotection may be employed following process step (i). Preferred conditions comprise boron trichloride or 1-chloroethylchloroformate in DCM at room temperature.

Compounds of formula (IA) may be prepared from compounds of formula (IB) according to process step (i), an amide bond formation step with compounds of formula (V) mediated by a suitable combination of amide bond coupling agent and organic base. Preferred conditions comprise HATU or HBTU with triethylamine or DIPEA in either DCM or DMF at room or elevated temperatures (e.g. about 80° C.), or using 2,4,6-tripropyl-1,3,5,2,4,6-trioxatriphosphinane 2,4,6-trioxide in THF or 2-methyl-THF with pyridine or DIPEA at either room or elevated temperature e.g. about 85° C.

Alternatively compounds of formula (IA) may be prepared directly from compounds of formula (IC) according to process step (iii), a nucleophilic displacement reaction of an ester with amines of formula (V). Preferred conditions comprise heating compounds of formula (V) with compounds of formula (IC) either neat or in a solution of methanol at elevated temperatures of 60-80° C.

Compounds of formula (IB) may be prepared from compounds of formula (IC) according to process step (ii), a hydrolysis step mediated by an inorganic base. Preferred conditions comprise lithium or sodium hydroxide in methanol or ethanol at room temperature.

Compounds of formula (IC) may be prepared from compounds of formula (IV) and (VI) according to process steps (iv) and/or (v), a Suzuki cross-coupling reaction preceeded if necessary by a boronic ester formation reaction. Typical Suzuki cross-coupling conditions comprise a palladium catalyst containing suitable phosphine ligands, in the presence of an inorganic base, in aqueous dioxane, at elevated temperatures either thermally or under microwave irradiation. Preferred conditions comprise $Pd(OAc)_2$, $Pd(dppf)Cl_2$ or $Pd(PPh_3)_4$ with either sodium, cesium or potassium carbonate in aqueous dioxane or methanol with or without cataxium A at from room temperature to 120° C. Typical boronic ester formation conditions comprise $Pd(dppf)Cl_2$ and potassium acetate with bispinacolatodiboron with compounds of formula (IV) or (VI) in dioxane at reflux.

According to a second process, compounds of formula (IA) may be prepared in an alternative sequence from compounds of formulae (IV) as illustrated by Scheme 2.

Scheme 2

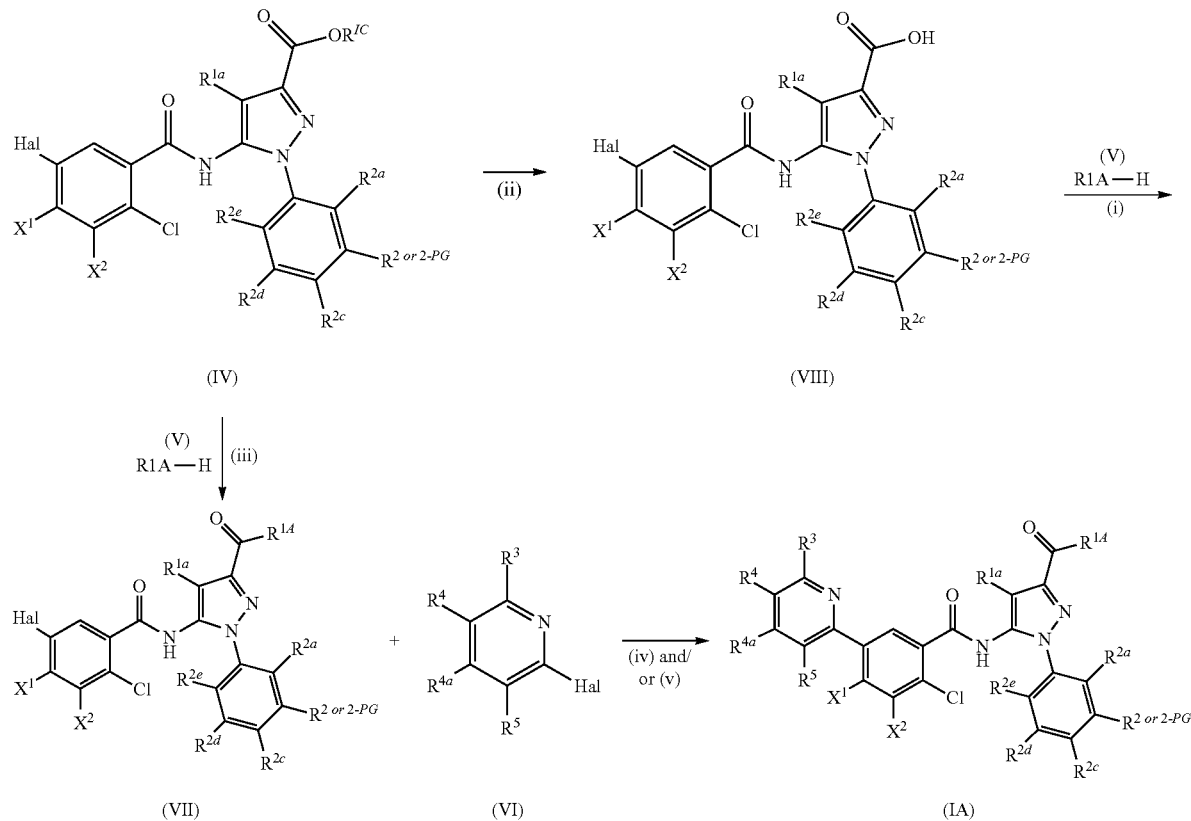

Wherein compounds of formula (IA) include a protecting group such as trimethylsilylethoxymethyl, or tertbutoxycarbonyl, deprotection may occur as necessary as described in Scheme 1.

Compounds of formula (IA) may be prepared from compounds of formula (VII) and (VI) according to process steps (iv) and/or (v) as described in Scheme 1.

Compounds of formula (VII) may be prepared from compounds of formulae (VIII) and (V) according to process step (i) as described in Scheme 1.

Compounds of formula (VIII) may be prepared from compounds of formula (IV) according to process step (ii) an hydrolysis step as described in Scheme 1.

Alternatively compounds of formula (VII) may be prepared from compound of formula (IV) according to process step (iii) a nucleophilic displacement reaction of an ester with amines of formula (V) as described in Scheme 1.

According to a third process, compounds of formula (I: ID; $R^1$ is CN) and (IE; $R^1$ is $CONH_2$) may be prepared from compounds of formulae (VI) and (X) as illustrated by Scheme 3.

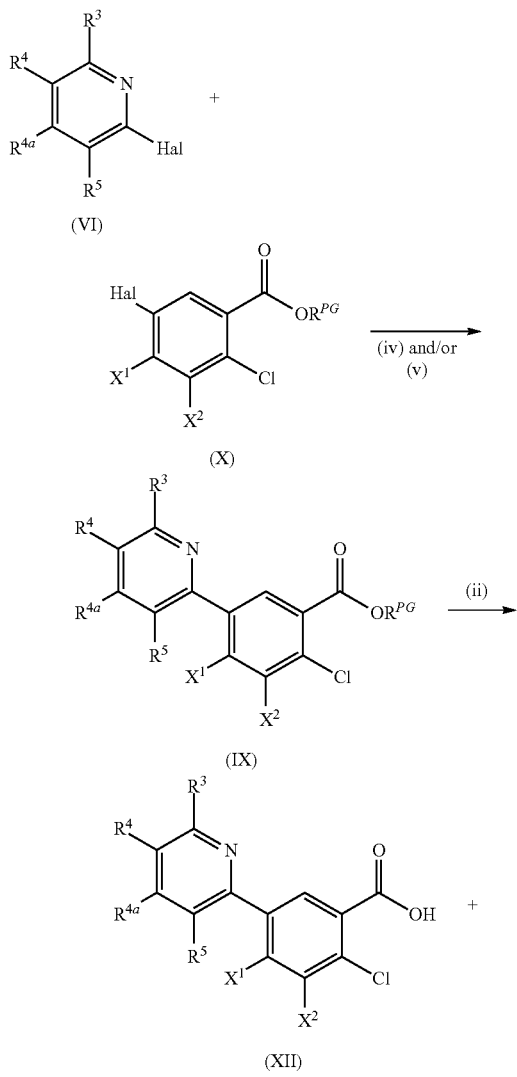

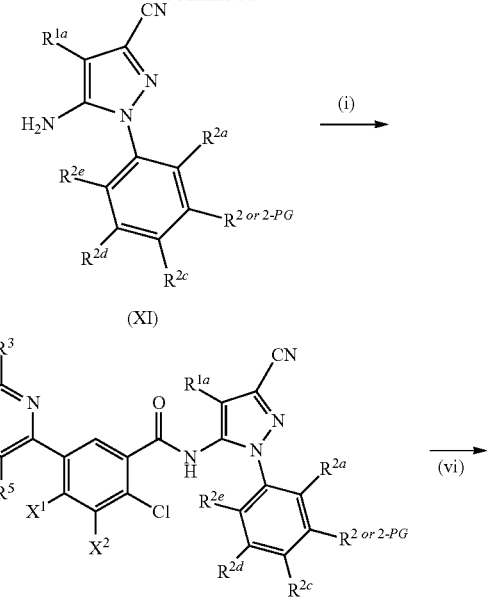

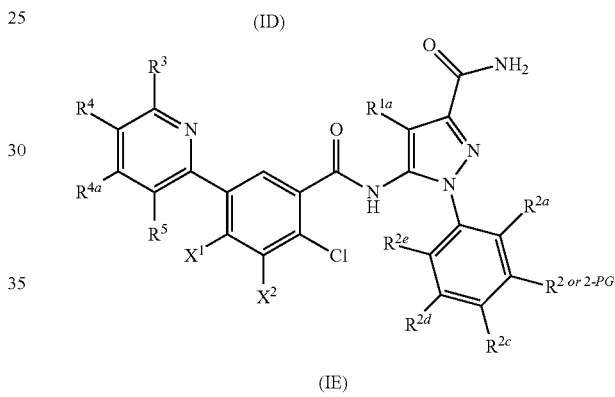

Wherein $R^{PG}$ is methyl or ethyl; Hal is chloro, bromo or iodo.

Compounds of formulae (X), (VI) and (XI) are commercially available or may be synthesized by those skilled in the art according to the literature or preparations described herein.

Wherein compounds of formulae (IX), (XII), (ID) and (IE) include a protecting group such as, benzyl, deprotection may occur as necessary as described in Scheme 1.

Compounds of formula (IE) may be prepared from compounds of formula (ID) according to process step (vi), an oxidative hydrolysis reaction. Preferred conditions comprise aqueous hydrogen peroxide with potassium carbonate in DMSO at room temperature.

Compounds of formula (ID) may be prepared from compounds of formula (XI) and (XII) according to process step (i), an amide bond formation reaction as described in Scheme 1.

Compounds of formula (XII) may be prepared from compounds of formula (IX) according to process step (ii) as described in Scheme 1.

Compounds of formula (IX) may be prepared from compounds of formulae (X) and (VI) according to process steps (iv) and/or (v) as described in Scheme 1.

According to a fourth process, compounds of formula (IE) may be prepared in an alternative sequence from compounds of formulae (XI) and (XIII) as illustrated by Scheme 4

Scheme 4

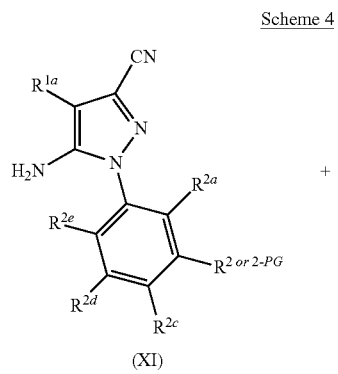

(XI)

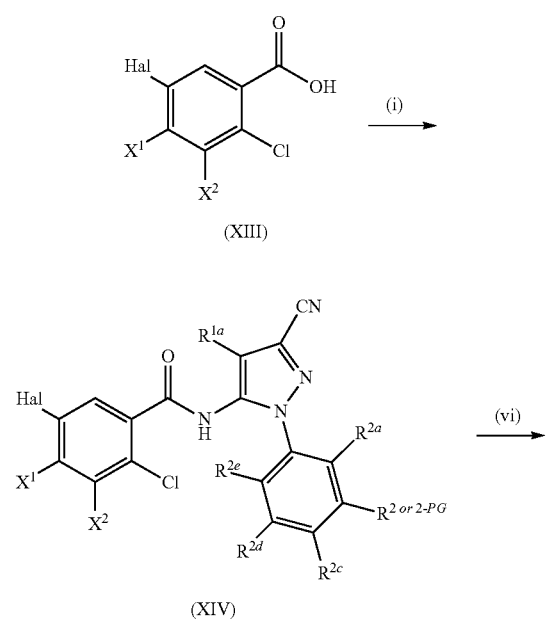

(XIII)

(XIV)

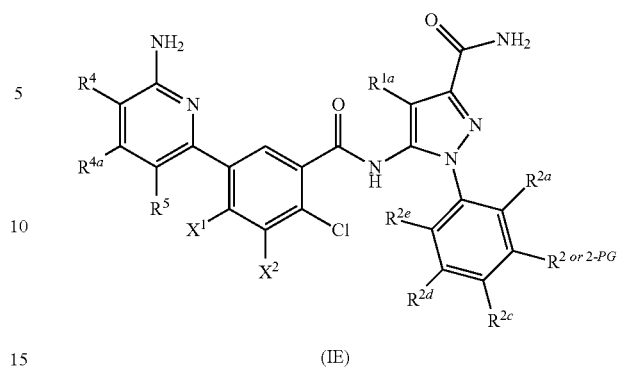

(IE)

Wherein Hal is chloro, bromo or iodo.

Compounds of formulae (XI), (XIII) and (VI) are commercially available or may be synthesized by those skilled in the art according to the literature or preparations described herein.

Wherein compounds of formulae (IE) include a protecting group such as benzyl, deprotection may occur as necessary as described in Scheme 1.

Compounds of formula (IE) may be prepared from compounds of formula (XV) and (VI) according to process steps (iv) and (v) as described in Scheme 1.

Compounds of formula (XV) may be prepared from compounds of formula (XIV) according to process step (vi) as described in Scheme 3.

Compounds of formula (XIV) may be prepared from compounds of formulae (XI) and (XIII) according to process step (i) as described in Scheme 1.

According to a fifth process, compounds of formula (IV) may be prepared from compounds of formulae (XIII) and (XVI) as illustrated by Scheme 5.

Scheme 5

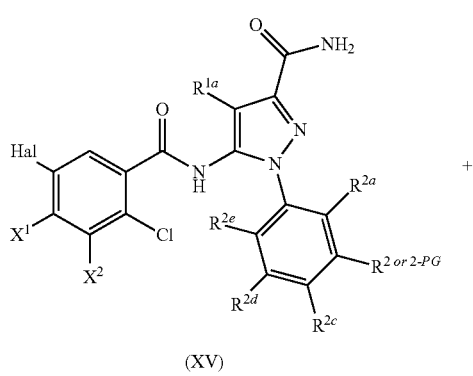

(XV)

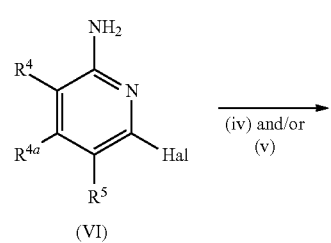

(VI)

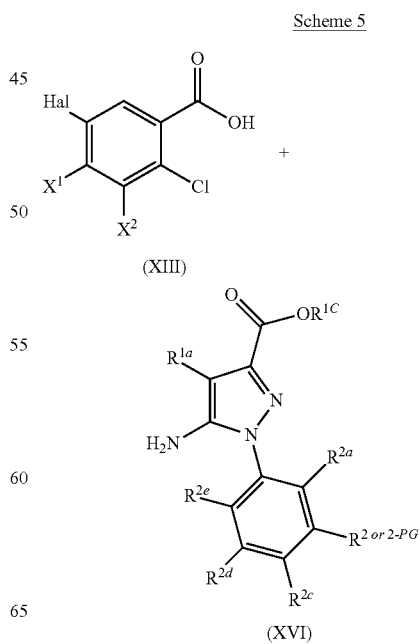

(XIII)

(XVI)

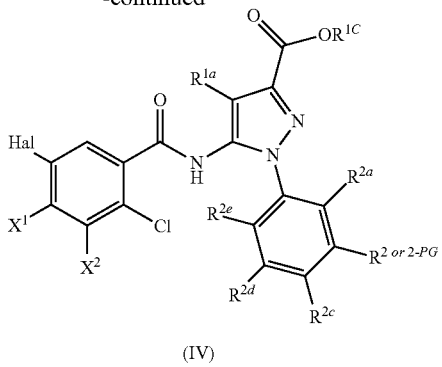

(IV)

Wherein Hal is chloro, bromo, iodo; $R^{PG}$ is methyl or ethyl;

Compounds of formulae (XIII) and (XVI) are commercially available or may be synthesized by those skilled in the art according to the literature or preparations described herein.

Compounds of formula (IV) may be prepared from compounds of formulae (XIII) and (XVI) according to process step (i) as described in Scheme 1.

According to a sixth process, compounds of formula (1 F; $R^1$ is an ester; $R^3$ is an amide) may be prepared from amine compounds of formulae (XVII) as illustrated by Scheme 6.

Scheme 6

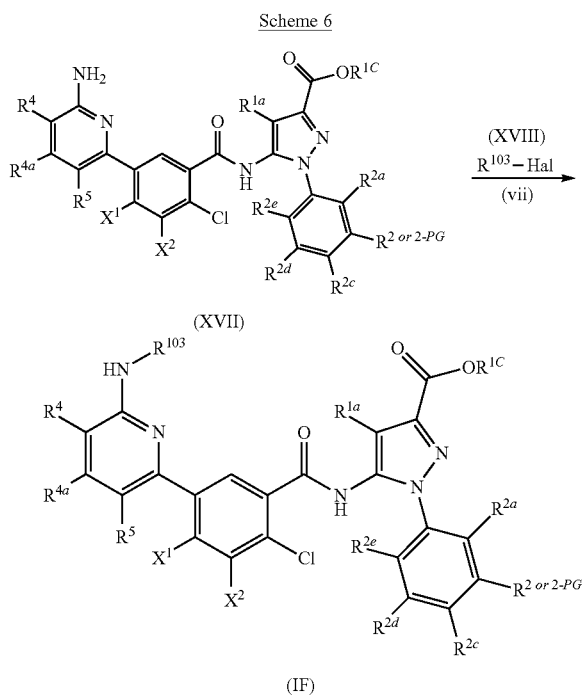

Wherein $R^{PG}$ is methyl or ethyl; $R^{103}$ is tert-butylcarbonyl or other suitable acyl moiety.

Compounds of formula (IF) may be prepared from compounds of formula (XVII) according to process (vii), an acylation step with compounds of formula (XVIII). Exemplary preferred conditions comprise pivaloyl chloride in anhydrous pyridine at room temperature.

Compounds of formula (XVII) may be prepared as described for compounds of formula (IC) illustrated in Scheme 1.

According to a further embodiment the present invention provides novel intermediate compounds.

Pharmaceutically acceptable salts of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention intended for pharmaceutical use may be administered alone or in combination with one or more other compounds of the invention or in combination with one or more other drug agent (or as any combination thereof). Generally, they will be administered as a formulation in association with one or more pharmaceutically acceptable excipients. The term "excipient" is used herein to describe any biologically inactive ingredient other than the compounds and salts of the invention. The choice of excipient will to a large extent depend on factors such as the particular mode of administration, the effect of the excipient on solubility and stability, and the nature of the dosage form. For example, a compound of the formula I, or a pharmaceutically acceptable salt or solvate thereof, as defined above, may be administered simultaneously (e.g. as a fixed dose combination), sequentially or separately in combination with one or more other drug agent.

A compound of formula I may be usefully combined with another pharmacologically active compound, or with two or more other pharmacologically active compounds, particularly in the treatment of pain. The skilled person will appreciate that such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A compound of formula (I), or a pharmaceutically acceptable salt thereof, as defined above, may be administered in combination with one or more agents selected from:

a selective Nav1.3 channel modulator, such as a compound disclosed in WO2008/118758;

a selective Nav1.7 channel modulator, such as a compound disclosed in WO2010/079443, e.g. 4-[2-(5-amino-1H-pyrazol-4-yl)-4-chlorophenoxy]-5-chloro-2-fluoro-N-1,3-thiazol-4-ylbenzenesulfonamide or 4-[2-(3-amino-1H-pyrazol-4-yl)-4-(trifluoromethyl)phenoxy]-5-chloro-2-fluoro-N-1,3-thiazol-4-ylbenzenesulfonamide, or a pharmaceutically acceptable salt of either;

a selective Nav1.8 channel modulator;

a selective Nav1.9 channel modulator;

a compound which modulates activity at more than one Nav channel, including a non-selective modulator such as bupivacaine, carbamazepine, lamotrigine, lidocaine, mexiletine or phenytoin;

any inhibitor of nerve growth factor (NGF) signaling, such as: an agent that binds to NGF and inhibits NGF biological activity and/or downstream pathway(s) mediated by NGF signaling (e.g. tanezumab), a TrkA antagonist or a p75 antagoinsist, or an agent that inhibits downstream signaling in regard to NGF stimulated TrkA or P75 signalling; an inhibitor of neurotrophic pathways, where such inhibition is achieved by: (a) an agent that binds to nerve growth factor (NGF) (e.g. tanezumab, fasinumab or fulranumab), brain-derived neurotrophic factor (BDNF), neurotrophin-3 (NT-3) or neurotrophin-4 (NT-4), or to more than one of the aforementioned neurotrophins (e.g. soluble P75); or (b) an agent that inhibits receptor function at one or more of TrKA, TrKB, TrKC or P75, either at the orthostatic site, an allosteric site or by inhibition of the catalytic activity of the receptor(s);

a compound which increases the levels of endocannabinoid, such as a compound with fatty acid amid hydrolase inhibitory (FAAH) or monoacylglycerol lipase (MAGL) activity; an analgesic, in particular paracetamol;

an opioid analgesic, such as: buprenorphine, butorphanol, cocaine, codeine, dihydrocodeine, fentanyl, heroin, hydrocodone, hydromorphone, levallorphan levorphanol, meperidine, methadone, morphine, nalmefene, nalorphine, naloxone, naltrexone, nalbuphine, oxycodone, oxymorphone, propoxyphene or pentazocine; an opioid analgesic which preferentially stimulates a specific intracellular pathway, for example G-protein as opposed to beta arrestin recruitment, such as TRV130; an opioid analgesic with additional pharmacology, such as: noradrenaline (norepinephrine) reuptake inhibitory (NRI) activity, e.g. tapentadol; serotonin and norepinephrine reuptake inhibitory (SNRI) activity, e.g. tramadol; or nociceptin receptor (NOP) agonist activity, such as GRT6005;

a nonsteroidal antiinflammatory drug (NSAID), such as a non-selective cyclooxygenase (COX) inhibitor, e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac; or a COX-2 selective inhibitor, e.g. celecoxib, deracoxib, etoricoxib, mavacoxib or parecoxib;

a prostaglandin $E_2$ subtype 4 (EP4) antagonist;

a microsomal prostaglandin E synthase type 1 (mPGES-1) inhibitor;

a sedative, such as glutethimide, meprobamate, methaqualone or dichloralphenazone;

a $GABA_A$ modulator with broad subtype modulatory effects mediated via the benzodiazepine binding site, such as chlordiazepoxide, alprazolam, diazepam, lorazepam, oxazepam, temazepam, triazolam, clonazepam or clobazam;

a $GABA_A$ modulator with subtype-selective modulatory effects mediated via the benzodiazepine binding site with reduced adverse effects, for example sedation, such as TPA023, TPA023B, L-838,417, CTP354 or NSD72;

a $GABA_A$ modulator acting via alternative binding sites on the receptor, such as barbiturates, e.g. amobarbital, aprobarbital, butalbital, mephobarbital, methohexital, pentobarbital, phenobarbital, secobarbital, or thiopental; neurosteroids such as alphaxalone, alphadolone or ganaxolone; β-subunit ligands, such as etifoxine; or δ-preferring ligands, such as gaboxadol;

a GlyR3 agonist or positive allosteric modulator;

a skeletal muscle relaxant, e.g. baclofen, carisoprodol, chlorzoxazone, cyclobenzaprine, metaxolone, methocarbamol or orphrenadine;

a glutamate receptor antagonist or negative allosteric modulator, such as an NMDA receptor antagonist, e.g. dextromethorphan, dextrorphan, ketamine or, memantine; or an mGluR antagonist or modulator;

an alpha-adrenergic, such as clonidine, guanfacine or dexmetatomidine;

a beta-adrenergic such as propranolol;

a tricyclic antidepressant, e.g. desipramine, imipramine, amitriptyline or nortriptyline;

a tachykinin (NK) antagonist, such as aprepitant or maropitant; a muscarinic antagonist, e.g oxybutynin, tolterodine, propiverine, tropsium chloride, darifenacin, solifenacin, temiverine and ipratropium;

a Transient Receptor Potential V1 (TRPV1) receptor agonist (e.g. resinferatoxin or capsaicin) or antagonist (e.g. capsazepine or mavatrap);

a Transient Receptor Potential A1 (TRPA1) receptor agonist (e.g. cinnamaldehyde or mustard oil) or antagonist (e.g. GRC17536 or CB-625);

a Transient Receptor Potential M8 (TRPM8) receptor agonist (e.g. menthol or icilin) or antagonist;

a Transient Receptor Potential V3 (TRPV3) receptor agonist or antagonist (e.g. GRC-15300);

a corticosteroid such as dexamethasone;

a 5-HT receptor agonist or antagonist, particularly a $5\text{-}HT_{1B/1D}$ agonist, such as eletriptan, sumatriptan, naratriptan, zolmitriptan or rizatriptan;

a $5\text{-}HT_{2A}$ receptor antagonist;

a cholinergic (nicotinic) analgesic, such as ispronicline (TC-1734), vareniclineor nicotine;

a PDEV inhibitor, such sildenafil, tadalafilor vardenafil;

an alpha-2-delta ligand such as gabapentin, gabapentin enacarbil or pregabalin;

a serotonin reuptake inhibitor (SRI) such as sertraline, demethylsertraline, fluoxetine, norfluoxetine, fluvoxamine, paroxetine, citalopram, desmethylcitalopram, escitalopram, d,l-fenfluramine, femoxetine, ifoxetine, cyanodothiepin, litoxetine, dapoxetine, nefazodone, cericlamine and trazodone;

an NRI, such as maprotiline, lofepramine, mirtazepine, oxaprotiline, fezolamine, tomoxetine, mianserin, buprorion, buprorion metabolite hydroxybuprorion, nomifensine and viloxazine, especially a selective noradrenaline reuptake inhibitor such as reboxetine;

an SNRI, such as venlafaxine, O-desmethylvenlafaxine, clomipramine, desmethylclomipramine, duloxetine, milnacipran and imipramine;

an inducible nitric oxide synthase (iNOS) inhibitor;

a leukotriene B4 antagonist;

a 5-lipoxygenase inhibitor, such as zileuton;

a potassium channel opener or positive modulator, such as an opener or positive modulator of KCNQ/Kv7 (e.g. retigabine or flupirtine), a G protein-coupled inwardly-rectifying potassium channel (GIRK), a calcium-activated potassium channel (Kca) or a potassium voltage-gated channel such as a member of subfamily A (e.g. Kv1.1), subfamily B (e.g. Kv2.2) or subfamily K (e.g. TASK, TREK or TRESK);

a $P2X_3$ receptor antagonist (e.g. AF219) or an antagonist of a receptor which contains as one of its subunits the $P2X_3$ subunit, such as a $P2X_{2/3}$ heteromeric receptor;

a $Ca_v2.2$ calcium channel blocker (N-type), such as ziconotide; and a $Ca_v3.2$ calcium channel blocker (T-type), such as ethosuximide.

Pharmaceutical compositions suitable for the delivery of compounds and salts of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Compounds and salts of the invention intended for pharmaceutical use may be prepared and administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations, such as tablets, capsules containing particulates, liquids, or powders; lozenges (including liquid-filled), chews; multi- and nano-particulates; gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

The foregoing formulations for the various types of administration discussed above may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parenteral Administration

The compounds and salts of the invention may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) and salts used in the preparation of parenteral solutions may be increased by the use of appropriate formulation techniques, such as the incorporation of solubility-enhancing agents.

Formulations for parenteral administration may be formulated to be immediate and/or modified release. Thus, compounds and salts of the invention may be formulated as a solid, semi-solid, or thixotropic liquid for administration as an implanted depot providing modified release of the active compound. An example of such formulations include drug-coated stents.

Topical Administration

The compounds and salts of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated [see, for example, Finnin and Morgan, J Pharm Sci, 88 (10), 955-958 (October 1999).] Other means of topical administration include delivery by electroporation, iontophoresis, phonophoresis, sonophoresis and microneedle or needle-free (e.g. Powderject™, Bioject™, etc.) injection.

Inhaled/Intranasal Administration

The compounds and salts of the invention may also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

A pressurised container, pump, spray, atomizer, or nebuliser may contain a solution or suspension of the compound(s) or salt(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound or salt of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound or salt of the invention per actuation and the actuation volume may vary from 1 μl to 100 μl. A typical formulation may comprise a compound of formula (I) or salt thereof, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by a prefilled capsule, blister or pocket or by a system that utilises a gravimetrically fed dosing chamber. Units in accordance with the invention are typically arranged to administer a metered dose or "puff" containing from 1 to 5000 μg of the compound or salt. The overall daily dose will typically be in the range 1 μg to 20 mg which may be administered in a single dose or, more usually, as divided doses throughout the day.

Rectal/Intravaginal Administration

The compounds and salts of the invention may be administered rectally or vaginally, for example, in the form of a suppository, pessary, or enema. Cocoa butter is a traditional suppository base, but various well known alternatives may be used as appropriate.

Ocular and Aural Administration

The compounds and salts of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid; a cellulosic polymer, for example, hydroxypropylmethylcellulose, hydroxyethylcellulose, or methyl cellulose; or a heteropolysaccharide polymer, for example, gelan gum, may be incorporated together with a preservative, such as benzalkonium chloride. Such formulations may also be delivered by iontophoresis.

Other Technologies

The compounds and salts of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds and salts of the invention is typically in the range 0.1 mg to 200 mg depending, of course, on the mode of administration, preferred in the range 1 mg to 100 mg and more preferred in the range 1 mg to 50 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the above-mentioned therapeutic uses, the dosage administered will, of course, vary with the compound or salt employed, the mode of administration, the treatment desired and the disorder indicated. The total daily dosage of the compound of formula (I)/salt/solvate (active ingredient) will, generally, be in the range from 1 mg to 1 gram, preferably 1 mg to 250 mg, more preferably 10 mg to 100 mg. The total daily dose may be administered in single or divided doses. The present invention also encompasses sustained release compositions.

The pharmaceutical composition may, for example, be in a form suitable for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

For parenteral dosages, this may conveniently be prepared as a solution or as a dry powder requiring dissolution by a pharmacist, medical practitioner or the patient. It may be provided in a bottle or sterile syringe. For example it may be provided as a powder in a multicompartment syringe which allows the dry powder and solvent to be mixed just prior to administration (to aid long-term stability and storage). Syringes could be used which allow multiple doses to be administered from a single device.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations as discussed below. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

A composition of the present invention can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, ed., Marcel Dekker, Inc., New York, (1978). Pharmaceutical compositions are preferably manufactured under GMP conditions.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

The precise dosage administered of each active ingredient will vary depending upon any number of factors, including but not limited to, the type of animal and type of disease state being treated, the age of the animal, and the route(s) of administration.

The following non-limiting Preparations and Examples illustrate the preparation of compounds and salts of the present invention. In the Examples and Preparations that are set out below, and in the aforementioned Schemes, the following abbreviations, definitions and analytical procedures may be referred to. Other abbreviations common in the art are also used. Standard IUPAC nomenclature has been used.

AcOH is acetic acid;
AIBN is azobisisobutyronitrile;
aq is aqueous;
Bn is benzyl;
Boc is tert-butoxycarbonyl;
br is broad;
tBu is tert-butyl;
° C. is degrees celcius;
CataXium A is Di(1-adamantyl)-n-butylphosphine;
$CDCl_3$ is deutero-chloroform;
$Cs_2CO_3$ is cesium carbonate;
CsF is cesium fluoride;
δ is chemical shift;
d is doublet;
DCM is dichloromethane; methylene chloride;
DIPEA is N-ethyldiisopropylamine, N,N-diisopropylethylamine;
DMF is N,N-dimethylformamide;
DMSO is dimethyl sulphoxide;
EDC=N-(3-Dimethylaminopropyl)-N'-ethylcarbodiimide hydrochloride and HOBt=1-Hydroxybenzotriazole hydrate are amide coupling reagents
EtOAc is ethyl acetate;
EtOH is ethanol;
$Et_3N$ is triethylamine;
g is gram;
HATU is 1-[Bis(dimethylamino)methylene]-1H-1,2,3-triazolo[4,5-b]pyridinium 3-oxid hexafluorophosphate;
HCl is hydrochloric acid;
$HCO_2H$ is formic acid;
HPLC is high pressure liquid chromatography;
$H_2O$ is water;
$H_2O_2$ is hydrogen peroxide;
IMS is industrial methylated spirit;
$[Ir(COD)OMe]_2$ is (1,5-cyclooctadiene)(methoxy)iridium(I) dimer
$K_2CO_3$ is potassium carbonate;
$KHSO_4$ is potassium hydrogen sulphate;
KOAc is potassium acetate
L is liter;
LCMS is liquid chromatography mass spectrometry (Rt=retention time);
LiOH is lithium hydroxide;
m is multiplet;
M is molar;
MeCN is acetonitrile;
MeOH is methanol;
mg is milligram;
$MgSO_4$ is magnesium sulphate;
MHz is mega Hertz;
min is minutes;
mL is milli liter;
mmol is millimole;
mol is mole;
MS m/z is mass spectrum peak;
NaCN is sodium cyanide;
$Na_2CO_3$ is sodium carbonate;
NaOH is sodium hydroxide;
NBS is N-bromosuccinimide;
$NH_3$ is ammonia;
$NH_4Cl$ is ammonium chloride;
$NH_4HCO_3$ is ammonium hydrogen carbonate;
$NH_4OH$ is ammonium hydroxide;
NMR is nuclear magnetic resonance;
Pd/C is palladium on carbon;
$Pd(dppf)Cl_2$ is 1,1-bis(diphenylphosphino)ferrocene-palladium(II)dichloride;
$Pd(OAc)_2$ is palladium acetate;
$Pd(PPh_3)_4$ is tetrakis(triphenylphosphine)palladium;
pH is power of hydrogen;
ppm is parts per million;
q is quartet;
Rt is retention time;
s is singlet;
SCX is strong cation exchange;
t is triplet;
T3P is propylphosphonic anhydride
TBAF is tert-butyl ammonium fluoride;
TBME is tert-butyl dimethyl ether;

TEA is triethylamine;
TFA is trifluoroacetic acid;
THF is tetrahydrofuran;
TPTU is 2-(2-pyridon-1-yl)-1,1,3,3-tetramethyluronium tetrafluoroborate, an amide coupling agent.
μL is microliter and
μmol is micromol $^1$H and $^{19}$F Nuclear magnetic resonance (NMR) spectra were in all cases consistent with the proposed structures. Characteristic chemical shifts (δ) are given in parts-per-million downfield from tetramethylsilane (for $^1$H-NMR) and upfield from trichloro-fluoro-methane (for $^{19}$F NMR) using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; d$_6$-DMSO, deuterodimethylsulphoxide; and CD$_3$OD, deuteromethanol. Where appropriate, tautomers may be recorded within the NMR data; and some exchangeable protons may not be visible.

Mass spectra, MS (m/z), were recorded using either electrospray ionisation (ESI) or atmospheric pressure chemical ionisation (APCI).
Where relevant and unless otherwise stated the m/z data provided are for isotopes $^{19}$F, $^{35}$Cl, $^{79}$Br and $^{127}$I.
Wherein preparative TLC or silica gel chromatography have been used, one skilled in the art may choose any combination of solvents to purify the desired compound.
Wherein an SCX-2 column has been used, the eluant conditions are MeOH followed by 7N NH$_3$ in MeOH.
Wherein reverse phase column chromatography has been used, either acidic or basic conditions were employed using a Biotage SNAP KP-C18 silica cartridge:
Acidic conditions: between 0 and 100% of acetonitrile (with 0.1% formic acid) in water (with 0.1% formic acid).
Basic conditions: between 0 and 100% of acetonitrile (with 0.1% ammonia) in water (with 0.1% ammonia, 33% aqueous ammonia used).
Wherein Preparative HPLC has been used, one of the following methods was employed:
Preparative HPLC using acid:
Column: Gemini 5 u C18 110 A 100*21.2 mm 5 micron
Mobile phase A: Water
Mobile phase B: Acetonitrile
Modifier: 0.1% formic acid
Room temperature; 10 minute run time; Initial: 95% A, 5% B to 5% A and 95% B at 7 minutes, hold time 2 minutes, then back to 95% A, 5% B at 9.1 minutes. Flow rate 18 mL/min.
Detectors
ELSD=Polymer labs PL-ELS 2100
UV=Waters 2487 detector at 225 and 255 nm
Mass spectrometer=Waters ZQ using electrospray ionisation
Preparative HPLC Using Base:
Column: Gemini 5 u C18 110 A 100*21.2 mm 5 micron
Mobile phase A: Water
Mobile phase B: Acetonitrile
Modifier: 0.1% diethylamine
Room temperature; 10 minute run time; Initial: 95% A, 5% B to 5% A and 95% B at 7 minutes, hold time 2 minutes, then back to 95% A, 5% B at 9.1 minutes. Flow rate 18 mL/min.
Detectors
ELSD=Polymer labs PL-ELS 2100
UV=Waters 2487 detector at 225 and 255 nm
Mass spectrometer=Waters ZQ using electrospray ionisation
Following Preparative HPLC the following analytical conditions were employed:

Acidic Analytical Conditions:
Column: Gemini 3 u C18 110 A 50*4.6 mm 3 micron
Mobile phase A: Water
Mobile phase B: Acetonitrile
Modifier: 0.1% formic acid
Room temperature; 5 minute run time; Initial: 95% A, 5% B to 5% A and 95% B at 3 minutes, hold time 1 minutes, then back to 95% A, 5% B at 4.1 minutes. Flow rate 1.5 mL/min.
Detectors
ELSD=Polymer labs PL-ELS 2100
UV=Waters 2487 detector at 225 and 255 nm
Mass spectrometer=Waters ZQ using electrospray ionisation
Basic Analytical Conditions:
Column: Gemini 3 u C18 110 A 50*4.6 mm 3 micron
Mobile phase A: Water
Mobile phase B: Acetonitrile
Modifier: 0.1% ammonia
Room temperature; 5 minute run time; Initial: 95% A, 5% B to 5% A and 95% B at 3 minutes, hold time 1 minutes, then back to 95% A, 5% B at 4.1 minutes. Flow rate 1.5 mL/min.
Detectors
ELSD=Polymer labs PL-ELS 2100
UV=Waters 2487 detector at 225 and 255 nm
Wherein LCMS was employed, LCMS Agilent 1100 with column XBridge analytical C18 5 um 4.6×50 mm was used with one of the four following conditions at 25° C.:
System 1 conditions:
Mobile phase A1: 0.05% formic acid in water
Mobile phase B1: 0.05% formic acid in acetonitrile

| Time (mins) | A1 (%) | B1 (%) | Flow (mL/min) |
|---|---|---|---|
| 0.00 | 95 | 5 | 2.00 |
| 3.50 | 5 | 95 | 2.00 |
| 4.50 | 5 | 95 | 2.00 |
| 4.60 | 95 | 5 | 2.00 |

System 2 Conditions:
Mobile phase A2: 10 mmol ammonia formate in water
Mobile phase B2: acetonitrile

| Time (mins) | A2 (%) | B2 (%) | Flow (mL/min) |
|---|---|---|---|
| 0.00 | 95 | 5 | 2.00 |
| 3.50 | 5 | 95 | 2.00 |
| 4.50 | 5 | 95 | 2.00 |
| 4.60 | 95 | 5 | 2.00 |

System 3 Conditions:
Mobile phase A: water
Mobile phase B: acetonitrile
Mobile phase C: 10 mmol ammonia formate in water
Mobile phase D: 0.05% formic acid in acetonitrile

| Time (mins) | A (%) | B (%) | C (%) | D (%) | Flow (mL/min) |
|---|---|---|---|---|---|
| 0 | 95 | 0 | 0 | 5 | 2 |
| 3.5 | 0 | 95 | 0 | 5 | 2 |
| 4.5 | 0 | 95 | 0 | 5 | 2 |
| 4.6 | 95 | 0 | 0 | 5 | 2 |

System 4 Conditions:
Mobile phase A: water
Mobile phase B: acetonitrile
Mobile phase C: 10 mmol ammonium formate in water Mobile phase D: 0.05% formic acid in acetonitrile

| Time (mins) | A (%) | B (%) | C (%) | D (%) | Flow (mL/min) |
|---|---|---|---|---|---|
| 0 | 0 | 0 | 100 | 0 | 2 |
| 3.5 | 0 | 95 | 5 | 0 | 2 |
| 4.5 | 0 | 95 | 5 | 0 | 2 |
| 4.6 | 0 | 0 | 100 | 0 | 2 |

Analytical Methods for Libraries

| Method |  |
|---|---|
| Column RESTEK C18(30 × 2.1) 3μ | |
| Temperature 50° C. | |
| Mobile Phase A 0.05% HCOOH in water | |
| Mobile Phase B ACETONITRILE | |
| Gradient | |
| Time Initial | 2% B |
| Time 0.75 mins | 2% B |
| Time 1.00 mins | 10% B |
| Time 2.00 mins | 98% B |
| Time 2.25 mins | 98% B |
| Time 2.90 mins | 2% B |
| Time 3.00 mins | 2% B |
| Flow rate | 1.5 ml/min |
| Injection volume | 3 μl |
| WATERS ACQUITY UPLC/WATERS 3100 MSD/ | |
| PL-ELS 2100 ICE ELSD | |
| Ionization Mode | API-ES |
| Polarity | Positive/Negative |

| Method |  |
|---|---|
| Column Gemini NX C18(50 × 4.6) 5μ | |
| Temperature 50° C. | |
| Mobile Phase A 10 mM NH4OAc in water | |
| Mobile Phase B ACETONITRILE | |
| Gradient | |
| Time Initial | 5% B |
| Time 0.75 mins | 5% B |
| Time 1.5 mins | 15% B |
| Time 3.00 mins | 90% B |
| Time 4.00 mins | 90% B |
| Time 5.00 mins | 5% B |
| Time 5.10 mins | 5% B |
| Flow rate | 1.5 ml/min |
| Injection volume | 3 μl |
| WATERS ACQUITY UPLC/WATERS 3100 MSD/ | |
| PL-ELS 2100 ICE ELSD | |
| Ionization Mode | API-ES |
| Polarity | Positive/Negative |

Example 1

N-((1H-1,2,3-triazol-5-yl)methyl)-5-(2,4-dichloro-5-(5-fluoropyridin-2-yl)benzamido)-1-phenyl-1H-pyrazole-3-carboxamide

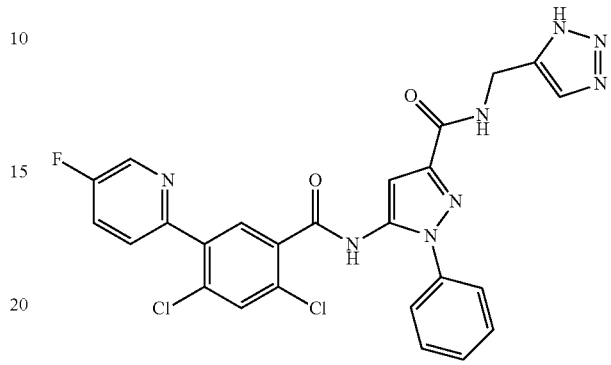

5-(2,4-dichloro-5-(5-fluoropyridin-2-yl)benzamido)-1-phenyl-1H-pyrazole-3-carboxylic acid (Example 102, 100 mg, 0.212 mmol), (1H-1,2,3-triazol-5-yl)methanamine hydrochloride (43 mg, 0.32 mmol) and HATU (121 mg, 0.32 mmol) were dissolved in dimethylformamide (5 mL) under nitrogen. Triethylamine (0.12 mL, 0.85 mmol) was added dropwise and the reaction stirred at room temperature for 1 hour. The reaction was concentrated in vacuo. The residue was partitioned between ethyl acetate (50 mL) and water (50 mL), the organic layer was collected, dried over magnesium sulphate and concentrated in vacuo. The residue was purified by silica gel column chromatography eluting with 95:5:0.5 dichloromethane:methanol:ammonia to afford the title compound as a white solid (48 mg, 42%).

$^1$H NMR (400 MHz, MeOH-$d_4$): δ ppm 4.66-4.70 (s, 2H), 7.02-7.05 (s, 1H), 7.44-7.55 (m, 3H), 7.57-7.60 (m, 1H), 7.60-7.63 (m, 1H), 7.65-7.68 (s, 1H), 7.71-7.73 (s, 1H), 7.73-7.77 (m, 3H), 8.58-8.61 (s, 1H).

LCMS Rt=2.76 minutes MS m/z 551 [M+H]$^+$

Example 2

5-(2,4-dichloro-5-(5-fluoropyridin-2-yl)benzamido)-N-(2-hydroxyethyl)-1-phenyl-1H-Pyrazole-3-carboxamide

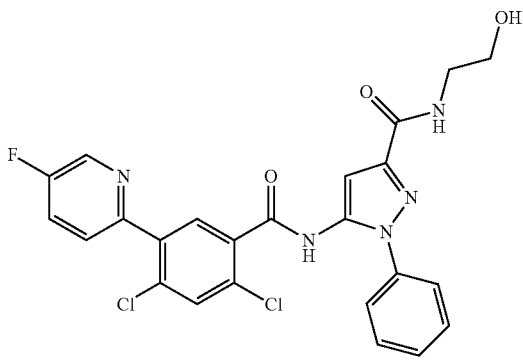 [SMILES: O=C(NCCO)c1cc(NC(=O)c2cc(-c3ccc(F)cn3)c(Cl)cc2Cl)n(-c2ccccc2)n1]

5-(2,4-dichloro-5-(5-fluoropyridin-2-yl)benzamido)-1-phenyl-1H-pyrazole-3-carboxylic acid (Example 102, 100 mg, 0.212 mmol), ethanolamine (0.2 mL, 0.32 mmol) and HATU (121 mg, 0.32 mmol) were dissolved in dimethylformamide (5 mL) under nitrogen. Triethylamine (0.12 mL, 0.85 mmol) was added and the reaction stirred at room temperature for 1 hour. The reaction was concentrated in vacuo. The residue was partitioned between ethyl acetate (50 mL) and water (30 mL), the organic layer was collected, dried over magnesium sulphate and concentrated in vacuo. The residue was purified by silica gel column chromatography eluting with 95:5:0.5 dichloromethane:methanol:ammonia to afford the title compound as a white solid (79 mg, 73%).

$^1$H NMR (400 MHz, DMSO-d$_6$): δ ppm 3.27-3.34 (m, 2H), 3.45-3.51 (q, 2H), 4.70-4.73 (t, 1H), 6.88-6.91 (s, 1H), 7.43-7.48 (m, 1H), 7.48-7.55 (m, 2H), 7.56-7.61 (m, 2H), 7.70-7.73 (s, 1H), 7.76-7.81 (m, 1H), 7.86-7.88 (s, 1H), 7.86-7.93 (m, 1H), 8.10-8.15 (m, 1H), 8.72-8.75 (d, 1H), 10.79-10.81 (s, 1H).

LCMS Rt=2.72 minutes MS m/z 514 [M+H]$^+$

Example 3

5-(2-chloro-5-(3-fluoropyridin-2-yl)benzamido)-N-(3-methyl-1H-pyrazol-4-yl)-1-phenyl-1H-pyrazole-3-carboxamide

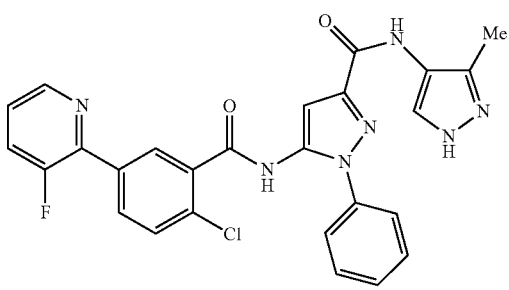 [SMILES: Cc1n[nH]cc1NC(=O)c1cc(NC(=O)c2cc(-c3ncccc3F)ccc2Cl)n(-c2ccccc2)n1]

To a solution of HATU (0.3 mmol, 113 mg) and 5-(2-chloro-5-(3-fluoropyridin-2-yl)benzamido)-1-phenyl-1H-pyrazole-3-carboxylic acid (Example 105, 0.23 mmol, 100 mg) in DMF (0.9 mL) was added DIPEA (1.10 mmol, 0.191 mL). The solution was stirred at room temperature for 15 minutes. 3-methyl-1H-pyrazol-4-amine (0.23 mmol, 100 mg) was added and the reaction stirred at room temperature for 18 hours. The reaction was diluted with EtOAc (20 mL), washed with NaHCO$_3$ (20 mL), 10% aqueous citric acid solution (20 mL) and brine (20 mL). The organic layer was dried over sodium sulphate and concentrated in vacuo. The residue was purified using reverse phase column chromatography to afford the title compound as a yellow solid (35 mg, 29%).

$^1$H NMR (400 MHz, DMSO-d$_6$): δ ppm 3.28 (br s, 3H), 7.02 (s, 1H), 7.46-7.58 (m, 5H), 7.65-7.69 (m, 3H), 7.87-7.92 (m, 1H), 8.02 (s, 1H), 8.03 (s, 1H), 8.58 (d, 1H), 9.48-9.54 (br d, 1H), 10.84 (s, 1H), 12.32-12.42 (br d, 1H).

LCMS Rt=2.66 minutes MS m/z 516 [M+H]$^+$

Example 4

N-((1H-1,2,3-triazol-4-yl)methyl)-5-(2-chloro-5-(3-fluoropyridin-2-yl)benzamido)-1-phenyl-1H-pyrazole-3-carboxamide

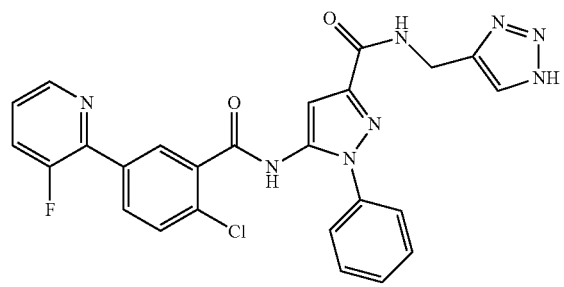 [SMILES: O=C(NCc1c[nH]nn1)c1cc(NC(=O)c2cc(-c3ncccc3F)ccc2Cl)n(-c2ccccc2)n1]

To a solution of 5-(2-chloro-5-(3-fluoropyridin-2-yl)benzamido)-1-phenyl-1H-pyrazole-3-carboxylic acid (Example 105, 200 mg, 0.458 mmol), (1H-1,2,3-triazol-4-yl)methanamine (74 mg, 0.549 mmol) and N,N-diisopropylethylamine (406 µL, 2.29 mmol) in dichloromethane (3 mL) and N,N-dimethylformamide (1 mL) was added HATU (261 mg, 0.687 mmol). The reaction was stirred at room temperature for 2 hours. Further HATU (87 mg, 0.229 mmol) was added and the reaction continued for 3 hours. The reaction solution was partitioned between water (10 mL) and ethyl acetate (10 mL). The aqueous layer was further extracted with ethyl acetate (2×10 mL), and the combined organic layers were washed with brine (20 mL), dried over magnesium sulphate and concentrated in vacuo. The residue was purified by elution through an SCX-2 column using MeOH followed by 7N NH$_3$ in MeOH followed by silica gel column chromatography eluting with 1% NH$_3$(aq) and 8% MeOH in DCM to afford the title compound as white solid (51 mg, 21%).

$^1$H NMR (400 MHz, MeOH-d$_4$): δ ppm 4.69 (s, 2H), 7.05 (s, 1H), 7.47 (m, 2H), 7.54 (t, 2H), 7.62 (m, 3H), 7.73 (m, 2H), 8.05 (m, 2H), 8.51 (d, 1H).

LCMS Rt=2.45 minutes MS m/z 517 [M+H]$^+$

Example 5

5-{[2-chloro-4-fluoro-5-(3-fluoropyridin-2-yl)benzoyl]amino}-N-[(2S)-2-hydroxypropyl]-1-phenyl-1H-pyrazole-3-carboxamide

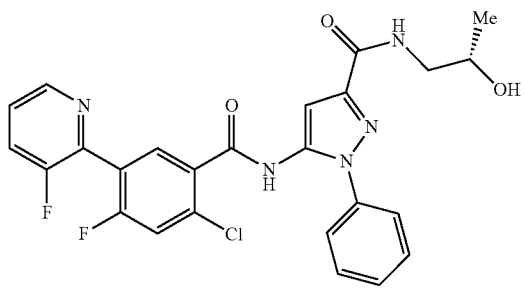 [SMILES: C[C@H](O)CNC(=O)c1cc(NC(=O)c2cc(-c3ncccc3F)c(F)cc2Cl)n(-c2ccccc2)n1]

To a solution of 5-(2-chloro-4-fluoro-5-(3-fluoropyridin-2-yl)benzamido)-1-phenyl-1H-pyrazole-3-carboxylic acid (Example 110, 100 mg, 0.22 mmol) in DMF (3 mL) was added DIPEA (0.23 mL, 1.32 mmol) and 2-(3H-[1,2,3]triazolo[4,5-b]pyridin-3-yl)-1,1,3,3-tetramethyluronium hexafluorophosphate (92 mg, 0.26 mmol). The reaction was stirred at room temperature for 10 minutes before the addition of (S)-1-aminopropan-2-ol (20 mg, 0.22 mmol) and the reaction was continued stirring for 18 hours. The reaction was diluted with EtOAc (50 mL) and extracted with water (3×5 mL) and brine (25 mL). The organic layer was collected, dried over anhydrous $Na_2SO_4$ before concentration in vacuo. The residue was purified using reverse phase column chromatography eluting with 0-80% MeCN in water to afford the title compound (18 mg, 16%).

$^1$H NMR (400 MHz, MeOH-$d_4$): δ ppm 1.20 (d, 3H), 3.35 (m, 1H), 3.45 (m, 1H), 3.95 (m, 1H), 7.05 (m, 1H), 7.40-7.70 (m, 7H), 7.80 (m, 2H), 8.60 (m, 1H).

LCMS Rt=2.61 minutes MS m/z 512 [M+H]$^+$

The following Examples were prepared according to the method described for Examples 1-5 using the appropriate acid and amine as described below. The crude residues were purified as above or according to the purification method described below:

Purification Method A: Silica gel column chromatography eluting with 70% EtOAc in heptanes.
Purification Method B: Reverse phase column chromatography using 3-50% MeCN in water containing 0.1% ammonia.
Purification Method C: Silica gel column chromatography eluting with 50% EtOAc in heptanes to 10% MeOH in EtOAc and if necessary, followed by elution through an SCX-2 column using MeOH followed by 7N $NH_3$ in MeOH or trituration with MeOH.
Purification Method D: Preparative HPLC and followed by, if necessary, silica gel column chromatography eluting with 10% ammonia in MeOH in DCM.
Purification Method E: Reverse phase column chromatography using 5 to 95% MeCN (with 0.1% formic acid) in water (with 0.1% formic acid).
Purification Method F: Silica gel column chromatography eluting with 99:1:0.1 to 92:8:0.8 DCM:MeOH:$NH_3$.
Purification Method G: Recrystalisation from 1:1 DCM:heptanes.
Purification Method H: Trituration with MeCN or MeOH.

| Example Number | Name/Structure | Starting Materials | Data/PM |
| --- | --- | --- | --- |
| 6 | 5-(2-chloro-5-(6-pivalamidopyridin-2-yl)benzamido)-N-cyclopropyl-1-phenyl-1H-pyrazole-3-carboxamide | 5-(2-chloro-5-(6-pivalamidopyridin-2-yl)benzamido)-1-phenyl-1H-pyrazole-3-carboxylic acid (Example 103) and cyclopropylamine. | $^1$H NMR (400 MHz DMSO-$d_6$): δ ppm 0.65 (m, 4H), 1.25 (s, 9H), 2.85 (m, 1H), 6.90 (s, 1H), 7.45 (m, 1H), 7.55 (m, 2H), 7.65 (m, 3H), 7.75 (d, 1H), 7.90 (t, 1H), 8.05 (d, 1H), 8.20 (m, 1H), 8.23 (s, 1H), 8.30 (m, 1H), 9.65 (s, 1H), 10.80 (s, 1H). LCMS Rt = 3.43 minutes MS m/z 557 [M + H]$^+$ PM A. |
| 7 | N-((1H-imidazol-2-yl)methyl)-5-(2-chloro-5-(3-fluoropyridin-2-yl)benzamido)-1-phenyl-1H-pyrazole-3-carboxamide | 5-(2-chloro-5-(3-fluoropyridin-2-yl)benzamido)-1-phenyl-1H-pyrazole-3-carboxylic acid (Example 105) and (1H-imidazol-2-yl)methanamine hydrochloride. | $^1$H NMR (400 MHz DMSO-$d_6$): δ ppm 4.48 (d, 2H), 6.80-6.98 (m, 3H), 7.48-7.70 (m, 7H), 7.86-7.92 (m, 1H), 8.01-8.07 (m, 2H), 8.60 (d, 1H), 8.65-8.68 (m, 1H), 10.85 (s, 1H), 11.78 (s, 1H). LCMS Rt = 2.58 minutes MS m/z 516 [M + H]$^+$ PM B. |

| Example Number | Name/Structure | Starting Materials | Data/PM |
|---|---|---|---|
| 8 | N-((1H-pyrazol-3-yl)methyl)-5-(2-chloro-5-(3-fluoropyridin-2-yl)benzamido)-1-phenyl-1H-pyrazole-3-carboxamide 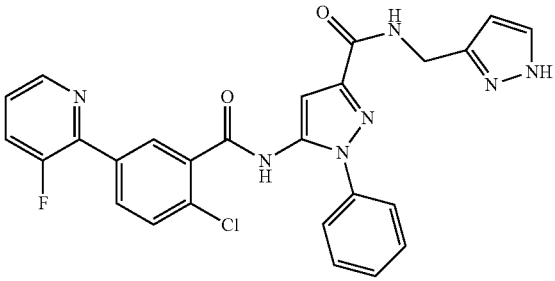 | 5-(2-chloro-5-(3-fluoropyridin-2-yl)benzamido)-1-phenyl-1H-pyrazole-3-carboxylic acid (Example 105) and (1H-pyrazol-3-yl)methanamine. | $^1$H NMR (400 MHz, MeOH-d$_4$): δ ppm 4.60 (s, 2H), 6.25 (s, 1H), 7.05 (s, 1H), 7.40-7.77 (m, 9H), 8.00-8.06 (m, 2H) and 8.51 (br s, 1H). LCMS Rt = 2.65 minutes MS m/z 516 [M + H]$^+$ PM C. |
| 9 | N-((5-amino-1H-pyrazol-3-yl)methyl)-5-(2-chloro-5-(3-fluoropyridin-2-yl)benzamido)-1-phenyl-1H-pyrazole-3-carboxamide 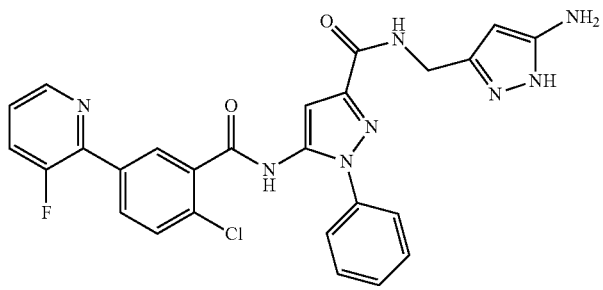 | 5-(2-chloro-5-(3-fluoropyridin-2-yl)benzamido)-1-phenyl-1H-pyrazole-3-carboxylic acid (Example 105) and 3-(aminomethyl)-1H-pyrazol-5-amine. | $^1$H NMR (400 MHz, MeOH-d$_4$): δ ppm 4.48 (s, 2H), 5.59 (br s, 1H), 7.05 (s, 1H), 7.46-7.65 (m, 7H), 7.71-7.76 (m, 1H), 8.04-8.06 (m, 2H), 8.52 (d, 1H). LCMS Rt = 2.50 minutes MS m/z 531 [M + H]$^+$ PM C. |
| 10 | Racemic 5-(2-chloro-5-(3-fluoropyridin-2-yl)benzamido)-N-(2,3-dihydroxypropyl)-1-phenyl-1H-pyrazole-3-carboxamide 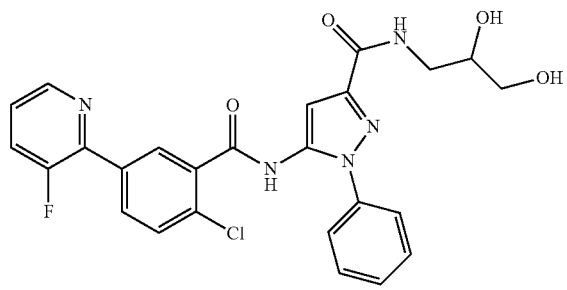 | 5-(2-chloro-5-(3-fluoropyridin-2-yl)benzamido)-1-phenyl-1H-pyrazole-3-carboxylic acid (Example 105) and racemic-3-aminopropane-1,2-diol. | $^1$H NMR (400 MHz, MeOH-d$_4$): δ ppm 3.40 (m, 1H), 3.56-3.62 (m, 3H), 3.79-3.85 (m, 1H), 7.03 (s, 1H), 7.45-7.50 (m, 2H), 7.53-7.57 (m, 2H), 7.60-7.64 (m, 3H), 7.71-7.76 (m, 1H), 8.03-8.05 (m, 2H), 8.52 (d, 1H). LCMS Rt = 2.44 minutes MS m/z 510 [M + H]$^+$ PM C. |
| 11 | N-((1H-pyrazol-4-yl)methyl)-5-(2-chloro-5-(3-fluoropyridin-2-yl)benzamido)-1-phenyl-1H-pyrazole-3-carboxamide 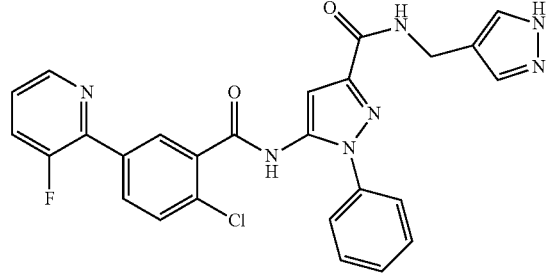 | 5-(2-chloro-5-(3-fluoropyridin-2-yl)benzamido)-1-phenyl-1H-pyrazole-3-carboxylic acid (Example 105) and (1H-pyrazol-4-yl)methanamine. | $^1$H NMR (400 MHz, MeOH-d$_4$): δ ppm 4.47 (s, 2H), 7.03 (s, 1H), 7.42-7.75 (m, 10H), 7.99-8.09 (m, 2H), 8.50 (d, 1H). LCMS Rt = 2.48 minutes MS m/z 516 [M + H]$^+$ PM D. |

| Example Number | Name/Structure | Starting Materials | Data/PM |
|---|---|---|---|
| 12 | (R)-5-(2-chloro-5-(3-fluoropyridin-2-yl)benzamido)-N-(2-hydroxypropyl)-1-phenyl-1H-pyrazole-3-carboxamide | 5-(2-chloro-5-(3-fluoropyridin-2-yl)benzamido)-1-phenyl-1H-pyrazole-3-carboxylic acid (Example 105) and (R)-1-aminopropan-2-ol. | $^1$H NMR (400 MHz, MeOH-d$_4$): δ ppm 1.21 (d, 3H), 3.31-3.35 (m, 1H), 3.45-3.51 (dd, 1H), 3.94-3.98 (m, 1H), 7.04 (s, 1H), 7.46-7.51 (m, 2H), 7.53-7.59 (m, 2H), 7.60-7.64 (m, 3H), 7.76 (m, 1H), 8.04-8.08 (m, 2H), 8.54 (d, 1H). LCMS Rt = 2.48 minutes MS m/z 494 [M + H]$^+$ PM D. |
| 13 | N-((4H-1,2,4-triazol-3-yl)methyl)-5-(2-chloro-5-(3-fluoropyridin-2-yl)benzamido)-1-phenyl-1H-pyrazole-3-carboxamide | 5-(2-chloro-5-(3-fluoropyridin-2-yl)benzamido)-1-phenyl-1H-pyrazole-3-carboxylic acid (Example 105) and (4H-1,2,4-triazol-3-yl)methanamine hydrochloride. | $^1$H NMR (400 MHz, MeOH-d$_4$): δ ppm 4.73 (s, 2H), 7.07 (s, 1H), 7.46-7.51 (m, 2H), 7.54-7.58 (m, 2H), 7.61-7.66 (m, 3H), 7.74 (m, 1H), 8.04-8.07 (m, 2H), 8.22 (br s, 1H), 8.52-8.55 (m, 1H). LCMS Rt = 2.48 minutes MS m/z 517 [M + H]$^+$ PM D. |
| 14 | 5-(2-chloro-5-(3-fluoropyridin-2-yl)benzamido)-N-((5-methyl-1H-1,2,4-triazol-3-yl)methyl)-1-phenyl-1H-pyrazole-3-carboxamide | 5-(2-chloro-5-(3-fluoropyridin-2-yl)benzamido)-1-phenyl-1H-pyrazole-3-carboxylic acid (Example 105) and (5-methyl-1H-1,2,4-triazol-3-yl)methanamine. | $^1$H NMR (400 MHz, MeOH-d$_4$): δ ppm 2.39 (s, 3H), 4.64 (s, 2H), 7.05 (s, 1H), 7.45-7.65 (m, 7H), 7.71-7.76 (m, 1H), 8.03-8.05 (m, 2H), 8.52 (d, 1H). LCMS Rt = 2.50 minutes MS m/z 531 [M + H]$^+$ |
| 15 | 5-(2-chloro-5-(3-fluoropyridin-2-yl)benzamido)-N-(1-hydroxy-2-methylpropan-2-yl)-1-phenyl-1H-pyrazole-3-carboxamide | 5-(2-chloro-5-(3-fluoropyridin-2-yl)benzamido)-1-phenyl-1H-pyrazole-3-carboxylic acid (Example 105) and 2-amino-2-methylpropan-1-ol. | $^1$H NMR (400 MHz DMSO-d$_6$): δ ppm 1.32 (s, 6H), 3.42 (d, 2H), 5.08 (t, 1H), 6.88 (s, 1H), 7.30 (s, 1H), 7.43-7.62 (m, 5H), 7.67 (d, 1H), 7.88 (dd, 1H), 8.02 (br s, 2H), 8.58 (d, 1H), 10.79 (br s, 1H). LCMS Rt = 2.70 minutes MS m/z 508 [M + H]$^+$ PM D. |

| Example Number | Name/Structure | Starting Materials | Data/PM |
|---|---|---|---|
| 16 | 5-(2-chloro-5-(3-fluoropyridin-2-yl)benzamido)-N-(4-methyl-1H-pyrazol-3-yl)-1-phenyl-1H-pyrazole-3-carboxamide 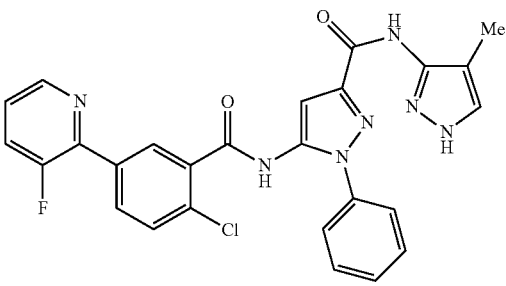 | 5-(2-chloro-5-(3-fluoro-pyridin-2-yl)benzamido)-1-phenyl-1H-pyrazole-3-carboxylic acid (Example 105) and 4-methyl-1H-pyrazol-3-amine. | $^1$H NMR (400 MHz DMSO-$d_6$): δ ppm 1.92 (s, 3H), 5.69 (br s, 2H), 7.38 (br s, 1H), 7.47-7.70 (m, 7H), 7.87-7.92 (m, 1H), 8.02 (br s, 1H), 8.04 (br s, 1H), 8.16 (br s, 1H), 8.58-8.59 (m, 1H), 10.87 (br s, 1H). LCMS Rt = 3.00 minutes MS m/z 516 [M + H]$^+$ PM E. |
| 17 | (S)-5-(2-chloro-5-(3-fluoropyridin-2-yl)benzamido)-N-(2-hydroxypropyl)-1-phenyl-1H-pyrazole-3-carboxamide 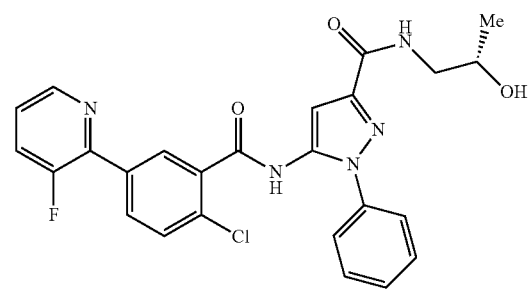 | 5-(2-chloro-5-(3-fluoro-pyridin-2-yl)benzamido)-1-phenyl-1H-pyrazole-3-carboxylic acid (Example 105) and (S)-1-aminopropan-2-ol. | $^1$H NMR (400 MHz, MeOH-$d_4$): δ ppm 1.21 (d, 3H), 3.31-3.36 (m, 1H), 3.45-3.51 (dd, 1H), 3.94-3.98 (m, 1H), 7.04 (s, 1H), 7.46-7.51 (m, 2H), 7.53-7.59 (m, 2H), 7.60-7.65 (m, 3H), 7.74 (m, 1H), 8.04-8.07 (m, 2H), 8.53 (d, 1H). LCMS Rt = 2.47 minutes MS m/z 494 [M + H]$^+$ PM E. |
| 18 | 5-(2-chloro-5-(3-fluoropyridin-2-yl)benzamido)-1-phenyl-N-(pyrimidin-4-ylmethyl)-1H-pyrazole-3-carboxamide 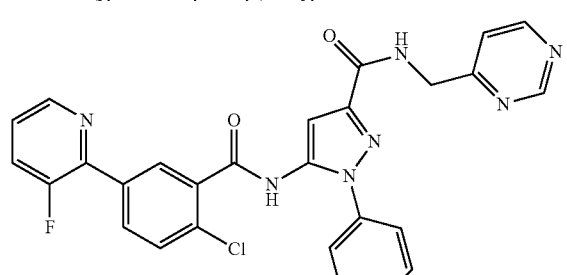 | 5-(2-chloro-5-(3-fluoro-pyridin-2-yl)benzamido)-1-phenyl-1H-pyrazole-3-carboxylic acid (Example 105) and pyrimidin-4-ylmethanamine. | $^1$H NMR (400 MHz DMSO-$d_6$): δ ppm 4.55 (s, 2H), 6.98 (s, 1H), 7.43-7.71 (m, 7H), 7.91 (m, 1H), 8.04 (m, 2H), 8.60 (s, 1H), 8.72 (m, 1H), 9.02 (m, 1H), 9.11 (s, 1H), 10.87 (br s, 1H). MS m/z 528 [M + H]$^+$ |
| 19 | 5-(2-chloro-5-(3-fluoropyridin-2-yl)benzamido)-1-phenyl-N-(pyrazin-2-ylmethyl)-1H-pyrazole-3-carboxamide 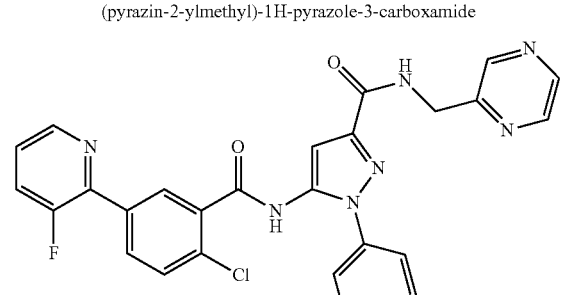 | 5-(2-chloro-5-(3-fluoro-pyridin-2-yl)benzamido)-1-phenyl-1H-pyrazole-3-carboxylic acid (Example 105) and pyrazin-2-ylmethanamine. | $^1$H NMR (400 MHz DMSO-$d_6$): δ ppm 4.63 (s, 2H), 6.97 (s, 1H), 7.47-7.70 (m, 7H), 7.88 (m, 1H), 7.93 (m, 1H), 8.53-8.63 (m, 4H), 8.99 (m, 1H), 10.85 (s, 1H). MS m/z 528 [M + H]$^+$ |

-continued

| Example Number | Name/Structure | Starting Materials | Data/PM |
|---|---|---|---|
| 20 | 5-(2-chloro-5-(3-fluoropyridin-2-yl)benzamido)-1-phenyl-N-(pyrimidin-2-ylmethyl)-1H-pyrazole-3-carboxamide 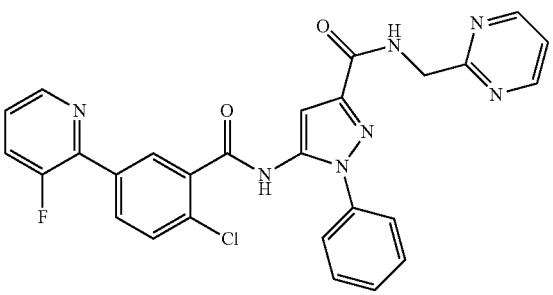 | 5-(2-chloro-5-(3-fluoro-pyridin-2-yl)benzamido)-1-phenyl-1H-pyrazole-3-carboxylic acid (Example 105) and pyrimidin-2-ylmethanamine. | $^1$H NMR (400 MHz DMSO-$d_6$): δ ppm 4.67 (s, 2H), 6.96 (s, 1H), 7.39-7.70 (m, 8H), 7.88 (m, 1H), 8.05 (m, 2H), 8.59 (m, 1H), 8.71-8.78 (m, 3H), 10.84 (br s, 1H). MS m/z 528 [M + H]$^+$ |
| 21 | 5-(2-chloro-5-(3-fluoropyridin-2-yl)benzamido)-N-((1-methyl-1H-1,2,3-triazol-5-yl)methyl)-1-phenyl-1H-pyrazole-3-carboxamide 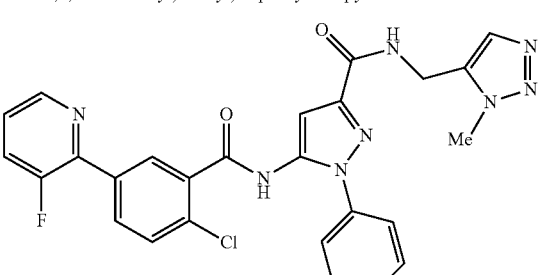 | 5-(2-chloro-5-(3-fluoro-pyridin-2-yl)benzamido)-1-phenyl-1H-pyrazole-3-carboxylic acid (Example 105) and (1-methyl-1H-1,2,3-triazol-5-yl)methanamine. | $^1$H NMR (400 MHz DMSO-$d_6$): δ ppm 4.04 (s, 3H), 4.56 (s, 2H), 6.96 (s, 1H), 7.48-7.70 (m, 7H), 7.88 (m, 1H), 8.03 (m, 2H), 8.60 (m, 1H), 8.96 (m, 1H), 10.84 (br s, 1H). MS m/z 531 [M + H]$^+$ |
| 22 | 5-(2-chloro-5-(3-fluoropyridin-2-yl)benzamido)-N-((1-methyl-1H-1,2,3-triazol-4-yl)methyl)-1-phenyl-1H-pyrazole-3-carboxamide 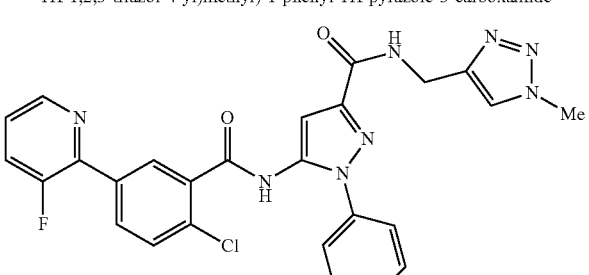 | 5-(2-chloro-5-(3-fluoro-pyridin-2-yl)benzamido)-1-phenyl-1H-pyrazole-3-carboxylic acid (Example 105) and (1-methyl-1H-1,2,3-triazol-4-yl)methanamine. | $^1$H NMR (400 MHz DMSO-$d_6$): δ ppm 4.09 (s, 3H), 4.49 (m, 2H), 6.95 (s, 1H), 7.46-7.70 (m, 7H), 7.88 (m, 1H), 8.03 (s, 1H), 8.59 (m, 1H), 8.82 (m, 1H), 10.82 (br s, 1H). MS m/z 531 [M + H]$^+$ |
| 23 | 5-(2-chloro-5-(3-fluoropyridin-2-yl)benzamido)-1-phenyl-N-(pyrimidin-5-ylmethyl)-1H-pyrazole-3-carboxamide 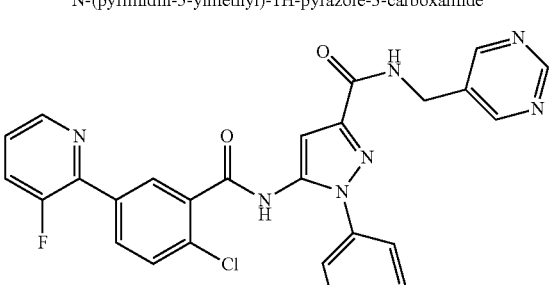 | 5-(2-chloro-5-(3-fluoro-pyridin-2-yl)benzamido)-1-phenyl-1H-pyrazole-3-carboxylic acid (Example 105) and pyrimidin-5-ylmethanamine. | $^1$H NMR (400 MHz DMSO-$d_6$): δ ppm 4.49 (m, 2H), 6.96 (s, 1H), 7.47-7.70 (m, 7H), 7.87 (m, 1H), 8.04 (m, 1H), 8.59 (m, 1H), 8.77 (s, 2H), 9.01 (m, 1H), 9.08 (s, 1H), 10.83 (br s, 1H). MS m/z 528 [M + H]$^+$ |

| Example Number | Name/Structure | Starting Materials | Data/PM |
|---|---|---|---|
| 24 | 5-(2-chloro-5-(3-fluoropyridin-2-yl)benzamido)-1-phenyl-N-(pyridazin-3-ylmethyl)-1H-pyrazole-3-carboxamide | 5-(2-chloro-5-(3-fluoropyridin-2-yl)benzamido)-1-phenyl-1H-pyrazole-3-carboxylic acid (Example 105) and pyridazin-3-ylmethanamine. | $^1$H NMR (400 MHz DMSO-$d_6$): δ ppm 4.77 (s, 2H), 6.98 (s, 1H), 7.47-7.70 (m, 9H), 7.88 (m, 1H), 8.04 (m, 1H), 8.60 (m, 1H), 9.07-9.14 (m, 2H), 10.86 (s, 1H). MS m/z 528 [M + H]$^+$ |
| 25 | 5-(2-chloro-5-(3-fluoropyridin-2-yl)benzamido)-1-phenyl-N-(1H-pyrazol-4-yl)-1H-pyrazole-3-carboxamide | 5-(2-chloro-5-(3-fluoropyridin-2-yl)benzamido)-1-phenyl-1H-pyrazole-3-carboxylic acid (Example 105) and 1H-pyrazol-4-amine. | $^1$H NMR (400 MHz DMSO-$d_6$): δ ppm 7.00 (s, 1H), 7.40-7.55 (m, 4H), 7.60-7.80 (m, 4H), 7.90 (m, 2H) 8.00 (m, 2H), 8.55 (m, 1H), 10.35 (s, 1H), 11.85 (s, 1H), 12.55 (br s, 1H). LCMS Rt = 2.66 minutes MS m/z 502 [M + H]$^+$ PM E. |
| 26 | N-((1H-1,2,3-triazol-4-yl)methyl)-5-(2-chloro-5-(3-chloropyridin-2-yl)benzamido)-1-phenyl-1H-pyrazole-3-carboxamide | 5-(2-chloro-5-(3-chloropyridin-2-yl)benzamido)-1-phenyl-1H-pyrazole-3-carboxylic acid (Example 106) and (1H-1,2,3-triazol-4-yl)methanamine hydrochloride. | $^1$H NMR (400 MHz DMSO-$d_6$): δ ppm 4.51 (d, 2H), 6.93 (s, 1H), 7.42-7.68 (s, 1H), 7.77-7.84 (m, 9H), 8.08 (dd, 1H), 8.65 (dd, 1H), 8.78 (br s, 1H), 10.80 (s, 1H). LCMS Rt = 2.60 minutes MS m/z 533 [M + H]$^+$ PM B. |
| 27 | Racemic N-(1-(1H-1,2,3-triazol-4-yl)ethyl)-5-(2-chloro-5-(3-fluoropyridin-2-yl)benzamido)-1-phenyl-1H-pyrazole-3-carboxamide | 5-(2-chloro-5-(3-fluoropyridin-2-yl)benzamido)-1-phenyl-1H-pyrazole-3-carboxylic acid (Example 105) and racemic-1-(1H-1,2,3-triazol-4-yl)ethanamine (Preparation 62). | $^1$H NMR (400 MHz, MeOH-$d_4$): δ ppm 1.65-1.67 (d, 3H), 5.46-5.50 (q, 1H), 7.06 (s, 1H), 7.45-7.63 (m, 7H), 7.71-7.76 (m, 2H), 8.03-8.05 (m, 2H), 8.51-8.53 (d, 1H). LCMS Rt = 2.74 minutes MS m/z 531 [M + H]$^+$ PM F. |

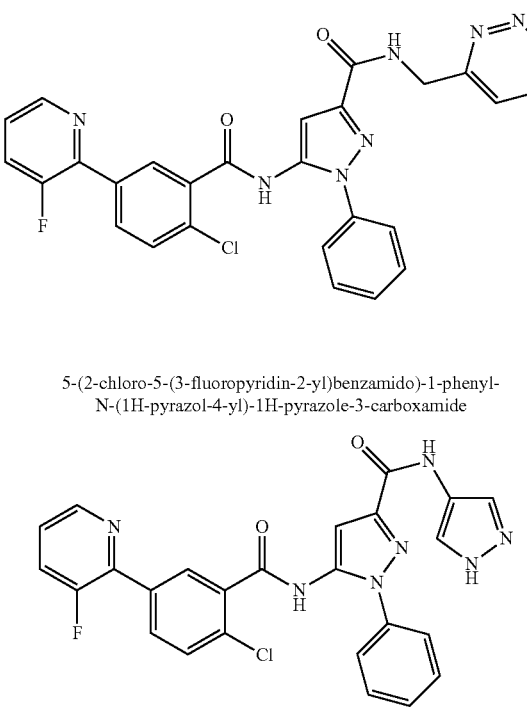

| Example Number | Name/Structure | Starting Materials | Data/PM |
|---|---|---|---|
| 28 | N-((1H-1,2,3-triazol-4-yl)methyl)-5-(2,4-dichloro-5-(pyridin-2-yl)benzamido)-1-phenyl-1H-pyrazole-3-carboxamide | 5-(2,4-dichloro-5-(pyridin-2-yl)benzamido)-1-phenyl-1H-pyrazole-3-carboxylic acid (Example 111) and and 1-(1H-1,2,3-triazol-4-yl)methanamine. | $^1$H NMR (400 MHz DMSO-$d_6$): δ ppm 4.53 (d, 2H), 6.95 (s, 1H), 7.41-7.52 (m, 4H), 7.65-7.69 (m, 5H), 7.71 (s, 1H), 7.85 (s, 1H), 7.97 (t, 1H), 8.73-8.77 (m, 2H). LCMS Rt = 2.63 minutes MS m/z 533 [M + H]$^+$ PM B. |
| 29 | N-((1H-1,2,3-triazol-4-yl)methyl)-5-(2-chloro-4-fluoro-5-(pyridin-2-yl)benzamido)-1-phenyl-1H-pyrazole-3-carboxamide | 5-(2-chloro-4-fluoro-5-(pyridin-2-yl)benzamido)-1-phenyl-1H-pyrazole-3-carboxylic acid (Example 108) and 1-(1H-1,2,3-triazol-4-yl)methanamine. | $^1$H NMR (400 MHz, MeOH-$d_4$): δ ppm 4.69 (s, 2H), 7.04 (s, 1H), 7.43-7.48 (m, 3H), 7.52-7.55 (m, 2H), 7.63 (d, 2H), 7.76 (s, 1H), 7.81 (d, 1H), 7.93 (td, 1H), 8.06 (d, 1H), 8.71 (d, 1H). LCMS Rt = 2.45 minutes MS m/z 517 [M + H]$^+$ |
| 30 | 5-(2-chloro-4-fluoro-5-(pyridin-2-yl)benzamido)-N-(3-methyl-1H-pyrazol-4-yl)-1-phenyl-1H-pyrazole-3-carboxamide | 5-(2-chloro-4-fluoro-5-(pyridin-2-yl)benzamido)-1-phenyl-1H-pyrazole-3-carboxylic acid (Example 108) and 3-methyl-1H-pyrazol-4-amine. PM F. | $^1$H NMR (400 MHz DMSO-$d_6$): δ ppm 2.16 (s, 3H), 7.01 (s, 1H), 7.45-7.50 (m, 2H), 7.56 (t, 3H), 7.65 (d, 2H), 7.72 (d, 1H), 7.82 (d, 1H), 7.95 (m, 1H), 8.12 (d, 1H), 8.76 (d, 1H), 9.51 (br s, 1H), 10.81 (br s, 1H), 12.37 (br s, 1H). LCMS Rt = 2.56 minutes MS m/z 516 [M + H]$^+$ |
| 31 | N-((1H-1,2,3-triazol-4-yl)methyl)-5-(2-chloro-4-fluoro-5-(5-fluoropyridin-2-yl)benzamido)-1-phenyl-1H-pyrazole-3-carboxamide | 5-(2-chloro-4-fluoro-5-(5-fluoropyridin-2-yl)benzamido)-1-phenyl-1H-pyrazole-3-carboxylic acid (Example 109) and 1-(1H-1,2,3-triazol-4-yl)ethanamine. | $^1$H NMR (400 MHz, CDCl$_3$): δ ppm 4.72 (d, 2H), 7.22-7.26 (m, 1H), 7.37-7.45 (m, 1H), 7.46-7.60 (m, 6H), 7.65-7.70 (m, 1H), 7.77-7.84 (m, 1H), 8.46-8.54 (m, 2H). LCMS Rt = 2.70 minutes MS m/z 535 [M + H]$^+$ |

| Example Number | Name/Structure | Starting Materials | Data/PM |
|---|---|---|---|
| 32 | (S)-5-(2-chloro-5-(3-fluoropyridin-2-yl)benzamido)-N-(1-hydroxypropan-2-yl)-1-phenyl-1H-pyrazole-3-carboxamide | 5-(2-chloro-5-(3-fluoro-pyridin-2-yl)benzamido)-1-phenyl-1H-pyrazole-3-carboxylic acid (Example 105) and (S)-2-aminopropan-1-ol. | $^1$H NMR (400 MHz, MeOH-d$_4$ and CDCl$_3$): δ ppm 1.26 (d, 3H), 3.60 (m, 2H), 4.12-4.25 (m, 1H), 7.03 (s, 1H), 7.44-7.78 (m, 8H), 8.00-8.06 (m, 2H), 8.52 (d, 1H). LCMS Rt = 2.49 minutes MS m/z 494 [M + H]$^+$ PM G. |
| 33 | (R)-5-(2-chloro-5-(3-fluoropyridin-2-yl)benzamido)-N-(1-hydroxypropan-2-yl)-1-phenyl-1H-pyrazole-3-carboxamide | 5-(2-chloro-5-(3-fluoro-pyridin-2-yl)benzamido)-1-phenyl-1H-pyrazole-3-carboxylic acid (Example 105) and (R)-2-aminopropan-1-ol. | $^1$H NMR (400 MHz, MeOH-d$_4$ and CDCl$_3$): δ ppm 1.26 (d, 3H), 3.60 (m, 2H), 4.12-4.25 (m, 1H), 7.03 (s, 1H), 7.44-7.78 (m, 8H), 8.00-8.06 (m, 2H), 8.52 (d, 1H). LCMS Rt = 2.49 minutes MS m/z 494 [M + H]$^+$ PM G. |
| 34 | (S)-5-(2,4-dichloro-5-(pyridin-2-yl)benzamido)-N-(1-hydroxypropan-2-yl)-1-phenyl-1H-pyrazole-3-carboxamide | 5-(2,4-dichloro-5-(pyridin-2-yl)benzamido)-1-phenyl-1H-pyrazole-3-carboxylic acid (Example 111) and (S)-2-aminopropan-1-ol. | $^1$H NMR (400 MHz, MeOH-d$_4$): δ ppm 1.25 (d, 3H), 3.60 (m, 2H), 4.17 (q, 1H), 7.02 (s, 1H), 7.47-7.54 (m, 4H), 7.59-7.63 (m, 3H), 7.69 (d, 1H), 7.73 (s, 1H), 7.96 (t, 1H), 8.67 (d, 1H). LCMS Rt = 2.66 minutes MS m/z 508 [M − H]$^-$ |
| 35 | (S)-5-(2,4-dichloro-5-(pyridin-2-yl)benzamido)-N-(2-hydroxypropyl)-1-phenyl-1H-pyrazole-3-carboxamide | 5-(2,4-dichloro-5-(pyridin-2-yl)benzamido)-1-phenyl-1H-pyrazole-3-carboxylic acid (Example 111) and (S)-1-aminopropan-2-ol. | $^1$H NMR (400 MHz, MeOH-d$_4$): δ ppm 1.19 (d, 3H), 3.26-3.31 (m, 1H), 3.45 (dd, 1H), 3.92-3.97 (m, 1H), 7.02 (s, 1H), 7.45-7.54 (m, 4H), 7.60-7.64 (m, 3H), 7.69 (d, 1H), 7.73 (s, 1H), 7.96 (m, 1H), 8.68 (d, 1H). LCMS Rt = 2.64 minutes MS m/z 510 [M + H]$^+$ |

| Example Number | Name/Structure | Starting Materials | Data/PM |
|---|---|---|---|
| 36 | 5-(2,4-dichloro-5-(pyridin-2-yl)benzamido)-1-phenyl-N-(pyridazin-4-ylmethyl)-1H-pyrazole-3-carboxamide | 5-(2,4-dichloro-5-(pyridin-2-yl)benzamido)-1-phenyl-1H-pyrazole-3-carboxylic acid (Example 111) and pyridazin-4-ylmethanamine. | $^1$H NMR (400 MHz, MeOH-$d_4$): δ ppm 4.66 (s, 2H), 7.06 (s, 1H), 7.46-7.55 (m, 4H), 7.62-7.65 (m, 3H), 7.69-7.73 (m, 3H), 7.96 (dt, 1H), 8.68 (d, 1H), 9.12 (d, 1H), 9.21 (s, 1H).<br>LCMS Rt = 2.63 minutes<br>MS m/z 544 [M + H]$^+$<br>PM B. |
| 37 | 5-(2-chloro-5-(3-fluoropyridin-2-yl)benzamido)-N-(3,5-dimethyl-1H-pyrazol-4-yl)-1-phenyl-1H-pyrazole-3-carboxamide | 5-(2-chloro-5-(3-fluoropyridin-2-yl)benzamido)-1-phenyl-1H-pyrazole-3-carboxylic acid (Example 105) and 3,5-dimethyl-1H-pyrazol-4-amine. | $^1$H NMR (400 MHz DMSO-$d_6$): δ ppm 2.04 (s, 6H), 7.00 (s, 1H), 7.46-7.56 (m, 4H), 7.66 (m, 3H), 7.89 (m, 1H), 8.02 (m, 2H), 8.58 (m, 1H), 9.36 (s, 1H), 10.8 (s, 1H), 12.1 (s, 1H).<br>LCMS Rt = 2.73 minutes<br>MS m/z 530 [M + H]$^+$<br>PM H. |
| 38 | 5-(2-chloro-5-(3-fluoropyridin-2-yl)benzamido)-N-((3-methyloxetan-3-yl)methyl)-1-phenyl-1H-pyrazole-3-carboxamide | 5-(2-chloro-5-(3-fluoropyridin-2-yl)benzamido)-1-phenyl-1H-pyrazole-3-carboxylic acid (Example 105) and (3-methyloxetan-3-yl)methanamine. | $^1$H NMR (400 MHz, MeOH-$d_4$): δ ppm 1.37 (s, 3H), 3.59 (s, 2H), 4.36 (d, 2H), 4.65 (d, 2H), 7.04 (s, 1H), 7.47 (m, 2H), 7.55 (m, 2H), 7.64 (m, 3H), 7.73 (dd, 1H), 8.05 (dd, 2H), 8.52 (m, 1H).<br>LCMS Rt = 2.75 minutes<br>MS m/z 520 [M + H]$^+$<br>PM H. |
| 39 | N-((1H-pyrazol-4-yl)methyl)-5-(2-chloro-4-fluoro-5-(3-fluoropyridin-2-yl)benzamido)-1-phenyl-1H-pyrazole-3-carboxamide | 5-(2-chloro-4-fluoro-5-(3-fluoropyridin-2-yl)benzamido)-1-phenyl-1H-pyrazole-3-carboxylic acid (Example 110) and (1H-pyrazol-4-yl)methanamine. | $^1$H NMR (400 MHz DMSO-$d_6$): δ ppm 4.31 (d, 2H), 6.92 (s, 1H), 7.40-7.70 (m, 8H), 7.75-7.80 (m, 2H), 7.90 (m, 1H), 8.60 (m, 2H), 10.80 (s, 1H), 12.60 (br s, 1H).<br>LCMS Rt = 2.62 minutes<br>MS m/z 534 [M + H]$^+$ |

| Example Number | Name/Structure | Starting Materials | Data/PM |
|---|---|---|---|
| 40 | 5-(2-chloro-4-fluoro-5-(3-fluoropyridin-2-yl)benzamido)-N-(3-methyl-1H-pyrazol-4-yl)-1-phenyl-1H-pyrazole-3-carboxamide | 5-(2-chloro-4-fluoro-5-(3-fluoropyridin-2-yl)benzamido)-1-phenyl-1H-pyrazole-3-carboxylic acid (Example 110) and 3-methyl-1H-pyrazol-4-amine. | $^1$H NMR (400 MHz DMSO-$d_6$): δ ppm 2.15 (s, 3H), 7.00 (s, 1H), 7.40-7.60 (m, 3H), 7.60-7.70 (m, 3H), 7.70-7.80 (m, 2H), 7.90 (m, 1H), 8.60 (m, 1H), 9.50 (br s, 1H), 10.85 (s, 1H). LCMS Rt = 2.84 minutes MS m/z 534 [M + H]$^+$ PM B. |
| 41 | 5-(2-chloro-4-fluoro-5-(3-fluoropyridin-2-yl)benzamido)-N-(2-hydroxy-2-methylpropyl)-1-phenyl-1H-pyrazole-3-carboxamide | 5-(2-chloro-4-fluoro-5-(3-fluoropyridin-2-yl)benzamido)-1-phenyl-1H-pyrazole-3-carboxylic acid (Example 110) and 1-amino-2-methylpropan-2-ol. | $^1$H NMR (400 MHz DMSO-$d_6$): δ ppm 1.00 (s, 6H), 3.20 (m, 2H), 4.60 (s, 1H), 6.90 (s, 1H), 7.40-7.70 (m, 7H), 7.75-7.82 (m, 3H), 7.90 (m, 1H), 8.60 (m, 1H). LCMS Rt = 2.68 minutes MS m/z 524 [M − H]$^-$ PM B. |
| 42 | N-((1H-pyrazol-5-yl)methyl)-5-(2,4-dichloro-5-(pyridin-2-yl)benzamido)-1-phenyl-1H-pyrazole-3-carboxamide | 5-(2,4-dichloro-5-(pyridin-2-yl)benzamido)-1-phenyl-1H-pyrazole-3-carboxylic acid (Example 111) and (1H-pyrazol-5-yl)methanamine. | $^1$H NMR (400 MHz, MeOH-$d_4$): δ ppm 4.60 (br s, 2H), 6.31 (br s, 1H), 7.03 (s, 1H), 7.40-7.55 (m, 6H), 7.60-7.70 (m, 3H), 7.70-7.75 (m, 1H), 7.95-8.00 (m, 1H), 8.70 (m, 1H). LCMS Rt = 2.76 minutes MS m/z 532 [M + H]$^+$ |
| 43 | 5-(2,4-dichloro-5-(3-fluoropyridin-2-yl)benzamido)-N-(2-hydroxyethyl)-1-phenyl-1H-pyrazole-3-carboxamide | 5-(2,4-dichloro-5-(3-fluoropyridin-2-yl)benzamido)-1-phenyl-1H-pyrazole-3-carboxylic acid (Example 107) and ethanolamine. | $^1$H NMR (400 MHz, MeOH-$d_4$): δ ppm 3.48-3.54 (t, 2H), 3.67-3.73 (t, 2H), 7.00-7.03 (s, 1H), 7.43-7.54 (m, 3H), 7.56-7.64 (m, 4H), 7.74-7.81 (m, 2H), 8.50-8.54 (m, 1H). LCMS Rt = 2.64 minutes MS m/z 514 [M + H]$^+$ |

-continued

| Example Number | Name/Structure | Starting Materials | Data/PM |
|---|---|---|---|
| 44 | 5-(2-chloro-5-(3-fluoropyridin-2-yl)benzamido)-N-methyl-1-phenyl-1H-pyrazole-3-carboxamide | 5-(2-chloro-5-(3-fluoropyridin-2-yl)benzamido)-1-phenyl-1H-pyrazole-3-carboxylic acid (Example 105) and methylamine hydrochloride. | 1H NMR (400 MHz, MeOH-d4): δ ppm 2.91 (s, 3H), 7.00 (s, 1H), 7.45-7.49 (m, 2H), 7.52-7.58 (m, 2H), 7.61-7.63 (m, 3H), 7.72-7.77 (m, 1H), 8.06-8.08 (m, 2H), 8.52 (d, 1H). LCMS Rt = 2.70 minutes MS m/z 450 [M + H]+ |

Example 45

5-(2,4-dichloro-5-(pyridin-2-yl)benzamido)-N-(3-methyl-1H-pyrazol-4-yl)-1-phenyl-1H-pyrazole-3-carboxamide

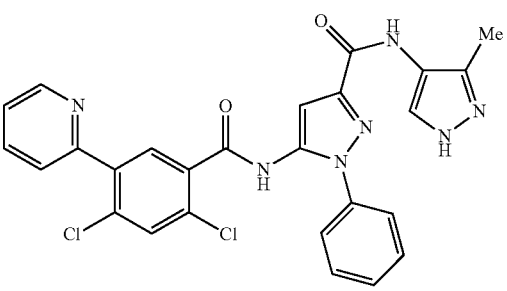 [SMILES: Cc1n[nH]cc1NC(=O)c1cc(NC(=O)c2cc(-c3ccccn3)c(Cl)cc2Cl)n(-c2ccccc2)n1]

To a solution of 5-(2,4-dichloro-5-(pyridin-2-yl)benzamido)-1-phenyl-1H-pyrazole-3-carboxylic acid (Example 111, 210 mg, 0.46 mmol), 3-methyl-1H-pyrazol-4-amine (68 mg, 0.69 mmol) and DIPEA (0.32 mL, 1.85 mmol) in anhydrous DMF (4 mL) was added 1-[bis(dimethylamino)methylene]-1H-1,2,3-triazolo[4,5-b]pyridinium 3-oxid hexafluorophosphate (264 mg, 0.69 mmol). The reaction was stirred at room temperature for 1 hour under nitrogen. The reaction was partitioned between EtOAc (20 mL) and water (20 mL). The organic layer was collected, washed with brine (15 mL), dried over sodium sulfate, filtered and concentrated in vacuo. The residue was purified by elution through an SCX-2 column using MeOH followed by 7N ammonia in MeOH, followed by purification using silica gel column chromatography eluting with EtOAc followed by 10% MeOH in DCM to afford the title compound (170 mg, 69%).

$^1$H NMR (400 MHz, CDCl$_3$): δ ppm 2.24 (s, 3H), 7.32 (br s, 1H), 7.38 (m, 1H), 7.45-7.58 (m, 6H), 7.79 (d, 1H), 7.83 (m, 1H), 7.95 (s, 1H), 8.04 (s, 1H), 8.30 (br s, 1H), 8.71 (d, 1H), 9.31 (br s, 1H).

LCMS Rt=2.72 minutes MS m/z 532 [M+H]$^+$

Example 46

N-((1H-pyrazol-4-yl)methyl)-5-(2,4-dichloro-5-(pyridin-2-yl)benzamido)-1-phenyl-1H-Pyrazole-3-carboxamide

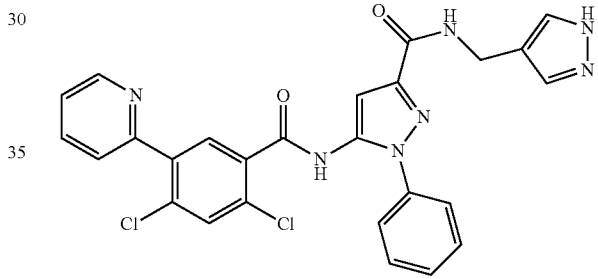

To solution of 5-(2,4-dichloro-5-(pyridin-2-yl)benzamido)-1-phenyl-1H-pyrazole-3-carboxylic acid (Example 111, 200 mg, 0.44 mmol) in DMF was added DIPEA (0.46 mL, 2.65 mmol) and 2-(3H-[1,2,3]triazolo[4,5-b]pyridin-3-yl)-1,1,3,3-tetramethyluronium hexafluorophosphate (201 mg, 0.53 mmol). The reaction was stirred at room temperature for 10 minutes before the addition of (1H-pyrazol-4-yl)methanamine hydrochloride (64 mg, 0.49 mmol). The reaction was stirred at room temperature for 18 hours. The reaction mixture was diluted with ethyl acetate (50 mL) and extracted with water (3×5 mL) and brine (25 mL). The organic layer was collected, dried over anhydrous sodium sulfate and concentrated in vacuo. The residue was purified using silica gel column chromatography eluting with 2% MeOH in DCM to afford the title compound (68 mg, 29%).

$^1$H NMR (400 MHz DMSO-d$_6$): δ ppm 4.30 (d, 2H), 6.90 (s, 1H), 7.42-7.52 (m, 5H), 7.57-7.59 (m, 3H), 7.68-7.72 (m, 2H), 7.86 (s, 1H), 7.92-7.96 (m, 1H), 8.57 (t, 1H), 8.72 (d, 1H), 10.79 (s, 1H), 12.60 (s, 1H).

LCMS Rt=2.65 minutes MS m/z 532 [M+H]$^+$

Example 47

5-(2,4-dichloro-5-(pyridin-2-yl)benzamido)-N-(2-hydroxy-2-methylpropyl)-1-phenyl-1H-pyrazole-3-carboxamide

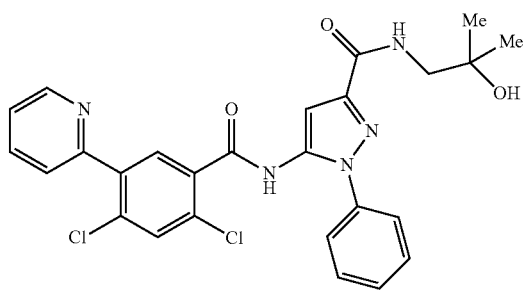 [SMILES: CC(C)(O)CNC(=O)c1cc(NC(=O)c2cc(-c3ccccn3)c(Cl)cc2Cl)n(-c2ccccc2)n1]

To a solution of 5-(2,4-dichloro-5-(pyridin-2-yl)benzamido)-1-phenyl-1H-pyrazole-3-carboxylic acid (Example 111, 150 mg, 0.33 mmol) and 1-amino-2-methylpropan-2-ol (50 mg, 0.66 mmol) in DMF (2 mL) was added DIPEA (0.11 mL, 0.66 mmol, 2 eq) and HATU (188 mg, 0.50 mmol). The reaction was stirred at room temperature for 18 hours. The reaction was partitioned between saturated aqueous sodium carbonate solution (50 mL) and EtOAc (50 mL). The organic layer was collected, washed with brine, dried over magnesium sulphate and concentrated in vacuo. The residue was triturated with acetonitrile to afford the title compound (63 mg, 36%).

$^1$H NMR (400 MHz DMSO-$d_6$): δ ppm 1.10 (s, 6H), 3.25 (d, 2H), 4.64 (s, 1H), 6.94 (s, 1H), 7.45-7.96 (m, 10H), 8.74 (d, 1H), 10.83 (s, 1H).

LCMS Rt=2.73 minutes MS m/z 524 [M+H]$^+$

Example 48

N-(2-(1H-1,2,3-triazol-4-yl)ethyl)-3-(2-chloro-5-(3-fluoropyridin-2-yl)benzamido)-1-phenyl-1H-pyrazole-5-carboxamide

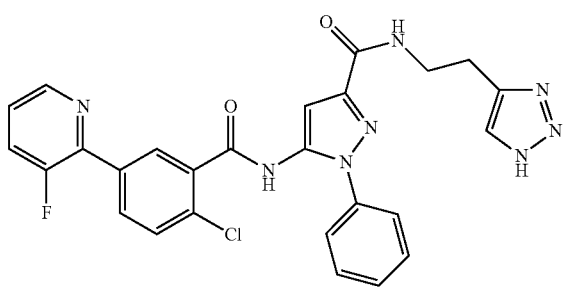 [SMILES: O=C(NCCc1c[nH]nn1)c1cc(NC(=O)c2cc(-c3ncccc3F)ccc2Cl)n(-c2ccccc2)n1]

To a solution of 5-(2-chloro-5-(3-fluoropyridin-2-yl)benzamido)-1-phenyl-1H-pyrazole-3-carboxylic acid (Example 105, 250 mg, 0.57 mmol) and diisopropylethylamine (350 μL, 2.0 mmol)) in dimethylformamide (5 mL) was added a mixture of 2-(1-((2-(trimethylsilyl)ethoxy)methyl)-1H-1,2,3-triazol-4-yl)ethanamine and 2-(2-((2-(trimethylsilyl)ethoxy)methyl)-2H-1,2,3-triazol-4-yl)ethanamine and 2-(1-((2-(trimethylsilyl)ethoxy)methyl)-1H-1,2,3-triazol-5-yl)ethanamine (Preparation 65, 210 mg, 0.84 mmol). The mixture was stirred for 5 minutes before the addition of HATU (220 mg, 0.57 mmol). The reaction was stirred at room temperature for 18 hours and concentrated in vacuo. The residue was partitioned between EtOAc (80 mL) and dilute aqueous sodium hydrogen carbonate solution (80 mL) with saturated aqueous sodium chloride solution (10 mL). The organic layer was collected, dried over anhydrous sodium sulphate and concentrated in vacuo. The residue was dissolved in DCM (20 mL) and treated with TFA (20 mL) with stirring at room temperature for 18 hours. After concentration in vacuo, the residue was partitioned between DCM (80 mL) with MeOH (4 mL) and dilute aqueous sodium hydrogen carbonate solution (50 mL). The organic layer was collected, dried over sodium sulphate and concentrated in vacuo. The residue was purified using silica gel column chromatography eluting with 95:5:0.5 to 90.10:1 DCM:MeOH:NH$_3$ followed by dissolving in hot MeCN (15 mL). The solution was cooled and decanted to afford a residue that was azeotroped with toluene and water to afford the title compound (31 mg, quant.).

$^1$H NMR (400 MHz DMSO-$d_6$): δ ppm 2.90 (m, 2H), 3.51 (m, 2H), 6.91 (m, 1H), 7.47-7.70 (m, 9H), 7.85-7.93 (m, 1H), 8.01 (m, 2H), 8.38-8.50 (m, 1H), 8.58 (s, 1H), 10.80 (s, 1H).

LCMS Rt=2.45 minutes MS m/z 531 [M+H]$^+$

Example 49

N-(2-aminoethyl)-5-(2-chloro-5-(3-fluoropyridin-2-yl)benzamido)-1-phenyl-1H-pyrazole-3-carboxamide

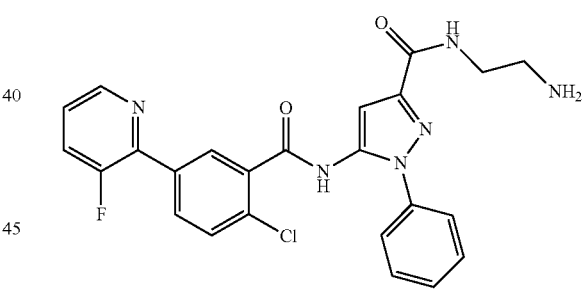

The title compound was prepared according to the method described for Example 3 using 5-(2-chloro-5-(3-fluoropyridin-2-yl)benzamido)-1-phenyl-1H-pyrazole-3-carboxylic acid (Example 105) and tert-butyl(2-aminoethyl)carbamate. The residue was dissolved in DCM (10 mL) and treated with 4M HCl in dioxane (5 mL) with stirring at room temperature for 4 hours. The reaction was concentrated in vacuo and eluted through an SCX-2 column using MeOH followed by 7N NH$_3$ in MeOH; followed by reverse phase chromatography eluting with 5-95% MeCN (with 0.1% NH$_3$) in water (with 0.1% NH$_3$); followed by silica gel column chromatography eluting with 1-5% 7N NH$_3$/MeOH in DCM and finally trituration with TBME.

$^1$H NMR (400 MHz, MeOH-$d_4$): δ ppm 2.89 (t, 2H), 3.50 (t, 2H), 7.03 (s, 1H), 7.45-7.75 (m, 9H), 8.00 (m, 2H), 8.50 (m, 1H).

LCMS Rt=2.37 minutes MS m/z 479 [M+H]$^+$

Example 50

Racemic-5-(2-chloro-5-(3-fluoropyridin-2-yl)benzamido)-N-(4,4-difluoropyrrolidin-3-yl)-1-phenyl-1H-pyrazole-3-carboxamide

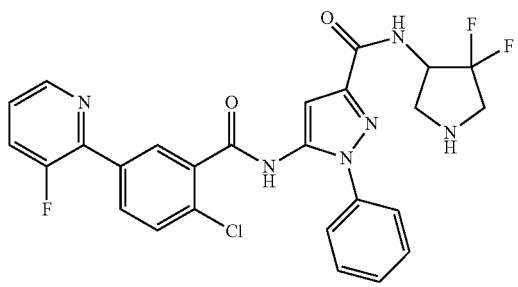 [SMILES: O=C(NC1CNCC1(F)F)c1cc(NC(=O)c2cc(-c3ncccc3F)ccc2Cl)n(-c2ccccc2)n1]

The title compound was prepared according to the method described for Example 49 using 5-(2-chloro-5-(3-fluoropyridin-2-yl)benzamido)-1-phenyl-1H-pyrazole-3-carboxylic acid (Example 105) and racemic tert-butyl 4-(aminomethyl)-3,3-difluoropyrrolidine-1-carboxylate.

$^1$H NMR (400 MHz, MeOH-d$_4$): δ ppm 3.01 (dd, 1H), 3.19 (dd, 1H), 3.33 (m, 1H), 3.46 (dd, 1H), 4.75 (m, 1H), 7.07 (s, 1H), 7.45-7.66 (m, 7H), 7.73 (m, 1H), 8.04 (m, 2H), 8.52 (d, 1H).

MS m/z 541 [M+H]$^+$

Example 51

N-(2-aminoethyl)-5-(2,4-dichloro-5-(pyridin-2-yl)benzamido)-1-phenyl-1H-pyrazole-3-carboxamide

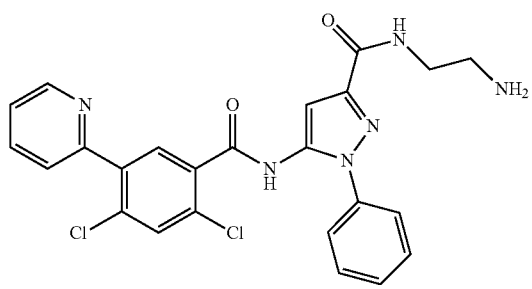 [SMILES: NCCNC(=O)c1cc(NC(=O)c2cc(-c3ccccn3)c(Cl)cc2Cl)n(-c2ccccc2)n1]

The title compound was prepared according to the method described for Example 49 using 5-(2,4-dichloro-5-(pyridin-2-yl)benzamido)-1-phenyl-1H-pyrazole-3-carboxylic acid (Example 111) and tert-butyl(2-aminoethyl)carbamate.

$^1$H NMR (400 MHz DMSO-d$_6$): δ ppm 2.98 (m, 2H), 3.50 (m, 2H), 6.94 (s, 1H), 7.48-7.60 (m, 6H), 7.71 (m, 2H), 7.89 (br m, 1H), 7.99 (m, 1H), 8.50 (t, 1H), 8.74 (s, 1H), 10.87 (s, 1H).

MS m/z 495 [M+H]$^+$

Example 52

(R)-5-(2-chloro-5-(3-fluoropyridin-2-yl)benzamido)-N-(morpholin-2-ylmethyl)-1-phenyl-1H-pyrazole-3-carboxamide

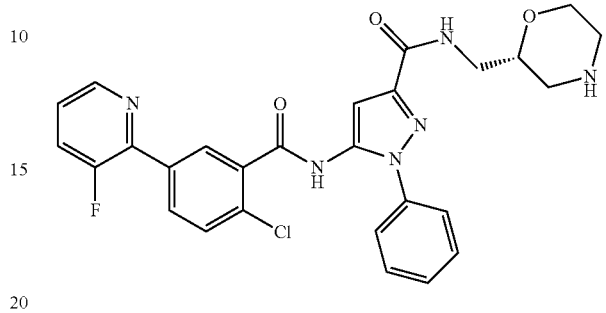

The title compound was prepared according to the method described for Example 3 using 5-(2-chloro-5-(3-fluoropyridin-2-yl)benzamido)-1-phenyl-1H-pyrazole-3-carboxylic acid (Example 105) and (S)-(4-benzylmorpholin-2-yl)methanamine. The residue was dissolved in DCM and treated with 1-chloroethyl chloroformate (37.2 μL, 0.192 mmol) and stirred at room temperature for 4 hours. The reaction was concentrated in vacuo, methanol (4 mL) was added, and the resulting solution stirred for 2 hours at 65° C. The reaction was concentrated in vacuo, and the residue purified by elution through an SCX cartridge followed by silica gel column chromatography eluting with 2% NH$_3$(aq) and 8% propan-2-ol in dichloromethane.

$^1$H NMR (400 MHz, MeOH-d$_4$): δ ppm 2.57 (dd, 1H), 2.78 (m, 2H), 2.93 (dd, 1H), 3.39 (dd, 1H), 3.48 (dd, 1H), 3.57-3.70 (m, 2H), 3.87 (m, 1H), 7.02 (s, 1H), 7.49 (m, 2H), 7.55 (m, 2H), 7.62 (m, 3H), 7.73 (m, 1H), 8.04 (m, 2H), 8.52 (m, 1H).

MS m/z 535 [M+H]$^+$

Example 53

(S)-5-(2-chloro-5-(3-fluoropyridin-2-yl)benzamido)-N-(morpholin-2-ylmethyl)-1-phenyl-1H-pyrazole-3-carboxamide

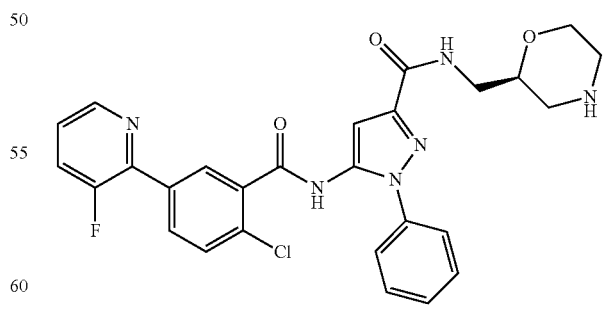

The title compound was prepared according to the method described for Example 52 using 5-(2-chloro-5-(3-fluoropyridin-2-yl)benzamido)-1-phenyl-1H-pyrazole-3-carboxylic acid (Example 105) and (R)-(4-benzylmorpholin-2-yl)methanamine.

$^1$H NMR (400 MHz, MeOH-d$_4$): δ ppm 2.56 (dd, 1H), 2.77 (m, 2H), 2.92 (dd, 1H), 3.39 (dd, 1H), 3.48 (dd, 1H), 3.57-3.69 (m, 2H), 3.87 (m, 1H), 7.03 (s, 1H), 7.49 (m, 2H), 7.55 (m, 2H), 7.62 (m, 3H), 7.74 (m, 1H), 8.04 (m, 2H), 8.52 (m, 1H).

MS m/z 535 [M+H]$^+$

Example 54

5-(2-chloro-5-(3-fluoropyridin-2-yl)benzamido)-N-(2-hydroxyethyl)-1-phenyl-1H-pyrazole-3-carboxamide

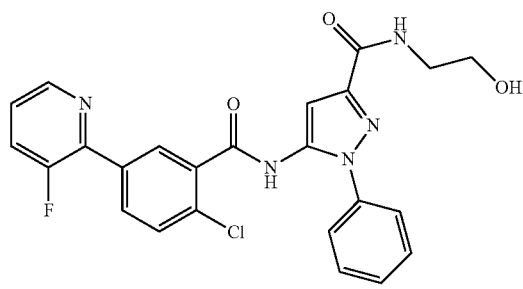 [SMILES: O=C(NCCO)c1cc(NC(=O)c2cc(-c3ncccc3F)ccc2Cl)n(-c2ccccc2)n1]

Ethyl 5-(2-chloro-5-(3-fluoropyridin-2-yl)benzamido)-1-phenyl-1H-pyrazole-3-carboxylate (Example 113, 40 mg, 0.09 mmol), ethanolamine (15.7 mg, 0.26 mmol) and N,N-diisopropylethylamine (33.3 mg, 0.26 mmol) in methanol (1 mL) was heated at 50° C. in a sealed vial for 17 hours. The reaction was cooled and purified using reverse phase column chromatography eluting with 3-50% MeCN in water with 0.1% ammonia to afford the title compound as a white solid (18 mg, 44%).

$^1$H NMR (400 MHz DMSO-d$_6$): δ ppm 3.28-3.32 (m, 2H), 3.49-3.53 (m, 2H), 4.75 (t, 1H), 6.91 (s, 1H), 7.44-7.70 (m, 7H), 7.85-7.92 (m, 1H), 8.02-8.06 (m, 2H), 8.13-8.18 (m, 1H), 8.59 (d, 1H), 10.80 (br s, 1H).

LCMS Rt=2.41 minutes MS m/z 480 [M+H]$^+$

Example 55

5-(2,4-dichloro-5-(pyridin-2-yl)benzamido)-1-phenyl-1H-pyrazole-3-carboxamide

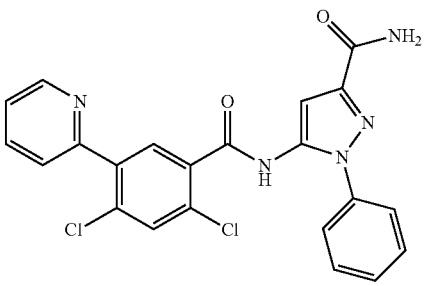 [SMILES: NC(=O)c1cc(NC(=O)c2cc(-c3ccccn3)c(Cl)cc2Cl)n(-c2ccccc2)n1]

To a solution of ethyl 5-(2,4-dichloro-5-(pyridin-2-yl)benzamido)-1-phenyl-1H-pyrazole-3-carboxylate (Example 125, 120 mg, 0.249 mmol) in MeOH (2 mL) was added 880NH$_3$ (4 mL) in a Reactivial™ and the reaction was heated at 50° C. for 16 hours. The reaction was concentrated in vacuo and the resulting solid was washed with water and dried to afford the title compound (68 mg, 60%).

$^1$H NMR (400 MHz, DMSO-d$_6$): δ ppm 6.90 (s, 1H), 7.37 (m, 1H), 7.44-7.74 (m, 9H), 7.88 (s, 1H), 7.96 (t, 1H), 8.73 (d, 1H), 10.70 (br s, 1H).

LCMS Rt=2.66 minutes MS m/z 452 [M+H]$^+$

The following Examples were prepared according to the methods described for Examples 54 and 55 using either 7N NH$_3$ in MeOH or ethanolamine or 3-aminopropan-1-ol with the appropriate ester as described below. The crude residues were purified as above or according to one of the purification methods described below:

Purification Method A: Silica gel column chromatography eluting with 20-100% EtOAc in heptanes.
Purification Method B: Silica gel column chromatography eluting with 0-5% MeOH in EtOAc followed by trituration with TBME.
Purification Method C: Reverse phase column chromatography eluting with water and MeCN containing 0.1% ammonia.
Purification Method D: Reverse phase column chromatography using 0-100% MeCN in water with 0.1% formic acid.
Purification Method E: Preparative HPLC.

| Example Number | Name/Structure | Starting Material | Data/PM |
|---|---|---|---|
| 56 | 5-(2-chloro-5-(6-(difluoromethyl)pyridin-2-yl)benzamido)-1-phenyl-1H-pyrazole-3-carboxamide | Ethyl 5-(2-chloro-5-(6-(difluoromethyl)pyridin-2-yl)benzamido)-1-phenyl-1H-pyrazole-3-carboxylate (Example 131). | $^1$H NMR (400 MHz, MeOH-d$_4$): δ ppm 6.65-6.95 (t, 1H), 7.00 (s, 1H), 7.40-7.70 (m, 8H), 8.10 (m, 1H), 8.20 (m, 2H). MS m/z 468 [M + H]$^+$ PM A. |

| Example Number | Name/Structure | Starting Material | Data/PM |
|---|---|---|---|
| 57 | 5-(2-chloro-5-(6-(1,1-difluoroethyl)pyridin-2-yl)benzamido)-1-phenyl-1H-pyrazole-3-carboxamide | Ethyl 5-(2-chloro-5-(6-(1,1-difluoroethyl)pyridin-2-yl)benzamido)-1-phenyl-1H-pyrazole-3-carboxylate (Example 120). | $^1$H NMR (400 MHz, CDCl$_3$): δ ppm 2.10 (t, 3H), 5.40 (br s, 1H), 6.80 (br s, 1H), 7.40 (s, 1H), 7.45-7.65 (m, 7H), 7.80 (m, 1H), 7.90 (m, 1H), 8.15 (m, 1H), 8.41 (m, 1H), 8.50 (s, 1H). MS m/z 482 [M + H]$^+$ PM A. |
| 58 | 5-(2-chloro-5-(6-(2,2-difluoroethyl)pyridin-2-yl)benzamido)-1-phenyl-1H-pyrazole-3-carboxamide | Ethyl 5-(2-chloro-5-(6-(2,2-difluoroethyl)pyridin-2-yl)benzamido)-1-phenyl-1H-pyrazole-3-carboxylate (Example 121). | $^1$H NMR (400 MHz, CDCl$_3$): δ ppm 3.40 (m, 1H), 5.40 (br s, 1H), 6.20-6.40 (t, 1H), 6.80 (br s, 1H), 7.20 (m, 1H), 7.40-7.80 (m, 9H), 8.10 (m, 1H), 8.40 (br s, 1H), 8.50 (s, 1H). MS m/z 482 [M + H]$^+$ |
| 59 | 5-(2,4-dichloro-5-(pyridin-2-yl)benzamido)-N-(2-hydroxy-ethyl)-1-phenyl-1H-pyrazole-3-carboxamide | Ethyl 5-(2,4-dichloro-5-(pyridin-2-yl)benzamido)-1-phenyl-1H-pyrazole-3-carboxylate (Example 124). | $^1$H NMR (400 MHz DMSO-d$_6$): δ ppm 3.33 (br s, 2H), 3.52 (m, 2H), 4.76 (t, 1H), 6.92 (s, 1H), 7.45-7.54 (m, 4H), 7.63 (d, 2H), 7.70-7.74 (m, 2H), 7.87 (s, 1H), 7.94-7.98 (m, 1H), 8.14 (t, 1H), 8.74 (s, 1H), 10.82 (s, 1H). LCMS Rt = 2.71 minutes MS m/z 496 [M + H]$^+$ |
| 60 | 5-(2,4-dichloro-5-(6-(methoxymethyl)pyridin-2-yl)benzamido)-N-(2-hydroxyethyl)-1-phenyl-1H-pyrazole-3-carboxamide | Ethyl 5-(2,4-dichloro-5-(6-(methoxymethyl)pyridin-2-yl)benzamido)-1-phenyl-1H-pyrazole-3-carboxylate (Example 118). | $^1$H NMR (400 MHz, MeOH-d$_4$): δ ppm 3.49 (s, 3H), 3.51 (t, 2H), 3.72 (t, 2H), 4.62 (s, 2H), 7.02 (s, 1H), 7.44-7.60 (m, 7H), 7.64 (s, 1H), 7.72 (s, 1H), 7.94 (t, 1H). LCMS Rt = 2.70 minutes MS m/z 540 [M + H]$^+$ |

-continued

| Example Number | Name/Structure | Starting Material | Data/PM |
|---|---|---|---|
| 61 | 5-(2,4-dichloro-5-(pyridin-2-yl)benzamido)-N-(3-hydroxypropyl)-1-phenyl-1H-pyrazole-3-carboxamide | Ethyl 5-(2,4-dichloro-5-(pyridin-2-yl)benzamido)-1-phenyl-1H-pyrazole-3-carboxylate (Example 124). | $^1$H NMR (400 MHz, MeOH-d$_4$): δ ppm 1.83 (m, 2H), 3.49 (t, 2H), 3.66 (t, 2H), 7.01 (s, 1H), 7.45-7.54 (m, 4H), 7.60-7.64 (m, 3H), 7.69-7.73 (m, 2H), 7.96 (m, 1H), 7.98-8.00 (d, 1H). LCMS Rt = 2.79 minutes MS m/z 510 [M + H]$^+$ PM B. |
| 62 | 5-(2-chloro-5-(6-methoxypyridin-2-yl)benzamido)-1-phenyl-1H-pyrazole-3-carboxamide | Ethyl 5-(2-chloro-5-(6-methoxypyridin-2-yl)benzamido)-1-phenyl-1H-pyrazole-3-carboxylate (Example 126). | $^1$H NMR (400 MHz, CDCl$_3$): δ ppm 4.00 (s, 3H), 5.39 (s, 1H), 6.75 (d, 1H), 6.81 (br s, 1H), 7.36 (d, 1H), 7.42-7.47 (m, 2H), 7.52-7.57 (m, 3H), 7.67 (t, 1H), 8.11 (m, 1H), 8.45 (br s, 1H), 8.51 (s, 1H). LCMS Rt = 3.07 minutes MS m/z 448 [M + H]$^+$ |
| 63 | 5-(2-chloro-5-(3-chloro-6-(cyanomethyl)pyridin-2-yl)benzamido)-1-phenyl-1H-pyrazole-3-carboxamide | Ethyl 5-(2-chloro-5-(3-chloro-6-(cyanomethyl)pyridin-2-yl)benzamido)-1-phenyl-1H-pyrazole-3-carboxylate (Example 115). | $^1$H NMR (400 MHz, DMSO-d$_6$): δ ppm 4.30 (s, 2H), 5.90 (s, 1H), 7.40 (m, 1H), 7.45 (m, 1H), 7.50 (m, 3H), 7.60 (m, 2H), 7.65 (m, 2H), 7.75 (s, 1H), 7.80 (m, 1H), 8.15 (d, 1H). LCMS Rt = 1.04 minutes MS m/z 491 [M + H]$^+$ PM D. |
| 64 | 5-(2-chloro-5-(6-(difluoromethoxy)pyridin-2-yl)benzamido)-1-phenyl-1H-pyrazole-3-carboxamide | Ethyl 5-(2-chloro-5-(6-(difluoromethoxy)pyridin-2-yl)benzamido)-1-phenyl-1H-pyrazole-3-carboxylate (Example 114). | $^1$H NMR (400 MHz, DMSO-d$_6$): δ ppm 6.95 (s, 1H), 7.11 (d, 1H), 7.39-8.35 (m, 13H), 10.77 (br s, 1H). LCMS Rt = 2.88 minutes MS m/z 484 [M + H]$^+$ PM C. |

| Example Number | Name/Structure | Starting Material | Data/PM |
|---|---|---|---|
| 65 | 5-(2-chloro-5-(6-((methylamino)methyl)pyridin-2-yl)benzamido)-1-phenyl-1H-pyrazole-3-carboxamide | Ethyl 5-(2-chloro-5-(6-((methyl-amino)methyl)pyridin-2-yl)benzamido)-1-phenyl-1H-pyrazole-3-carboxylate (Example 127). | $^1$H NMR (400 MHz, MeOH-$d_4$): δ ppm 2.42 (s, 3H), 3.91 (s, 2H), 7.02 (s, 1H), 7.35 (d, 1H), 7.43-7.59 (m, 5H), 7.61-7.63 (m, 1H), 7.78 (d, 1H), 7.81-7.84 (m, 1H), 8.17 (s, 1H), 8.21 (s, 1H). LCMS Rt = 2.45 minutes MS m/z 461 [M + H]$^+$ PM E. |
| 66 | 5-(2-chloro-5-(6-(1-methoxyethyl)pyridin-2-yl)benzamido)-1-phenyl-1H-pyrazole-3-carboxamide | Racemic ethyl 5-(2-chloro-5-(6-(1-methoxyethyl)pyridin-2-yl)benzamido)-1-phenyl-1H-pyrazole-3-carboxylate (Example 129) at 135°C. for 3 hours under microwave irradiation. | $^1$H NMR (400 MHz, DMSO-$d_6$): δ ppm 1.44 (d, 3H), 3.32 (s, 3H), 4.48 (q, 1H), 6.93 (s, 1H), 7.38 (s, 1H), 7.43 (d, 1H), 7.49 (d, 1H), 7.57 (t, 2H), 7.64-7.69 (m, 3H), 7.95 (m, 2H), 8.20 (s, 2H), 10.80 (s, 1H). LCMS Rt = 2.80 minutes MS m/z 476 [M + H]$^+$ PM A. |
| 67 | 5-(2-chloro-5-(3-chloro-6-(methoxymethyl)pyridin-2-yl)benzamido)-1-phenyl-1H-pyrazole-3-carboxamide | Ethyl 5-(2-chloro-5-(3-chloro-6-(methoxymethyl)pyridin-2-yl)benzamido)-1-phenyl-1H-pyrazole-3-carboxylate (Example 132). | $^1$H NMR (400 MHz, CDCl$_3$): δ ppm 3.44 (s, 3H), 4.58 (s, 2H), 5.32 (s, 1H), 6.78 (s, 1H) 7.36-7.58 (m, 8H), 7.76-7.80 (m, 2H), 8.18 (s, 1H), 8.38 (s, 1H). LCMS Rt = 2.78 minutes MS m/z 496 [M + H]$^+$ |

Example 68

5-(2-chloro-4-fluoro-5-(3-fluoropyridin-2-yl)benzamido)-1-phenyl-1H-pyrazole-3-carboxamide

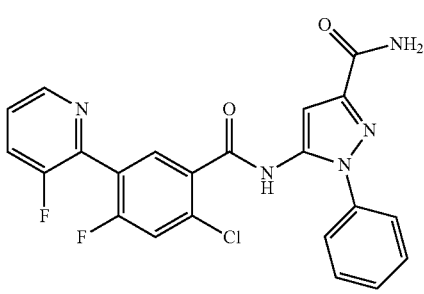 [SMILES: NC(=O)c1cc(NC(=O)c2cc(-c3ncccc3F)c(F)cc2Cl)n(-c2ccccc2)n1]

To a solution of 2-chloro-N-(3-cyano-1-phenyl-1H-pyrazol-5-yl)-4-fluoro-5-(3-fluoropyridin-2-yl)benzamide (Example 98, 89 mg, 0.20 mmol) in DMSO (5 mL) was added K$_2$CO$_3$ (56 mg, 0.41 mmol) followed by H$_2$O$_2$ (30% aqueous solution, 926 mg, 8.17 mmol). The reaction was stirred at room temperature for 3 hours. The reaction was quenched by the addition of water (20 mL) and extracted into EtOAc (2×20 mL). The combined organic layers were washed with water (2×40 mL), brine (40 mL), dried over magnesium sulphate and concentrated in vacuo. The residue was purified using reverse phase column chromatography eluting from 5-45% MeCN (with 0.1% HCO$_2$H) in water (with 0.1% HCO$_2$H) to afford the title compound as a white solid (70 mg, 75%).

$^1$H NMR (400 MHz, DMSO-$d_6$): δ ppm 6.88 (s, 1H), 7.34 (s, 1H), 7.43-7.46 (m, 1H), 7.52 (t, 2H), 7.58-7.65 (m, 2H), 7.76 (dd, 2H), 7.91 (m, 1H), 8.61 (d, 1H), 10.78 (br s, 1H).

LCMS Rt=2.54 minutes MS m/z 454 [M+H]$^+$

Example 69

5-(2-chloro-5-(3-fluoro-6-(methoxymethyl)pyridin-2-yl)benzamido)-1-phenyl-1H-pyrazole-3-carboxamide

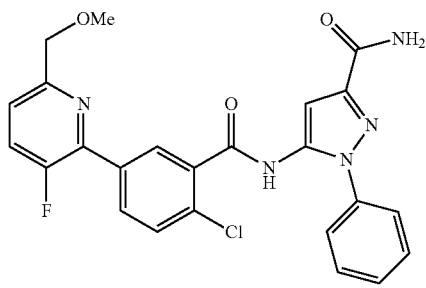 [SMILES: COCc1ccc(F)c(-c2ccc(Cl)c(C(=O)Nc3cc(C(N)=O)nn3-c3ccccc3)c2)n1]

To a solution of 2-chloro-N-(3-cyano-1-phenyl-1H-pyrazol-5-yl)-5-(3-fluoro-6-(methoxymethyl)pyridin-2-yl)benzamide (Example 89, 200 mg, 0.43 mmol) in DMSO (4 mL) was added potassium carbonate (120 mg, 0.87 mmol) followed by $H_2O_2$ (1.79 mL, 17 mmol, 30% w/w in water) slowly, maintaining the internal temperature below 30° C. The reaction was stirred at room temperature for 3 hours before quenching with the addition of water (15 mL). The solution was extracted into ethyl acetate (3×15 mL), the organic extracts were collected, dried over sodium sulphate, and concentrated in vacuo. The residue was purified using silica gel column chromatography eluting with ethyl acetate 0-10% MeOH in EtOAc followed by preparative HPLC. The residue was dissolved in DCM (5 mL) and washed with water (4 mL). The organic layer was dried over sodium sulphate and concentrated in vacuo to afford the title compound (29 mg, 14%).

$^1$H NMR (400 MHz, MeOH-d$_4$): δ ppm 8.10 (br s, 2H), 7.75-7.43 (m, 8H), 7.02 (s, 1H), 4.60 (s, 2H), 3.50 (s, 3H).
LCMS Rt=2.74 minutes MS m/z 480 [M+H]$^+$

Example 70

5-(2-chloro-5-(3-fluoropyridin-2-yl)benzamido)-1-phenyl-1H-pyrazole-3-carboxamide

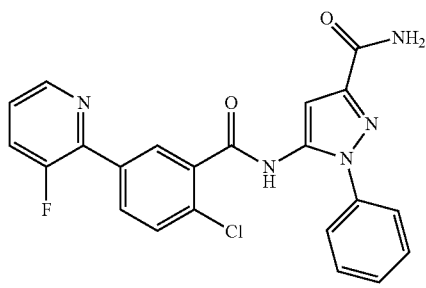 [SMILES: NC(=O)c1cc(NC(=O)c2cc(-c3ncccc3F)ccc2Cl)n(-c2ccccc2)n1]

To a solution of 2-chloro-N-(3-cyano-1-phenyl-1H-pyrazol-5-yl)-5-(3-fluoropyridin-2-yl)benzamide (Example 90, 100 mg, 0.24 mmol) in DMSO (3 mL) was added $K_2CO_3$ (66 mg, 0.48 mmol) and $H_2O_2$ (30% aqueous solution, 1.5 mL) and the reaction was stirred at room temperature for 18 hours. The reaction was diluted with water (1 mL), and 2M aqueous HCl (3 mL) was added resulting in precipitation of a white solid. The solid was filtered, washed with water and dried to afford the title compound as a colourless solid (52.8 mg, 51%).

$^1$H NMR (400 MHz, MeOH-d$_4$): δ ppm 7.04 (s, 1H), 7.45-7.66 (m, 7H), 7.70-7.76 (m, 1H), 8.02-8.06 (m, 2H), 8.50-8.54 (m, 1H).
LCMS Rt=4.5 minutes MS m/z 436 [M+H]$^+$

Example 71

5-(5-(6-acetamido-3-fluoropyridin-2-yl)-2-chlorobenzamido)-1-phenyl-1H-pyrazole-3-carboxamide

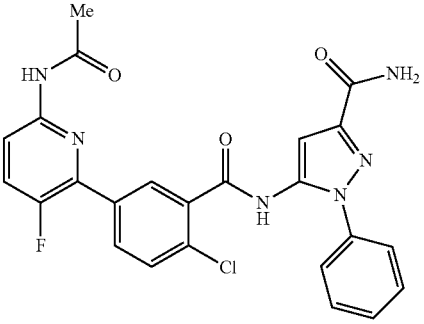 [SMILES: CC(=O)Nc1ccc(F)c(-c2ccc(Cl)c(C(=O)Nc3cc(C(N)=O)nn3-c3ccccc3)c2)n1]

To a solution of 5-(5-(6-amino-3-fluoropyridin-2-yl)-2-chlorobenzamido)-1-phenyl-1H-pyrazole-3-carboxamide (Preparation 1, 23 mg, 0.05 mmol) in acetic acid (2 mL) was added acetic anhydride (0.5 mL) and the reaction was stirred at room temperature for 18 hours. The reaction was poured into water (50 mL) and basified by the addition of solid potassium carbonate. The aqueous solution was extracted with ethyl acetate (50 mL) and the organic layer was washed with brine (50 mL), dried over magnesium sulphate and concentrated in vacuo. The residue was purified using silica gel column chromatography eluting with 40-60% EtOAc in heptanes followed by trituration in TBME to afford the title compound as a white solid (10 mg, 40%).

$^1$H NMR (400 MHz, MeOH-d$_4$): δ ppm 2.19 (s, 3H), 7.04 (s, 1H), 7.47-7.71 (m, 7H), 8.11-8.15 (m, 3H).
LCMS Rt=2.69 minutes MS m/z 493 [M+H]$^+$

Example 72

5-(5-(6-acetamidopyridin-2-yl)-2-chlorobenzamido)-1-phenyl-1H-pyrazole-3-carboxamide

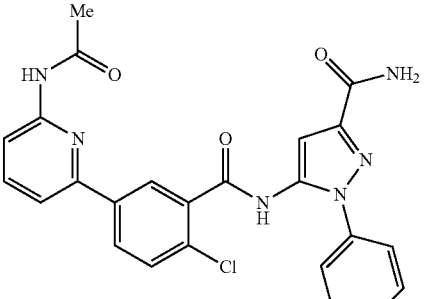

To a solution of 5-(6-acetamidopyridin-2-yl)-2-chloro-N-(3-cyano-1-phenyl-1H-pyrazol-5-yl)benzamide (Example 88, 100 mg, 0.22 mmol) in dimethylsulfoxide (3 mL) was added potassium carbonate (60 mg, 0.44 mmol) followed by hydrogen peroxide (30% w/w solution in water, 441 μL, 4.4 mmol) and the reaction was stirred at room temperature for 2.5 hours. Additional hydrogen peroxide was added (882 μL, 8.8 mmol) and the reaction was stirred for 1 hour. The reaction was diluted with water (5 mL) then neutralised with 2M aqueous hydrochloric acid and extracted into ethyl acetate (3×10 mL). The combined organic extracts were dried over magnesium sulphate and concentrated in vacuo. The residue was purified by silica gel column chromatography eluting with 80% ethyl acetate in heptanes to furnish the title compound as a colourless solid (65 mg, 62%).

$^1$H NMR (400 MHz, DMSO-d$_6$): δ ppm 2.41 (s, 3H), 6.84 (s, 1H), 7.30-7.64 (m, 7H), 7.82 (t, 1H), 7.99 (d, 1H), 8.09-8.12 (m, 2H), 10.46 (s, 1H), 10.73 (s, 1H).

LCMS Rt=2.64 minutes MS m/z 475 [M+H]$^+$

The following Examples were prepared according to the method described for Example 72 using the appropriate nitrile as described below. The crude residues were purified as above or according to one of the purification methods described below:

Purification Method A: Silica gel column chromatography eluting with 50-100% EtOAc in heptanes followed by trituration with 16% DCM in pentane.

Purification Method B: The reaction was quenched with saturated aqueous KHSO$_3$ and extracted with DCM. The aqueous layer was neutralized with 2M NaOH and extracted with DCM. The combined organic layers were washed with brine, dried over sodium sulphate and concentrated in vacuo. The residue was purified using silica gel column chromatography eluting with 40-100% EtOAc in heptanes followed by 0-1% MeOH in EtOAc.

Purification Method C: Preparative HPLC followed by trituration with DCM or TBME.

Purification Method D: Elution through an SCX-2 cartridge using MeOH followed by 7N NH$_3$ in MeOH.

| Example Number | Name/Structure | Starting Material | Data/Nitrile/PM |
|---|---|---|---|
| 73 | 5-(2-chloro-5-(3-chloropyridin-2-yl)benzamido)-1-phenyl-1H-pyrazole-3-carboxamide | 2-chloro-5-(3-chloropyridin-2-yl)-N-(3-cyano-1-phenyl-1H-pyrazol-5-yl)benzamide (Example 91). | $^1$H NMR (400 MHz, CDCl$_3$): δ ppm 5.44 (bs, 1H), 6.80 (bs, 1H), 7.29 (dd, 1H), 7.37 (s, 1H), 7.46-7.58 (m, 5H), 7.82 (m, 2H), 8.24 (d, 1H), 8.46 (s, 1H), 8.58 (d, 1H). LCMS Rt = 2.90 minutes MS m/z 452 [M + H]$^+$ PM A. |
| 74 | 5-(2-chloro-5-(3-chloro-5-fluoropyridin-2-yl)benzamido)-1-phenyl-1H-pyrazole-3-carboxamide | 2-chloro-5-(3-chloro-5-fluoropyridin-2-yl)-N-(3-cyano-1-phenyl-1H-pyrazol-5-yl)benzamide (Example 92). | $^1$H NMR (400 MHz, CDCl$_3$): δ ppm 5.44 (br s, 1H), 6.82 (br s, 1H), 7.39 (s, 1H), 7.46-7.58 (m, 5H), 7.62 (dd, 1H), 7.78 (dd, 1H), 8.22 (d, 1H), 8.42 (s, 1H), 8.48 (d, 1H). LCMS Rt = 3.03 minutes MS m/z 470 [M + H]$^+$ PM A. |
| 75 | 5-(2-chloro-5-(6-(methylamino)pyridin-2-yl)benzamido)-1-phenyl-1H-pyrazole-3-carboxamide | 2-chloro-N-(3-cyano-1-phenyl-1H-pyrazol-5-yl)-5-(6-(methylamino)pyridin-2-yl)benzamide (Example 93). | $^1$H NMR (400 MHz, Acetone-d$_6$): δ ppm 2.96-2.99 (m, 3H), 5.93 (br s, 1H), 6.51 (d, 1H), 6.56 (br s, 1H), 7.10-7.14 (m, 2H), 7.24 (br s, 1H), 7.45-7.59 (m, 5H), 7.68-7.72 (m, 2H), 8.15 (dd, 1H), 8.26 (d, 1H), 9.76 (br s, 1H). LCMS Rt = 2.11 minutes MS m/z 447 [M + H]$^+$ PM B. |

| Example Number | Name/Structure | Starting Material | Data/Nitrile/PM |
|---|---|---|---|
| 76 | 6-(3-((3-carbamoyl-1-phenyl-1H-pyrazol-5-yl)carbamoyl)-4-chlorophenyl)picolinamide | 6-(4-chloro-3-((3-cyano-1-phenyl-1H-pyrazol-5-yl)carbamoyl)phenyl)picolinamide (Example 94). | $^1$H NMR (400 MHz, DMSO-$d_6$): δ ppm 6.97 (s, 1H), 7.38 (br s, 1H), 7.46 (m, 1H), 7.54 (t, 2H), 7.64-7.70 (m, 4H), 7.81 (br s, 1H), 8.03 (d, 1H), 8.11 (t, 1H), 8.24 (d, 1H), 8.41 (m, 1H), 8.45 (br s, 1H), 8.53 (d, 1H), 10.80 (br s, 1H). LCMS Rt = 2.47 minutes MS m/z 461 [M + H]$^+$ PM C. |
| 77 | 5-(2-chloro-5-(3,5-difluoropyridin-2-yl)benzamido)-1-phenyl-1H-pyrazole-3-carboxamide | 2-chloro-N-(3-cyano-1-phenyl-1H-pyrazol-5-yl)-5-(3,5-difluoropyridin-2-yl)benzamide (Example 95). | $^1$H NMR (400 MHz, DMSO-$d_6$): δ ppm 6.90 (s, 1H), 7.35 (s, 1H), 7.45-7.60 (m, 7H), 7.95-7.98 (m, 2H), 8.13 (t, 1H), 8.68 (d, 1H), 10.79 (br s, 1H). LCMS Rt = 2.96 minutes MS m/z 454 [M + H]$^+$ |
| 78 | 5-(2-chloro-3-fluoro-5-(3-fluoropyridin-2-yl)benzamido)-1-phenyl-1H-pyrazole-3-carboxamide | 2-chloro-N-(3-cyano-1-phenyl-1H-pyrazol-5-yl)-3-fluoro-5-(3-fluoropyridin-2-yl)benzamide (Example 96). | $^1$H NMR (400 MHz, DMSO-$d_6$): δ ppm 6.92 (s, 1H), 7.36 (s, 1H), 7.45-7.49 (m, 1H), 7.53-7.66 (m, 6H), 7.90-7.95 (m, 2H), 8.02 (d, 1H), 8.59 (d, 1H), 10.89 (br s, 1H). LCMS Rt = 2.62 minutes MS m/z 454 [M + H]$^+$ |
| 79 | 5-(6-chloro-2-fluoro-3-(3-fluoropyridin-2-yl)benzamido)-1-phenyl-1H-pyrazole-3-carboxamide | 6-chloro-N-(3-cyano-1-phenyl-1H-pyrazol-5-yl)-2-fluoro-3-(3-fluoropyridin-2-yl)benzamide (Example 97). | $^1$H NMR (400 MHz, DMSO-$d_6$): δ ppm 6.89 (s, 1H), 7.36 (s, 1H), 7.45-7.63 (m, 7H), 7.68-7.73 (m, 2H), 7.88-7.93 (m, 1H), 8.57 (d, 1H), 11.14 (br s, 1H). LCMS Rt = 2.40 minutes MS m/z 454 [M + H]$^+$ PM C. |

| Example Number | Name/Structure | Starting Material | Data/Nitrile/PM |
|---|---|---|---|
| 80 | 5-(2-chloro-4-methyl-5-(pyridin-2-yl)benzamido)-1-phenyl-1H-pyrazole-3-carboxamide | 2-chloro-N-(3-cyano-1-phenyl-1H-pyrazol-5-yl)-4-methyl-5-(pyridin-2-yl)benzamide (Example 99). | $^1$H NMR (400 MHz, MeOH-$d_4$): δ ppm 2.30 (s, 3H), 6.99 (s, 1H), 7.43-7.50 (m, 7H), 7.59 (d, 2H), 7.95 (m, 1H), 8.62 (d, 1H). LCMS Rt = 1.82 minutes MS m/z 432 [M + H]$^+$ PM D. |
| 81 | 5-(2-chloro-4-fluoro-5-(pyridin-2-yl)benzamido)-1-phenyl-1H-pyrazole-3-carboxamide | 2-chloro-N-(3-cyano-1-phenyl-1H-pyrazol-5-yl)-4-fluoro-5-(pyridin-2-yl)benzamide (Example 100). | $^1$H NMR (400 MHz, MeOH-$d_4$): δ ppm 7.02 (s, 1H), 7.61-7.45 (m, 8H), 7.81 (d, 1H), 7.94 (m, 1H), 8.05 (d, 1H), 8.69 (d, 1H). MS m/z 436 [M + H]$^+$ |
| 82 | 5-(2-chloro-4-methoxy-5-(pyridin-2-yl)benzamido)-1-phenyl-1H-pyrazole-3-carboxamide | 2-chloro-N-(3-cyano-1-phenyl-1H-pyrazol-5-yl)-4-methoxy-5-(pyridin-2-yl)benzamide (Example 101). | $^1$H NMR (400 MHz, MeOH-$d_4$): δ ppm 3.91 (s, 3H), 7.01 (s, 1H), 7.24 (s, 1H), 7.37-7.40 (m, 1H), 7.46-7.48 (m, 1H), 7.51-7.54 (m, 2H), 7.63 (d, 2H), 7.80-7.88 (m, 3H), 8.62 (d, 1H). LCMS Rt = 2.23 minutes MS m/z 448 [M + H]$^+$ |

Example 83

5-(2-chloro-5-(3-fluoropyridin-2-yl)benzamido)-N-cyclopropyl-1-phenyl-1H-pyrazole-3-carboxamide

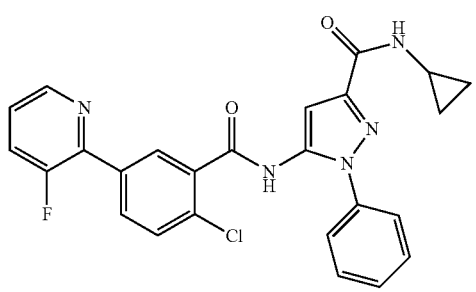 [SMILES: O=C(NC1CC1)c1cc(NC(=O)c2cc(-c3ncccc3F)ccc2Cl)n(-c2ccccc2)n1]

To the solution of 5-(2-chloro-5-(4,4,5,5-tetramethyl-1,3,2-dioxaborolan-2-yl)benzamido)-N-cyclopropyl-1-phenyl-1H-pyrazole-3-carboxamide in dioxane (Preparation 10, 0.63 mmol, 15 mL) was added 2-bromo-3-fluoropyridine (58 mg, 0.33 mmol), $Na_2CO_3$ (46.6 mg, 0.44 mmol) in water (1 mL) and Pd(dppf)$Cl_2$ (9 mg, 0.01 mmol). The reaction was degassed with nitrogen for 30 minutes and heated to 110° C. for 17 hours. The reaction was cooled and concentrated in vacuo. The residue was eluted through a small plug of silica with EtOAc followed by reverse phase column chromatography eluting with 3-60% MeCN (containing 0.1% $NH_4OH$) in water (containing 0.1% $NH_4OH$) to afford the title compound (20 mg, 19%).

$^1$H NMR (400 MHz, MeOH-$d_4$): δ ppm 0.65-0.70 (m, 2H), 0.82-0.88 (m, 2H), 2.83-2.89 (m, 1H), 7.02 (s, 1H), 7.46-7.65 (m, 7H), 7.71-7.77 (m, 1H), 8.04-8.08 (m, 2H), 8.51 (d, 1H).

LCMS Rt=2.77 minutes MS m/z 476 [M+H]$^+$

Example 84

5-(2-chloro-5-(3-cyanopyridin-2-yl)benzamido)-N-cyclopropyl-1-phenyl-1H-pyrazole-3-carboxamide

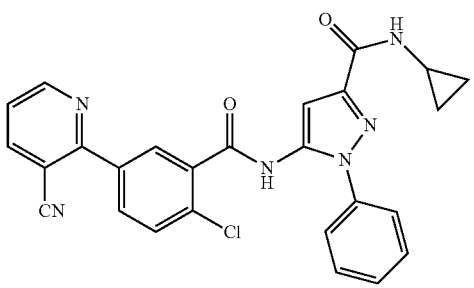 [SMILES: N#Cc1cccnc1-c1ccc(Cl)c(C(=O)Nc2cc(C(=O)NC3CC3)nn2-c2ccccc2)c1]

The title compound was prepared according to the method described for Example 83 using 5-(2-chloro-5-(4,4,5,5-tetramethyl-1,3,2-dioxaborolan-2-yl)benzamido)-N-cyclopropyl-1-phenyl-1H-pyrazole-3-carboxamide in dioxane (Preparation 10) and 2-chloronicotinonitrile with potassium carbonate as base.

$^1$H NMR (400 MHz, MeOH-d$_4$): δ ppm 0.66 (m, 2H), 0.80 (m, 2H), 2.85 (m, 1H), 7.02 (s, 1H), 7.46 (t, 1H), 7.52-7.61 (m, 6H), 8.00 (m, 2H), 8.31 (d, 1H), 8.89 (d, 1H).

LCMS Rt=2.74 minutes MS m/z 483 [M+H]$^+$

Example 85

5-(2-chloro-5-(3-fluoropyridin-2-yl)benzamido)-1-(3-hydroxyphenyl)-1H-pyrazole-3-carboxamide

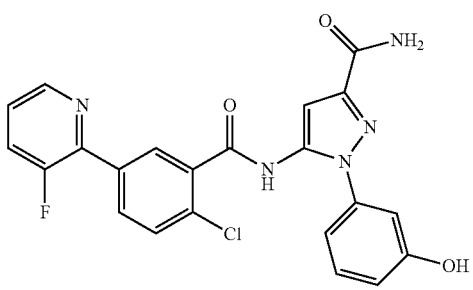 [SMILES: NC(=O)c1cc(NC(=O)c2cc(-c3ncccc3F)ccc2Cl)n(-c2cccc(O)c2)n1]

To a solution of ethyl 1-(3-(benzyloxy)phenyl)-5-(2-chloro-5-(3-fluoropyridin-2-yl)benzamido)-1H-pyrazole-3-carboxylate (Example 128, 220 mg, 0.385 mmol) in methanol (3 mL) was added 880 ammonia (7 mL) and the reaction was heated at 60° C. for 18 hours in a Reactivial™. The reaction was cooled, concentrated in vacuo and dissolved in DCM (5 mL). The solution was cooled to 0° C. and boron trichloride (1M in DCM, 3.41 mL, 3.41 mmol) was added dropwise. The reaction was stirred at room temperature for 30 minutes before being quenched by the addition of methanol (20 mL) and stirred for 18 hours. The reaction was concentrated in vacuo azeotroping with MeOH. The residue was purified using preparative HPLC followed by trituration with TBME to afford the title compound (12 mg, 6%).

$^1$H NMR (400 MHz, DMSO-d$_6$): δ ppm 6.84 (dd, 1H), 6.87 (br s, 1H), 6.96 (br s, 1H), 7.00 (d, 1H), 7.53 (m, 1H), 7.63 (br s, 1H), 7.68 (m, 1H), 7.85-7.90 (m, 1H), 8.02 (br s, 2H), 8.57-8.58 (m, 1H), 9.83 (br s, 1H), 10.74 (br s, 1H).

LCMS Rt=2.61 minutes MS m/z 452 [M+H]$^+$

Example 86

5-(2-chloro-5-(3-fluoropyridin-2-yl)benzamido)-N-(2-hydroxyethyl)-1-(3-hydroxyphenyl)-1H-pyrazole-3-carboxamide

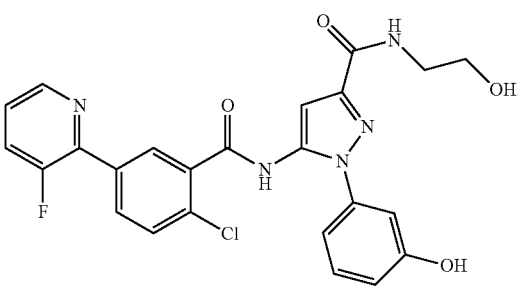 [SMILES: O=C(NCCO)c1cc(NC(=O)c2cc(-c3ncccc3F)ccc2Cl)n(-c2cccc(O)c2)n1]

The title compound was prepared according to the method described for Example 85 using ethyl 1-(3-(benzyloxy)phenyl)-5-(2-chloro-5-(3-fluoropyridin-2-yl)benzamido)-1H-pyrazole-3-carboxylate (Example 128) and ethanolamine. The residue was purified using reverse phase column chromatography eluting with 0-100% MeCN in water with 0.1% NH$_3$.

$^1$H NMR (400 MHz, MeOH-d$_4$): δ ppm 3.52 (t, 2H), 3.72 (t, 2H), 6.90 (m, 1H), 7.03-7.08 (m, 3H), 7.32-7.36 (m, 1H), 7.46-7.50 (m, 1H), 7.62 (d, 1H), 7.71-7.77 (m, 1H), 8.02-8.06 (m, 1H), 8.07 (br s, 1H), 8.52-8.53 (m, 1H).

LCMS Rt=2.44 minutes MS m/z 496 [M+H]$^+$

Example 87

5-(2-chloro-5-(3-fluoropyridin-2-yl)benzamido)-N-cyclopropyl-1-(3-hydroxyphenyl)-1H-Pyrazole-3-carboxamide

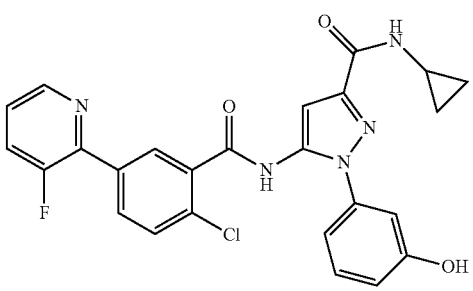 [SMILES: O=C(NC1CC1)c1cc(NC(=O)c2cc(-c3ncccc3F)ccc2Cl)n(-c2cccc(O)c2)n1]

To a solution of 1-(3-(benzyloxy)phenyl)-5-(2-chloro-5-(3-fluoropyridin-2-yl)benzamido)-1H-pyrazole-3-carboxylic acid (Example 104, 220 mg, 0.373 mmol) in DMF (5 mL) was added cyclopropylamine (26 mg, 0.448 mmol) and DIPEA (241 mg, 1.87 mmol, 0.325 mL) followed by HATU (213 mg, 0.560 mmol). The reaction was stirred at room temperature for 30 minutes. The reaction was diluted with water (70 mL) and extracted with 2-MeTHF (50 mL). The organic layer was washed with brine (50 mL) dried over sodium sulphate and concentrated in vacuo. The residue was purified by silica gel column chromatography eluting with 20-25% EtOAc in DCM and the residue was dissolved in DCM (5 mL). Boron trichloride (1M in DCM, 1.72 mL, 1.72 mmol) was added at 0° C. and the reaction was stirred at this temperature for 40 minutes. The reaction was quenched by the addition of MeOH (1 mL) and stirred for 20 minutes. The reaction was concentrated in vacuo and purified using silica gel column chromatography eluting with 2-6% MeOH in DCM to afford the title compound (103 mg, 79%).

$^1$H NMR (400 MHz, DMSO-$d_6$): δ ppm 0.57-0.61 (m, 2H), 0.63-0.67 (m, 2H), 2.79-2.86 (m, 1H), 6.83 (d, 1H), 6.87 (br s, 1H), 6.95 (t, 1H), 6.98-7.00 (m, 1H), 7.29 (t, 1H), 7.51-7.55 (m, 1H), 7.66-7.69 (m, 1H), 7.85-7.90 (m, 1H), 8.01-8.02 (m, 2H), 8.26 (m, 1H), 8.56-8.57 (m, 1H), 9.83 (br s, 1H), 10.75 (br s, 1H).

LCMS Rt=2.84 minutes MS m/z 492 [M+H]$^+$

Example 88

5-(6-acetamidopyridin-2-yl)-2-chloro-N-(3-cyano-1-phenyl-1H-pyrazol-5-yl)benzamide

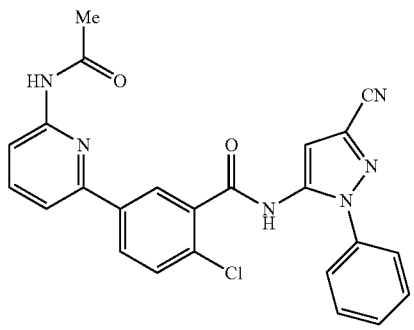 [SMILES: CC(=O)Nc1cccc(-c2ccc(Cl)c(C(=O)Nc3cc(C#N)nn3-c3ccccc3)c2)n1]

To a solution of 2-chloro-N-(3-cyano-1-phenyl-1H-pyrazol-5-yl)-5-(4,4,5,5-tetramethyl-1,3,2-dioxaborolan-2-yl)benzamide (Preparation 7, 0.5 mmol) in dioxane (5 mL) was added N-(6-bromopyridin-2-yl)acetamide (118 mg, 0.55 mmol), [1,1'-bis(diphenylphosphino)ferrocene]dichloropalladium(II) (41 mg, 0.05 mmol), sodium carbonate (183 mg, 1.72 mmol) and water (1 mL). The reaction was heated to 100° C. for 18 hours. The reaction was allowed to cool to room temperature and diluted with ethyl acetate (10 mL) and water (10 mL). The layers were separated and the aqueous phase extracted with ethyl acetate (3×10 mL). The combined organic extracts were dried over sodium sulphate and concentrated in vacuo. The residue was purified by silica gel column chromatography eluting with 40-50% ethyl acetate in heptanes to afford the title compound as a yellow solid (104 mg, 46%).

$^1$H NMR (400 MHz, DMSO-$d_6$): δ ppm 2.13 (s, 3H), 7.30 (s, 1H), 7.54-7.71 (m, 7H), 7.91 (t, 1H), 8.08 (d, 1H), 8.18-8.20 (m, 2H).

Example 89

2-chloro-N-(3-cyano-1-phenyl-1H-pyrazol-5-yl)-5-(3-fluoro-6-(methoxymethyl)pyridin-2-yl)benzamide

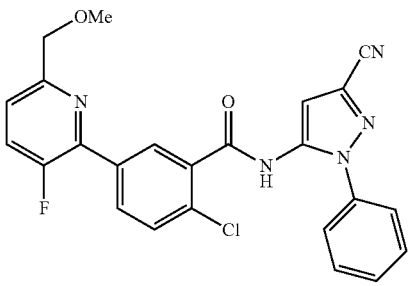 [SMILES: COCc1ccc(F)c(-c2ccc(Cl)c(C(=O)Nc3cc(C#N)nn3-c3ccccc3)c2)n1]

To a degassed solution of 2-chloro-N-(3-cyano-1-phenyl-1H-pyrazol-5-yl)-5-(4,4,5,5-tetramethyl-1,3,2-dioxaborolan-2-yl)benzamide (Preparation 7, 325 mg, 0.72 mmol), 2-chloro-3-fluoro-6-(methoxymethyl)pyridine (Preparation 52, 191 mg, 1.09 mmol) and potassium carbonate (200 mg, 1.45 mmol) in 1,4-dioxane (5 mL) and water (1 mL) was added Pd(PPh$_3$)$_4$ (83 mg, 0.072 mmol) and the reaction was heated to 80° C. for 18 hours. The reaction was cooled and concentrated in vacuo. The resulting residue was partitioned between EtOAc (15 mL) and water (15 mL). The aqueous layer was extracted with EtOAc (2×15 mL) and the organic extracts were combined, dried over sodium sulphate and concentrated in vacuo. The residue was purified using silica gel column chromatography eluting with 1:1 EtOAc in heptanes to afford the title compound (250 mg, 75%).

$^1$H NMR (400 MHz, CDCl$_3$): δ ppm 3.42 (s, 3H), 4.50 (s, 2H), 7.21 (s, 1H), 7.39-7.58 (m, 8H), 8.02 (d, 1H), 8.42 (s, 1H), 8.53 (br s, 1H).

MS m/z 462 [M+H]$^+$

Example 90

2-chloro-N-(3-cyano-1-phenyl-1H-pyrazol-5-yl)-5-(3-fluoropyridin-2-yl)benzamide

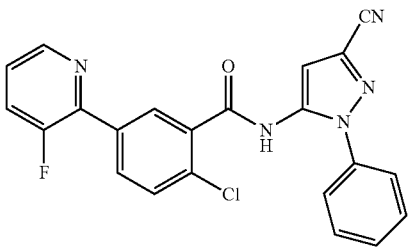

To a degassed solution of 2-chloro-N-(3-cyano-1-phenyl-1H-pyrazol-5-yl)-5-(4,4,5,5-tetramethyl-1,3,2-dioxaborolan-2-yl)benzamide (Preparation 7, 223 mg, 0.49 mmol) in dioxane (2 mL) was added 3-fluoro-2-iodopyridine (167 mg, 0.75 mmol), Pd(dppf)Cl$_2$ (36 mg, 0.049 mmol), K$_2$CO$_3$ (206 mg, 1.49 mmol) and water (1 mL). The reaction was heated at 100° C. for 18 hours before cooling and concentrating in vacuo. The residue was suspended in DCM (20 mL) and filtered through a pad of celite. The filtrate was purified directly by silica gel column chromatography eluting with 0-80% EtOAc in heptanes to afford the title compound as a brown solid (100 mg, 48%).

$^1$H NMR (400 MHz, CDCl$_3$): δ ppm 7.31-7.38 (m, 2H), 7.49-7.62 (m, 6H), 8.09 (d, 1H), 8.51-8.54 (m, 2H), 8.60 (s, 1H).

LCMS Rt=4.5 minutes MS m/z 418 [M+H]$^+$

The following Preparations were prepared according to the method described for Preparation 89 or 90 using 2-chloro-N-(3-cyano-1-phenyl-1H-pyrazol-5-yl)-5-(4,4,5,5-tetramethyl-1,3,2-dioxaborolan-2-yl)benzamide (Preparation 7) or an alternative as described and the appropriate 2-halopyridine at either 100 or 110° C. The crude residues were purified as above or according to one of the purification methods described below:

Purification Method A: Silica gel column chromatography eluting with 4% MeOH in DCM.

Purification Method B: Silica gel column chromatography eluting from 10-40% EtOAc in heptanes followed by reverse phase chromatography eluting from 5-50% MeCN (with 0.1% HCO$_2$H) in water (with 0.1% HCO$_2$H).

| Example Number | Name | Structure | Data/Halopyridine |
|---|---|---|---|
| 91 | 2-chloro-5-(3-chloropyridin-2-yl)-N-(3-cyano-1-phenyl-1H-pyrazol-5-yl)benzamide | 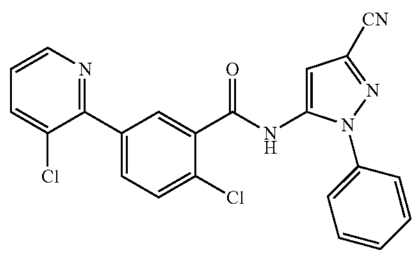 [SMILES: N#Cc1cc(NC(=O)c2cc(-c3ncccc3F)ccc2Cl)n(-c2ccccc2)n1] | $^1$H NMR (400 MHz, CDCl$_3$): δ ppm 7.20-7.26 (m, 2H), 7.42-7.55 (m, 5H), 7.76-7.80 (m, 2H), 8.22 (d, 1H), 8.52 (d, 1H), 8.58 (s, 1H). LCMS Rt = 3.14 minutes MS m/z 434 [M + H]$^+$ Using 2-bromo-3-chloropyridine. |
| 92 | 2-chloro-5-(3-chloro-5-fluoropyridin-2-yl)-N-(3-cyano-1-phenyl-1H-pyrazol-5-yl)benzamide | 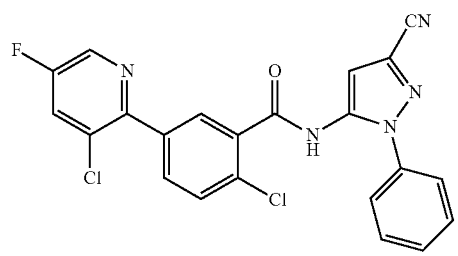 [SMILES: N#Cc1cc(NC(=O)c2cc(-c3ncc(F)cc3Cl)ccc2Cl)n(-c2ccccc2)n1] | $^1$H NMR (400 MHz, CDCl$_3$): δ ppm 7.19 (s, 2H), 7.41-7.57 (m, 5H), 7.74 (dd, 1H), 8.20 (s, 1H), 8.41 (d, 1H), 8.56 (s, 1H). Using 2-bromo-3-chloro-5-fluoropyridine. |
| 93 | 2-chloro-N-(3-cyano-1-phenyl-1H-pyrazol-5-yl)-5-(6-(methylamino)pyridin-2-yl)benzamide | 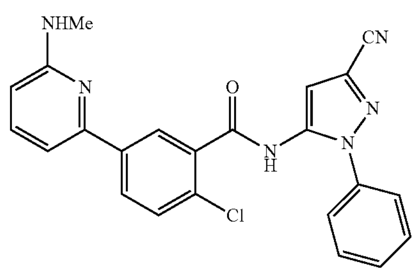 [SMILES: CNc1cccc(-c2ccc(Cl)c(C(=O)Nc3cc(C#N)nn3-c3ccccc3)c2)n1] | $^1$H NMR (400 MHz, DMSO-d$_6$): δ ppm 2.86 (s, 3H), 6.43-6.49 (m, 1H), 6.58-6.67 (m, 1H), 7.04-7.13 (m, 1H), 7.25-7.32 (m, 1H), 7.47-7.65 (m, 7H), 8.06-8.17 (m, 2H), 11.01 (s, 1H). LCMS Rt = 2.61 minutes MS m/z 429 [M + H]$^+$ Using 6-bromo-N-methylpyridin-2-amine. |
| 94 | 6-(4-chloro-3-((3-cyano-1-phenyl-1H-pyrazol-5-yl)carbamoyl)phenyl)picolinamide | 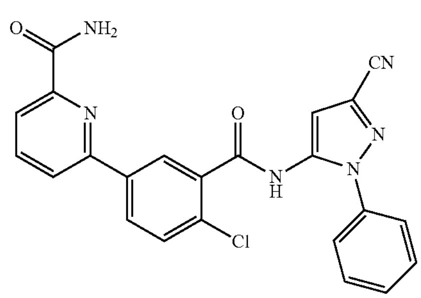 [SMILES: N#Cc1cc(NC(=O)c2cc(-c3cccc(C(N)=O)n3)ccc2Cl)n(-c2ccccc2)n1] | $^1$H NMR (400 MHz, DMSO-d$_6$): δ ppm 7.27-7.30 (s, 1H), 7.47-7.60 (m, 4H), 7.60-7.70 (m, 2H), 7.79-7.83 (m, 1H), 7.99-8.04 (m, 1H), 8.06-8.14 (m, 1H), 8.19-8.25 (m, 1H), 8.39-8.44 (m, 2H), 8.48-8.55 (s, 1H), 11.03-11.09 (s, 1H). LCMS Rt = 2.87 minutes MS m/z 443 [M + H]$^+$ Using 6-iodopicolinamide |

| Example Number | Name | Structure | Data/Halopyridine |
|---|---|---|---|
| 95 | 2-chloro-N-(3-cyano-1-phenyl-1H-pyrazol-5-yl)-5-(3,5-difluoropyridin-2-yl)benzamide | 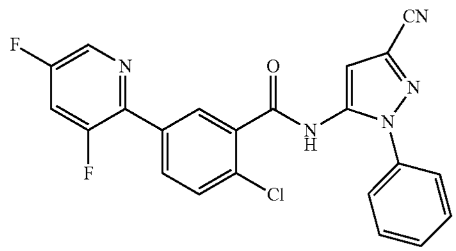 [SMILES: N#Cc1cc(NC(=O)c2cc(-c3ncc(F)cc3F)ccc2Cl)n(-c2ccccc2)n1] | $^1$H NMR (400 MHz, DMSO-d$_6$): δ ppm 7.30 (s, 1H), 7.52-7.61 (m, 5H), 7.68 (d, 1H), 7.96-7.98 (m, 2H), 8.10-8.16 (m, 1H), 8.68 (d, 1H), 11.02 (br s, 1H). Using 2-bromo-3,5-difluoropyridine. |
| 96 | 2-chloro-N-(3-cyano-1-phenyl-1H-pyrazol-5-yl)-3-fluoro-5-(3-fluoropyridin-2-yl)benzamide | 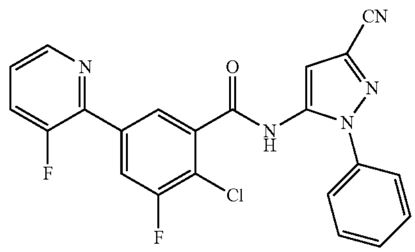 | $^1$H NMR (400 MHz, DMSO-d$_6$): δ ppm 7.32 (s, 1H), 7.53-7.61 (m, 6H), 7.89-7.94 (m, 2H), 8.03 (d, 1H), 8.59 (d, 1H), 11.12 (br s, 1H). Using 2-chloro-N-(3-cyano-1-phenyl-1H-pyrazol-5-yl)-3-fluoro-5-(4,4,5,5-tetramethyl-1,3,2-dioxaborolan-2-yl)benzamide (Preparation 8) and 2-bromo-3-fluoropyridine. PM B. |
| 97 | 6-chloro-N-(3-cyano-1-phenyl-1H-pyrazol-5-yl)-2-fluoro-3-(3-fluoropyridin-2-yl)benzamide | 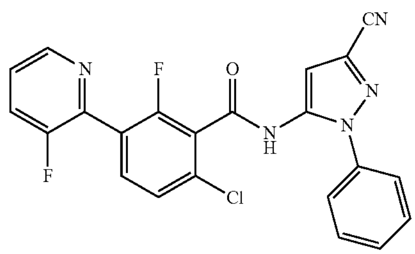 [SMILES: N#Cc1cc(NC(=O)c2c(Cl)ccc(-c3ncccc3F)c2F)n(-c2ccccc2)n1] | $^1$H NMR (400 MHz, DMSO-d$_6$): δ ppm 7.30 (s, 1H), 7.51-7.57 (m, 6H), 7.59-7.63 (m, 1H), 7.07-7.74 (m, 1H), 7.88-7.93 (m, 1H), 8.57-8.58 (m, 1H), 11.38 (br s, 1H). Using 6-chloro-N-(3-cyano-1-phenyl-1H-pyrazol-5-yl)-2-fluoro-3-(4,4,5,5-tetramethyl-1,3,2-dioxaborolan-2-yl)benzamide (Preparation 9) and 2-bromo-3-fluoropyridine. |

Example 98

2-chloro-N-(3-cyano-1-phenyl-1H-pyrazol-5-yl)-4-fluoro-5-(3-fluoropyridin-2-yl)benzamide

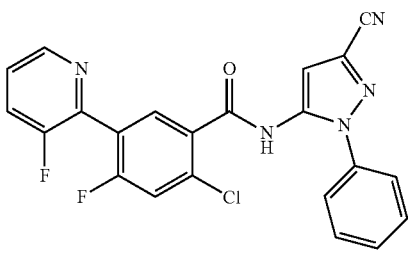 [SMILES: N#Cc1cc(NC(=O)c2cc(-c3ncccc3F)c(F)cc2Cl)n(-c2ccccc2)n1]

To a solution of 2-chloro-4-fluoro-5-(3-fluoropyridin-2-yl)benzoic acid (Preparation 21, 160 mg, 0.59 mmol) in 2-Methyl-THF (3 mL) was added 5-amino-1-phenyl-1H-pyrazole-3-carbonitrile (Preparation 53, 120 mg, 0.65 mmol) and pyridine (0.14 mL, 1.77 mmol). The reaction was heated to 90° C. before the addition of propylphosphonic anhydride (752 mg, 1.18 mmol) and the reaction was continued heating at 90° C. for 16 hours. Further propylphosphonic anhydride (752 mg, 1.18 mmol) was added and the reaction continued to heat at 90° C. for 3 hours. The reaction was cooled to room temperature, diluted with EtOAc (20 mL) and washed with 2M NaOH(aq) (2×20 mL), saturated aqueous NH$_4$Cl solution (20 mL), water (20 mL) and brine (20 mL). The organic layer was dried over magnesium sulphate and concentrated in vacuo. The residue was purified using reverse phase column chromatography eluting from 5-60% MeCN (with 0.1% HCO$_2$H) in water (with 0.1% HCO$_2$H) to afford the title compound (89 mg, 34%).

$^1$H NMR (400 MHz, CDCl$_3$): δ ppm 7.25-7.28 (m, 2H), 7.39-7.44 (m, 1H), 7.51-7.55 (m, 3H), 7.57-7.62 (m, 3H), 8.22 (d, 1H), 8.54 (m, 1H), 8.57 (br s, 1H).

LCMS Rt=3.12 minutes MS m/z 436 [M+H]$^+$

Example 99

2-chloro-N-(3-cyano-1-phenyl-1H-pyrazol-5-yl)-4-methyl-5-(pyridin-2-yl)benzamide

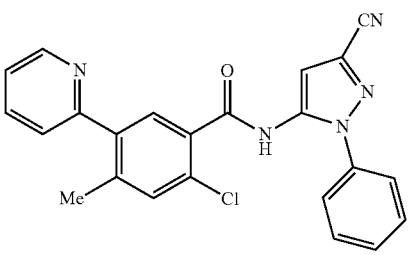 [SMILES: Cc1cc(Cl)c(C(=O)Nc2cc(C#N)nn2-c2ccccc2)cc1-c1ccccn1]

A mixture of 2-chloro-4-methyl-5-(pyridin-2-yl)benzoic acid (Preparation 25, 234 mg, 0.94 mmol), 5-amino-1-phenyl-1H-pyrazole-3-carbonitrile (Preparation 53, 191 mg, 1.04 mmol) and pyridine (0.23 mL, 2.83 mmol) in 2-methyl tetrahydrofuran (20 mL) was heated at reflux for 10 minutes. To this refluxing mixture was added propylphosphonic anhydride solution (2.8 mL, 50% w/w in EtOAc) and the reaction heated at reflux under an atmosphere of argon for 18 hours. The reaction mixture was cooled to room temperature and partitioned between EtOAc (100 mL) and 2M aqueous sodium hydroxide solution (50 mL). The organic layer was washed with 2M aqueous sodium hydroxide solution (50 mL), saturated aqueous ammonium chloride solution (50 mL), water (50 mL), dried over magnesium sulphate and concentrated in vacuo. The residue was purified using silica gel column chromatography eluting with 0-20% EtOAc in DCM followed by trituration with diethylether to afford the title compound as a white solid (119 mg, 31%).

$^1$H NMR (400 MHz, MeOH-d$_4$): δ ppm 2.31 (s, 3H), 7.09 (s, 1H), 7.55-7.09 (m, 9H), 7.94 (m, 1H), 8.62 (d, 1H).

LCMS Rt=2.27 minutes MS m/z 414 [M+H]$^+$

Example 100

2-chloro-N-(3-cyano-1-phenyl-1H-pyrazol-5-yl)-4-fluoro-5-(pyridin-2-yl)benzamide

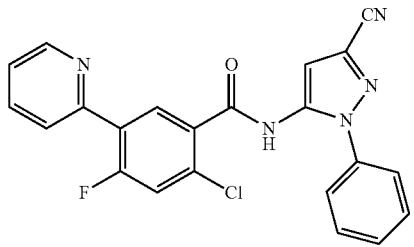 [SMILES: N#Cc1cc(NC(=O)c2cc(-c3ccccn3)c(F)cc2Cl)n(-c2ccccc2)n1]

The title compound was prepared according to the method described for Example 99 using 2-chloro-4-fluoro-5-(pyridin-2-yl)benzoic acid (Preparation 22) and 5-amino-1-phenyl-1H-pyrazole-3-carbonitrile (Preparation 53). The residue was purified using silica gel column chromatography eluting with 10% MeOH in EtOAc followed by a second chromatography eluting with 50% EtOAc in heptanes.

$^1$H NMR (400 MHz, CDCl$_3$): δ ppm 7.29-7.25 (m, 3H), 7.40 (br s, 1H), 7.61-7.53 (m, 5H), 7.92-7.79 (m, 2H), 7.58 (d, 1H), 7.72 (d, 1H).

Example 101

2-chloro-N-(3-cyano-1-phenyl-1H-pyrazol-5-yl)-4-methoxy-5-(pyridin-2-yl)benzamide

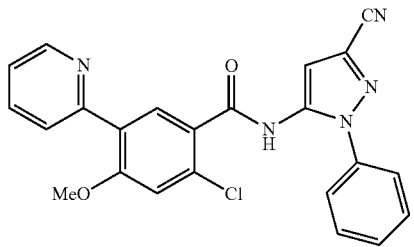 [SMILES: COc1cc(Cl)c(C(=O)Nc2cc(C#N)nn2-c2ccccc2)cc1-c1ccccn1]

The title compound was prepared according to the method described for Example 99 using 2-chloro-4-methoxy-5-(pyridin-2-yl)benzoic acid (Preparation 26) and 5-amino-1-phenyl-1H-pyrazole-3-carbonitrile (Preparation 53). The residue was purified using reverse phase chromatography eluting with 5-60% MeCN (with 0.1% formic acid) in water (with 0.1% formic acid).

$^1$H NMR (400 MHz, DMSO-d$_6$): δ ppm 3.90 (s, 3H), 7.26 (s, 1H), 7.30 (s, 1H), 7.34-7.39 (m, 1H), 7.50-7.59 (m, 5H), 7.81-7.87 (m, 2H), 7.94 (s, 1H), 8.68 (d, 1H), 10.80 (br s, 1H).

LCMS Rt=3.00 minutes MS m/z 430 [M+H]$^+$

Example 102

5-(2,4-dichloro-5-(5-fluoropyridin-2-yl)benzamido)-1-phenyl-1H-pyrazole-3-carboxylic acid

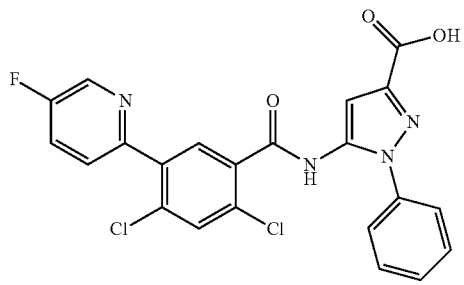 [SMILES: O=C(O)c1cc(NC(=O)c2cc(-c3ccc(F)cn3)c(Cl)cc2Cl)n(-c2ccccc2)n1]

To a suspension of ethyl 5-(2,4-dichloro-5-(5-fluoropyridin-2-yl)benzamido)-1-phenyl-1H-pyrazole-3-carboxylate (Example 116, 822 mg, 1.65 mmol) in ethanol (15 mL) was added 2M aqueous sodium hydroxide (4.1 mL, 8.23 mmol) and the reaction was stirred at room temperature for 1 hour. The reaction mixture was concentrated in vacuo. The residue was diluted with water (25 mL) and neutralised with 2M aqueous hydrochloric acid. The resultant solid was filtered, washed with water and dried in vacuo to afford the title compound as a white solid (700 mg, 90%).

LCMS Rt=2.27 minutes MS m/z 469 [M−H]$^-$

The following Preparations were prepared according to the method described for Example 102 using the appropriate ester with either NaOH or LiOH. The crude residues were purified as above or according to the purification method described below:

Purification Method A: Reverse phase column chromatography eluting with 0-100% MeCN in water with 0.1% ammonia.

Purification Method B: Trituration with IMS.

| Example Number | Name/Structure | Starting Material | Data |
|---|---|---|---|
| 103 | 5-(2-chloro-5-(6-pivalamidopyridin-2-yl)benzamido)-1-phenyl-1H-pyrazole-3-carboxylic acid | Ethyl 5-(2-chloro-5-(6-pivalamidopyridin-2-yl)benzamido)-1-phenyl-1H-pyrazole-3-carboxylate (Example 112). | $^1$H NMR (400 MHz, DMSO-$d_6$): δ ppm 1.15 (s, 9H), 6.95 (s, 1H) 7.40-7.70 (m, 7H), 7.90 (t, 1H), 8.05 (d, 1H), 8.15 (m, 2H), 9.70 (s, 1H), 10.85 (s, 1H), 13.00 (br s, 1H). LCMS Rt = 3.19 minutes MS m/z 518 [M + H]$^+$ |
| 104 | 1-(3-(benzyloxy)phenyl)-5-(2-chloro-5-(3-fluoropyridin-2-yl)benzamido)-1H-pyrazole-3-carboxylic acid | Ethyl 1-(3-(benzyloxy)phenyl)-5-(2-chloro-5-(3-fluoropyridin-2-yl)benzamido)-1H-pyrazole-3-carboxylate (Example 128). | $^1$H NMR (400 MHz, DMSO-$d_6$): δ ppm 5.09 (br s, 2H), 6.96 (s, 1H), 7.11 (dd, 1H), 7.18 (dd, 1H), 7.24 (br s, 1H), 7.29-7.37 (m, 5H), 7.43-7.52 (m, 2H), 7.68 (d, 1H), 7.81-7.86 (m, 1H), 8.01 (m, 1H), 8.03 (br s, 1H), 8.51-8.52 (m, 1H), 10.86 (br s, 1H), 13.01 (br s, 1H). LCMS Rt = 3.29 minutes MS m/z 541 [M − H]$^−$ |
| 105 | 5-(2-chloro-5-(3-fluoropyridin-2-yl)benzamido)-1-phenyl-1H-pyrazole-3-carboxylic acid | Ethyl 5-(2-chloro-5-(3-fluoropyridin-2-yl)benzamido)-1-phenyl-1H-pyrazole-3-carboxylate (Example 113). | $^1$H NMR (400 MHz, DMSO-$d_6$): δ ppm 6.96 (s, 1H), 7.40-7.63 (m, 6H), 7.67 (d, 1H), 7.89 (m, 1H), 8.02 (m, 2H), 8.57 (d, 1H), 10.83 (s, 1H), 12.97 (s, 1H). LCMS Rt = 2.19 minutes MS m/z 437 [M + H]$^+$ |
| 106 | 5-(2-chloro-5-(3-chloropyridin-2-yl)benzamido)-1-phenyl-1H-pyrazole-3-carboxylic acid | Ethyl 5-(2-chloro-5-(3-chloropyridin-2-yl)benzamido)-1-phenyl-1H-pyrazole-3-carboxylate (Example 130) at 40° C. | $^1$H NMR (400 MHz, DMSO-$d_6$): δ ppm 6.94 (s, 1H), 7.44-7.77 (m, 7H), 7.78-7.84 (m, 2H), 8.09 (dd, 1H), 8.65 (dd, 1H), 10.82 (s, 1H), 12.98 (s, 1H). |

-continued

| Example Number | Name/Structure | Starting Material | Data |
|---|---|---|---|
| 107 | 5-(2,4-dichloro-5-(3-fluoropyridin-2-yl)benzamido)-1-phenyl-1H-pyrazole-3-carboxylic acid | Ethyl 5-(2,4-dichloro-5-(3-fluoropyridin-2-yl)benzamido)-1-phenyl-1H-pyrazole-3-carboxylate (Example 122). | $^1$H NMR (400 MHz, DMSO-$d_6$): δ ppm 6.91-6.95 (s, 1H), 7.42-7.48 (m, 1H), 7.48-7.54 (m, 2H), 7.54-7.59 (m, 2H), 7.60-7.65 (m, 1H), 7.66-7.70 (s, 1H), 7.87-7.95 (m, 2H), 8.54-8.60 (m, 1H), 10.80-10.93 (br s, 1H), 12.85-13.09 (br s, 1H). MS m/z 471 [M + H]$^+$ |
| 108 | 5-(2-chloro-4-fluoro-5-(pyridin-2-yl)benzamido)-1-phenyl-1H-pyrazole-3-carboxylic acid | Ethyl 5-(2-chloro-4-fluoro-5-(pyridin-2-yl)benzamido)-1-phenyl-1H-pyrazole-3-carboxylate (Example 117). | $^1$H NMR (400 MHz, DMSO-$d_6$): δ ppm 6.96 (s, 1H), 7.44-7.50 (m, 2H), 7.52-7.60 (m, 4H), 7.71 (d, 1H), 7.81 (d, 1H), 7.95 (m, 1H), 8.10 (d, 1H), 8.76 (d, 1H), 10.80 (br s, 1H), 12.98 (br s, 1H). LCMS Rt = 2.49 minutes MS m/z 437 [M + H]$^+$ |
| 109 | 5-(2-chloro-4-fluoro-5-(5-fluoropyridin-2-yl)benzamido)-1-phenyl-1H-pyrazole-3-carboxylic acid | Ethyl 5-(2-chloro-4-fluoro-5-(5-fluoropyridin-2-yl)benzamido)-1-phenyl-1H-pyrazole-3-carboxylate (Example 119). | $^1$H NMR (400 MHz, DMSO-$d_6$): δ ppm 6.95 (s, 1H), 7.46-7.61 (m, 6H), 7.72 (d, 1H), 7.88-7.91 (m, 2H), 8.05 (d, 1H), 8.78 (s, 1H), 10.82 (s, 1H). MS m/z 455 [M + H]$^+$ |
| 110 | 5-(2-chloro-4-fluoro-5-(3-fluoropyridin-2-yl)benzamido)-1-phenyl-1H-pyrazole-3-carboxylic acid | Ethyl 5-(2-chloro-4-fluoro-5-(3-fluoropyridin-2-yl)benzamido)-1-phenyl-1H-pyrazole-3-carboxylate (Example 123). | Used as an intermediate and taken on directly to the next step. |

Example 107A

Alternative Method for Synthesis of Example 107

5-(2,4-dichloro-5-(3-fluoropyridin-2-yl)benzamido)-1-phenyl-1H-pyrazole-3-carboxylic acid To a suspension of ethyl 5-(2,4-dichloro-5-(3-fluoropyridin-2-yl)benzamido)-1-phenyl-1H-pyrazole-3-carboxylate (Example 122A, 58.3 g, 0.117 mol) in IMS (580 mL), was added 2M aqueous sodium hydroxide solution (176 mL, 0.352 mol) and the reaction stirred at room temperature for 5 hours. The reaction mixture was diluted with water (600 mL) and acidified to pH1 with hydrochloric acid solution (40 mL, 36%). The resulting solid was filtered and washed with water (50 mL) to give the title compound as a white solid (53.1 g, 97%).

$^1$H NMR (300 MHz, DMSO-$d_6$): δ ppm 6.95 (s, 1H), 7.46-7.69 (m, 6H), 7.90-7.91 (m, 2H), 8.55-8.57 (d, 1H), 10.90 (s, 1H), 13.00 (br s, 1H).
MS m/z 471.15 [M+H]$^+$, 469.28 [M−H]$^−$

Example 108A

Alternative Method for Synthesis of Example 108

5-(2-chloro-4-fluoro-5-(pyridin-2-yl)benzamido)-1-phenyl-1H-pyrazole-3-carboxylic acid To a suspension of ethyl 5-(2-chloro-4-fluoro-5-(pyridin-2-yl)benzamido)-1-phenyl-1H-pyrazole-3-carboxylate (Example 117A, 15.0 g, 32.3 mmol) in IMS (150 mL), was added 2M aqueous sodium hydroxide solution (83 mL) and the reaction stirred at room temperature for 3 hours. Aqueous hydrochloric acid solution (90 mL, 2 M) was then added. The resulting solid was collected by filtration, washed with water (10 mL) and dried under vacuum to give the title compound (12.7 g, 90%).

$^1$H NMR (400 MHz, DMSO-$d_6$): δ ppm 6.94 (s, 1H), 7.43-7.48 (m, 2H), 7.52-7.60 (m, 4H), 7.69-7.71 (d, 1H), 7.79-7.81 (d, 1H), 7.90-7.95 (m, 1H), 8.09-8.11 (d, 1H), 8.73-8.74 (d, 1H), 10.87 (s, 1H).
MS m/z 437.10 [M+H]$^+$

Example 111

5-(2,4-dichloro-5-(pyridin-2-yl)benzamido)-1-phenyl-1H-pyrazole-3-carboxylic acid

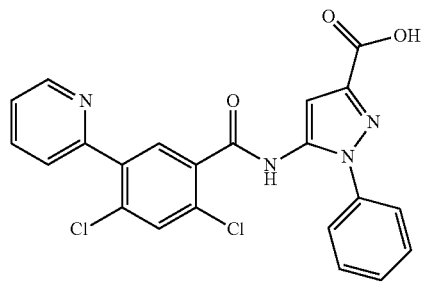 [SMILES: O=C(O)c1cc(NC(=O)c2cc(-c3ccccn3)c(Cl)cc2Cl)n(-c2ccccc2)n1]

To a solution of ethyl 5-(2,4-dichloro-5-(pyridin-2-yl)benzamido)-1-phenyl-1H-pyrazole-3-carboxylate (Example 124, 2.5 g, 5.19 mmol) in industrial methylated spirit (50 mL) was added a 1M LiOH solution in water (26 mL, 26 mmol) and the reaction was stirred at room temperature for 3 hours. The reaction was acidified with 2M HCl (aq) (13 mL, 26 mmol) to afford a precipitate that was filtered and washed with industrial methylated spirit to afford the title compound (1.96 g, 83%).

$^1$H NMR (400 MHz, DMSO-$d_6$): δ ppm 6.97 (s, 1H), 7.47-7.60 (m, 5H), 7.72 (d, 1H), 7.75 (s, 1H), 7.89 (s, 1H), 7.98 (t, 1H), 8.74 (d, 1H), 10.80 (s, 1H), 13.01 (br s, 1H).
LCMS Rt=2.75 minutes MS m/z 452 [M+H]$^+$

Example 112

Ethyl 5-(2-chloro-5-(6-pivalamidopyridin-2-yl)benzamido)-1-phenyl-1H-pyrazole-3-carboxylate

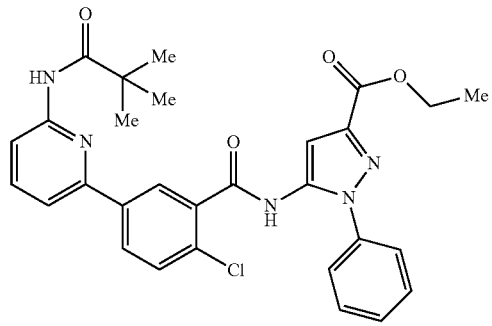 [SMILES: CCOC(=O)c1cc(NC(=O)c2cc(-c3cccc(NC(=O)C(C)(C)C)n3)ccc2Cl)n(-c2ccccc2)n1]

To a solution of 5-(5-(6-aminopyridin-2-yl)-2-chlorobenzamido)-1-phenyl-1H-pyrazole-3-carboxylic acid ethyl ester (Preparation 2, 4.61 g, 10 mmol) in anhydrous pyridine (50 mL) was added pivaloyl chloride (1.32 g, 11 mmol) over 10 minutes with stirring at room temperature. The reaction was stirred for 90 minutes before concentrating in vacuo to low volume. The solution was partitioned between EtOAc (250 mL) and water (100 mL). The organic layer was separated, washed with brine (10 mL), dried over magnesium sulphate and concentrated in vacuo. The residue was purified using silica gel column chromatography eluting with 50% EtOAc in heptanes to afford the title compound (5 g, 92%).

$^1$H NMR (400 MHz, CDCl$_3$): δ ppm 1.40 (s, 9H), 1.45 (t, 3H), 4.45 (q, 2H), 7.40-7.60 (m, 8H), 7.80 (m, 1H), 8.00 (d, 1H), 8.05 (br s, 1H), 8.25 (m, 1H), 8.55 (m, 2H).
LCMS Rt=1.77 minutes MS m/z 546 [M+H]$^+$

Example 113

Ethyl 5-(2-chloro-5-(3-fluoropyridin-2-yl)benzamido)-1-phenyl-1H-pyrazole-3-carboxylate

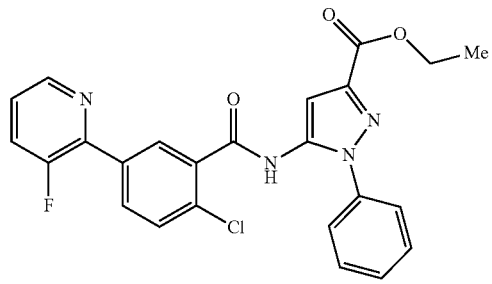 [SMILES: CCOC(=O)c1cc(NC(=O)c2cc(-c3ncccc3F)ccc2Cl)n(-c2ccccc2)n1]

The title compound was prepared according to the method described for Preparation 2 using 5-(2-chloro-5-(4,4,5,5-tetramethyl-1,3,2-dioxaborolan-2-yl)benzamido)-1-phenyl-1H-pyrazole-3-carboxylate (Preparation 5) and 2-bromo-3-fluoropyridine. The residue was purified using silica gel column chromatography eluting with 0-100% DCM in TBME followed by EtOAc, followed by a second chromatography eluting with 5% acetone in DCM.

¹H NMR (400 MHz, MeOH-d₄): δ ppm 1.41 (t, 3H), 4.41 (q, 2H), 7.08 (s, 1H), 7.44-7.65 (m, 8H), 7.73 (dd, 1H), 8.05 (s, 1H), 8.51 (d, 1H).

Example 114

Ethyl 5-(2-chloro-5-(6-(difluoromethoxy)pyridin-2-yl)benzamido)-1-phenyl-1H-pyrazole-3-carboxylate

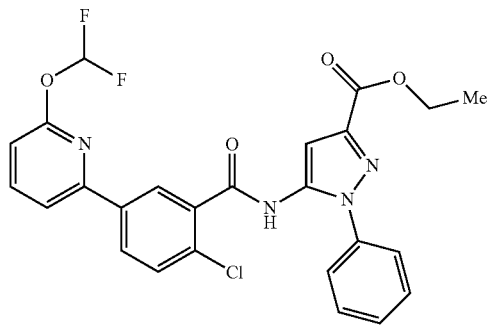 [SMILES: CCOC(=O)c1cc(NC(=O)c2cc(-c3cccc(OC(F)F)n3)ccc2Cl)n(-c2ccccc2)n1]

To a degassed solution of ethyl 5-(2-chloro-5-(4,4,5,5-tetramethyl-1,3,2-dioxaborolan-2-yl)benzamido)-1-phenyl-1H-pyrazole-3-carboxylate (Preparation 5, 229 mg, 0.44 mmol) in dioxane (4 mL) and water (0.5 mL) heated to 50° C. was added Na₂CO₃ (228 mg, 1.32 mmol), Cataxium A (16 mg, 0.044 mmol), a solution of 2-bromo-6-(difluoromethoxy)pyridine (Preparation 58, 100 mg, 0.44 mmol) in dioxane (1 mL) and Pd(OAc)₂ (5 mg, 0.022 mmol). The reaction was heated at 80° C. for 3 hours. Further Cataxium A (16 mg, 0.044 mmol) and Pd(OAc)₂ (5 mg, 0.022 mmol) were added and the reaction continued at 90° C. for 3 hours. The reaction was cooled and concentrated in vacuo. The residue was purified using silica gel column chromatography eluting with 10-40% EtOAc in heptanes to afford the title compound (146 mg, 60%).

¹H NMR (400 MHz, CDCl₃): δ ppm 1.42 (t, 3H), 4.44 (q, 2H), 6.90 (d, 1H), 7.38-7.74 (m, 8H), 7.82 (t, 1H), 8.05 (m, 1H), 8.44 (d, 1H), 8.54 (s, 1H).

LCMS Rt=3.42 minutes MS m/z 513 [M+H]⁺

Example 115

Ethyl 5-(2-chloro-5-(3-chloro-6-(cyanomethyl)pyridin-2-yl)benzamido)-1-phenyl-1H-pyrazole-3-carboxylate

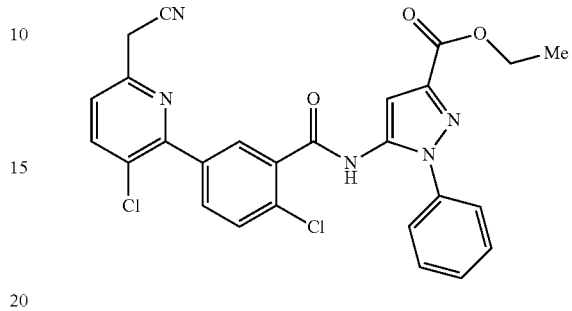

To a degassed solution of ethyl 5-(2-chloro-5-(4,4,5,5-tetramethyl-1,3,2-dioxaborolan-2-yl)benzamido)-1-phenyl-1H-pyrazole-3-carboxylate (Preparation 5, 1.01 g, 1.34 mmol) and 2-(5,6-dichloropyridin-2-yl)acetonitrile (Preparation 59, 300 mg, 1.60 mmol) in dioxane (10 mL) was added Na₂CO₃ (213 mg, 2.01 mmol), water (1 drop) and Pd(PPh₃)₄ (144 mg, 0.134 mmol). The reaction was further degassed and heated to 80° C. for 1 hour. Further water (1 mL) was added and heating continued for 5 hours before cooling to room temperature. The reaction was filtered through Celite washing through with EtOAc, and concentrated in vacuo. The residue was purified using reverse phase column chromatography eluting with 0-100% MeCN in water with 0.1% formic acid to afford the title compound (360 mg, 49%).

¹H NMR (400 MHz, MeOH-d₄): δ ppm 1.40 (t, 3H), 4.10 (s, 2H), 4.40 (q, 2H), 7.10 (s, 1H), 7.50 (m, 7H), 7.90 (m, 2H), 8.00 (d, 1H).

LCMS Rt=1.64 minutes MS m/z 520 [M+H]⁺

Example 116

Ethyl 5-(2,4-dichloro-5-(5-fluoropyridin-2-yl)benzamido)-1-phenyl-1H-pyrazole-3-carboxylate

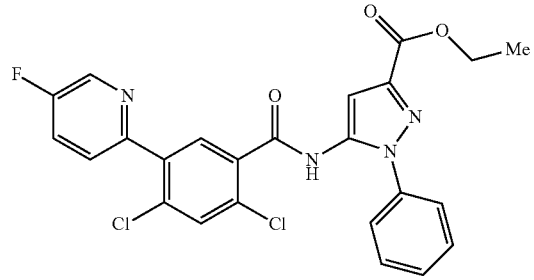 [SMILES: CCOC(=O)c1cc(NC(=O)c2cc(-c3ccc(F)cn3)c(Cl)cc2Cl)n(-c2ccccc2)n1]

2,4-dichloro-5-(5-fluoropyridin-2-yl)benzoic acid hydrochloride (Preparation 20, 900 mg, 3.15 mmol), ethyl 5-amino-1-phenyl-1H-pyrazole-3-carboxylate (683 mg, 2.95 mmol) and diisopropylethylamine (3.28 mL, 18.88 mmol) were added to EtOAc (30 mL) and heated to reflux under an atmosphere of nitrogen. A 50% solution of propylphosphonic cyclic anhydride in EtOAc (9 g, 14.16 mmol) was added dropwise, and the reaction was kept at reflux for 3 hours. After cooling, the reaction was basified with saturated aqueous sodium hydrogen carbonate solution. The organic layer was collected, dried over magnesium sulphate and concentrated in vacuo. The residue was dissolved in ethanol (30 mL) and solid sodium carbonate (~2 g) was added with rapid stirring for 1 hour. The mixture was filtered and the filtrate concentrated in vacuo. The residue was stirred with dilute aqueous sodium hydrogen carbonate, filtered, washed with water and dried in vacuo. The resulting solid was triturated with TBME to afford the title compound (822 mg, 52%).

$^1$H NMR (400 MHz, MeOH-$d_4$): δ ppm 1.35-1.42 (t, 3H), 4.32-4.39 (q, 2H), 6.86-6.90 (s, 1H), 7.30-7.36 (m, 1H), 7.38-7.45 (m, 2H), 7.53-7.56 (s, 1H), 7.64-7.74 (m, 5H), 8.53-8.56 (m, 1H).

LCMS Rt=3.31 minutes MS m/z 499 [M+H]$^+$

The following Preparations were prepared according to the method described for Example 116 using ethyl-5-amino-1-phenyl-1H-pyrazole-3-carboxylate and the appropriate acid as described below. The crude residues were purified as above or according to one of the Purification Methods (PM) described below:

Purification Method A: Reverse phase column chromatography eluting with 5-50% MeCN (with 0.1% formic acid) in water (with 0.1% formic acid).

Purification Method B: Silica gel column chromatography eluting with 0-50% EtOAc in heptanes.

| Example Number | Name/Structure | Starting Material | Data |
| --- | --- | --- | --- |
| 117 | Ethyl 5-(2-chloro-4-fluoro-5-(pyridin-2-yl)benzamido)-1-phenyl-1H-pyrazole-3-carboxylate | 2-chloro-4-fluoro-5-(pyridin-2-yl)benzoic acid (Preparation 22). | $^1$H NMR (400 MHz, DMSO-$d_6$): δ ppm 1.30 (t, 3H), 4.31 (q, 2H), 7.03 (s, 1H), 7.44-7.50 (m, 2H), 7.53-7.60 (m, 4H), 7.71 (d, 1H), 7.81 (d, 1H), 7.95 (m, 1H), 8.11 (d, 1H), 8.76 (d, 1H), 10.84 (br s, 1H). LCMS Rt = 3.02 minutes MS m/z 465 [M + H]$^+$ PM A. |
| 118 | Ethyl 5-(2,4-dichloro-5-(6-(methoxymethyl)pyridin-2-yl)benzamido)-1-phenyl-1H-pyrazole-3-carboxylate | 2,4-dichloro-5-(6-(methoxymethyl)pyridin-2-yl)benzoic acid (Preparation 29). | $^1$H NMR (400 MHz, CDCl$_3$): δ ppm 1.42 (t, 3H), 3.52 (s, 3H), 4.44 (q, 2H), 4.66 (br s, 2H), 7.38 (s, 1H), 7.50-7.62 (m, 9H), 7.84 (br s, 1H), 8.14 (s, 1H). |
| 119 | Ethyl 5-(2-chloro-4-fluoro-5-(5-fluoropyridin-2-yl)benzamido)-1-phenyl-1H-pyrazole-3-carboxylate | 2-chloro-4-fluoro-5-(5-fluoropyridin-2-yl)benzoic acid (Preparation 24). | $^1$H NMR (400 MHz, DMSO-$d_6$): δ ppm 1.32 (t, 3H), 4.32 (q, 2H), 7.05 (s, 1H), 7.46-7.73 (m, 6H), 7.90 (d, 2H), 8.09 (d, 1H), 8.79 (d, 1H), 10.86 (s, 1H). MS m/z 483 [M + H]$^+$ |

-continued

| Example Number | Name/Structure | Starting Material | Data |
|---|---|---|---|
| 120 | Ethyl 5-(2-chloro-5-(6-(1,1-difluoroethyl)pyridin-2-yl)benzamido)-1-phenyl-1H-pyrazole-3-carboxylate 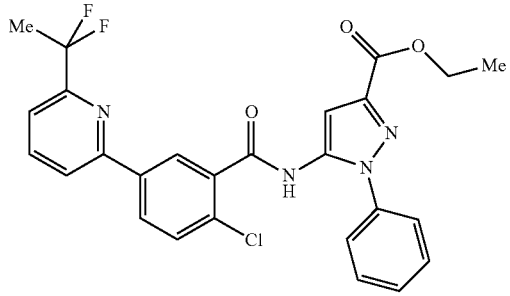 | 2-chloro-5-(6-(1,1-difluoroethyl)pyridin-2-yl)benzoic acid (Preparation 23). | $^1$H NMR (400 MHz, CDCl$_3$): δ ppm 1.40 (t, 3H), 2.10 (t, 3H), 4.40 (q, 2H), 7.40-7.70 (m, 7H), 7.80 (m, 1H), 7.90 (m, 1H), 8.15 (m, 1H), 8.50 (m, 2H). PM B. |
| 121 | Ethyl 5-(2-chloro-5-(6-(2,2-difluoroethyl)pyridin-2-yl)benzamido)-1-phenyl-1H-pyrazole-3-carboxylate 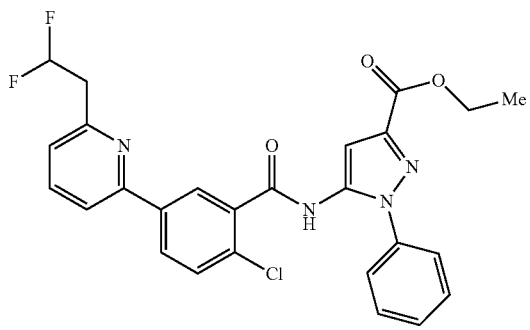 | 2-chloro-5-(6-(2,2-difluoroethyl)pyridin-2-yl)benzoic acid (Preparation 28). | $^1$H NMR (400 MHz, CDCl$_3$): δ ppm 1.40 (m, 3H), 3.40 (m, 2H), 4.50 (t, 2H), 6.20-6.40 (t, 1H), 7.20 (m, 1H), 7.40-7.60 (m, 8H), 7.70 (m, 1H), 7.80 (m, 1H), 8.10 (m, 1H), 8.50 (br s, 1H). |
| 122 | Ethyl 5-(2,4-dichloro-5-(3-fluoropyridin-2-yl)benzamido)-1-phenyl-1H-pyrazole-3-carboxylate 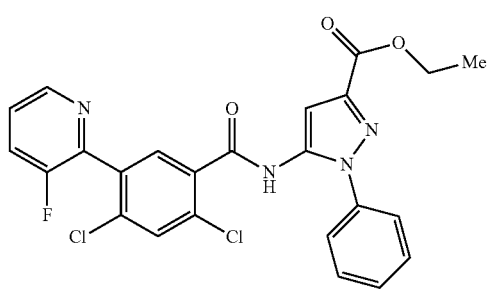 [SMILES: CCOC(=O)c1cc(NC(=O)c2cc(-c3ccccn3)c(Cl)cc2Cl)n(-c2ccccc2)n1] | 2,4-dichloro-5-(3-fluoropyridin-2-yl)benzoic acid (Preparation 27). | $^1$H NMR (400 MHz, CDCl$_3$): δ ppm 1.39-1.44 (t, 3H), 4.41-4.48 (q, 2H), 7.35-7.39 (s, 1H), 7.39-7.45 (m, 1H), 7.50-7.58 (m, 7H), 8.00-8.04 (s, 1H), 8.42-8.47 (s, 1H), 8.50-8.55 (m, 1H). |
| 123 | Ethyl 5-(4-chloro-2-fluoro-5-(3-fluoropyridin-2-yl)benzamido)-1-phenyl-1H-pyrazole-3-carboxylate 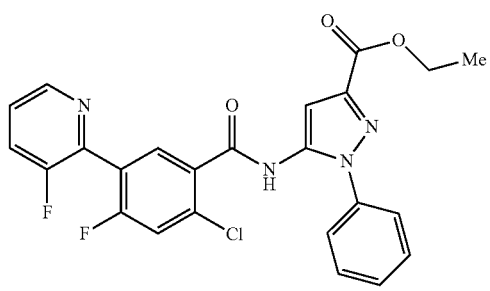 | 2-chloro-4-fluoro-5-(3-fluoropyridin-2-yl)benzoic acid (Preparation 21). | Used as an intermediate and taken on directly to the next step. |

Example 117A

Alternative Method for Synthesis of Example 117

Ethyl 5-(2-chloro-4-fluoro-5-(pyridin-2-yl)benzamido)-1-phenyl-1H-pyrazole-3-carboxylate To a refluxing mixture of 2-chloro-4-fluoro-5-(pyridin-2-yl)benzoic acid (Preparation 22A, 9.2 g, 36.6 mmol), ethyl 5-amino-1-phenyl-1H-pyrazole-3-carboxylate (8.45 g, 36.6 mmol), N,N-diisopropylethylamine (19.2 mL, 110 mmol) and 2-methyltetrahydrofuran (320 mL), was added propylphosphonic anhydride solution (255 mL, 429 mmol, >50% by weight in EtOAc) dropwise under argon, and the reaction maintained at reflux for 5 hours. After cooling to room temperature, the reaction was filtered and the filtrate concentrated in vacuo. The residue was dissolved in ethyl acetate (350 mL) and washed with saturated aqueous sodium hydrogen carbonate solution (300 mL). The organic layer was filtered under vacuum and the solids washed with EtOAc (20 mL) and TBME (200 mL) to give the title compound (51 g, 78%).

$^1$H NMR (300 MHz, CDCl$_3$): δ ppm 1.38-1.44 (t, 3H), 4.41-4.44 (q, 2H), 5.24 (br s, 1H), 7.19-7.21 (d, 1H), 7.25-7.34 (m, 2H), 7.45-7.55 (m, 4H), 7.70-7.80 (m, 2H), 8.45-8.47 (d, 1H), 8.53 (s, 1H), 8.66-8.67 (d, 1H).

UPLC Rt=0.81 minutes, MS m/z 463.3 [M−H]$^−$, 465.2 [M+H]$^+$

Example 122A

Alternative Method for Synthesis of Example 122

Ethyl 5-(2,4-dichloro-5-(3-fluoropyridin-2-yl)benzamido)-1-phenyl-1H-pyrazole-3-carboxylate To a refluxing mixture of 2,4-dichloro-5-(3-fluoropyridin-2-yl)benzoic acid (Preparation 27A, 159 g, 0.554 mol), ethyl 5-amino-1-phenyl-1H-pyrazole-3-carboxylate (154 g, 0.665 mol), N,N-diisopropylethylamine (215 g, 1.66 mol) and 2-methyltetrahydrofuran (4.8 L), was added propylphosphonic anhydride solution (989 mL, 1.66 mol, >50% by weight in EtOAc) and the reaction maintained at reflux for 6 hours. After cooling to room temperature, the reaction was diluted with water (6 L) and extracted with 2-methyltetrahydrofuran (2×1.5 L). The combined organic layers were concentrated in vacuo to provide a slurry which was filtered and the solid washed with ethyl acetate (3×200 mL) to give the title compound as a white solid (215 g, 79%).

$^1$H NMR (300 MHz, DMSO-d$_6$): δ ppm 1.26-1.30 (t, 3H), 4.27-4.30 (q, 2H), 7.00 (s, 1H), 7.48-7.65 (m, 6H), 7.69 (s, 1H), 7.87-7.93 (m, 2H), 8.55-8.57 (m, 1H), 10.94 (br s, 1H).

LCMS Rt=1.75 minutes, MS m/z 497.0 [M−H]$^−$, 498.9 [M+H]$^+$

LCMS basic analytical conditions:

Column: XBridge C18 2.5 μm 2.1×20 mm IS

Mobile phase A: 10 mM NH$_4$HCO$_3$ in water (pH 10)

Mobile phase B: Acetonitrile

Run time=3.0 minutes; Initial: 80% A, 20% B to 30% A and 70% B at 1.6 minutes, to 95% B at 2 minutes, hold to 2.4 minutes.

Detectors: UV and mass spectrometer

Example 124

Ethyl 5-(2,4-dichloro-5-(pyridin-2-yl)benzamido)-1-phenyl-1H-pyrazole-3-carboxylate

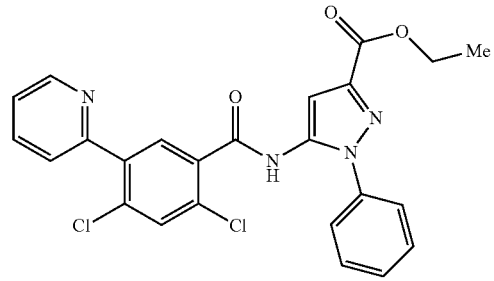 [SMILES: CCOC(=O)c1cc(NC(=O)c2cc(-c3ccccn3)c(Cl)cc2Cl)n(-c2ccccc2)n1]

To a solution of 2,4-dichloro-5-(pyridin-2-yl)benzoic acid (Preparation 30, 3.76 g, 14.02 mmol) and ethyl 5-amino-1-phenyl-1H-pyrazole-3-carboxylate (3.89 g, 16.83 mmol) in 2-methyltetrahydrofuran (150 mL) was added DIPEA (7.33 mL, 42 mmol) and the reaction was heated to 95° C. T3P (50% solution in EtOAc, 16.53 mL, 28 mmol) was added and the reaction was stirred at 95° C. for 18 hours. The reaction was cooled and partitioned between saturated aqueous sodium carbonate solution (200 mL) and EtOAc (200 mL). The organic layer was collected, washed with brine, dried over magnesium sulphate and concentrated in vacuo. The residue was triturated with TBME to afford the title compound (5.72 g, 85%).

$^1$H NMR (400 MHz, DMSO-d$_6$): δ ppm 1.33 (t, 3H), 4.35 (q, 2H), 7.03 (s, 1H), 7.47-7.55 (m, 4H), 7.61 (d, 2H), 7.72 (d, 2H), 7.75 (s, 1H), 7.98 (t, 1H), 8.74 (d, 1H), 10.88 (1H).

LCMS Rt=3.24 minutes MS m/z 481 [M+H]$^+$

Example 125

Ethyl 5-(2,4-dichloro-5-(pyridin-2-yl)benzamido)-1-phenyl-1H-pyrazole-3-carboxylate

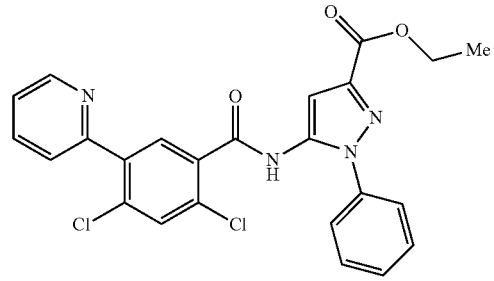

To the solution of ethyl 5-(2,4-dichloro-5-(4,4,5,5-tetramethyl-1,3,2-dioxaborolan-2-yl)benzamido)-1-phenyl-1H-pyrazole-3-carboxylate in dioxane (Preparation 4, 675 mg, 1.27 mmol) was added water (2.2 mL), 2-bromopyridine (302 mg, 1.91 mmol) and K$_2$CO$_3$ (352 mg, 2.546 mmol). The reaction was degassed for 10 minutes before the addition of tetrakis(triphenylphosphine)palladium(0) (147 mg, 0.127 mmol) and heating at reflux for 2 hours. The reaction was cooled and concentrated in vacuo. The residue was purified using silica gel chromatography eluting with 20-50% EtOAc in heptanes to afford the title compound (128 mg, 21%).

$^1$H NMR (400 MHz, DMSO-d$_6$): δ ppm 1.40 (t, 3H), 4.42 (q, 2H), 7.32-7.35 (m, 2H), 7.50-7.53 (m, 5H), 7.63 (d, 1H), 7.80 (m, 1H), 8.07 (s, 1H), 8.53 (br s, 1H), 8.68 (br s, 1H).

LCMS Rt=1.69 minutes MS m/z 481 [M+H]$^+$

Example 126

Ethyl 5-(2-chloro-5-(6-methoxypyridin-2-yl)benzamido)-1-phenyl-1H-pyrazole-3-carboxylate

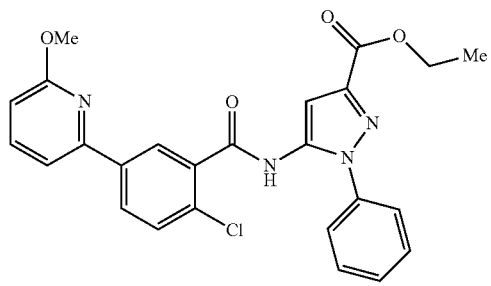 [SMILES: CCOC(=O)c1cc(NC(=O)c2cc(-c3cccc(OC)n3)ccc2Cl)n(-c2ccccc2)n1]

Step 1

To a solution of ethyl 5-(5-bromo-2-chlorobenzamido)-1-phenyl-1H-pyrazole-3-carboxylate (Preparation 13, 500 mg, 1.1 mmol) in dioxane (20 mL) was added bis-pinacolatodiboron (420 mg, 1.65 mmol) and potassium acetate (320 mg, 3.3 mmol). The reaction was degassed at 60° C. for 10 minutes before the addition of Pd(dppf)Cl$_2$ (40 mg, 0.05 mmol) and further heated at reflux for 3 hours to obtain the boronic ester.

Step 2

The reaction was cooled to 60° C. and to the reaction was added water (0.1 mL), 2-bromo-6-methoxypyridine (210 mg, 1.1 mmol) and Na$_2$CO$_3$ (570 mg, 3.3 mmol). The reaction was degassed for 5 minutes before the addition of Pd(dppf)Cl$_2$ (40 mg, 0.05 mmol) and heating at reflux for 18 hours. The reaction was cooled, filtered through Celite and concentrated in vacuo. The residue was purified by silica gel column chromatography eluting with 5-80% DCM in TBME to afford the title compound (340 mg, 65%).

$^1$H NMR (400 MHz, CDCl$_3$): δ ppm 1.39-1.43 (m, 3H), 4.00 (s, 3H), 4.41-4.47 (m, 2H), 6.74 (d, 1H), 7.34-7.56 (m, 6H), 7.70 (t, 1H), 7.80 (dd, 1H), 8.11 (dd, 1H), 8.23 (s, 1H), 8.53 (d, 1H).

LCMS Rt=3.63 minutes MS m/z 477 [M+H]$^+$

The following Preparations were prepared according to the Method described by Preparation 125 or Preparation 126 Step 2 using ethyl 5-(2-chloro-5-(4,4,5,5-tetramethyl-1,3,2-dioxaborolan-2-yl)benzamido)-1-phenyl-1H-pyrazole-3-carboxylate (Preparation 5) or ethyl 1-(3-(benzyloxy)phenyl)-5-(2-chloro-5-(4,4,5,5-tetramethyl-1,3,2-dioxaborolan-2-yl)benzamido)-1H-pyrazole-3-carboxylate (Preparation 6) and the appropriate halopyridine as described below. The crude residues were purified as above or according to one of the purification methods described below:

Purification Method A: Silica gel column chromatography eluting with from 0-100% EtOAc in heptanes to 10% MeOH in EtOAc to 10% MeOH in EtOAc or DCM with 0.4% ammonia.

Purification Method B: Silica gel column chromatography eluting with from 0-45% EtOAc in heptanes.

| Example Number | Name | Structure | Data/Halopyridine |
|---|---|---|---|
| 127 | Ethyl 5-(2-chloro-5-(6-((methylamino)methyl)pyridin-2-yl)benzamido)-1-phenyl-1H-pyrazole-3-carboxylate | 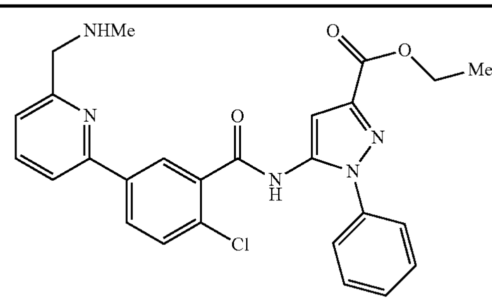 | $^1$H NMR (400 MHz, CDCl$_3$): δ ppm 1.28 (t, 3H), 2.16 (s, 3H), 3.70 (s, 2H), 4.34 (q, 2H), 7.18 (d, 1H), 7.18-7.22 (m, 2H), 7.30-7.55 (m, 6H), 7.60-7.63 (m, 1H), 7.99 (s, 1H), 8.33 (s, 1H). 1-(6-bromopyridin-2-yl)-N-methylmethanamine |
| 128 | Ethyl 1-(3-(benzyloxy)phenyl)-5-(2-chloro-5-(3-fluoropyridin-2-yl)benzamido)-1H-pyrazole-3-carboxylate | 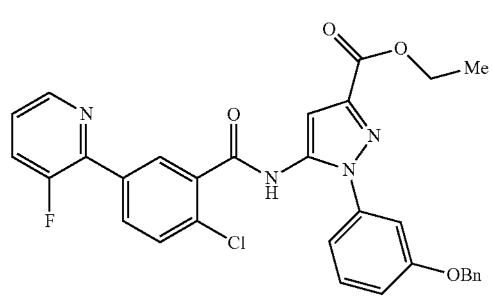 [SMILES: CCOC(=O)c1cc(NC(=O)c2cc(-c3ncccc3F)ccc2Cl)n(-c2cccc(OCc3ccccc3)c2)n1] | $^1$H NMR (400 MHz, DMSO-d$_6$): δ ppm 1.31 (t, 3H), 4.32 (q, 2H), 5.10 (s, 2H), 7.04 (s, 1H), 7.12-7.52 (m, 9H), 7.68 (d, 1H), 7.81-7.86 (m, 1H), 8.01-8.04 (m, 2H), 8.51 (d, 1H), 10.89 (br s, 1H). 2-bromo-3-fluoropyridine. |

-continued

| Example Number | Name | Structure | Data/Halopyridine |
|---|---|---|---|
| 129 | Racemic ethyl 5-(2-chloro-5-(6-(1-methoxyethyl)pyridin-2-yl)benzamido)-1-phenyl-1H-pyrazole-3-carboxylate | 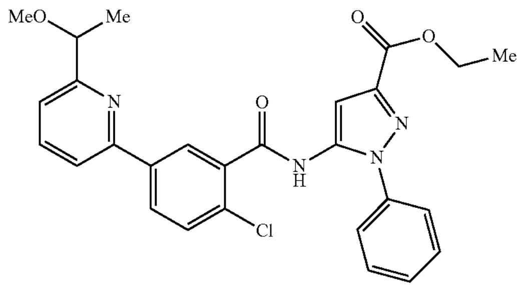 [SMILES: CCOC(=O)c1cc(NC(=O)c2cc(-c3cccc(C(C)OC)n3)ccc2Cl)n(-c2ccccc2)n1] | $^1$H NMR (400 MHz, MeOH-d$_4$): δ ppm 1.41 (t, 3H), 1.48 (d, 3H), 3.34 (s, 3H), 4.40 (q, 2H), 4.50 (q, 1H), 7.10 (s, 1H), 7.43 (d, 1H), 7.52-7.64 (m, 6H), 7.77 (d, 1H), 7.90 (t, 1H), 8.11 (dd, 1H), 8.17 (s, 1H). LCMS Rt = 3.40 minutes MS m/z 505 [M + H]$^+$ Racemic 2-bromo-6-(1-methoxyethyl)pyridine. |
| 130 | Ethyl 5-(2-chloro-5-(3-chloropyridin-2-yl)benzamido)-1-phenyl-1H-pyrazole-3-carboxylate | 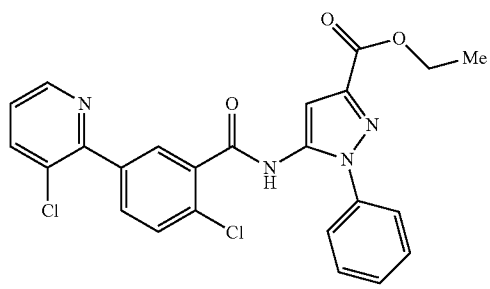 [SMILES: CCOC(=O)c1cc(NC(=O)c2cc(-c3ncccc3Cl)ccc2Cl)n(-c2ccccc2)n1] | $^1$H NMR (400 MHz, DMSO-d$_6$): δ ppm 1.32 (t, 3H), 4.33 (q, 2H), 7.03 (s, 1H), 7.46-7.68 (m, 7H), 7.80-7.86 (m, 2H), 8.10 (m, 1H), 8.66 (m, 1H), 10.88 (s, 1H). 2-bromo-3-chloropyridine. PM A. |
| 131 | Ethyl 5-(2-chloro-5-(6-(difluoromethyl)pyridin-2-yl)benzamido)-1-phenyl-1H-pyrazole-3-carboxylate | 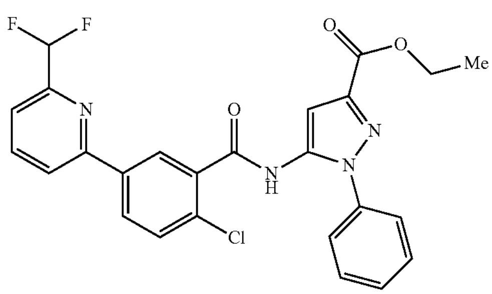 [SMILES: CCOC(=O)c1cc(NC(=O)c2cc(-c3cccc(C(F)F)n3)ccc2Cl)n(-c2ccccc2)n1] | $^1$H NMR (400 MHz, CDCl$_3$): δ ppm 1.40 (t, 3H), 4.45 (q, 2H), 6.60-6.80 (t, 1H), 7.40-7.60 (m, 7H), 7.90-8.00 (m, 2H), 8.15 (m, 1H), 8.50-8.60 (m, 2H). 2-bromo-6-(difluoromethyl)pyridine. PM B. |
| 132 | Ethyl 5-(2-chloro-5-(3-chloro-6-(methoxymethyl)pyridin-2-yl)benzamido)-1-phenyl-1H-pyrazole-3-carboxylate | 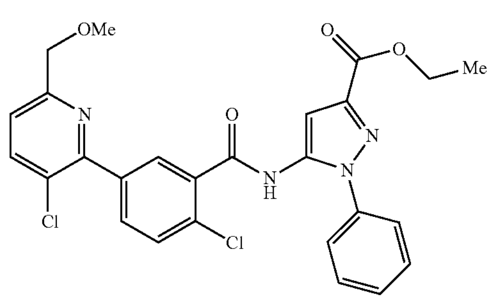 [SMILES: CCOC(=O)c1cc(NC(=O)c2cc(-c3nc(COC)ccc3Cl)ccc2Cl)n(-c2ccccc2)n1] | $^1$H NMR (400 MHz, CDCl$_3$): δ ppm 1.44 (t, 3H), 3.50 (s, 3H), 4.44 (q, 2H), 4.60 (s, 2H), 7.44 (d, 1H), 7.48 (d, 1H), 7.48-7.60 (m, 6H), 7.84 (d, 2H), 8.26 (s, 1H), 8.52 (s, 1H). 2,3-dichloro-6-(methoxymethyl)pyridine (Preparation 56). PM A. |

Example 133

5-{[2,4-dichloro-5-(pyridin-2-yl)benzoyl]amino}-N-(3,5-dimethyl-1H-pyrazol-4-yl)-1-phenyl-1H-pyrazole-3-carboxamide

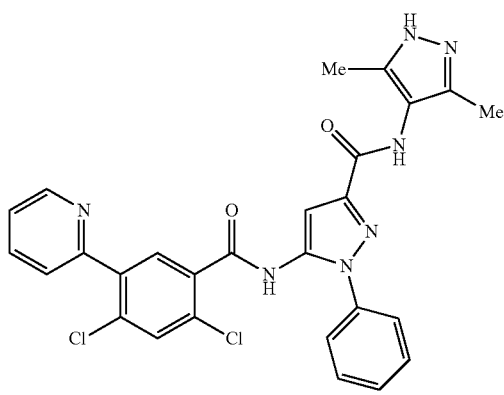 [SMILES: Cc1n[nH]c(C)c1NC(=O)c1cc(NC(=O)c2cc(-c3ccccn3)c(Cl)cc2Cl)n(-c2ccccc2)n1]

To a solution of 5-(2,4-dichloro-5-(pyridin-2-yl)benzamido)-1-phenyl-1H-pyrazole-3-carboxylic acid (Example 111, 110 mg, 0.24 mmol), 3,5-dimethyl-1H-pyrazol-4-amine (30 mg, 0.27 mmol) and DIPEA (0.17 mL, 0.97 mmol) in DMF (1.5 mL) was added 1-[bis(dimethylamino)methylene]-1H-1,2,3-triazolo[4,5-b]pyridinium 3-oxid hexafluorophosphate (101 mg, 0.26 mmol) and the reaction was stirred for 2 hours at room temperature. The reaction was concentrated in vacuo and the residue purified using Preparative HPLC to afford the title compound (65 mg, 49%).

$^1$H NMR (400 MHz, MeOH-d$_4$): δ ppm 2.19 (s, 6H), 7.10 (s, 1H), 7.47-7.52 (m, 4H), 7.64-7.74 (m, 5H), 7.97 (m, 1H), 8.68 (d, 1H).

LCMS Rt=2.59 minutes MS m/z 546 [M+H]$^+$

Example 134

5-{[2,4-dichloro-5-(3-fluoropyridin-2-yl)benzoyl]amino}-N-(2-hydroxy-2-methylpropyl)-1-phenyl-1H-pyrazole-3-carboxamide

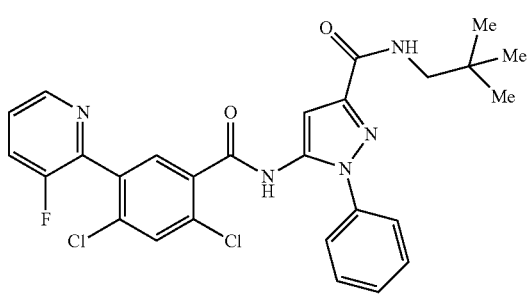 [SMILES: CC(C)(C)CNC(=O)c1cc(NC(=O)c2cc(-c3ncccc3F)c(Cl)cc2Cl)n(-c2ccccc2)n1]

5-(2,4-dichloro-5-(3-fluoropyridin-2-yl)benzamido)-1-phenyl-1H-pyrazole-3-carboxylic acid (Example 107, 78 g, 166 mmol) was sonicated in DMF (300 mL) with N,N-diisopropylethylamine (58 mL, 332 mmol) to give a clear solution, which was cooled to 10° C. TPTU (74 g, 249 mmol) was added portionwise and the mixture stirred at 10° C. for 20 minutes. A solution of 1-amino-2-methylpropan-2-ol (22.1 g, 249 mmol) in DMF (50 mL) was added dropwise at 10° C. and the mixture then allowed to warm to room temperature and stirred for 16 hours. The reaction mixture was partitioned between EtOAc (600 mL) and water (600 mL). The aqueous layer was separated and extracted with additional EtOAc (3×200 mL). The combined organic layers were washed with saturated aqueous ammonium chloride solution (300 mL), water (5×200 mL), dried (magnesium sulphate) and concentrated in vacuo to give an orange oil. The oil was treated with acetonitrile (300 mL) and the resulting solid collected by filtration, washed with acetonitrile and dried under vacuum to afford the title compound as a colourless solid (60 g, 66%).

$^1$H NMR (400 MHz, DMSO-d$_6$): δ ppm 1.09 (s, 6H), 3.21-3.22 (d, 2H), 4.63 (s, 1H), 6.93 (s, 1H), 7.45-7.49 (m, 1H), 7.50-7.55 (t, 2H), 7.58-7.65 (m, 3H), 7.69 (s, 1H), 7.80-7.85 (t, 1H), 7.87-7.95 (m, 2H), 8.56-8.58 (d, 1H), 10.89 (s, 1H).

MS m/z 540.45 [M−H]$^−$

Example 135

5-{[2-chloro-4-fluoro-5-(pyridin-2-yl)benzoyl]amino}-N-(2-hydroxyethyl)-1-phenyl-1H-Pyrazole-3-carboxamide

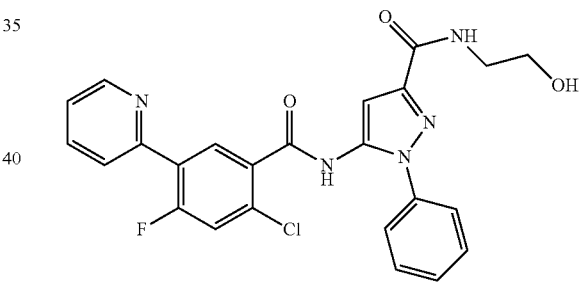

TPTU (510 mg, 1.72 mmol) and 5-(2-chloro-4-fluoro-5-(pyridin-2-yl)benzamido)-1-phenyl-1H-pyrazole-3-carboxylic acid (Example 108, 500 mg, 1.14 mmol) were dissolved in DMF (2.5 mL) at 0° C. N,N-diisopropylethylamine (0.6 mL, 3.43 mmol) was then added and the mixture stirred at 0° C. for 15 minutes. Ethanolamine (99.5 mL, 1.65 mmol) was then added and the mixture stirred at room temperature for 2 hours. The solvent was removed in vacuo and the resulting brown solid triturated with dichloromethane/TBME/heptane (4:2:0.5, 5 mL) to give a white solid, which was further triturated with MeOH (5 mL) to afford the title compound as a white solid (262 mg, 48%).

$^1$H NMR (400 MHz, DMSO-d$_6$): δ ppm 3.28-3.34 (q, 2H), 3.45-3.50 (q, 2H), 4.71-4.75 (t, 1H), 6.92 (s, 1H), 7.45-7.49 (m, 2H), 7.50-7.57 (t, 2H), 7.58-7.62 (d, 2H), 7.69-7.71 (d, 1H), 7.79-7.83 (d, 1H), 7.92-7.98 (t, 1H), 8.08-8.16 (m, 2H), 8.74-8.76 (d, 1H), 10.70-10.82 (br s, 1H).

MS m/z 478.66 [M−H]$^−$, 480.55 [M+H]$^+$

Example 136

2-{[(5-{[2-chloro-4-fluoro-5-(pyridin-2-yl)benzoyl]
amino}-1-phenyl-1H-pyrazol-3-yl)carbonyl]
amino}ethyl dihydrogen phosphate

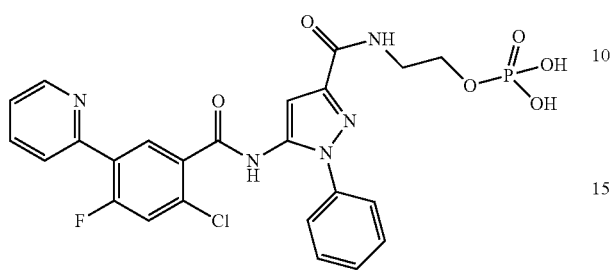

To a solution of 5-(2-chloro-4-fluoro-5-(pyridin-2-yl)benzamido)-1-phenyl-1H-pyrazole-3-carboxylic acid (Example 108, 3.00 g, 6.87 mmol), 2-aminoethyl di-tert-butyl phosphate (*Angew. Chem. Int. Ed.* 2011; 50(11):2606-2609) (2.5 g, 10.3 mmol) and N,N-diisopropylethylamine (3.55 g, 27.5 mmol) in DMF (20 mL) at 0° C., was added TPTU (3.06 g, 10.3 mmol) and the mixture stirred for 1 h at 0° C. and 2 h at room temperature. The mixture was diluted with EtOAc (150 mL), and washed sequentially with saturated aqueous ammonium chloride solution (150 mL), saturated aqueous sodium hydrogen carbonate solution (150 mL) and saturated aqueous ammonium chloride solution (150 mL) again. The organic layer was concentrated in vacuo, then azeotroped with dichloromethane (50 mL) and azeotroped with TBME (50 mL) to give di-tert-butyl (2-(5-(2-chloro-4-fluoro-5-(pyridin-2-yl)benzamido)-1-phenyl-1H-pyrazole-3-carboxamido)ethyl) phosphate as an off-white foam (3.8 g, 82%).

$^1$H NMR (400 MHz, CDCl$_3$): δ ppm 1.48 (s, 18H), 3.69-3.75 (q, 2H), 4.07-4.14 (q, 2H), 7.21-7.40 (m, 4H), 7.45-7.58 (m, 5H), 7.73-7.80 (m, 2H), 8.40 (s, 1H), 8.45-8.50 (d, 1H), 8.69-8.71 (d, 1H).

MS m/z 672.0 [M+H]$^+$

To a solution of di-tert-butyl (2-(5-(2-chloro-4-fluoro-5-(pyridin-2-yl)benzamido)-1-phenyl-1H-pyrazole-3-carboxamido)ethyl)phosphate (3.8 g, 5.65 mmol) in dichloromethane (30 mL) was added TFA (2 mL) and the mixture stirred at room temperature for 4 hours. The mixture was concentrated in vacuo and azeotroped twice with methanol (40 mL). The resulting oil was dissolved in methanol (10 mL) and treated with water (15 mL). The resulting precipitate was collected by filtration, then suspended in methanol (30 mL) and concentrated in vacuo, then azeotroped twice with methanol (30 mL). The resulting off-white solid was azeotroped with acetonitrile, then recrystallised from methanol and dried under vacuum for 72 hours to afford the title compound as a colourless solid.

$^1$H NMR (400 MHz, DMSO-d$_6$): δ ppm 3.45-3.50 (q, 2H), 3.87-3.95 (q, 2H), 6.92 (s, 1H), 7.43-7.49 (m, 2H), 7.50-7.58 (t, 2H), 7.59-7.62 (d, 2H), 7.70-7.73 (d, 1H), 7.79-7.82 (d, 1H), 7.90-7.98 (t, 1H), 8.08-8.12 (d, 1H), 8.35-8.40 (m, 1H), 8.73-8.77 (d, 1H), 10.80 (s, 1H).

MS m/z 560.39 [M+H]$^+$

Example 137

5-{[2,4-dichloro-5-(3-fluoropyridin-2-yl)benzoyl]
amino}-N-[1-(methylcarbamoyl)cyclopropyl]-1-
phenyl-1H-pyrazole-3-carboxamide

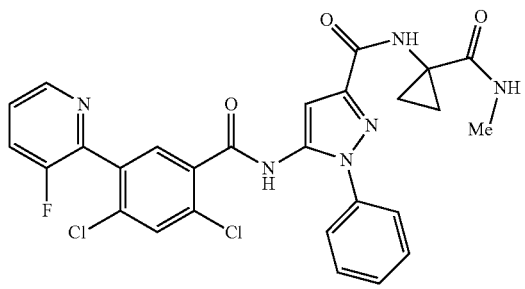 [SMILES: CNC(=O)C1(NC(=O)c2cc(NC(=O)c3cc(-c4ncccc4F)c(Cl)cc3Cl)n(-c3ccccc3)n2)CC1]

To a solution of 5-(2,4-dichloro-5-(3-fluoropyridin-2-yl)benzamido)-1-phenyl-1H-pyrazole-3-carboxylic acid (Example 107, 961 mg, 2.04 mmol) in DMF (20 mL), were added N,N-diisopropylethylamine (0.8 mL, 5.5 mmol) and TPTU (848 mg, 2.85 mmol) and the mixture stirred at room temperature for 5 minutes. 1-Amino-N-methylcyclopropanecarboxamide (PCT Int. Appl., 2008051547) (300 mg, 2.65 mmol) was then added and the mixture stirred for 30 minutes. The reaction mixture was diluted with water (100 mL) and extracted with EtOAc (3×20 mL). The combined organic layers were washed with saturated aqueous brine solution, dried (magnesium sulphate) and concentrated in vacuo. The residue was purified by column chromatography over silica gel, eluting with EtOAc to afford the title compound as a white solid (916 mg, 79%). Crystallisation by vapour diffusion using methanol as the solvent and acetonitrile as the anti-solvent also afforded the title compound as crystalline colourless needles.

$^1$H NMR (400 MHz, CDCl$_3$): δ ppm 1.11-1.13 (t, 2H), 1.65-1.67 (t, 2H), 2.82 (d, 3H), 6.50-6.55 (m, 1H), 7.34-7.38 (d, 2H), 7.41-7.43 (m, 1H), 7.48-7.60 (m, 7H), 8.00 (s, 1H), 8.43 (s, 1H), 8.52 (s, 1H).

MS m/z 565.70 [M−H]$^-$, 567.60 [M+H]$^+$

Examples 138-841

The following Examples 138-841 were prepared according to the general synthetic schemes and methods outlined above, using the corresponding acid and appropriate amine, in an amide coupling reaction, followed by appropriate deprotection where required.

| Example Number | Name | Data |
|---|---|---|
| 138 | N-[(6-aminopyridin-3-yl)methyl-d$_2$]-5-{[2-chloro-4-fluoro-5-(pyridin-2-yl)benzoyl]amino}-1-phenyl-1H-pyrazole-3-carboxamide | LCMS Rt = 2.36 minutes<br>MS m/z 542.71 [M − H]$^-$ |
| 139 | 2-{[(5-{[2,4-dichloro-5-(3-fluoropyridin-2-yl)benzoyl]amino}-1-phenyl-1H-pyrazol-3-yl)carbonyl]amino}ethyl dihydrogen phosphate | LCMS Rt = 2.18 minutes<br>MS m/z 594.47 [M]$^+$ |

| Example Number | Name | Data |
|---|---|---|
| 140 | 5-{[2-chloro-5-(pyridin-2-yl)-4-(trifluoromethyl)benzoyl]amino}-N-(2-hydroxyethyl)-1-phenyl-1H-pyrazole-3-carboxamide | LCMS Rt = 2.55 minutes MS m/z 530.37 [M + H]+ |
| 141 | N-[(3-aminooxetan-3-yl)methyl]-5-{[2,4-dichloro-5-(3-fluoropyridin-2-yl)benzoyl]amino}-1-phenyl-1H-pyrazole-3-carboxamide | LCMS Rt = 2.54 minutes MS m/z 555.00 [M]+ |
| 142 | 5-{[2-chloro-4-fluoro-5-(3-fluoropyridin-2-yl)benzoyl]amino}-N-(oxetan-3-yl)-1-phenyl-1H-pyrazole-3-carboxamide | LCMS Rt = 2.74 minutes MS m/z 510.26 [M + H]+ |
| 143 | 5-{[2-chloro-4-fluoro-5-(3-fluoropyridin-2-yl)benzoyl]amino}-N-[(3S,4R)-4-hydroxytetrahydrofuran-3-yl]-1-phenyl-1H-pyrazole-3-carboxamide | LCMS Rt = 2.54 minutes MS m/z 540.22 [M + H]+ |
| 144 | 5-(2,4-dichloro-5-(3-fluoropyridin-2-yl)benzamido)-N-((3S,4R)-3-hydroxytetrahydro-2H-pyran-4-yl)-1-phenyl-1H-pyrazole-3-carboxamide | LCMS Rt = 2.62 minutes MS m/z 570.21 [M]+ |
| 145 | 2,4-dichloro-5-(3-fluoropyridin-2-yl)-N-[1-phenyl-3-(piperazin-1-ylcarbonyl)-1H-pyrazol-5-yl]benzamide | LCMS Rt = 2.50 minutes MS m/z 539.32 [M]+ |
| 146 | 5-{[2-chloro-4-methoxy-5-(pyridin-2-yl)benzoyl]amino}-N-(3,5-dimethyl-1H-pyrazol-4-yl)-1-phenyl-1H-pyrazole-3-carboxamide | LCMS Rt = 2.57 minutes MS m/z 542.55 [M]+ |
| 147 | N-[(5-amino-1H-pyrazol-4-yl)methyl]-5-{[2,4-dichloro-5-(3-fluoropyridin-2-yl)benzoyl]amino}-1-phenyl-1H-pyrazole-3-carboxamide | LCMS Rt = 2.51 minutes MS m/z 565.26 [M]+ |
| 148 | 5-{[2-chloro-5-(3-fluoropyridin-2-yl)-4-methylbenzoyl]amino}-N-(2-hydroxy-2-methylpropyl)-1-phenyl-1H-pyrazole-3-carboxamide | LCMS Rt = 2.77 minutes MS m/z 520.31 [M − H]− |
| 149 | N-(2-aminoethyl)-5-{[2-chloro-5-(3-fluoropyridin-2-yl)-4-methylbenzoyl]amino}-1-phenyl-1H-pyrazole-3-carboxamide | LCMS Rt = 2.41 minutes MS m/z 491.22 [M − H]− |
| 150 | 5-{[2-chloro-5-(3-fluoropyridin-2-yl)-4-methoxybenzoyl]amino}-1-phenyl-N-(1H-pyrazol-4-ylmethyl)-1H-pyrazole-3-carboxamide | LCMS Rt = 2.47 minutes MS m/z 546.39 [M + H]+ |
| 151 | N-[(6-aminopyridin-3-yl)methyl]-5-{[2-chloro-4-fluoro-5-(3-fluoropyridin-2-yl)benzoyl]amino}-1-phenyl-1H-pyrazole-3-carboxamide | LCMS Rt = 2.60 minutes MS m/z 560.31 [M + H]+ |
| 152 | 5-{[2,4-dichloro-5-(3-fluoropyridin-2-yl)benzoyl]amino}-N-[(3S,4R)-4-hydroxytetrahydrofuran-3-yl]-1-phenyl-1H-pyrazole-3-carboxamide | LCMS Rt = 2.78 minutes MS m/z 556.13 [M]+ |
| 153 | 5-{[2,4-dichloro-5-(3-fluoropyridin-2-yl)benzoyl]amino}-N-[(3R,4S)-4-hydroxytetrahydrofuran-3-yl]-1-phenyl-1H-pyrazole-3-carboxamide | LCMS Rt = 2.79 minutes MS m/z 556.14 [M]+ |
| 154 | 2,4-dichloro-5-(3-fluoropyridin-2-yl)-N-{3-[(3-oxopiperazin-1-yl)carbonyl]-1-phenyl-1H-pyrazol-5-yl}benzamide | LCMS Rt = 2.59 minutes MS m/z 553.15 [M]+ |
| 155 | N-[(3-amino-1-methyl-1H-pyrazol-5-yl)methyl]-5-{[2,4-dichloro-5-(3-fluoropyridin-2-yl)benzoyl]amino}-1-phenyl-1H-pyrazole-3-carboxamide | LCMS Rt = 2.63 minutes MS m/z 579.23 [M]+ |
| 156 | N-[(3-amino-1H-pyrazol-4-yl)methyl]-5-{[2-chloro-4-fluoro-5-(3-fluoropyridin-2-yl)benzoyl]amino}-1-phenyl-1H-pyrazole-3-carboxamide | LCMS Rt = 2.50 minutes MS m/z 549.16 [M + H]+ |
| 157 | N-(2-aminoethyl)-5-{[2-chloro-4-fluoro-5-(3-fluoropyridin-2-yl)benzoyl]amino}-1-phenyl-1H-pyrazole-3-carboxamide | LCMS Rt = 2.35 minutes MS m/z 495.40 [M − H]− |
| 158 | 5-{[2,4-dichloro-5-(3-fluoropyridin-2-yl)benzoyl]amino}-N-[(2-methyl-1H-imidazol-5-yl)methyl]-1-phenyl-1H-pyrazole-3-carboxamide | LCMS Rt = 2.59 minutes MS m/z 564.17 [M]+ |
| 159 | N-(azetidin-3-yl)-5-{[2,4-dichloro-5-(3-fluoropyridin-2-yl)benzoyl]amino}-1-phenyl-1H-pyrazole-3-carboxamide | LCMS Rt = 2.44 minutes MS m/z 525.18 [M]+ |
| 160 | 5-{[2,4-dichloro-5-(3-fluoropyridin-2-yl)benzoyl]amino}-N-[(2R)-2-hydroxy-3-methoxypropyl]-1-phenyl-1H-pyrazole-3-carboxamide | LCMS Rt = 2.69 minutes MS m/z 558.17 [M]+ |
| 161 | 5-{[2,4-dichloro-5-(3-fluoropyridin-2-yl)benzoyl]amino}-N-[2-(2-hydroxyethoxy)ethyl]-1-phenyl-1H-pyrazole-3-carboxamide | LCMS Rt = 2.63 minutes MS m/z 558.18 [M]+ |
| 162 | 5-{[2,4-dichloro-5-(3-fluoropyridin-2-yl)benzoyl]amino}-N-[(2S)-2-hydroxy-3-methoxypropyl]-1-phenyl-1H-pyrazole-3-carboxamide | LCMS Rt = 2.68 minutes MS m/z 558.22 [M]+ |

-continued

| Example Number | Name | Data |
|---|---|---|
| 163 | N-[(2S)-2-amino-3-methoxypropyl]-5-{[2,4-dichloro-5-(3-fluoropyridin-2-yl)benzoyl]amino}-1-phenyl-1H-pyrazole-3-carboxamide | LCMS Rt = 2.54 minutes MS m/z 557.5 [M]+ |
| 164 | N-[(2S)-2-amino-3-hydroxypropyl]-5-{[2,4-dichloro-5-(3-fluoropyridin-2-yl)benzoyl]amino}-1-phenyl-1H-pyrazole-3-carboxamide | LCMS Rt = 2.39 minutes MS m/z 543.98 [M]+ |
| 165 | 5-{[2,4-dichloro-5-(3-fluoropyridin-2-yl)benzoyl]amino}-N-(3,5-dimethyl-1H-pyrazol-4-yl)-1-phenyl-1H-pyrazole-3-carboxamide | LCMS Rt = 2.75 minutes MS m/z 564.15 [M]+ |
| 166 | 5-{[2,4-dichloro-5-(3-fluoropyridin-2-yl)benzoyl]amino}-N-[(2R)-2,3-dihydroxypropyl]-1-phenyl-1H-pyrazole-3-carboxamide | LCMS Rt = 2.61 minutes MS m/z 544.19 [M]+ |
| 167 | 5-{[2,4-dichloro-5-(3-fluoropyridin-2-yl)benzoyl]amino}-N-[(2S)-2,3-dihydroxypropyl]-1-phenyl-1H-pyrazole-3-carboxamide | LCMS Rt = 2.53 minutes MS m/z 544.12 [M]+ |
| 168 | 5-{[2,4-dichloro-5-(pyridin-2-yl)benzoyl]amino}-N-(trans-4-hydroxycyclohexyl)-1-phenyl-1H-pyrazole-3-carboxamide | LCMS Rt = 2.59 minutes MS m/z 550.18 [M]+ |
| 169 | 5-{[2,4-dichloro-5-(3-fluoropyridin-2-yl)benzoyl]amino}-N-[(3-hydroxyoxetan-3-yl)methyl]-1-phenyl-1H-pyrazole-3-carboxamide | LCMS Rt = 2.65 minutes MS m/z 556.05 [M]+ |
| 170 | 5-{[2,4-dichloro-5-(3-fluoropyridin-2-yl)benzoyl]amino}-N-(trans-4-hydroxycyclohexyl)-1-phenyl-1H-pyrazole-3-carboxamide | LCMS Rt = 2.81 minutes MS m/z 568.24 [M]+ |
| 171 | N-(2-aminoethyl)-5-{[2,4-dichloro-5-(3-fluoropyridin-2-yl)benzoyl]amino}-1-phenyl-1H-pyrazole-3-carboxamide | LCMS Rt = 2.53 minutes MS m/z 513.06 [M]+ |
| 172 | N-[(3-amino-1H-pyrazol-5-yl)methyl]-5-{[2,4-dichloro-5-(3-fluoropyridin-2-yl)benzoyl]amino}-1-phenyl-1H-pyrazole-3-carboxamide | LCMS Rt = 2.60 minutes MS m/z 565.14 [M]+ |
| 173 | 5-{[2,4-dichloro-5-(3-fluoropyridin-2-yl)benzoyl]amino}-1-phenyl-1H-pyrazole-3-carboxylic acid | LCMS Rt = 2.23 minutes MS m/z 471.00 [M + H]+ |
| 174 | 5-{[2,4-dichloro-5-(3-fluoropyridin-2-yl)benzoyl]amino}-1-phenyl-N-(2H-1,2,3-triazol-4-ylmethyl)-1H-pyrazole-3-carboxamide | LCMS Rt = 2.73 minutes MS m/z 551.16 [M]+ |
| 175 | 5-{[2-chloro-4-fluoro-5-(3-fluoropyridin-2-yl)benzoyl]amino}-N-[(5-methyl-1H-pyrazol-4-yl)methyl]-1-phenyl-1H-pyrazole-3-carboxamide | LCMS Rt = 2.62 minutes MS m/z 548.19 [M + H]+ |
| 176 | 5-{[2,4-dichloro-5-(5-fluoropyridin-2-yl)benzoyl]amino}-1-phenyl-N-(1H-pyrazol-4-ylmethyl)-1H-pyrazole-3-carboxamide | LCMS Rt = 2.68 minutes MS m/z 551.29 [M + H]+ |
| 177 | 5-{[2-chloro-4-fluoro-5-(5-fluoropyridin-2-yl)benzoyl]amino}-1-phenyl-N-(1H-pyrazol-4-ylmethyl)-1H-pyrazole-3-carboxamide | LCMS Rt = 2.66 minutes MS m/z 534.21 [M + H]+ |
| 178 | 5-{[2-chloro-4-fluoro-5-(pyridin-2-yl)benzoyl]amino}-1-phenyl-N-(1H-pyrazol-4-ylmethyl)-1H-pyrazole-3-carboxamide | LCMS Rt = 2.56 minutes MS m/z 516.15 [M + H]+ |
| 179 | 5-{[2,4-dichloro-5-(3-fluoropyridin-2-yl)benzoyl]amino}-1-phenyl-N-(1H-pyrazol-4-ylmethyl)-1H-pyrazole-3-carboxamide | LCMS Rt = 2.63 minutes MS m/z 550.18 [M]+ |
| 180 | 5-{[2,4-dichloro-5-(3-fluoropyridin-2-yl)benzoyl]amino}-1-phenyl-N-(1H-pyrazol-3-ylmethyl)-1H-pyrazole-3-carboxamide | LCMS Rt = 2.73 minutes MS m/z 550.16 [M]+ |
| 181 | 5-{[2,4-dichloro-5-(pyridin-2-yl)benzoyl]amino}-N-[(3-hydroxyoxetan-3-yl)methyl]-1-phenyl-1H-pyrazole-3-carboxamide | LCMS Rt = 2.51 minutes MS m/z 538.12 [M]+ |
| 182 | 5-{[2,4-dichloro-5-(pyridin-2-yl)benzoyl]amino}-N-[3-(hydroxymethyl)oxetan-3-yl]-1-phenyl-1H-pyrazole-3-carboxamide | LCMS Rt = 2.65 minutes MS m/z 538.27 [M]+ |
| 183 | 5-{[2-chloro-4-fluoro-5-(3-fluoropyridin-2-yl)benzoyl]amino}-N-[(3-hydroxyoxetan-3-yl)methyl]-1-phenyl-1H-pyrazole-3-carboxamide | LCMS Rt = 2.46 minutes MS m/z 540.15 [M + H]+ |
| 184 | N-[(3-aminooxetan-3-yl)methyl]-5-{[2,4-dichloro-5-(pyridin-2-yl)benzoyl]amino}-1-phenyl-1H-pyrazole-3-carboxamide | LCMS Rt = 2.57 minutes MS m/z 537.20 [M]+ |
| 185 | 5-{[2-chloro-4-(difluoromethoxy)-5-(pyridin-2-yl)benzoyl]amino}-1-phenyl-1H-pyrazole-3-carboxamide | LCMS Rt = 2.63 minutes MS m/z 484.15 [M + H]+ |

-continued

| Example Number | Name | Data |
|---|---|---|
| 186 | 5-{[2-chloro-4-cyclopropyl-5-(pyridin-2-yl)benzoyl]amino}-1-phenyl-1H-pyrazole-3-carboxamide | LCMS Rt = 2.72 minutes MS m/z 458.17 [M + H]+ |
| 187 | 5-{[2,4-dichloro-5-(pyridin-2-yl)benzoyl]amino}-N-(1,2-oxazol-5-ylmethyl)-1-phenyl-1H-pyrazole-3-carboxamide | MS m/z 533.0 [M]+ |
| 188 | 5-{[2,4-dichloro-5-(pyridin-2-yl)benzoyl]amino}-N-[(3-fluorooxetan-3-yl)methyl]-1-phenyl-1H-pyrazole-3-carboxamide | MS m/z 540.6 [M]+ |
| 189 | 5-{[2,4-dichloro-5-(pyridin-2-yl)benzoyl]amino}-N-[(1-methyl-1H-1,2,3-triazol-5-yl)methyl]-1-phenyl-1H-pyrazole-3-carboxamide | MS m/z 547.2 [M]+ |
| 190 | N-(2-amino-2-oxoethyl)-5-{[2,4-dichloro-5-(pyridin-2-yl)benzoyl]amino}-1-phenyl-1H-pyrazole-3-carboxamide | MS m/z 509.2 [M]+ |
| 191 | 5-{[2,4-dichloro-5-(pyridin-2-yl)benzoyl]amino}-N-[(1-hydroxycyclopropyl)methyl]-1-phenyl-1H-pyrazole-3-carboxamide | MS m/z 522.2 [M]+ |
| 192 | 5-{[2,4-dichloro-5-(pyridin-2-yl)benzoyl]amino}-N-[2-(methylamino)-2-oxoethyl]-1-phenyl-1H-pyrazole-3-carboxamide | LCMS Rt = 2.47 minutes MS m/z 523.22 [M]+ |
| 193 | 5-{[2,4-dichloro-5-(pyridin-2-yl)benzoyl]amino}-N-(3-hydroxy-3-methylbutyl)-1-phenyl-1H-pyrazole-3-carboxamide | LCMS Rt = 2.64 minutes MS m/z 538.26 [M]+ |
| 194 | 5-{[2,4-dichloro-5-(pyridin-2-yl)benzoyl]amino}-N-(oxetan-3-ylmethyl)-1-phenyl-1H-pyrazole-3-carboxamide | LCMS Rt = 2.55 minutes MS m/z 522.15 [M]+ |
| 195 | 5-{[2,4-dichloro-5-(pyridin-2-yl)benzoyl]amino}-N-(oxetan-3-yl)-1-phenyl-1H-pyrazole-3-carboxamide | LCMS Rt = 2.60 minutes MS m/z 508.23 [M]+ |
| 196 | 5-{[2,4-dichloro-5-(pyridin-2-yl)benzoyl]amino}-N-(trans-4-hydroxy-4-methylcyclohexyl)-1-phenyl-1H-pyrazole-3-carboxamide | LCMS Rt = 2.78 minutes MS m/z 564.25 [M]+ |
| 197 | 5-{[2,4-dichloro-5-(pyridin-2-yl)benzoyl]amino}-1-phenyl-N-(4H-1,2,4-triazol-3-ylmethyl)-1H-pyrazole-3-carboxamide | LCMS Rt = 2.54 minutes MS m/z 533.15 [M]+ |
| 198 | 5-{[2,4-dichloro-5-(pyridin-2-yl)benzoyl]amino}-N-{[3-(hydroxymethyl)oxetan-3-yl]methyl}-1-phenyl-1H-pyrazole-3-carboxamide | LCMS Rt = 2.65 minutes MS m/z 552.21 [M]+ |
| 199 | 5-{[2,4-dichloro-5-(pyridin-2-yl)benzoyl]amino}-N-[(2R)-2-hydroxypropyl]-1-phenyl-1H-pyrazole-3-carboxamide | LCMS Rt = 2.65 minutes MS m/z 510.25 [M]+ |
| 200 | 5-{[2,4-dichloro-5-(pyridin-2-yl)benzoyl]amino}-N-[(2R)-1-hydroxypropan-2-yl]-1-phenyl-1H-pyrazole-3-carboxamide | LCMS Rt = 2.67 minutes MS m/z 510.25 [M]+ |
| 201 | 5-{[2-chloro-4-fluoro-5-(3-fluoropyridin-2-yl)benzoyl]amino}-N-(trans-4-hydroxycyclohexyl)-1-phenyl-1H-pyrazole-3-carboxamide | LCMS Rt = 2.80 minutes MS m/z 552.04 [M + H]+ |
| 202 | 5-{[2-chloro-4-fluoro-5-(3-fluoropyridin-2-yl)benzoyl]amino}-N-[(2R)-2-hydroxypropyl]-1-phenyl-1H-pyrazole-3-carboxamide | LCMS Rt = 2.75 minutes MS m/z 512.01 [M + H]+ |
| 203 | 5-{[2-chloro-4-fluoro-5-(3-fluoropyridin-2-yl)benzoyl]amino}-N-[(2R)-2,3-dihydroxypropyl]-1-phenyl-1H-pyrazole-3-carboxamide | LCMS Rt = 2.46 minutes MS m/z 528.25 [M + H]+ |
| 204 | 5-{[2-chloro-4-fluoro-5-(3-fluoropyridin-2-yl)benzoyl]amino}-N-(1,2-oxazol-3-ylmethyl)-1-phenyl-1H-pyrazole-3-carboxamide | LCMS Rt = 2.85 minutes MS m/z 535.18 [M + H]+ |
| 205 | 5-{[2-chloro-4-fluoro-5-(3-fluoropyridin-2-yl)benzoyl]amino}-1-phenyl-N-(1H-pyrazol-5-ylmethyl)-1H-pyrazole-3-carboxamide | LCMS Rt = 2.66 minutes MS m/z 534.20 [M + H]+ |
| 206 | 5-{[2-chloro-4-fluoro-5-(3-fluoropyridin-2-yl)benzoyl]amino}-N-[(2S)-2,3-dihydroxypropyl]-1-phenyl-1H-pyrazole-3-carboxamide | LCMS Rt = 2.46 minutes MS m/z 526.19 [M − H]− |
| 207 | N-[(6-aminopyridin-2-yl)methyl]-5-{[2-chloro-4-fluoro-5-(3-fluoropyridin-2-yl)benzoyl]amino}-1-phenyl-1H-pyrazole-3-carboxamide | LCMS Rt = 2.81 minutes MS m/z 560.26 [M + H]+ |
| 208 | N-[(2-aminopyridin-3-yl)methyl]-5-{[2-chloro-4-fluoro-5-(3-fluoropyridin-2-yl)benzoyl]amino}-1-phenyl-1H-pyrazole-3-carboxamide | LCMS Rt = 2.83 minutes MS m/z 558.16 [M − H]− |
| 209 | N-[(5-amino-1H-pyrazol-4-yl)methyl]-5-{[2-chloro-5-(3-fluoropyridin-2-yl)benzoyl]amino}-1-phenyl-1H-pyrazole-3-carboxamide | LCMS Rt = 2.51 minutes MS m/z 531.27 [M + H]+ |
| 210 | N-[(3-amino-1-methyl-1H-pyrazol-5-yl)methyl]-5-{[2-chloro-5-(3-fluoropyridin-2-yl)benzoyl]amino}-1-phenyl-1H-pyrazole-3-carboxamide | LCMS Rt = 2.43 minutes MS m/z 545.18 [M + H]+ |

-continued

| Example Number | Name | Data |
|---|---|---|
| 211 | 5-{[2-chloro-4-fluoro-5-(pyridin-2-yl)benzoyl]amino}-1-phenyl-N-(1H-pyrazol-5-ylmethyl)-1H-pyrazole-3-carboxamide | LCMS Rt = 2.53 minutes MS m/z 516.27 [M + H]+ |
| 212 | N-[(5-amino-1H-pyrazol-3-yl)methyl]-5-{[2,4-dichloro-5-(pyridin-2-yl)benzoyl]amino}-1-phenyl-1H-pyrazole-3-carboxamide | LCMS Rt = 2.56 minutes MS m/z 547.23 [M]+ |
| 213 | 5-{[2-chloro-4-fluoro-5-(3-fluoropyridin-2-yl)benzoyl]amino}-N-(trans-4-hydroxy-4-methylcyclohexyl)-1-phenyl-1H-pyrazole-3-carboxamide | LCMS Rt = 2.89 minutes MS m/z 566.07 [M]+ |
| 214 | 5-{[2-chloro-4-fluoro-5-(3-fluoropyridin-2-yl)benzoyl]amino}-1-phenyl-N-(1H-1,2,3-triazol-5-ylmethyl)-1H-pyrazole-3-carboxamide | LCMS Rt = 2.44 minutes MS m/z 535.18 [M + H]+ |
| 215 | 5-{[2-chloro-4-fluoro-5-(3-fluoropyridin-2-yl)benzoyl]amino}-N-(2-hydroxyethyl)-1-phenyl-1H-pyrazole-3-carboxamide | LCMS Rt = 2.55 minutes MS m/z 496.26 [M − H]− |
| 216 | 5-{[2-chloro-4-fluoro-5-(3-fluoropyridin-2-yl)benzoyl]amino}-N-(3-hydroxypropyl)-1-phenyl-1H-pyrazole-3-carboxamide | LCMS Rt = 2.59 minutes MS m/z 512.22 [M + H]+ |
| 217 | 5-{[2-chloro-5-(3-fluoropyridin-2-yl)benzoyl]amino}-N-[(5-methyl-1H-1,2,3-triazol-4-yl)methyl]-1-phenyl-1H-pyrazole-3-carboxamide | LCMS Rt = 2.48 minutes MS m/z 531.26 [M + H]+ |
| 218 | N-[(4-amino-1H-pyrazol-3-yl)methyl]-5-{[2,4-dichloro-5-(pyridin-2-yl)benzoyl]amino}-1-phenyl-1H-pyrazole-3-carboxamide | MS m/z 547.2 [M]+ |
| 219 | 5-{[2,4-dichloro-5-(pyridin-2-yl)benzoyl]amino}-1-phenyl-N-(pyridazin-3-ylmethyl)-1H-pyrazole-3-carboxamide | MS m/z 544.1 [M]+ |
| 220 | 5-{[2,4-dichloro-5-(pyridin-2-yl)benzoyl]amino}-N-(3,5-dimethyl-1H-pyrazol-4-yl)-1-phenyl-1H-pyrazole-3-carboxamide | MS m/z 546.21 [M]+ |
| 221 | N-(trans-3-aminocyclobutyl)-5-{[2-chloro-4-fluoro-5-(pyridin-2-yl)benzoyl]amino}-1-phenyl-1H-pyrazole-3-carboxamide | LCMS Rt = 1.38 minutes MS m/z 505.05 [M + H]+ |
| 222 | N-[(2-aminopyridin-4-yl)methyl]-5-{[2-chloro-5-(3-fluoropyridin-2-yl)benzoyl]amino}-1-phenyl-1H-pyrazole-3-carboxamide | MS m/z 542.1 [M + H]+ |
| 223 | 5-{[2-chloro-5-(3-fluoropyridin-2-yl)benzoyl]amino}-1-phenyl-N-(pyridazin-4-ylmethyl)-1H-pyrazole-3-carboxamide | MS m/z 528.2 [M + H]+ |
| 224 | N-[(6-aminopyridin-2-yl)methyl]-5-{[2-chloro-5-(3-fluoropyridin-2-yl)benzoyl]amino}-1-phenyl-1H-pyrazole-3-carboxamide | LCMS Rt = 1.42 minutes MS m/z 542.29 [M + H]+ |
| 225 | 5-{[2-chloro-5-(3-fluoropyridin-2-yl)benzoyl]amino}-N-(oxetan-3-yl)-1-phenyl-1H-pyrazole-3-carboxamide | LCMS Rt = 1.59 minutes MS m/z 492.29 [M + H]+ |
| 226 | 5-{[2-chloro-5-(3-fluoropyridin-2-yl)benzoyl]amino}-N-(3-hydroxypropyl)-1-phenyl-1H-pyrazole-3-carboxamide | LCMS Rt = 1.55 minutes MS m/z 494.29 [M + H]+ |
| 227 | 5-{[2-chloro-5-(3-fluoropyridin-2-yl)benzoyl]amino}-N-(2-methoxyethyl)-1-phenyl-1H-pyrazole-3-carboxamide | LCMS Rt = 1.62 minutes MS m/z 494.33 [M + H]+ |
| 228 | 5-{[2-chloro-5-(3-fluoropyridin-2-yl)benzoyl]amino}-N-[1-(hydroxymethyl)cyclopropyl]-1-phenyl-1H-pyrazole-3-carboxamide | LCMS Rt = 1.57 minutes MS m/z 506.3 [M + H]+ |
| 229 | 5-{[2-chloro-5-(3-fluoropyridin-2-yl)benzoyl]amino}-N-(trans-3-hydroxycyclobutyl)-1-phenyl-1H-pyrazole-3-carboxamide | LCMS Rt = 1.55 minutes MS m/z 506.32 [M + H]+ |
| 230 | 5-{[2-chloro-5-(3-fluoropyridin-2-yl)benzoyl]amino}-1-phenyl-N-(tetrahydrofuran-3-yl)-1H-pyrazole-3-carboxamide | LCMS Rt = 1.61 minutes MS m/z 506.24 [M + H]+ |
| 231 | 5-{[2-chloro-5-(3-fluoropyridin-2-yl)benzoyl]amino}-N-(oxetan-2-ylmethyl)-1-phenyl-1H-pyrazole-3-carboxamide | LCMS Rt = 1.61 minutes MS m/z 506.32 [M + H]+ |
| 232 | 5-{[2-chloro-5-(3-fluoropyridin-2-yl)benzoyl]amino}-N-(1,3-dihydroxypropan-2-yl)-1-phenyl-1H-pyrazole-3-carboxamide | LCMS Rt = 1.5 minutes MS m/z 510.27 [M + H]+ |
| 233 | 5-{[2-chloro-5-(3-fluoropyridin-2-yl)benzoyl]amino}-1-phenyl-N-(tetrahydro-2H-pyran-3-yl)-1H-pyrazole-3-carboxamide | LCMS Rt = 1.65 minutes MS m/z 520.36 [M + H]+ |
| 234 | 5-{[2-chloro-5-(3-fluoropyridin-2-yl)benzoyl]amino}-1-phenyl-N-(tetrahydrofuran-3-ylmethyl)-1H-pyrazole-3-carboxamide | LCMS Rt = 1.63 minutes MS m/z 520.36 [M + H]+ |
| 235 | 5-{[2-chloro-5-(3-fluoropyridin-2-yl)benzoyl]amino}-N-[trans-3-(hydroxymethyl)cyclobutyl]-1-phenyl-1H-pyrazole-3-carboxamide | LCMS Rt = 1.58 minutes MS m/z 520.17 [M + H]+ |

-continued

| Example Number | Name | Data |
|---|---|---|
| 236 | 5-{[2-chloro-5-(3-fluoropyridin-2-yl)benzoyl]amino}-N-[(1-hydroxycyclobutyl)methyl]-1-phenyl-1H-pyrazole-3-carboxamide | LCMS Rt = 1.61 minutes MS m/z 520.32 [M + H]$^+$ |
| 237 | 5-{[2-chloro-5-(3-fluoropyridin-2-yl)benzoyl]amino}-1-phenyl-N-(tetrahydro-2H-pyran-4-yl)-1H-pyrazole-3-carboxamide | LCMS Rt = 1.63 minutes MS m/z 520.36 [M + H]$^+$ |
| 238 | 5-{[2-chloro-5-(3-fluoropyridin-2-yl)benzoyl]amino}-1-phenyl-N-(tetrahydrofuran-2-ylmethyl)-1H-pyrazole-3-carboxamide | LCMS Rt = 1.66 minutes MS m/z 520.31 [M + H]$^+$ |
| 239 | 5-{[2-chloro-5-(3-fluoropyridin-2-yl)benzoyl]amino}-N-(4-hydroxy-2-methylbutan-2-yl)-1-phenyl-1H-pyrazole-3-carboxamide | LCMS Rt = 1.62 minutes MS m/z 522.38 [M + H]$^+$ |
| 240 | 5-{[2-chloro-5-(3-fluoropyridin-2-yl)benzoyl]amino}-N-[(3-fluorooxetan-3-yl)methyl]-1-phenyl-1H-pyrazole-3-carboxamide | LCMS Rt = 1.61 minutes MS m/z 524.31 [M + H]$^+$ |
| 241 | 5-{[2-chloro-5-(3-fluoropyridin-2-yl)benzoyl]amino}-N-[(1-methyl-1H-imidazol-5-yl)methyl]-1-phenyl-1H-pyrazole-3-carboxamide | LCMS Rt = 1.41 minutes MS m/z 530.2 [M + H]$^+$ |
| 242 | 5-{[2-chloro-5-(3-fluoropyridin-2-yl)benzoyl]amino}-N-[(4-methyl-1H-imidazol-2-yl)methyl]-1-phenyl-1H-pyrazole-3-carboxamide | LCMS Rt = 1.42 minutes MS m/z 528.26 [M − H]$^-$ |
| 243 | 5-{[2-chloro-5-(3-fluoropyridin-2-yl)benzoyl]amino}-N-[(1-methyl-1H-imidazol-4-yl)methyl]-1-phenyl-1H-pyrazole-3-carboxamide | LCMS Rt = 1.41 minutes MS m/z 530.3 [M + H]$^+$ |
| 244 | 5-{[2-chloro-5-(3-fluoropyridin-2-yl)benzoyl]amino}-N-[(1-methyl-1H-imidazol-2-yl)methyl]-1-phenyl-1H-pyrazole-3-carboxamide | LCMS Rt = 1.41 minutes MS m/z 530.3 [M + H]$^+$ |
| 245 | 5-{[2-chloro-5-(3-fluoropyridin-2-yl)benzoyl]amino}-1-phenyl-N-[2-(1H-1,2,4-triazol-5-yl)ethyl]-1H-pyrazole-3-carboxamide | LCMS Rt = 1.54 minutes MS m/z 531.32 [M + H]$^+$ |
| 246 | 5-{[2-chloro-5-(3-fluoropyridin-2-yl)benzoyl]amino}-N-[(4-methyl-1,2,5-oxadiazol-3-yl)methyl]-1-phenyl-1H-pyrazole-3-carboxamide | LCMS Rt = 1.66 minutes MS m/z 532.16 [M + H]$^+$ |
| 247 | 5-{[2-chloro-5-(3-fluoropyridin-2-yl)benzoyl]amino}-N-[(5-methyl-1,3,4-oxadiazol-2-yl)methyl]-1-phenyl-1H-pyrazole-3-carboxamide | LCMS Rt = 1.58 minutes MS m/z 532.29 [M + H]$^+$ |
| 248 | 5-{[2-chloro-5-(3-fluoropyridin-2-yl)benzoyl]amino}-N-[(1S,2S)-2-hydroxycyclohexyl]-1-phenyl-1H-pyrazole-3-carboxamide | LCMS Rt = 1.63 minutes MS m/z 534.34 [M + H]$^+$ |
| 249 | 5-{[2-chloro-5-(3-fluoropyridin-2-yl)benzoyl]amino}-N-[(1S,2R)-2-hydroxycyclohexyl]-1-phenyl-1H-pyrazole-3-carboxamide | LCMS Rt = 1.65 minutes MS m/z 534.3 [M + H]$^+$ |
| 250 | 5-{[2-chloro-5-(3-fluoropyridin-2-yl)benzoyl]amino}-N-[3-(2-hydroxyethyl)oxetan-3-yl]-1-phenyl-1H-pyrazole-3-carboxamide | LCMS Rt = 1.54 minutes MS m/z 536.34 [M + H]$^+$ |
| 251 | 5-(2-chloro-5-(3-fluoropyridin-2-yl)benzamido)-N-((3R,4S)-3-hydroxytetrahydro-2H-pyran-4-yl)-1-phenyl-1H-pyrazole-3-carboxamide | LCMS Rt = 1.55 minutes MS m/z 536.3 [M + H]$^+$ |
| 252 | 5-{[2-chloro-5-(3-fluoropyridin-2-yl)benzoyl]amino}-N-(trans-4-hydroxy-4-methylcyclohexyl)-1-phenyl-1H-pyrazole-3-carboxamide | LCMS Rt = 1.63 minutes MS m/z 548.38 [M + H]$^+$ |
| 253 | 5-{[2-chloro-5-(3-fluoropyridin-2-yl)benzoyl]amino}-N-[(4-methylmorpholin-2-yl)methyl]-1-phenyl-1H-pyrazole-3-carboxamide | LCMS Rt = 1.41 minutes MS m/z 549.35 [M + H]$^+$ |
| 254 | 5-{[2-chloro-5-(3-fluoropyridin-2-yl)benzoyl]amino}-N-[(4-hydroxytetrahydro-2H-pyran-4-yl)methyl]-1-phenyl-1H-pyrazole-3-carboxamide | LCMS Rt = 1.57 minutes MS m/z 550.33 [M + H]$^+$ |
| 255 | 5-{[2-chloro-5-(3-fluoropyridin-2-yl)benzoyl]amino}-N-(cis-3-hydroxy-2,2,4,4-tetramethylcyclobutyl)-1-phenyl-1H-pyrazole-3-carboxamide | LCMS Rt = 1.67 minutes MS m/z 562.38 [M + H]$^+$ |
| 256 | 5-{[2-chloro-5-(3-fluoropyridin-2-yl)benzoyl]amino}-N-(trans-3-hydroxy-2,2,4,4-tetramethylcyclobutyl)-1-phenyl-1H-pyrazole-3-carboxamide | LCMS Rt = 1.68 minutes MS m/z 562.36 [M + H]$^+$ |
| 257 | 5-{[2-chloro-5-(3-fluoropyridin-2-yl)benzoyl]amino}-N-[(4-methyl-5-oxomorpholin-2-yl)methyl]-1-phenyl-1H-pyrazole-3-carboxamide | LCMS Rt = 1.58 minutes MS m/z 563.29 [M + H]$^+$ |
| 258 | 5-{[2-chloro-5-(3-fluoropyridin-2-yl)benzoyl]amino}-N-[(4-hydroxy-1-methylpiperidin-4-yl)methyl]-1-phenyl-1H-pyrazole-3-carboxamide | LCMS Rt = 1.4 minutes MS m/z 563.34 [M + H]$^+$ |
| 259 | 5-{[2-chloro-5-(3-fluoropyridin-2-yl)benzoyl]amino}-N-(1,1-dioxidotetrahydro-2H-thiopyran-4-yl)-1-phenyl-1H-pyrazole-3-carboxamide | LCMS Rt = 1.58 minutes MS m/z 568.27 [M + H]$^+$ |
| 260 | 5-{[2-chloro-5-(3-fluoropyridin-2-yl)benzoyl]amino}-N-{[1-(2-hydroxyethyl)piperidin-4-yl]methyl}-1-phenyl-1H-pyrazole-3-carboxamide | LCMS Rt = 1.41 minutes MS m/z 575.28 [M − H]$^-$ |

| Example Number | Name | Data |
|---|---|---|
| 261 | 5-{[2-chloro-4-fluoro-5-(pyridin-2-yl)benzoyl]amino}-N-methyl-1-phenyl-1H-pyrazole-3-carboxamide | LCMS Rt = 1.6 minutes MS m/z 450.32 [M + H]$^+$ |
| 262 | 5-{[2-chloro-4-fluoro-5-(pyridin-2-yl)benzoyl]amino}-N-cyclopropyl-1-phenyl-1H-pyrazole-3-carboxamide | LCMS Rt = 1.65 minutes MS m/z 476.35 [M + H]$^+$ |
| 263 | 5-{[2-chloro-4-fluoro-5-(pyridin-2-yl)benzoyl]amino}-N-(oxetan-3-yl)-1-phenyl-1H-pyrazole-3-carboxamide | LCMS Rt = 1.59 minutes MS m/z 492.33 [M + H]$^+$ |
| 264 | N-(2-amino-2-oxoethyl)-5-{[2-chloro-4-fluoro-5-(pyridin-2-yl)benzoyl]amino}-1-phenyl-1H-pyrazole-3-carboxamide | LCMS Rt = 1.51 minutes MS m/z 493.31 [M + H]$^+$ |
| 265 | 5-{[2-chloro-4-fluoro-5-(pyridin-2-yl)benzoyl]amino}-N-(3-hydroxypropyl)-1-phenyl-1H-pyrazole-3-carboxamide | LCMS Rt = 1.55 minutes MS m/z 494.33 [M + H]$^+$ |
| 266 | 5-{[2-chloro-4-fluoro-5-(pyridin-2-yl)benzoyl]amino}-N-[(2S)-2-hydroxypropyl]-1-phenyl-1H-pyrazole-3-carboxamide | LCMS Rt = 1.56 minutes MS m/z 494.33 [M + H]$^+$ |
| 267 | 5-{[2-chloro-4-fluoro-5-(pyridin-2-yl)benzoyl]amino}-N-(1-methylazetidin-3-yl)-1-phenyl-1H-pyrazole-3-carboxamide | LCMS Rt = 1.4 minutes MS m/z 503.3 [M − H]$^-$ |
| 268 | 5-{[2-chloro-4-fluoro-5-(pyridin-2-yl)benzoyl]amino}-1-phenyl-N-[(3R)-tetrahydrofuran-3-yl]-1H-pyrazole-3-carboxamide | LCMS Rt = 1.62 minutes MS m/z 506.32 [M + H]$^+$ |
| 269 | 5-{[2-chloro-4-fluoro-5-(pyridin-2-yl)benzoyl]amino}-1-phenyl-N-[(3S)-tetrahydrofuran-3-yl]-1H-pyrazole-3-carboxamide | LCMS Rt = 1.62 minutes MS m/z 506.32 [M + H]$^+$ |
| 270 | 5-{[2-chloro-4-fluoro-5-(pyridin-2-yl)benzoyl]amino}-N-[2-(methylamino)-2-oxoethyl]-1-phenyl-1H-pyrazole-3-carboxamide | LCMS Rt = 1.54 minutes MS m/z 507.3 [M + H]$^+$ |
| 271 | 5-{[2-chloro-4-fluoro-5-(pyridin-2-yl)benzoyl]amino}-N-(3-hydroxy-2-methylpropyl)-1-phenyl-1H-pyrazole-3-carboxamide | LCMS Rt = 1.59 minutes MS m/z 508.32 [M + H]$^+$ |
| 272 | 5-{[2-chloro-4-fluoro-5-(pyridin-2-yl)benzoyl]amino}-N-(2-hydroxy-2-methylpropyl)-1-phenyl-1H-pyrazole-3-carboxamide | LCMS Rt = 1.59 minutes MS m/z 508.32 [M + H]$^+$ |
| 273 | 5-{[2-chloro-4-fluoro-5-(pyridin-2-yl)benzoyl]amino}-N-[(2S)-2,3-dihydroxypropyl]-1-phenyl-1H-pyrazole-3-carboxamide | LCMS Rt = 1.5 minutes MS m/z 510.32 [M + H]$^+$ |
| 274 | 5-{[2-chloro-4-fluoro-5-(pyridin-2-yl)benzoyl]amino}-N-(1H-imidazol-5-ylmethyl)-1-phenyl-1H-pyrazole-3-carboxamide | LCMS Rt = 1.4 minutes MS m/z 514.27 [M − H]$^-$ |
| 275 | 5-{[2-chloro-4-fluoro-5-(pyridin-2-yl)benzoyl]amino}-N-(1,3-oxazol-4-ylmethyl)-1-phenyl-1H-pyrazole-3-carboxamide | LCMS Rt = 1.61 minutes MS m/z 517.29 [M + H]$^+$ |
| 276 | 5-{[2-chloro-4-fluoro-5-(pyridin-2-yl)benzoyl]amino}-N-(1,2-oxazol-3-ylmethyl)-1-phenyl-1H-pyrazole-3-carboxamide | LCMS Rt = 1.62 minutes MS m/z 517.29 [M + H]$^+$ |
| 277 | 5-{[2-chloro-4-fluoro-5-(pyridin-2-yl)benzoyl]amino}-N-(cis-3-hydroxycyclobutyl)-1-phenyl-1H-pyrazole-3-carboxamide | LCMS Rt = 1.55 minutes MS m/z 506.32 [M + H]$^+$ |
| 278 | 5-{[2-chloro-4-fluoro-5-(pyridin-2-yl)benzoyl]amino}-N-(1,3-oxazol-2-ylmethyl)-1-phenyl-1H-pyrazole-3-carboxamide | LCMS Rt = 1.61 minutes MS m/z 517.25 [M + H]$^+$ |
| 279 | 5-{[2-chloro-4-fluoro-5-(pyridin-2-yl)benzoyl]amino}-1-phenyl-N-(4H-1,2,4-triazol-3-ylmethyl)-1H-pyrazole-3-carboxamide | LCMS Rt = 1.53 minutes MS m/z 517.29 [M + H]$^+$ |
| 280 | 5-{[2-chloro-4-fluoro-5-(pyridin-2-yl)benzoyl]amino}-N-(1-methylpyrrolidin-3-yl)-1-phenyl-1H-pyrazole-3-carboxamide | LCMS Rt = 1.41 minutes MS m/z 517.32 [M − H]$^-$ |
| 281 | 5-{[2-chloro-4-fluoro-5-(pyridin-2-yl)benzoyl]amino}-N-[(1S,3R)-3-hydroxycyclopentyl]-1-phenyl-1H-pyrazole-3-carboxamide | LCMS Rt = 1.59 minutes MS m/z 520.31 [M + H]$^+$ |
| 282 | 5-{[2-chloro-4-fluoro-5-(pyridin-2-yl)benzoyl]amino}-1-phenyl-N-(tetrahydrofuran-3-ylmethyl)-1H-pyrazole-3-carboxamide | LCMS Rt = 1.64 minutes MS m/z 520.31 [M + H]$^+$ |
| 283 | 5-{[2-chloro-4-fluoro-5-(pyridin-2-yl)benzoyl]amino}-N-[cis-3-(hydroxymethyl)cyclobutyl]-1-phenyl-1H-pyrazole-3-carboxamide | LCMS Rt = 1.58 minutes MS m/z 520.35 [M + H]$^+$ |
| 284 | 5-{[2-chloro-4-fluoro-5-(pyridin-2-yl)benzoyl]amino}-N-[trans-3-(hydroxymethyl)cyclobutyl]-1-phenyl-1H-pyrazole-3-carboxamide | LCMS Rt = 1.58 minutes MS m/z 520.37 [M + H]$^+$ |
| 285 | 5-{[2-chloro-4-fluoro-5-(pyridin-2-yl)benzoyl]amino}-N-(trans-3-hydroxycyclobutyl)-1-phenyl-1H-pyrazole-3-carboxamide | LCMS Rt = 1.55 minutes MS m/z 506.32 [M + H]$^+$ |

| Example Number | Name | Data |
|---|---|---|
| 286 | 5-{[2-chloro-4-fluoro-5-(pyridin-2-yl)benzoyl]amino}-N-[2-(dimethylamino)-2-oxoethyl]-1-phenyl-1H-pyrazole-3-carboxamide | LCMS Rt = 1.6 minutes MS m/z 521.3 [M + H]+ |
| 287 | 5-{[2-chloro-4-fluoro-5-(pyridin-2-yl)benzoyl]amino}-N-[(3-hydroxyoxetan-3-yl)methyl]-1-phenyl-1H-pyrazole-3-carboxamide | LCMS Rt = 1.54 minutes MS m/z 522.34 [M + H]+ |
| 288 | 5-{[2-chloro-4-fluoro-5-(pyridin-2-yl)benzoyl]amino}-N-[(3R,4S)-4-hydroxytetrahydrofuran-3-yl]-1-phenyl-1H-pyrazole-3-carboxamide | LCMS Rt = 1.54 minutes MS m/z 522.31 [M + H]+ |
| 289 | 5-{[2-chloro-4-fluoro-5-(pyridin-2-yl)benzoyl]amino}-N-(3-hydroxy-2,2-dimethylpropyl)-1-phenyl-1H-pyrazole-3-carboxamide | LCMS Rt = 1.64 minutes MS m/z 522.35 [M + H]+ |
| 290 | 5-{[2-chloro-4-fluoro-5-(pyridin-2-yl)benzoyl]amino}-N-[(2R)-2-hydroxypropyl]-1-phenyl-1H-pyrazole-3-carboxamide | LCMS Rt = 1.56 minutes MS m/z 494.29 [M + H]+ |
| 291 | 5-{[2-chloro-4-fluoro-5-(pyridin-2-yl)benzoyl]amino}-N-(2-hydroxy-3-methoxypropyl)-1-phenyl-1H-pyrazole-3-carboxamide | LCMS Rt = 1.56 minutes MS m/z 524.35 [M + H]+ |
| 292 | 5-{[2-chloro-4-fluoro-5-(pyridin-2-yl)benzoyl]amino}-1-phenyl-N-(pyridazin-4-ylmethyl)-1H-pyrazole-3-carboxamide | LCMS Rt = 1.59 minutes MS m/z 526.21 [M − H]− |
| 293 | 5-{[2-chloro-4-fluoro-5-(pyridin-2-yl)benzoyl]amino}-1-phenyl-N-(pyrimidin-2-ylmethyl)-1H-pyrazole-3-carboxamide | LCMS Rt = 1.63 minutes MS m/z 528.31 [M + H]+ |
| 294 | 5-{[2-chloro-4-fluoro-5-(pyridin-2-yl)benzoyl]amino}-N-[(1-methyl-1H-pyrazol-4-yl)methyl]-1-phenyl-1H-pyrazole-3-carboxamide | LCMS Rt = 1.65 minutes MS m/z 530.3 [M + H]+ |
| 295 | 5-{[2-chloro-4-fluoro-5-(pyridin-2-yl)benzoyl]amino}-N-[(1-methyl-1H-imidazol-5-yl)methyl]-1-phenyl-1H-pyrazole-3-carboxamide | LCMS Rt = 1.41 minutes MS m/z 528.3 [M − H]− |
| 296 | 5-{[2-chloro-4-fluoro-5-(pyridin-2-yl)benzoyl]amino}-N-[(1-methyl-1H-1,2,3-triazol-4-yl)methyl]-1-phenyl-1H-pyrazole-3-carboxamide | LCMS Rt = 1.61 minutes MS m/z 531.32 [M + H]+ |
| 297 | 5-{[2-chloro-4-fluoro-5-(pyridin-2-yl)benzoyl]amino}-N-[(1-methyl-1H-1,2,3-triazol-5-yl)methyl]-1-phenyl-1H-pyrazole-3-carboxamide | LCMS Rt = 1.58 minutes MS m/z 531.28 [M + H]+ |
| 298 | 5-{[2-chloro-4-fluoro-5-(pyridin-2-yl)benzoyl]amino}-1-phenyl-N-[2-(1H-1,2,4-triazol-1-yl)ethyl]-1H-pyrazole-3-carboxamide | LCMS Rt = 1.58 minutes MS m/z 529.27 [M − H]− |
| 299 | 5-{[2-chloro-4-fluoro-5-(pyridin-2-yl)benzoyl]amino}-N-[(2R)-2,3-dihydroxypropyl]-1-phenyl-1H-pyrazole-3-carboxamide | LCMS Rt = 1.5 minutes MS m/z 510.32 [M + H]+ |
| 300 | 5-{[2-chloro-4-fluoro-5-(pyridin-2-yl)benzoyl]amino}-N-(trans-4-hydroxycyclohexyl)-1-phenyl-1H-pyrazole-3-carboxamide | LCMS Rt = 1.59 minutes MS m/z 534.34 [M + H]+ |
| 301 | 5-{[2-chloro-4-fluoro-5-(pyridin-2-yl)benzoyl]amino}-N-(cis-4-hydroxycyclohexyl)-1-phenyl-1H-pyrazole-3-carboxamide | LCMS Rt = 1.59 minutes MS m/z 534.34 [M + H]+ |
| 302 | 5-{[2-chloro-4-fluoro-5-(pyridin-2-yl)benzoyl]amino}-N-{3-(hydroxymethyl)oxetan-3-yl]methyl}-1-phenyl-1H-pyrazole-3-carboxamide | LCMS Rt = 1.55 minutes MS m/z 536.39 [M + H]+ |
| 303 | 5-{[2-chloro-4-fluoro-5-(pyridin-2-yl)benzoyl]amino}-N-(trans-4-hydroxy-4-methylcyclohexyl)-1-phenyl-1H-pyrazole-3-carboxamide | LCMS Rt = 1.63 minutes MS m/z 548.33 [M + H]+ |
| 304 | N-[(2-aminopyridin-4-yl)methyl]-5-{[2-chloro-4-fluoro-5-(pyridin-2-yl)benzoyl]amino}-1-phenyl-1H-pyrazole-3-carboxamide | LCMS Rt = 1.42 minutes MS m/z 540.28 [M − H]− |
| 305 | 5-{[2-chloro-4-fluoro-5-(pyridin-2-yl)benzoyl]amino}-N-(3,5-dimethyl-1H-pyrazol-4-yl)-1-phenyl-1H-pyrazole-3-carboxamide | LCMS Rt = 1.6 minutes MS m/z 528.26 [M − H]− |
| 306 | N-[(2R)-1-aminopropan-2-yl]-5-{[2-chloro-5-(3-fluoropyridin-2-yl)benzoyl]amino}-1-phenyl-1H-pyrazole-3-carboxamide | LCMS Rt = 1.41 minutes MS m/z 493.26 [M + H]+ |
| 307 | N-(3-aminopropyl)-5-{[2-chloro-5-(3-fluoropyridin-2-yl)benzoyl]amino}-1-phenyl-1H-pyrazole-3-carboxamide | LCMS Rt = 1.4 minutes MS m/z 493.26 [M + H]+ |
| 308 | N-(1-aminopropan-2-yl)-5-{[2-chloro-5-(3-fluoropyridin-2-yl)benzoyl]amino}-1-phenyl-1H-pyrazole-3-carboxamide | LCMS Rt = 1.41 minutes MS m/z 493.22 [M + H]+ |
| 309 | N-[(2R)-2-aminopropyl]-5-{[2-chloro-5-(3-fluoropyridin-2-yl)benzoyl]amino}-1-phenyl-1H-pyrazole-3-carboxamide | LCMS Rt = 1.41 minutes MS m/z 493.22 [M + H]+ |
| 310 | N-[(2S)-2-aminopropyl]-5-{[2-chloro-5-(3-fluoropyridin-2-yl)benzoyl]amino}-1-phenyl-1H-pyrazole-3-carboxamide | LCMS Rt = 1.41 minutes MS m/z 493.22 [M + H]+ |

| Example Number | Name | Data |
|---|---|---|
| 311 | N-[(2S)-1-aminopropan-2-yl]-5-{[2-chloro-5-(3-fluoropyridin-2-yl)benzoyl]amino}-1-phenyl-1H-pyrazole-3-carboxamide | LCMS Rt = 1.42 minutes MS m/z 493.25 [M + H]+ |
| 312 | 5-{[2-chloro-5-(3-fluoropyridin-2-yl)benzoyl]amino}-N-[2-(methylamino)ethyl]-1-phenyl-1H-pyrazole-3-carboxamide | LCMS Rt = 1.41 minutes MS m/z 493.22 [M + H]+ |
| 313 | N-(cis-3-aminocyclobutyl)-5-{[2-chloro-5-(3-fluoropyridin-2-yl)benzoyl]amino}-1-phenyl-1H-pyrazole-3-carboxamide | LCMS Rt = 1.41 minutes MS m/z 505.21 [M + H]+ |
| 314 | N-(trans-3-aminocyclobutyl)-5-{[2-chloro-5-(3-fluoropyridin-2-yl)benzoyl]amino}-1-phenyl-1H-pyrazole-3-carboxamide | LCMS Rt = 1.41 minutes MS m/z 505.21 [M + H]+ |
| 315 | 5-{[2-chloro-5-(3-fluoropyridin-2-yl)benzoyl]amino}-1-phenyl-N-(pyrrolidin-3-yl)-1H-pyrazole-3-carboxamide | LCMS Rt = 1.41 minutes MS m/z 505.25 [M + H]+ |
| 316 | 5-{[2-chloro-5-(3-fluoropyridin-2-yl)benzoyl]amino}-1-phenyl-N-[(3R)-pyrrolidin-3-yl]-1H-pyrazole-3-carboxamide | LCMS Rt = 1.41 minutes MS m/z 505.25 [M + H]+ |
| 317 | 5-{[2-chloro-5-(3-fluoropyridin-2-yl)benzoyl]amino}-1-phenyl-N-[(3S)-pyrrolidin-3-yl]-1H-pyrazole-3-carboxamide | LCMS Rt = 1.41 minutes MS m/z 505.25 [M + H]+ |
| 318 | N-(azetidin-3-ylmethyl)-5-{[2-chloro-5-(3-fluoropyridin-2-yl)benzoyl]amino}-1-phenyl-1H-pyrazole-3-carboxamide | LCMS Rt = 1.43 minutes MS m/z 505.25 [M + H]+ |
| 319 | N-(3-amino-2-methylpropyl)-5-{[2-chloro-5-(3-fluoropyridin-2-yl)benzoyl]amino}-1-phenyl-1H-pyrazole-3-carboxamide | LCMS Rt = 1.42 minutes MS m/z 507.21 [M + H]+ |
| 320 | N-[(2R)-4-aminobutan-2-yl]-5-{[2-chloro-5-(3-fluoropyridin-2-yl)benzoyl]amino}-1-phenyl-1H-pyrazole-3-carboxamide | LCMS Rt = 1.42 minutes MS m/z 507.25 [M + H]+ |
| 321 | N-(1-amino-2-methylpropan-2-yl)-5-{[2-chloro-5-(3-fluoropyridin-2-yl)benzoyl]amino}-1-phenyl-1H-pyrazole-3-carboxamide | LCMS Rt = 1.43 minutes MS m/z 507.21 [M + H]+ |
| 322 | N-(2-amino-2-methylpropyl)-5-{[2-chloro-5-(3-fluoropyridin-2-yl)benzoyl]amino}-1-phenyl-1H-pyrazole-3-carboxamide | LCMS Rt = 1.41 minutes MS m/z 507.25 [M + H]+ |
| 323 | 5-{[2-chloro-5-(3-fluoropyridin-2-yl)benzoyl]amino}-N-[(2S)-2-(methylamino)propyl]-1-phenyl-1H-pyrazole-3-carboxamide | LCMS Rt = 1.42 minutes MS m/z 507.25 [M + H]+ |
| 324 | N-[(3S)-3-aminobutyl]-5-{[2-chloro-5-(3-fluoropyridin-2-yl)benzoyl]amino}-1-phenyl-1H-pyrazole-3-carboxamide | LCMS Rt = 1.41 minutes MS m/z 507.25 [M + H]+ |
| 325 | 5-{[2-chloro-5-(3-fluoropyridin-2-yl)benzoyl]amino}-N-[3-(methylamino)propyl]-1-phenyl-1H-pyrazole-3-carboxamide | LCMS Rt = 1.41 minutes MS m/z 507.25 [M + H]+ |
| 326 | N-(3-amino-2-hydroxypropyl)-5-{[2-chloro-5-(3-fluoropyridin-2-yl)benzoyl]amino}-1-phenyl-1H-pyrazole-3-carboxamide | LCMS Rt = 1.4 minutes MS m/z 509.22 [M + H]+ |
| 327 | N-(2-amino-3-fluoropropyl)-5-{[2-chloro-5-(3-fluoropyridin-2-yl)benzoyl]amino}-1-phenyl-1H-pyrazole-3-carboxamide | LCMS Rt = 1.41 minutes MS m/z 511.2 [M + H]+ |
| 328 | N-[(1R,5S,6s)-3-azabicyclo[3.1.0]hex-6-yl]-5-{[2-chloro-5-(3-fluoropyridin-2-yl)benzoyl]amino}-1-phenyl-1H-pyrazole-3-carboxamide | LCMS Rt = 1.42 minutes MS m/z 515.17 [M − H]− |
| 329 | 2-chloro-N-{3-[(1R,4R)-2,5-diazabicyclo[2.2.1]hept-2-ylcarbonyl]-1-phenyl-1H-pyrazol-5-yl}-5-(3-fluoropyridin-2-yl)benzamide | LCMS Rt = 1.41 minutes MS m/z 517.24 [M + H]+ |
| 330 | 2-chloro-N-{3-[(1S,4S)-2,5-diazabicyclo[2.2.1]hept-2-ylcarbonyl]-1-phenyl-1H-pyrazol-5-yl}-5-(3-fluoropyridin-2-yl)benzamide | LCMS Rt = 1.41 minutes MS m/z 517.24 [M + H]+ |
| 331 | 5-{[2-chloro-5-(3-fluoropyridin-2-yl)benzoyl]amino}-1-phenyl-N-(piperidin-4-yl)-1H-pyrazole-3-carboxamide | LCMS Rt = 1.41 minutes MS m/z 519.24 [M + H]+ |
| 332 | 5-{[2-chloro-5-(3-fluoropyridin-2-yl)benzoyl]amino}-1-phenyl-N-(piperidin-3-yl)-1H-pyrazole-3-carboxamide | LCMS Rt = 1.43 minutes MS m/z 519.24 [M + H]+ |
| 333 | N-[(1-aminocyclobutyl)methyl]-5-{[2-chloro-5-(3-fluoropyridin-2-yl)benzoyl]amino}-1-phenyl-1H-pyrazole-3-carboxamide | LCMS Rt = 1.43 minutes MS m/z 519.24 [M + H]+ |
| 334 | N-[(1S,3S)-3-aminocyclopentyl]-5-{[2-chloro-5-(3-fluoropyridin-2-yl)benzoyl]amino}-1-phenyl-1H-pyrazole-3-carboxamide | LCMS Rt = 1.42 minutes MS m/z 517.16 [M − H]− |
| 335 | N-[(1R,3R)-3-aminocyclopentyl]-5-{[2-chloro-5-(3-fluoropyridin-2-yl)benzoyl]amino}-1-phenyl-1H-pyrazole-3-carboxamide | LCMS Rt = 1.42 minutes MS m/z 517.2 [M − H]− |

| Example Number | Name | Data |
| --- | --- | --- |
| 336 | N-[(1R,2R)-2-aminocyclopentyl]-5-{[2-chloro-5-(3-fluoropyridin-2-yl)benzoyl]amino}-1-phenyl-1H-pyrazole-3-carboxamide | LCMS Rt = 1.43 minutes MS m/z 519.24 [M + H]+ |
| 337 | 5-{[2-chloro-5-(3-fluoropyridin-2-yl)benzoyl]amino}-1-phenyl-N-[(2S)-pyrrolidin-2-ylmethyl]-1H-pyrazole-3-carboxamide | LCMS Rt = 1.44 minutes MS m/z 519.24 [M + H]+ |
| 338 | 5-{[2-chloro-5-(3-fluoropyridin-2-yl)benzoyl]amino}-1-phenyl-N-(pyrrolidin-2-ylmethyl)-1H-pyrazole-3-carboxamide | LCMS Rt = 1.43 minutes MS m/z 519.24 [M + H]+ |
| 339 | 5-{[2-chloro-5-(3-fluoropyridin-2-yl)benzoyl]amino}-1-phenyl-N-(pyrrolidin-3-ylmethyl)-1H-pyrazole-3-carboxamide | LCMS Rt = 1.42 minutes MS m/z 519.24 [M + H]+ |
| 340 | 5-{[2-chloro-5-(3-fluoropyridin-2-yl)benzoyl]amino}-1-phenyl-N-[(3S)-pyrrolidin-3-ylmethyl]-1H-pyrazole-3-carboxamide | LCMS Rt = 1.42 minutes MS m/z 519.26 [M + H]+ |
| 341 | 5-{[2-chloro-5-(3-fluoropyridin-2-yl)benzoyl]amino}-1-phenyl-N-[(3R)-pyrrolidin-3-ylmethyl]-1H-pyrazole-3-carboxamide | LCMS Rt = 1.42 minutes MS m/z 519.28 [M + H]+ |
| 342 | 5-{[2-chloro-5-(3-fluoropyridin-2-yl)benzoyl]amino}-N-methyl-1-phenyl-N-(pyrrolidin-3-yl)-1H-pyrazole-3-carboxamide | LCMS Rt = 1.42 minutes MS m/z 519.24 [M + H]+ |
| 343 | 5-{[2-chloro-5-(3-fluoropyridin-2-yl)benzoyl]amino}-N-[(3R,4R)-4-hydroxypyrrolidin-3-yl]-1-phenyl-1H-pyrazole-3-carboxamide | LCMS Rt = 1.39 minutes MS m/z 521.24 [M + H]+ |
| 344 | 5-{[2-chloro-5-(3-fluoropyridin-2-yl)benzoyl]amino}-N-(4-hydroxypyrrolidin-3-yl)-1-phenyl-1H-pyrazole-3-carboxamide | LCMS Rt = 1.4 minutes MS m/z 521.24 [M + H]+ |
| 345 | 5-{[2-chloro-5-(3-fluoropyridin-2-yl)benzoyl]amino}-N-[(3S,4S)-4-hydroxypyrrolidin-3-yl]-1-phenyl-1H-pyrazole-3-carboxamide | LCMS Rt = 1.4 minutes MS m/z 521.24 [M + H]+ |
| 346 | 5-{[2-chloro-5-(3-fluoropyridin-2-yl)benzoyl]amino}-N-[(3S,4R)-4-hydroxypyrrolidin-3-yl]-1-phenyl-1H-pyrazole-3-carboxamide | LCMS Rt = 1.4 minutes MS m/z 521.24 [M + H]+ |
| 347 | 5-{[2-chloro-5-(3-fluoropyridin-2-yl)benzoyl]amino}-N-[(3-hydroxyazetidin-3-yl)methyl]-1-phenyl-1H-pyrazole-3-carboxamide | LCMS Rt = 1.4 minutes MS m/z 521.19 [M + H]+ |
| 348 | N-[2-(2-aminoethoxy)ethyl]-5-{[2-chloro-5-(3-fluoropyridin-2-yl)benzoyl]amino}-1-phenyl-1H-pyrazole-3-carboxamide | LCMS Rt = 1.41 minutes MS m/z 523.24 [M + H]+ |
| 349 | 5-{[2-chloro-5-(3-fluoropyridin-2-yl)benzoyl]amino}-N-{2-[(2-hydroxyethyl)amino]ethyl}-1-phenyl-1H-pyrazole-3-carboxamide | LCMS Rt = 1.4 minutes MS m/z 523.2 [M + H]+ |
| 350 | N-(3-amino-2,2-difluoropropyl)-5-{[2-chloro-5-(3-fluoropyridin-2-yl)benzoyl]amino}-1-phenyl-1H-pyrazole-3-carboxamide | LCMS Rt = 1.41 minutes MS m/z 529.23 [M + H]+ |
| 351 | 5-{[2-chloro-5-(3-fluoropyridin-2-yl)benzoyl]amino}-N-[(3R,4R)-4-cyanopyrrolidin-3-yl]-1-phenyl-1H-pyrazole-3-carboxamide | LCMS Rt = 1.42 minutes MS m/z 530.21 [M + H]+ |
| 352 | N-(trans-4-aminocyclohexyl)-5-{[2-chloro-5-(3-fluoropyridin-2-yl)benzoyl]amino}-1-phenyl-1H-pyrazole-3-carboxamide | LCMS Rt = 1.42 minutes MS m/z 531.21 [M − H]− |
| 353 | N-(cis-4-aminocyclohexyl)-5-{[2-chloro-5-(3-fluoropyridin-2-yl)benzoyl]amino}-1-phenyl-1H-pyrazole-3-carboxamide | LCMS Rt = 1.42 minutes MS m/z 533.23 [M + H]+ |
| 354 | 5-{[2-chloro-5-(3-fluoropyridin-2-yl)benzoyl]amino}-1-phenyl-N-(piperidin-4-ylmethyl)-1H-pyrazole-3-carboxamide | LCMS Rt = 1.43 minutes MS m/z 533.28 [M + H]+ |
| 355 | 5-{[2-chloro-5-(3-fluoropyridin-2-yl)benzoyl]amino}-N-[(3S,5S)-5-(hydroxymethyl)pyrrolidin-3-yl]-1-phenyl-1H-pyrazole-3-carboxamide | LCMS Rt = 1.4 minutes MS m/z 535.26 [M + H]+ |
| 356 | 5-{[2-chloro-5-(3-fluoropyridin-2-yl)benzoyl]amino}-N-(3-fluoropiperidin-4-yl)-1-phenyl-1H-pyrazole-3-carboxamide | LCMS Rt = 1.42 minutes MS m/z 537.23 [M + H]+ |
| 357 | 5-{[2-chloro-5-(3-fluoropyridin-2-yl)benzoyl]amino}-N-[2-(morpholin-2-yl)ethyl]-1-phenyl-1H-pyrazole-3-carboxamide | LCMS Rt = 1.42 minutes MS m/z 549.21 [M + H]+ |
| 358 | 2-chloro-4-fluoro-N-{3-[(3-methoxyazetidin-1-yl)carbonyl]-1-phenyl-1H-pyrazol-5-yl}-5-(pyridin-2-yl)benzamide | LCMS Rt = 1.66 minutes MS m/z 506.09 [M + H]+ |
| 359 | 2-chloro-4-fluoro-N-(3-{[(3S)-3-hydroxypyrrolidin-1-yl]carbonyl}-1-phenyl-1H-pyrazol-5-yl)-5-(pyridin-2-yl)benzamide | LCMS Rt = 1.56 minutes MS m/z 506.14 [M + H]+ |
| 360 | 2-chloro-4-fluoro-N-{3-[(3-hydroxypyrrolidin-1-yl)carbonyl]-1-phenyl-1H-pyrazol-5-yl}-5-(pyridin-2-yl)benzamide | LCMS Rt = 1.56 minutes MS m/z 506.23 [M + H]+ |

-continued

| Example Number | Name | Data |
|---|---|---|
| 361 | 2-chloro-4-fluoro-N-(3-{[(3R)-3-hydroxypyrrolidin-1-yl]carbonyl}-1-phenyl-1H-pyrazol-5-yl)-5-(pyridin-2-yl)benzamide | LCMS Rt = 1.56 minutes MS m/z 506.18 [M + H]+ |
| 362 | 5-{[2-chloro-4-fluoro-5-(pyridin-2-yl)benzoyl]amino}-N-[2-(dimethylamino)ethyl]-1-phenyl-1H-pyrazole-3-carboxamide | LCMS Rt = 1.41 minutes MS m/z 507.25 [M + H]+ |
| 363 | 2-chloro-N-{3-[(3-cyano-3-methylazetidin-1-yl)carbonyl]-1-phenyl-1H-pyrazol-5-yl}-4-fluoro-5-(pyridin-2-yl)benzamide | LCMS Rt = 1.66 minutes MS m/z 515.1 [M + H]+ |
| 364 | N-(3-(3-oxa-6-azabicyclo[3.1.1]heptane-6-carbonyl)-1-phenyl-1H-pyrazol-5-yl)-2-chloro-4-fluoro-5-(pyridin-2-yl)benzamide | LCMS Rt = 1.66 minutes MS m/z 518.1 [M + H]+ |
| 365 | 5-{[2-chloro-4-fluoro-5-(pyridin-2-yl)benzoyl]amino}-N-[(3R)-1-methylpyrrolidin-3-yl]-1-phenyl-1H-pyrazole-3-carboxamide | LCMS Rt = 1.41 minutes MS m/z 519.29 [M + H]+ |
| 366 | 5-{[2-chloro-4-fluoro-5-(pyridin-2-yl)benzoyl]amino}-N-[(3S)-1-methylpyrrolidin-3-yl]-1-phenyl-1H-pyrazole-3-carboxamide | LCMS Rt = 1.41 minutes MS m/z 519.15 [M + H]+ |
| 367 | 5-{[2-chloro-4-fluoro-5-(pyridin-2-yl)benzoyl]amino}-N-[(1-methylazetidin-3-yl)methyl]-1-phenyl-1H-pyrazole-3-carboxamide | LCMS Rt = 1.41 minutes MS m/z 519.1 [M + H]+ |
| 368 | 2-chloro-4-fluoro-N-{3-[(4-methylpiperazin-1-yl)carbonyl]-1-phenyl-1H-pyrazol-5-yl}-5-(pyridin-2-yl)benzamide | LCMS Rt = 1.4 minutes MS m/z 519.24 [M + H]+ |
| 369 | 2-chloro-4-fluoro-N-(3-{[2-(hydroxymethyl)pyrrolidin-1-yl]carbonyl}-1-phenyl-1H-pyrazol-5-yl)-5-(pyridin-2-yl)benzamide | LCMS Rt = 1.62 minutes MS m/z 520.23 [M + H]+ |
| 370 | 2-chloro-4-fluoro-N-(3-{[(3R)-3-methoxypyrrolidin-1-yl]carbonyl}-1-phenyl-1H-pyrazol-5-yl)-5-(pyridin-2-yl)benzamide | LCMS Rt = 1.67 minutes MS m/z 520.24 [M + H]+ |
| 371 | 2-chloro-4-fluoro-N-(3-{[(2S)-2-(hydroxymethyl)pyrrolidin-1-yl]carbonyl}-1-phenyl-1H-pyrazol-5-yl)-5-(pyridin-2-yl)benzamide | LCMS Rt = 1.62 minutes MS m/z 520.26 [M + H]+ |
| 372 | 2-chloro-N-(3-{[(3R,4S)-3,4-dihydroxypyrrolidin-1-yl]carbonyl}-1-phenyl-1H-pyrazol-5-yl)-4-fluoro-5-(pyridin-2-yl)benzamide | LCMS Rt = 1.5 minutes MS m/z 522.12 [M + H]+ |
| 373 | 2-chloro-N-(3-{[(3R,4R)-3,4-dihydroxypyrrolidin-1-yl]carbonyl}-1-phenyl-1H-pyrazol-5-yl)-4-fluoro-5-(pyridin-2-yl)benzamide | LCMS Rt = 1.49 minutes MS m/z 522.12 [M + H]+ |
| 374 | 5-{[2-chloro-4-fluoro-5-(pyridin-2-yl)benzoyl]amino}-N-(2-hydroxy-2-methylpropyl)-N-methyl-1-phenyl-1H-pyrazole-3-carboxamide | LCMS Rt = 1.61 minutes MS m/z 522.17 [M + H]+ |
| 375 | 5-{[2-chloro-4-fluoro-5-(pyridin-2-yl)benzoyl]amino}-N-(2,3-dihydroxypropyl)-N-methyl-1-phenyl-1H-pyrazole-3-carboxamide | LCMS Rt = 1.51 minutes MS m/z 524.26 [M + H]+ |
| 376 | 5-{[2-chloro-4-fluoro-5-(pyridin-2-yl)benzoyl]amino}-N-[2-(2-hydroxyethoxy)ethyl]-1-phenyl-1H-pyrazole-3-carboxamide | LCMS Rt = 1.55 minutes MS m/z 524.12 [M + H]+ |
| 377 | 5-{[2-chloro-4-fluoro-5-(pyridin-2-yl)benzoyl]amino}-N-[(4-methyl-4H-1,2,4-triazol-3-yl)methyl]-1-phenyl-1H-pyrazole-3-carboxamide | LCMS Rt = 1.57 minutes MS m/z 531.09 [M + H]+ |
| 378 | 5-{[2-chloro-4-fluoro-5-(pyridin-2-yl)benzoyl]amino}-N-[(3-methyl-1,2,4-oxadiazol-5-yl)methyl]-1-phenyl-1H-pyrazole-3-carboxamide | LCMS Rt = 1.62 minutes MS m/z 532.16 [M + H]+ |
| 379 | 2-chloro-4-fluoro-N-{3-[(4-methyl-3-oxopiperazin-1-yl)carbonyl]-1-phenyl-1H-pyrazol-5-yl}-5-(pyridin-2-yl)benzamide | LCMS Rt = 1.59 minutes MS m/z 533.13 [M + H]+ |
| 380 | 2-chloro-N-(3-{[(3S)-3-(dimethylamino)pyrrolidin-1-yl]carbonyl}-1-phenyl-1H-pyrazol-5-yl)-4-fluoro-5-(pyridin-2-yl)benzamide | LCMS Rt = 1.4 minutes MS m/z 533.27 [M + H]+ |
| 381 | 2-chloro-N-(3-{[(3R)-3-(dimethylamino)pyrrolidin-1-yl]carbonyl}-1-phenyl-1H-pyrazol-5-yl)-4-fluoro-5-(pyridin-2-yl)benzamide | LCMS Rt = 1.41 minutes MS m/z 533.23 [M + H]+ |
| 382 | N-{2-[acetyl(methyl)amino]ethyl}-5-{[2-chloro-4-fluoro-5-(pyridin-2-yl)benzoyl]amino}-1-phenyl-1H-pyrazole-3-carboxamide | LCMS Rt = 1.57 minutes MS m/z 535.23 [M + H]+ |
| 383 | 5-(2-chloro-4-fluoro-5-(pyridin-2-yl)benzamido)-N-((3S,4R)-4-hydroxytetrahydro-2H-pyran-3-yl)-1-phenyl-1H-pyrazole-3-carboxamide | LCMS Rt = 1.58 minutes MS m/z 536.11 [M + H]+ |
| 384 | 5-(2-chloro-4-fluoro-5-(pyridin-2-yl)benzamido)-N-((3S,4S)-4-hydroxytetrahydro-2H-pyran-3-yl)-1-phenyl-1H-pyrazole-3-carboxamide | LCMS Rt = 1.55 minutes MS m/z 536.11 [M + H]+ |
| 385 | 5-(2-chloro-4-fluoro-5-(pyridin-2-yl)benzamido)-N-((3R,4S)-4-hydroxytetrahydro-2H-pyran-3-yl)-1-phenyl-1H-pyrazole-3-carboxamide | LCMS Rt = 1.58 minutes MS m/z 536.06 [M + H]+ |

| Example Number | Name | Data |
| --- | --- | --- |
| 386 | N-(1-acetylpyrrolidin-3-yl)-5-{[2-chloro-4-fluoro-5-(pyridin-2-yl)benzoyl]amino}-1-phenyl-1H-pyrazole-3-carboxamide | LCMS Rt = 1.61 minutes MS m/z 547.12 [M + H]+ |
| 387 | 2-chloro-4-fluoro-N-(3-{[(3S)-3-(hydroxymethyl)morpholin-4-yl]carbonyl}-1-phenyl-1H-pyrazol-5-yl)-5-(pyridin-2-yl)benzamide | LCMS Rt = 1.56 minutes MS m/z 536.11 [M + H]+ |
| 388 | 2-chloro-4-fluoro-N-(3-{[(3R)-3-(hydroxymethyl)morpholin-4-yl]carbonyl}-1-phenyl-1H-pyrazol-5-yl)-5-(pyridin-2-yl)benzamide | LCMS Rt = 1.56 minutes MS m/z 536.11 [M + H]+ |
| 389 | 5-{[2-chloro-4-fluoro-5-(pyridin-2-yl)benzoyl]amino}-N-(2-hydroxyethyl)-N-(3-hydroxypropyl)-1-phenyl-1H-pyrazole-3-carboxamide | LCMS Rt = 1.52 minutes MS m/z 538.19 [M + H]+ |
| 390 | 5-{[2-chloro-4-fluoro-5-(pyridin-2-yl)benzoyl]amino}-N-[1,3-dihydroxy-2-(hydroxymethyl)propan-2-yl]-1-phenyl-1H-pyrazole-3-carboxamide | LCMS Rt = 1.52 minutes MS m/z 540.06 [M + H]+ |
| 391 | 5-{[2-chloro-4-fluoro-5-(pyridin-2-yl)benzoyl]amino}-1-phenyl-N-[(2S,3S)-2,3,4-trihydroxybutyl]-1H-pyrazole-3-carboxamide | LCMS Rt = 1.47 minutes MS m/z 540.2 [M + H]+ |
| 392 | 5-{[2-chloro-4-fluoro-5-(pyridin-2-yl)benzoyl]amino}-1-phenyl-N-[1-(pyrimidin-5-yl)ethyl]-1H-pyrazole-3-carboxamide | LCMS Rt = 1.63 minutes MS m/z 542.09 [M + H]+ |
| 393 | 5-{[2-chloro-4-fluoro-5-(pyridin-2-yl)benzoyl]amino}-N-methyl-1-phenyl-N-(pyrimidin-4-ylmethyl)-1H-pyrazole-3-carboxamide | LCMS Rt = 1.64 minutes MS m/z 542.1 [M + H]+ |
| 394 | 5-{[2-chloro-4-fluoro-5-(pyridin-2-yl)benzoyl]amino}-1-phenyl-N-[1-(pyrimidin-2-yl)ethyl]-1H-pyrazole-3-carboxamide | LCMS Rt = 1.67 minutes MS m/z 542.09 [M + H]+ |
| 395 | 5-{[2-chloro-4-fluoro-5-(pyridin-2-yl)benzoyl]amino}-N-[1-(1-methyl-1H-imidazol-4-yl)ethyl]-1-phenyl-1H-pyrazole-3-carboxamide | LCMS Rt = 1.42 minutes MS m/z 544.22 [M + H]+ |
| 396 | 5-{[2-chloro-4-fluoro-5-(pyridin-2-yl)benzoyl]amino}-N-[(1R)-1-(1-methyl-1H-imidazol-2-yl)ethyl]-1-phenyl-1H-pyrazole-3-carboxamide | LCMS Rt = 1.42 minutes MS m/z 544.24 [M + H]+ |
| 397 | 5-{[2-chloro-4-fluoro-5-(pyridin-2-yl)benzoyl]amino}-N-[(1S)-1-(1-methyl-1H-imidazol-2-yl)ethyl]-1-phenyl-1H-pyrazole-3-carboxamide | LCMS Rt = 1.43 minutes MS m/z 544.19 [M + H]+ |
| 398 | 5-{[2-chloro-4-fluoro-5-(pyridin-2-yl)benzoyl]amino}-N-[2-(1-methyl-1H-1,2,3-triazol-4-yl)ethyl]-1-phenyl-1H-pyrazole-3-carboxamide | LCMS Rt = 1.59 minutes MS m/z 545.17 [M + H]+ |
| 399 | 5-{[2-chloro-4-fluoro-5-(pyridin-2-yl)benzoyl]amino}-N-[1-(4-methyl-4H-1,2,4-triazol-3-yl)ethyl]-1-phenyl-1H-pyrazole-3-carboxamide | LCMS Rt = 1.59 minutes MS m/z 545.08 [M + H]+ |
| 400 | 5-{[2-chloro-4-fluoro-5-(pyridin-2-yl)benzoyl]amino}-N-[2-(4-methyl-4H-1,2,4-triazol-3-yl)ethyl]-1-phenyl-1H-pyrazole-3-carboxamide | LCMS Rt = 1.57 minutes MS m/z 545.19 [M + H]+ |
| 401 | 5-{[2-chloro-4-fluoro-5-(pyridin-2-yl)benzoyl]amino}-N-[2-(3-methyl-1,2,4-oxadiazol-5-yl)ethyl]-1-phenyl-1H-pyrazole-3-carboxamide | LCMS Rt = 1.63 minutes MS m/z 546.15 [M + H]+ |
| 402 | 5-{[2-chloro-4-fluoro-5-(pyridin-2-yl)benzoyl]amino}-N-[(1-methyl-5-oxopyrrolidin-3-yl)methyl]-1-phenyl-1H-pyrazole-3-carboxamide | LCMS Rt = 1.59 minutes MS m/z 547.22 [M + H]+ |
| 403 | N-{3-[(4-acetylpiperazin-1-yl)carbonyl]-1-phenyl-1H-pyrazol-5-yl}-2-chloro-4-fluoro-5-(pyridin-2-yl)benzamide | LCMS Rt = 1.6 minutes MS m/z 547.12 [M + H]+ |
| 404 | 2-chloro-N-(3-{[4-(dimethylamino)piperidin-1-yl]carbonyl}-1-phenyl-1H-pyrazol-5-yl)-4-fluoro-5-(pyridin-2-yl)benzamide | LCMS Rt = 1.4 minutes MS m/z 547.25 [M + H]+ |
| 405 | 5-{[2-chloro-4-fluoro-5-(pyridin-2-yl)benzoyl]amino}-1-phenyl-N-(1,1,1-trifluoro-3-hydroxypropan-2-yl)-1H-pyrazole-3-carboxamide | LCMS Rt = 1.63 minutes MS m/z 548.15 [M + H]+ |
| 406 | 5-{[2-chloro-4-fluoro-5-(pyridin-2-yl)benzoyl]amino}-N-[2-(morpholin-4-yl)ethyl]-1-phenyl-1H-pyrazole-3-carboxamide | LCMS Rt = 1.41 minutes MS m/z 549.24 [M + H]+ |
| 407 | N-(3-{[2,2-bis(hydroxymethyl)pyrrolidin-1-yl]carbonyl}-1-phenyl-1H-pyrazol-5-yl)-2-chloro-4-fluoro-5-(pyridin-2-yl)benzamide | LCMS Rt = 1.59 minutes MS m/z 550.1 [M + H]+ |
| 408 | 2-chloro-4-fluoro-N-(3-{[4-hydroxy-4-(hydroxymethyl)piperidin-1-yl]carbonyl}-1-phenyl-1H-pyrazol-5-yl)-5-(pyridin-2-yl)benzamide | LCMS Rt = 1.51 minutes MS m/z 550.1 [M + H]+ |
| 409 | 5-{[2-chloro-4-fluoro-5-(pyridin-2-yl)benzoyl]amino}-N-[4-(dimethylamino)-2-hydroxybutyl]-1-phenyl-1H-pyrazole-3-carboxamide | LCMS Rt = 1.4 minutes MS m/z 551.21 [M + H]+ |
| 410 | 5-{[2-chloro-4-fluoro-5-(pyridin-2-yl)benzoyl]amino}-N-[1-(dimethylamino)-3-methoxypropan-2-yl]-1-phenyl-1H-pyrazole-3-carboxamide | LCMS Rt = 1.43 minutes MS m/z 551.21 [M + H]+ |

| Example Number | Name | Data |
|---|---|---|
| 411 | 2-chloro-N-(3-{[(2S,3S,4S)-3,4-dihydroxy-2-(hydroxymethyl)pyrrolidin-1-yl]carbonyl}-1-phenyl-1H-pyrazol-5-yl)-4-fluoro-5-(pyridin-2-yl)benzamide | LCMS Rt = 1.48 minutes MS m/z 552.14 [M + H]+ |
| 412 | 5-{[2-chloro-4-fluoro-5-(pyridin-2-yl)benzoyl]amino}-N-[2-(4-methylpiperazin-1-yl)ethyl]-1-phenyl-1H-pyrazole-3-carboxamide | LCMS Rt = 1.4 minutes MS m/z 562.14 [M + H]+ |
| 413 | 5-{[2-chloro-4-fluoro-5-(pyridin-2-yl)benzoyl]amino}-N-[2-(morpholin-4-yl)-2-oxoethyl]-1-phenyl-1H-pyrazole-3-carboxamide | LCMS Rt = 1.59 minutes MS m/z 563.2 [M + H]+ |
| 414 | 5-{[2-chloro-4-fluoro-5-(pyridin-2-yl)benzoyl]amino}-N-(1,3-oxazol-5-ylmethyl)-1-phenyl-1H-pyrazole-3-carboxamide | LCMS Rt = 1.61 minutes MS m/z 517.22 [M + H]+ |
| 415 | 5-{[2-chloro-4-fluoro-5-(pyridin-2-yl)benzoyl]amino}-N-(1,2-oxazol-5-ylmethyl)-1-phenyl-1H-pyrazole-3-carboxamide | LCMS Rt = 1.62 minutes MS m/z 517.1 [M + H]+ |
| 416 | 5-{[2,4-dichloro-5-(5-fluoropyridin-2-yl)benzoyl]amino}-N-[(1-methyl-1H-1,2,3-triazol-5-yl)methyl]-1-phenyl-1H-pyrazole-3-carboxamide | LCMS Rt = 1.63 minutes MS m/z 565.15 [M + H]+ |
| 417 | 5-{[2,4-dichloro-5-(5-fluoropyridin-2-yl)benzoyl]amino}-N-(1,2-oxazol-3-ylmethyl)-1-phenyl-1H-pyrazole-3-carboxamide | LCMS Rt = 1.67 minutes MS m/z 551.12 [M + H]+ |
| 418 | 5-{[2,4-dichloro-5-(5-fluoropyridin-2-yl)benzoyl]amino}-N-[3-(2-hydroxyethyl)oxetan-3-yl]-1-phenyl-1H-pyrazole-3-carboxamide | LCMS Rt = 1.59 minutes MS m/z 570.13 [M + H]+ |
| 419 | 5-{[2,4-dichloro-5-(5-fluoropyridin-2-yl)benzoyl]amino}-N-[(3-fluorooxetan-3-yl)methyl]-1-phenyl-1H-pyrazole-3-carboxamide | LCMS Rt = 1.66 minutes MS m/z 558.19 [M + H]+ |
| 420 | 5-{[2,4-dichloro-5-(5-fluoropyridin-2-yl)benzoyl]amino}-N-(1,3,4-oxadiazol-2-ylmethyl)-1-phenyl-1H-pyrazole-3-carboxamide | LCMS Rt = 1.63 minutes MS m/z 552.09 [M + H]+ |
| 421 | 5-{[2,4-dichloro-5-(5-fluoropyridin-2-yl)benzoyl]amino}-N-[1-(hydroxymethyl)cyclopropyl]-1-phenyl-1H-pyrazole-3-carboxamide | LCMS Rt = 1.62 minutes MS m/z 540.11 [M + H]+ |
| 422 | 5-{[2,4-dichloro-5-(5-fluoropyridin-2-yl)benzoyl]amino}-N-(trans-4-hydroxy-4-methylcyclohexyl)-1-phenyl-1H-pyrazole-3-carboxamide | LCMS Rt = 1.65 minutes MS m/z 582.16 [M + H]+ |
| 423 | 5-{[2,4-dichloro-5-(5-fluoropyridin-2-yl)benzoyl]amino}-N-(1,3-oxazol-2-ylmethyl)-1-phenyl-1H-pyrazole-3-carboxamide | LCMS Rt = 1.65 minutes MS m/z 551.09 [M + H]+ |
| 424 | 5-{[2,4-dichloro-5-(5-fluoropyridin-2-yl)benzoyl]amino}-1-phenyl-N-(pyridin-2-ylmethyl)-1H-pyrazole-3-carboxamide | LCMS Rt = 1.62 minutes MS m/z 561.11 [M + H]+ |
| 425 | 5-{[2,4-dichloro-5-(5-fluoropyridin-2-yl)benzoyl]amino}-1-phenyl-N-(tetrahydrofuran-3-ylmethyl)-1H-pyrazole-3-carboxamide | LCMS Rt = 1.67 minutes MS m/z 554.14 [M + H]+ |
| 426 | 5-{[2,4-dichloro-5-(5-fluoropyridin-2-yl)benzoyl]amino}-1-phenyl-N-(1H-pyrazol-3-ylmethyl)-1H-pyrazole-3-carboxamide | LCMS Rt = 1.62 minutes MS m/z 550.14 [M + H]+ |
| 427 | 5-{[2,4-dichloro-5-(5-fluoropyridin-2-yl)benzoyl]amino}-N-[3-(hydroxymethyl)oxetan-3-yl]-1-phenyl-1H-pyrazole-3-carboxamide | LCMS Rt = 1.58 minutes MS m/z 556.09 [M + H]+ |
| 428 | 5-{[2,4-dichloro-5-(5-fluoropyridin-2-yl)benzoyl]amino}-1-phenyl-N-(4H-1,2,4-triazol-3-ylmethyl)-1H-pyrazole-3-carboxamide | LCMS Rt = 1.57 minutes MS m/z 551.12 [M + H]+ |
| 429 | 5-{[2,4-dichloro-5-(5-fluoropyridin-2-yl)benzoyl]amino}-N-[2-(dimethylamino)-2-oxoethyl]-1-phenyl-1H-pyrazole-3-carboxamide | LCMS Rt = 1.65 minutes MS m/z 555.12 [M + H]+ |
| 430 | 5-{[2,4-dichloro-5-(5-fluoropyridin-2-yl)benzoyl]amino}-N-[(5-methyl-1,3,4-oxadiazol-2-yl)methyl]-1-phenyl-1H-pyrazole-3-carboxamide | LCMS Rt = 1.63 minutes MS m/z 566.1 [M + H]+ |
| 431 | 5-{[2,4-dichloro-5-(5-fluoropyridin-2-yl)benzoyl]amino}-1-phenyl-N-[(3S)-tetrahydrofuran-3-yl]-1H-pyrazole-3-carboxamide | LCMS Rt = 1.66 minutes MS m/z 540.12 [M + H]+ |
| 432 | 5-{[2,4-dichloro-5-(5-fluoropyridin-2-yl)benzoyl]amino}-N-(1-hydroxypropan-2-yl)-1-phenyl-1H-pyrazole-3-carboxamide | LCMS Rt = 1.61 minutes MS m/z 528.12 [M + H]+ |
| 433 | 5-{[2,4-dichloro-5-(5-fluoropyridin-2-yl)benzoyl]amino}-N-[(1-methyl-1H-pyrazol-4-yl)methyl]-1-phenyl-1H-pyrazole-3-carboxamide | LCMS Rt = 1.66 minutes MS m/z 564.14 [M + H]+ |
| 434 | 5-{[2,4-dichloro-5-(5-fluoropyridin-2-yl)benzoyl]amino}-N-(1,3-oxazol-4-ylmethyl)-1-phenyl-1H-pyrazole-3-carboxamide | LCMS Rt = 1.65 minutes MS m/z 551.11 [M + H]+ |

| Example Number | Name | Data |
|---|---|---|
| 435 | N-cyclopropyl-5-{[2,4-dichloro-5-(5-fluoropyridin-2-yl)benzoyl]amino}-1-phenyl-1H-pyrazole-3-carboxamide | LCMS Rt = 1.68 minutes MS m/z 510.09 [M + H]+ |
| 436 | 5-{[2,4-dichloro-5-(5-fluoropyridin-2-yl)benzoyl]amino}-N-ethyl-1-phenyl-1H-pyrazole-3-carboxamide | LCMS Rt = 1.68 minutes MS m/z 498.1 [M + H]+ |
| 437 | 5-{[2,4-dichloro-5-(5-fluoropyridin-2-yl)benzoyl]amino}-1-phenyl-N-(tetrahydro-2H-pyran-4-yl)-1H-pyrazole-3-carboxamide | LCMS Rt = 1.67 minutes MS m/z 554.15 [M + H]+ |
| 438 | 5-{[2,4-dichloro-5-(5-fluoropyridin-2-yl)benzoyl]amino}-1-phenyl-N-(pyrazin-2-ylmethyl)-1H-pyrazole-3-carboxamide | LCMS Rt = 1.66 minutes MS m/z 562.12 [M + H]+ |
| 439 | 5-{[2,4-dichloro-5-(5-fluoropyridin-2-yl)benzoyl]amino}-N-(oxetan-3-yl)-1-phenyl-1H-pyrazole-3-carboxamide | LCMS Rt = 1.63 minutes MS m/z 526.12 [M + H]+ |
| 440 | 5-(2,4-dichloro-5-(5-fluoropyridin-2-yl)benzamido)-N-((3R,4S)-3-hydroxytetrahydro-2H-pyran-4-yl)-1-phenyl-1H-pyrazole-3-carboxamide | LCMS Rt = 1.6 minutes MS m/z 570.13 [M + H]+ |
| 441 | 5-{[2,4-dichloro-5-(5-fluoropyridin-2-yl)benzoyl]amino}-N-[2-(methylamino)-2-oxoethyl]-1-phenyl-1H-pyrazole-3-carboxamide | LCMS Rt = 1.59 minutes MS m/z 541.13 [M + H]+ |
| 442 | 5-{[2,4-dichloro-5-(5-fluoropyridin-2-yl)benzoyl]amino}-N-[(2R)-1-hydroxy-3-methoxypropan-2-yl]-1-phenyl-1H-pyrazole-3-carboxamide | LCMS Rt = 1.61 minutes MS m/z 558.15 [M + H]+ |
| 443 | 5-{[2,4-dichloro-5-(5-fluoropyridin-2-yl)benzoyl]amino}-N-[(3S,4R)-4-hydroxytetrahydrofuran-3-yl]-1-phenyl-1H-pyrazole-3-carboxamide | LCMS Rt = 1.59 minutes MS m/z 556.12 [M + H]+ |
| 444 | 5-{[2,4-dichloro-5-(5-fluoropyridin-2-yl)benzoyl]amino}-N-(3-methyl-1H-pyrazol-4-yl)-1-phenyl-1H-pyrazole-3-carboxamide | LCMS Rt = 1.64 minutes MS m/z 550.14 [M + H]+ |
| 445 | 5-{[2,4-dichloro-5-(5-fluoropyridin-2-yl)benzoyl]amino}-N-(oxetan-3-ylmethyl)-1-phenyl-1H-pyrazole-3-carboxamide | LCMS Rt = 1.64 minutes MS m/z 540.06 [M + H]+ |
| 446 | 5-{[2,4-dichloro-5-(5-fluoropyridin-2-yl)benzoyl]amino}-N-(3,5-dimethyl-1H-pyrazol-4-yl)-1-phenyl-1H-pyrazole-3-carboxamide | LCMS Rt = 1.64 minutes MS m/z 564.13 [M + H]+ |
| 447 | 5-{[2,4-dichloro-5-(5-fluoropyridin-2-yl)benzoyl]amino}-N-[(2R)-2-hydroxypropyl]-1-phenyl-1H-pyrazole-3-carboxamide | LCMS Rt = 1.61 minutes MS m/z 528.12 [M + H]+ |
| 448 | 2,4-dichloro-5-(5-fluoropyridin-2-yl)-N-{3-[(3-oxopiperazin-1-yl)carbonyl]-1-phenyl-1H-pyrazol-5-yl}benzamide | LCMS Rt = 1.59 minutes MS m/z 553.07 [M + H]+ |
| 449 | N-(2-amino-2-oxoethyl)-5-{[2,4-dichloro-5-(5-fluoropyridin-2-yl)benzoyl]amino}-1-phenyl-1H-pyrazole-3-carboxamide | LCMS Rt = 1.56 minutes MS m/z 527.09 [M + H]+ |
| 450 | 5-{[2,4-dichloro-5-(5-fluoropyridin-2-yl)benzoyl]amino}-N-[(2R)-2,3-dihydroxypropyl]-1-phenyl-1H-pyrazole-3-carboxamide | LCMS Rt = 1.55 minutes MS m/z 544.06 [M + H]+ |
| 451 | 5-{[2,4-dichloro-5-(5-fluoropyridin-2-yl)benzoyl]amino}-N-[(1-methyl-1H-1,2,3-triazol-4-yl)methyl]-1-phenyl-1H-pyrazole-3-carboxamide | LCMS Rt = 1.65 minutes MS m/z 565.07 [M + H]+ |
| 452 | N-[(2-aminopyridin-4-yl)methyl]-5-{[2,4-dichloro-5-(5-fluoropyridin-2-yl)benzoyl]amino}-1-phenyl-1H-pyrazole-3-carboxamide | LCMS Rt = 1.45 minutes MS m/z 576.21 [M + H]+ |
| 453 | 5-{[2,4-dichloro-5-(5-fluoropyridin-2-yl)benzoyl]amino}-N-(cis-4-hydroxycyclohexyl)-1-phenyl-1H-pyrazole-3-carboxamide | LCMS Rt = 1.63 minutes MS m/z 568.09 [M + H]+ |
| 454 | 5-{[2,4-dichloro-5-(5-fluoropyridin-2-yl)benzoyl]amino}-N-[(5-oxopyrrolidin-2-yl)methyl]-1-phenyl-1H-pyrazole-3-carboxamide | LCMS Rt = 1.6 minutes MS m/z 567.2 [M + H]+ |
| 455 | 5-{[2,4-dichloro-5-(5-fluoropyridin-2-yl)benzoyl]amino}-N-(2-hydroxy-2-methylpropyl)-1-phenyl-1H-pyrazole-3-carboxamide | LCMS Rt = 1.63 minutes MS m/z 542.1 [M + H]+ |
| 456 | 5-{[2,4-dichloro-5-(5-fluoropyridin-2-yl)benzoyl]amino}-N-[2-(2-hydroxyethoxy)ethyl]-1-phenyl-1H-pyrazole-3-carboxamide | LCMS Rt = 1.59 minutes MS m/z 558.09 [M + H]+ |
| 457 | 5-{[2,4-dichloro-5-(5-fluoropyridin-2-yl)benzoyl]amino}-1-phenyl-N-(pyrimidin-2-ylmethyl)-1H-pyrazole-3-carboxamide | LCMS Rt = 1.66 minutes MS m/z 562.12 [M + H]+ |
| 458 | (3S)-1-[(5-{[2,4-dichloro-5-(5-fluoropyridin-2-yl)benzoyl]amino}-1-phenyl-1H-pyrazol-3-yl)carbonyl]piperidine-3-carboxamide | LCMS Rt = 1.6 minutes MS m/z 581.22 [M + H]+ |

-continued

| Example Number | Name | Data |
|---|---|---|
| 459 | 5-{[2,4-dichloro-5-(5-fluoropyridin-2-yl)benzoyl]amino}-N-(1-methylazetidin-3-yl)-1-phenyl-1H-pyrazole-3-carboxamide | LCMS Rt = 1.43 minutes MS m/z 539.13 [M + H]$^+$ |
| 460 | 5-{[2,4-dichloro-5-(5-fluoropyridin-2-yl)benzoyl]amino}-N-(cis-3-hydroxycyclobutyl)-1-phenyl-1H-pyrazole-3-carboxamide | LCMS Rt = 1.6 minutes MS m/z 540.13 [M + H]$^+$ |
| 461 | 5-{[2,4-dichloro-5-(5-fluoropyridin-2-yl)benzoyl]amino}-N-methyl-1-phenyl-1H-pyrazole-3-carboxamide | LCMS Rt = 1.64 minutes MS m/z 484.12 [M + H]$^+$ |
| 462 | 2,4-dichloro-5-(5-fluoropyridin-2-yl)-N-{3-[(3-hydroxyazetidin-1-yl)carbonyl]-1-phenyl-1H-pyrazol-5-yl}benzamide | LCMS Rt = 1.6 minutes MS m/z 526.07 [M + H]$^+$ |
| 463 | 5-{[2,4-dichloro-5-(5-fluoropyridin-2-yl)benzoyl]amino}-N-[(3R,4S)-4-hydroxytetrahydrofuran-3-yl]-1-phenyl-1H-pyrazole-3-carboxamide | LCMS Rt = 1.59 minutes MS m/z 556.1 [M + H]$^+$ |
| 464 | 5-{[2,4-dichloro-5-(5-fluoropyridin-2-yl)benzoyl]amino}-N-(1,2-oxazol-5-ylmethyl)-1-phenyl-1H-pyrazole-3-carboxamide | LCMS Rt = 1.66 minutes MS m/z 551.19 [M + H]$^+$ |
| 465 | 5-{[2,4-dichloro-5-(5-fluoropyridin-2-yl)benzoyl]amino}-N-[(3S)-5-oxopyrrolidin-3-yl]-1-phenyl-1H-pyrazole-3-carboxamide | LCMS Rt = 1.58 minutes MS m/z 553.12 [M + H]$^+$ |
| 466 | 5-{[2,4-dichloro-5-(5-fluoropyridin-2-yl)benzoyl]amino}-N-[(3-methyl-1H-1,2,4-triazol-5-yl)methyl]-1-phenyl-1H-pyrazole-3-carboxamide | LCMS Rt = 1.58 minutes MS m/z 565.11 [M + H]$^+$ |
| 467 | 5-{[2,4-dichloro-5-(5-fluoropyridin-2-yl)benzoyl]amino}-N-(trans-4-hydroxycyclohexyl)-1-phenyl-1H-pyrazole-3-carboxamide | LCMS Rt = 1.63 minutes MS m/z 568.26 [M + H]$^+$ |
| 468 | 5-{[2,4-dichloro-5-(5-fluoropyridin-2-yl)benzoyl]amino}-N-[(2R)-1-hydroxypropan-2-yl]-1-phenyl-1H-pyrazole-3-carboxamide | LCMS Rt = 1.61 minutes MS m/z 528.13 [M + H]$^+$ |
| 469 | 5-{[2,4-dichloro-5-(5-fluoropyridin-2-yl)benzoyl]amino}-1-phenyl-N-(pyridazin-3-ylmethyl)-1H-pyrazole-3-carboxamide | LCMS Rt = 1.64 minutes MS m/z 562.21 [M + H]$^+$ |
| 470 | 5-{[2,4-dichloro-5-(5-fluoropyridin-2-yl)benzoyl]amino}-N-(3-methyloxetan-3-yl)-1-phenyl-1H-pyrazole-3-carboxamide | LCMS Rt = 1.66 minutes MS m/z 540.09 [M + H]$^+$ |
| 471 | 5-{[2,4-dichloro-5-(5-fluoropyridin-2-yl)benzoyl]amino}-N-(1,3-oxazol-5-ylmethyl)-1-phenyl-1H-pyrazole-3-carboxamide | LCMS Rt = 1.65 minutes MS m/z 551.18 [M + H]$^+$ |
| 472 | 1-[(5-{[2,4-dichloro-5-(5-fluoropyridin-2-yl)benzoyl]amino}-1-phenyl-1H-pyrazol-3-yl)carbonyl]pyrrolidine-3-carboxamide | LCMS Rt = 1.59 minutes MS m/z 567.06 [M + H]$^+$ |
| 473 | 5-{[2,4-dichloro-5-(5-fluoropyridin-2-yl)benzoyl]amino}-1-phenyl-N-(pyrimidin-4-ylmethyl)-1H-pyrazole-3-carboxamide | LCMS Rt = 1.65 minutes MS m/z 562.07 [M + H]$^+$ |
| 474 | 5-{[2,4-dichloro-5-(5-fluoropyridin-2-yl)benzoyl]amino}-1-phenyl-N-[(3R)-tetrahydrofuran-3-yl]-1H-pyrazole-3-carboxamide | LCMS Rt = 1.66 minutes MS m/z 540.11 [M + H]$^+$ |
| 475 | 5-{[2,4-dichloro-5-(5-fluoropyridin-2-yl)benzoyl]amino}-N-(2-methoxyethyl)-1-phenyl-1H-pyrazole-3-carboxamide | LCMS Rt = 1.67 minutes MS m/z 528.07 [M + H]$^+$ |
| 476 | 5-{[2,4-dichloro-5-(5-fluoropyridin-2-yl)benzoyl]amino}-N-(3-hydroxypropyl)-1-phenyl-1H-pyrazole-3-carboxamide | LCMS Rt = 1.6 minutes MS m/z 528.09 [M + H]$^+$ |
| 477 | 5-{[2,4-dichloro-5-(5-fluoropyridin-2-yl)benzoyl]amino}-N-[(1-hydroxycyclopropyl)methyl]-1-phenyl-1H-pyrazole-3-carboxamide | LCMS Rt = 1.63 minutes MS m/z 540.09 [M + H]$^+$ |
| 478 | 5-{[2,4-dichloro-5-(5-fluoropyridin-2-yl)benzoyl]amino}-N-[(2S)-2-hydroxypropyl]-1-phenyl-1H-pyrazole-3-carboxamide | LCMS Rt = 1.61 minutes MS m/z 528.12 [M + H]$^+$ |
| 479 | 5-{[2,4-dichloro-5-(5-fluoropyridin-2-yl)benzoyl]amino}-N-(trans-3-hydroxycyclobutyl)-1-phenyl-1H-pyrazole-3-carboxamide | LCMS Rt = 1.6 minutes MS m/z 540.12 [M + H]$^+$ |
| 480 | 5-{[2,4-dichloro-5-(5-fluoropyridin-2-yl)benzoyl]amino}-N-[(2S)-1-hydroxypropan-2-yl]-1-phenyl-1H-pyrazole-3-carboxamide | LCMS Rt = 1.61 minutes MS m/z 528.12 [M + H]$^+$ |
| 481 | 5-{[2-chloro-4-fluoro-5-(3-fluoropyridin-2-yl)benzoyl]amino}-1-phenyl-N-(pyridin-2-ylmethyl)-1H-pyrazole-3-carboxamide | LCMS Rt = 1.58 minutes MS m/z 545.22 [M + H]$^+$ |
| 482 | 5-{[2-chloro-4-fluoro-5-(3-fluoropyridin-2-yl)benzoyl]amino}-N-[(5-oxopyrrolidin-2-yl)methyl]-1-phenyl-1H-pyrazole-3-carboxamide | LCMS Rt = 1.57 minutes MS m/z 551.21 [M + H]$^+$ |

| Example Number | Name | Data |
|---|---|---|
| 483 | 2-chloro-4-fluoro-5-(3-fluoropyridin-2-yl)-N-{3-[(3-oxopiperazin-1-yl)carbonyl]-1-phenyl-1H-pyrazol-5-yl}benzamide | LCMS Rt = 1.55 minutes MS m/z 537.18 [M + H]+ |
| 484 | 5-{[2-chloro-4-fluoro-5-(3-fluoropyridin-2-yl)benzoyl]amino}-N-(2-hydroxy-3-methoxypropyl)-1-phenyl-1H-pyrazole-3-carboxamide | LCMS Rt = 1.56 minutes MS m/z 542.15 [M + H]+ |
| 485 | 5-{[2-chloro-4-fluoro-5-(3-fluoropyridin-2-yl)benzoyl]amino}-1-phenyl-N-(pyrimidin-4-ylmethyl)-1H-pyrazole-3-carboxamide | LCMS Rt = 1.61 minutes MS m/z 546.26 [M + H]+ |
| 486 | 5-{[2-chloro-4-fluoro-5-(3-fluoropyridin-2-yl)benzoyl]amino}-1-phenyl-N-(tetrahydrofuran-3-ylmethyl)-1H-pyrazole-3-carboxamide | LCMS Rt = 1.63 minutes MS m/z 538.2 [M + H]+ |
| 487 | 5-{[2-chloro-4-fluoro-5-(3-fluoropyridin-2-yl)benzoyl]amino}-N-[(3S)-5-oxopyrrolidin-3-yl]-1-phenyl-1H-pyrazole-3-carboxamide | LCMS Rt = 1.54 minutes MS m/z 537.19 [M + H]+ |
| 488 | 5-{[2-chloro-4-fluoro-5-(3-fluoropyridin-2-yl)benzoyl]amino}-N-(1-methylpyrrolidin-3-yl)-1-phenyl-1H-pyrazole-3-carboxamide | LCMS Rt = 1.43 minutes MS m/z 537.23 [M + H]+ |
| 489 | 5-{[2-chloro-4-fluoro-5-(3-fluoropyridin-2-yl)benzoyl]amino}-N-[(1-methyl-1H-1,2,3-triazol-4-yl)methyl]-1-phenyl-1H-pyrazole-3-carboxamide | LCMS Rt = 1.61 minutes MS m/z 549.26 [M + H]+ |
| 490 | 5-{[2-chloro-4-fluoro-5-(3-fluoropyridin-2-yl)benzoyl]amino}-1-phenyl-N-(4H-1,2,4-triazol-3-ylmethyl)-1H-pyrazole-3-carboxamide | LCMS Rt = 1.54 minutes MS m/z 535.13 [M + H]+ |
| 491 | 5-{[2-chloro-4-fluoro-5-(3-fluoropyridin-2-yl)benzoyl]amino}-N-(1-methylazetidin-3-yl)-1-phenyl-1H-pyrazole-3-carboxamide | LCMS Rt = 1.42 minutes MS m/z 523.24 [M + H]+ |
| 492 | (3S)-1-[(5-{[2-chloro-4-fluoro-5-(3-fluoropyridin-2-yl)benzoyl]amino}-1-phenyl-1H-pyrazol-3-yl)carbonyl]piperidine-3-carboxamide | LCMS Rt = 1.57 minutes MS m/z 565.22 [M + H]+ |
| 493 | 5-{[2-chloro-4-fluoro-5-(3-fluoropyridin-2-yl)benzoyl]amino}-1-phenyl-N-(tetrahydro-2H-pyran-4-yl)-1H-pyrazole-3-carboxamide | LCMS Rt = 1.63 minutes MS m/z 538.3 [M + H]+ |
| 494 | 5-{[2-chloro-4-fluoro-5-(3-fluoropyridin-2-yl)benzoyl]amino}-N-{[3-(hydroxymethyl)oxetan-3-yl]methyl}-1-phenyl-1H-pyrazole-3-carboxamide | LCMS Rt = 1.55 minutes MS m/z 554.19 [M + H]+ |
| 495 | 5-{[2-chloro-4-fluoro-5-(3-fluoropyridin-2-yl)benzoyl]amino}-N-(1,3-oxazol-4-ylmethyl)-1-phenyl-1H-pyrazole-3-carboxamide | LCMS Rt = 1.61 minutes MS m/z 535.14 [M + H]+ |
| 496 | 5-{[2-chloro-4-fluoro-5-(3-fluoropyridin-2-yl)benzoyl]amino}-N-(3-hydroxy-3-methylbutyl)-1-phenyl-1H-pyrazole-3-carboxamide | LCMS Rt = 1.61 minutes MS m/z 540.21 [M + H]+ |
| 497 | 5-{[2-chloro-4-fluoro-5-(3-fluoropyridin-2-yl)benzoyl]amino}-N-[(2S)-1-hydroxy-3-methoxypropan-2-yl]-1-phenyl-1H-pyrazole-3-carboxamide | LCMS Rt = 1.57 minutes MS m/z 542.24 [M + H]+ |
| 498 | 5-{[2-chloro-4-fluoro-5-(3-fluoropyridin-2-yl)benzoyl]amino}-N-[2-(dimethylamino)-2-oxoethyl]-1-phenyl-1H-pyrazole-3-carboxamide | LCMS Rt = 1.61 minutes MS m/z 539.14 [M + H]+ |
| 499 | 5-{[2-chloro-4-fluoro-5-(3-fluoropyridin-2-yl)benzoyl]amino}-N-[3-(2-hydroxyethyl)oxetan-3-yl]-1-phenyl-1H-pyrazole-3-carboxamide | LCMS Rt = 1.55 minutes MS m/z 554.28 [M + H]+ |
| 500 | 5-{[2-chloro-4-fluoro-5-(3-fluoropyridin-2-yl)benzoyl]amino}-N-(3,5-dimethyl-1H-pyrazol-4-yl)-1-phenyl-1H-pyrazole-3-carboxamide | LCMS Rt = 1.6 minutes MS m/z 548.24 [M + H]+ |
| 501 | 5-{[2-chloro-4-fluoro-5-(3-fluoropyridin-2-yl)benzoyl]amino}-1-phenyl-N-[2-(1H-1,2,3-triazol-1-yl)ethyl]-1H-pyrazole-3-carboxamide | LCMS Rt = 1.58 minutes MS m/z 549.15 [M + H]+ |
| 502 | 5-{[2-chloro-4-fluoro-5-(3-fluoropyridin-2-yl)benzoyl]amino}-N-cyclopropyl-1-phenyl-1H-pyrazole-3-carboxamide | LCMS Rt = 1.64 minutes MS m/z 494.19 [M + H]+ |
| 503 | 5-{[2-chloro-4-fluoro-5-(3-fluoropyridin-2-yl)benzoyl]amino}-1-phenyl-N-(pyrimidin-2-ylmethyl)-1H-pyrazole-3-carboxamide | LCMS Rt = 1.62 minutes MS m/z 546.19 [M + H]+ |
| 504 | 5-{[2-chloro-4-fluoro-5-(3-fluoropyridin-2-yl)benzoyl]amino}-N-[3-(hydroxymethyl)oxetan-3-yl]-1-phenyl-1H-pyrazole-3-carboxamide | LCMS Rt = 1.54 minutes MS m/z 540.2 [M + H]+ |
| 505 | 5-{[2-chloro-4-fluoro-5-(3-fluoropyridin-2-yl)benzoyl]amino}-N-[(1-methyl-1H-pyrazol-4-yl)methyl]-1-phenyl-1H-pyrazole-3-carboxamide | LCMS Rt = 1.62 minutes MS m/z 548.22 [M + H]+ |
| 506 | 5-{[2-chloro-4-fluoro-5-(3-fluoropyridin-2-yl)benzoyl]amino}-N-methyl-1-phenyl-1H-pyrazole-3-carboxamide | LCMS Rt = 1.6 minutes MS m/z 468.12 [M + H]+ |
| 507 | 5-{[2-chloro-4-fluoro-5-(3-fluoropyridin-2-yl)benzoyl]amino}-N-[2-(2-hydroxyethoxy)ethyl]-1-phenyl-1H-pyrazole-3-carboxamide | LCMS Rt = 1.55 minutes MS m/z 542.2 [M + H]+ |

| Example Number | Name | Data |
|---|---|---|
| 508 | 5-(2-chloro-4-fluoro-5-(3-fluoropyridin-2-yl)benzamido)-N-((3S,4R)-3-hydroxytetrahydro-2H-pyran-4-yl)-1-phenyl-1H-pyrazole-3-carboxamide | LCMS Rt = 1.56 minutes MS m/z 554.19 [M + H]+ |
| 509 | 5-{[2-chloro-4-fluoro-5-(3-fluoropyridin-2-yl)benzoyl]amino}-1-phenyl-N-(pyridazin-3-ylmethyl)-1H-pyrazole-3-carboxamide | LCMS Rt = 1.6 minutes MS m/z 546.15 [M + H]+ |
| 510 | 5-{[2-chloro-4-fluoro-5-(3-fluoropyridin-2-yl)benzoyl]amino}-1-phenyl-N-(pyrazin-2-ylmethyl)-1H-pyrazole-3-carboxamide | LCMS Rt = 1.62 minutes MS m/z 546.23 [M + H]+ |
| 511 | 5-{[2-chloro-4-fluoro-5-(3-fluoropyridin-2-yl)benzoyl]amino}-N-[(2R)-1-hydroxy-3-methoxypropan-2-yl]-1-phenyl-1H-pyrazole-3-carboxamide | LCMS Rt = 1.58 minutes MS m/z 542.15 [M + H]+ |
| 512 | 5-{[2-chloro-4-fluoro-5-(3-fluoropyridin-2-yl)benzoyl]amino}-N-[(2R)-1-hydroxypropan-2-yl]-1-phenyl-1H-pyrazole-3-carboxamide | LCMS Rt = 1.57 minutes MS m/z 512.21 [M + H]+ |
| 513 | 5-{[2-chloro-4-fluoro-5-(3-fluoropyridin-2-yl)benzoyl]amino}-1-phenyl-N-[(3R)-tetrahydrofuran-3-yl]-1H-pyrazole-3-carboxamide | LCMS Rt = 1.62 minutes MS m/z 524.18 [M + H]+ |
| 514 | 5-{[2-chloro-4-fluoro-5-(3-fluoropyridin-2-yl)benzoyl]amino}-N-[(2S)-1-hydroxypropan-2-yl]-1-phenyl-1H-pyrazole-3-carboxamide | LCMS Rt = 1.57 minutes MS m/z 512.18 [M + H]+ |
| 515 | 5-{[2-chloro-4-fluoro-5-(3-fluoropyridin-2-yl)benzoyl]amino}-N-[2-(methylamino)-2-oxoethyl]-1-phenyl-1H-pyrazole-3-carboxamide | LCMS Rt = 1.55 minutes MS m/z 525.19 [M + H]+ |
| 516 | 5-{[2-chloro-4-fluoro-5-(3-fluoropyridin-2-yl)benzoyl]amino}-1-phenyl-N-[(3S)-tetrahydrofuran-3-yl]-1H-pyrazole-3-carboxamide | LCMS Rt = 1.62 minutes MS m/z 524.21 [M + H]+ |
| 517 | 5-{[2-chloro-4-fluoro-5-(3-fluoropyridin-2-yl)benzoyl]amino}-N-(3-methyloxetan-3-yl)-1-phenyl-1H-pyrazole-3-carboxamide | LCMS Rt = 1.62 minutes MS m/z 524.17 [M + H]+ |
| 518 | 5-{[2-chloro-4-fluoro-5-(3-fluoropyridin-2-yl)benzoyl]amino}-N-(trans-3-hydroxycyclobutyl)-1-phenyl-1H-pyrazole-3-carboxamide | LCMS Rt = 1.56 minutes MS m/z 524.21 [M + H]+ |
| 519 | 5-{[2-chloro-4-fluoro-5-(3-fluoropyridin-2-yl)benzoyl]amino}-N-(1,3-oxazol-5-ylmethyl)-1-phenyl-1H-pyrazole-3-carboxamide | LCMS Rt = 1.61 minutes MS m/z 535.13 [M + H]+ |
| 520 | 2-chloro-4-fluoro-5-(3-fluoropyridin-2-yl)-N-{3-[(3-hydroxyazetidin-1-yl)carbonyl]-1-phenyl-1H-pyrazol-5-yl}benzamide | LCMS Rt = 1.55 minutes MS m/z 510.21 [M + H]+ |
| 521 | 5-{[2-chloro-4-fluoro-5-(3-fluoropyridin-2-yl)benzoyl]amino}-N-(1,2-oxazol-5-ylmethyl)-1-phenyl-1H-pyrazole-3-carboxamide | LCMS Rt = 1.62 minutes MS m/z 535.09 [M + H]+ |
| 522 | 5-{[2-chloro-4-fluoro-5-(3-fluoropyridin-2-yl)benzoyl]amino}-N-[(3-methyl-1H-1,2,4-triazol-5-yl)methyl]-1-phenyl-1H-pyrazole-3-carboxamide | LCMS Rt = 1.54 minutes MS m/z 549.21 [M + H]+ |
| 523 | 5-{[2-chloro-4-fluoro-5-(3-fluoropyridin-2-yl)benzoyl]amino}-1-phenyl-N-[2-(1H-1,2,4-triazol-1-yl)ethyl]-1H-pyrazole-3-carboxamide | LCMS Rt = 1.59 minutes MS m/z 549.19 [M + H]+ |
| 524 | 1-[(5-{[2-chloro-4-fluoro-5-(3-fluoropyridin-2-yl)benzoyl]amino}-1-phenyl-1H-pyrazol-3-yl)carbonyl]pyrrolidine-3-carboxamide | LCMS Rt = 1.55 minutes MS m/z 551.14 [M + H]+ |
| 525 | 5-{[2-chloro-4-fluoro-5-(3-fluoropyridin-2-yl)benzoyl]amino}-N-(cis-3-hydroxycyclobutyl)-1-phenyl-1H-pyrazole-3-carboxamide | LCMS Rt = 1.55 minutes MS m/z 524.23 [M + H]+ |
| 526 | 5-{[2-chloro-4-fluoro-5-(3-fluoropyridin-2-yl)benzoyl]amino}-N-[(1-methyl-1H-1,2,3-triazol-5-yl)methyl]-1-phenyl-1H-pyrazole-3-carboxamide | LCMS Rt = 1.58 minutes MS m/z 549.21 [M + H]+ |
| 527 | 5-{[2-chloro-4-fluoro-5-(3-fluoropyridin-2-yl)benzoyl]amino}-N-[1-(hydroxymethyl)cyclopropyl]-1-phenyl-1H-pyrazole-3-carboxamide | LCMS Rt = 1.58 minutes MS m/z 524.21 [M + H]+ |
| 528 | 5-{[2-chloro-4-fluoro-5-(3-fluoropyridin-2-yl)benzoyl]amino}-N-[(1-hydroxycyclopropyl)methyl]-1-phenyl-1H-pyrazole-3-carboxamide | LCMS Rt = 1.59 minutes MS m/z 524.13 [M + H]+ |
| 529 | (3S)-1-[(5-{[2,4-dichloro-5-(3-fluoropyridin-2-yl)benzoyl]amino}-1-phenyl-1H-pyrazol-3-yl)carbonyl]piperidine-3-carboxamide | LCMS Rt = 1.58 minutes MS m/z 581.15 [M + H]+ |
| 530 | 5-{[2,4-dichloro-5-(3-fluoropyridin-2-yl)benzoyl]amino}-N-[2-(methylamino)-2-oxoethyl]-1-phenyl-1H-pyrazole-3-carboxamide | LCMS Rt = 1.57 minutes MS m/z 541.13 [M + H]+ |
| 531 | 5-{[2,4-dichloro-5-(3-fluoropyridin-2-yl)benzoyl]amino}-N-[1-(hydroxymethyl)cyclopropyl]-1-phenyl-1H-pyrazole-3-carboxamide | LCMS Rt = 1.6 minutes MS m/z 540.15 [M + H]+ |

| Example Number | Name | Data |
|---|---|---|
| 532 | 5-{[2,4-dichloro-5-(3-fluoropyridin-2-yl)benzoyl]amino}-1-phenyl-N-[2-(1H-1,2,4-triazol-1-yl)ethyl]-1H-pyrazole-3-carboxamide | LCMS Rt = 1.6 minutes MS m/z 565.15 [M + H]⁺ |
| 533 | 5-{[2,4-dichloro-5-(3-fluoropyridin-2-yl)benzoyl]amino}-N-[(2R)-1-hydroxypropan-2-yl]-1-phenyl-1H-pyrazole-3-carboxamide | LCMS Rt = 1.59 minutes MS m/z 528.16 [M + H]⁺ |
| 534 | 5-{[2,4-dichloro-5-(3-fluoropyridin-2-yl)benzoyl]amino}-N-(1-methylazetidin-3-yl)-1-phenyl-1H-pyrazole-3-carboxamide | LCMS Rt = 1.43 minutes MS m/z 539.18 [M + H]⁺ |
| 535 | 5-{[2,4-dichloro-5-(3-fluoropyridin-2-yl)benzoyl]amino}-1-phenyl-N-(pyridin-2-ylmethyl)-1H-pyrazole-3-carboxamide | LCMS Rt = 1.6 minutes MS m/z 561.16 [M + H]⁺ |
| 536 | 5-{[2,4-dichloro-5-(3-fluoropyridin-2-yl)benzoyl]amino}-N-(1,3-oxazol-5-ylmethyl)-1-phenyl-1H-pyrazole-3-carboxamide | LCMS Rt = 1.62 minutes MS m/z 551.13 [M + H]⁺ |
| 537 | 5-{[2,4-dichloro-5-(3-fluoropyridin-2-yl)benzoyl]amino}-N-[3-(2-hydroxyethyl)oxetan-3-yl]-1-phenyl-1H-pyrazole-3-carboxamide | LCMS Rt = 1.57 minutes MS m/z 570.12 [M + H]⁺ |
| 538 | 5-{[2,4-dichloro-5-(3-fluoropyridin-2-yl)benzoyl]amino}-N-(cis-4-hydroxycyclohexyl)-1-phenyl-1H-pyrazole-3-carboxamide | LCMS Rt = 1.61 minutes MS m/z 568.18 [M + H]⁺ |
| 539 | 5-{[2,4-dichloro-5-(3-fluoropyridin-2-yl)benzoyl]amino}-N-(1-methylpyrrolidin-3-yl)-1-phenyl-1H-pyrazole-3-carboxamide | LCMS Rt = 1.43 minutes MS m/z 553.26 [M + H]⁺ |
| 540 | 5-{[2,4-dichloro-5-(3-fluoropyridin-2-yl)benzoyl]amino}-N-(3-methyl-1H-pyrazol-4-yl)-1-phenyl-1H-pyrazole-3-carboxamide | LCMS Rt = 1.62 minutes MS m/z 550.1 [M + H]⁺ |
| 541 | 5-{[2,4-dichloro-5-(3-fluoropyridin-2-yl)benzoyl]amino}-N-[(2R)-2-hydroxypropyl]-1-phenyl-1H-pyrazole-3-carboxamide | LCMS Rt = 1.58 minutes MS m/z 528.16 [M + H]⁺ |
| 542 | 5-{[2,4-dichloro-5-(3-fluoropyridin-2-yl)benzoyl]amino}-N-[(3S)-5-oxopyrrolidin-3-yl]-1-phenyl-1H-pyrazole-3-carboxamide | LCMS Rt = 1.56 minutes MS m/z 553.16 [M + H]⁺ |
| 543 | 5-{[2,4-dichloro-5-(3-fluoropyridin-2-yl)benzoyl]amino}-N-(trans-3-hydroxycyclobutyl)-1-phenyl-1H-pyrazole-3-carboxamide | LCMS Rt = 1.58 minutes MS m/z 540.18 [M + H]⁺ |
| 544 | 5-{[2,4-dichloro-5-(3-fluoropyridin-2-yl)benzoyl]amino}-N-[(1-methyl-1H-pyrazol-4-yl)methyl]-1-phenyl-1H-pyrazole-3-carboxamide | LCMS Rt = 1.64 minutes MS m/z 564.12 [M + H]⁺ |
| 545 | 5-{[2,4-dichloro-5-(3-fluoropyridin-2-yl)benzoyl]amino}-N-[(3-methyl-1H-1,2,4-triazol-5-yl)methyl]-1-phenyl-1H-pyrazole-3-carboxamide | LCMS Rt = 1.56 minutes MS m/z 565.15 [M + H]⁺ |
| 546 | 5-{[2,4-dichloro-5-(3-fluoropyridin-2-yl)benzoyl]amino}-N-{[3-(hydroxymethyl)oxetan-3-yl]methyl}-1-phenyl-1H-pyrazole-3-carboxamide | LCMS Rt = 1.57 minutes MS m/z 570.17 [M + H]⁺ |
| 547 | 5-{[2,4-dichloro-5-(3-fluoropyridin-2-yl)benzoyl]amino}-1-phenyl-N-(4H-1,2,4-triazol-3-ylmethyl)-1H-pyrazole-3-carboxamide | LCMS Rt = 1.55 minutes MS m/z 551.12 [M + H]⁺ |
| 548 | 5-{[2,4-dichloro-5-(3-fluoropyridin-2-yl)benzoyl]amino}-1-phenyl-N-(pyrimidin-2-ylmethyl)-1H-pyrazole-3-carboxamide | LCMS Rt = 1.64 minutes MS m/z 562.17 [M + H]⁺ |
| 549 | 5-{[2,4-dichloro-5-(3-fluoropyridin-2-yl)benzoyl]amino}-1-phenyl-N-(tetrahydrofuran-3-ylmethyl)-1H-pyrazole-3-carboxamide | LCMS Rt = 1.65 minutes MS m/z 554.19 [M + H]⁺ |
| 550 | 5-{[2,4-dichloro-5-(3-fluoropyridin-2-yl)benzoyl]amino}-N-(1,3-oxazol-4-ylmethyl)-1-phenyl-1H-pyrazole-3-carboxamide | LCMS Rt = 1.63 minutes MS m/z 551.15 [M + H]⁺ |
| 551 | 5-{[2,4-dichloro-5-(3-fluoropyridin-2-yl)benzoyl]amino}-N-[(5-methyl-1,3,4-oxadiazol-2-yl)methyl]-1-phenyl-1H-pyrazole-3-carboxamide | LCMS Rt = 1.6 minutes MS m/z 566.18 [M + H]⁺ |
| 552 | 5-{[2,4-dichloro-5-(3-fluoropyridin-2-yl)benzoyl]amino}-N-[2-(dimethylamino)-2-oxoethyl]-1-phenyl-1H-pyrazole-3-carboxamide | LCMS Rt = 1.62 minutes MS m/z 555.22 [M + H]⁺ |
| 553 | 5-{[2,4-dichloro-5-(3-fluoropyridin-2-yl)benzoyl]amino}-N-[(2S)-2-hydroxypropyl]-1-phenyl-1H-pyrazole-3-carboxamide | LCMS Rt = 1.58 minutes MS m/z 528.16 [M + H]⁺ |
| 554 | 1-[(5-{[2,4-dichloro-5-(3-fluoropyridin-2-yl)benzoyl]amino}-1-phenyl-1H-pyrazol-3-yl)carbonyl]pyrrolidine-3-carboxamide | LCMS Rt = 1.57 minutes MS m/z 567.18 [M + H]⁺ |
| 555 | 5-{[2,4-dichloro-5-(3-fluoropyridin-2-yl)benzoyl]amino}-1-phenyl-N-[(3R)-tetrahydrofuran-3-yl]-1H-pyrazole-3-carboxamide | LCMS Rt = 1.63 minutes MS m/z 540.19 [M + H]⁺ |
| 556 | 5-{[2,4-dichloro-5-(3-fluoropyridin-2-yl)benzoyl]amino}-N-[(2R)-1-hydroxy-3-methoxypropan-2-yl]-1-phenyl-1H-pyrazole-3-carboxamide | LCMS Rt = 1.59 minutes MS m/z 558.17 [M + H]⁺ |

| Example Number | Name | Data |
| --- | --- | --- |
| 557 | N-[(2-aminopyridin-4-yl)methyl]-5-{[2,4-dichloro-5-(3-fluoropyridin-2-yl)benzoyl]amino}-1-phenyl-1H-pyrazole-3-carboxamide | LCMS Rt = 1.44 minutes MS m/z 576.21 [M + H]⁺ |
| 558 | N-cyclopropyl-5-{[2,4-dichloro-5-(3-fluoropyridin-2-yl)benzoyl]amino}-1-phenyl-1H-pyrazole-3-carboxamide | LCMS Rt = 1.66 minutes MS m/z 510.14 [M + H]⁺ |
| 559 | 5-{[2,4-dichloro-5-(3-fluoropyridin-2-yl)benzoyl]amino}-1-phenyl-N-(pyrimidin-4-ylmethyl)-1H-pyrazole-3-carboxamide | LCMS Rt = 1.63 minutes MS m/z 562.18 [M + H]⁺ |
| 560 | 5-{[2,4-dichloro-5-(3-fluoropyridin-2-yl)benzoyl]amino}-1-phenyl-N-[2-(1H-1,2,3-triazol-1-yl)ethyl]-1H-pyrazole-3-carboxamide | LCMS Rt = 1.6 minutes MS m/z 565.16 [M + H]⁺ |
| 561 | 5-{[2,4-dichloro-5-(3-fluoropyridin-2-yl)benzoyl]amino}-N-(trans-4-hydroxy-4-methylcyclohexyl)-1-phenyl-1H-pyrazole-3-carboxamide | LCMS Rt = 1.66 minutes MS m/z 582.22 [M + H]⁺ |
| 562 | 5-{[2,4-dichloro-5-(3-fluoropyridin-2-yl)benzoyl]amino}-N-(oxetan-3-yl)-1-phenyl-1H-pyrazole-3-carboxamide | LCMS Rt = 1.61 minutes MS m/z 526.18 [M + H]⁺ |
| 563 | 5-{[2,4-dichloro-5-(3-fluoropyridin-2-yl)benzoyl]amino}-N-methyl-1-phenyl-1H-pyrazole-3-carboxamide | LCMS Rt = 1.62 minutes MS m/z 484.2 [M + H]⁺ |
| 564 | 5-{[2,4-dichloro-5-(3-fluoropyridin-2-yl)benzoyl]amino}-N-ethyl-1-phenyl-1H-pyrazole-3-carboxamide | LCMS Rt = 1.65 minutes MS m/z 498.19 [M + H]⁺ |
| 565 | 5-{[2,4-dichloro-5-(3-fluoropyridin-2-yl)benzoyl]amino}-1-phenyl-N-(tetrahydro-2H-pyran-4-yl)-1H-pyrazole-3-carboxamide | LCMS Rt = 1.65 minutes MS m/z 554.22 [M + H]⁺ |
| 566 | 5-{[2,4-dichloro-5-(3-fluoropyridin-2-yl)benzoyl]amino}-N-(1-hydroxypropan-2-yl)-1-phenyl-1H-pyrazole-3-carboxamide | LCMS Rt = 1.59 minutes MS m/z 528.16 [M + H]⁺ |
| 567 | 5-{[2,4-dichloro-5-(3-fluoropyridin-2-yl)benzoyl]amino}-N-[(1-methyl-1H-1,2,3-triazol-4-yl)methyl]-1-phenyl-1H-pyrazole-3-carboxamide | LCMS Rt = 1.63 minutes MS m/z 565.2 [M + H]⁺ |
| 568 | 5-{[2,4-dichloro-5-(3-fluoropyridin-2-yl)benzoyl]amino}-N-[(5-oxopyrrolidin-2-yl)methyl]-1-phenyl-1H-pyrazole-3-carboxamide | LCMS Rt = 1.58 minutes MS m/z 567.17 [M + H]⁺ |
| 569 | 5-{[2,4-dichloro-5-(3-fluoropyridin-2-yl)benzoyl]amino}-1-phenyl-N-[(3S)-tetrahydrofuran-3-yl]-1H-pyrazole-3-carboxamide | LCMS Rt = 1.63 minutes MS m/z 540.22 [M + H]⁺ |
| 570 | 5-{[2,4-dichloro-5-(3-fluoropyridin-2-yl)benzoyl]amino}-N-[(2S)-1-hydroxypropan-2-yl]-1-phenyl-1H-pyrazole-3-carboxamide | LCMS Rt = 1.59 minutes MS m/z 528.12 [M + H]⁺ |
| 571 | 5-{[2,4-dichloro-5-(3-fluoropyridin-2-yl)benzoyl]amino}-N-(3-methyloxetan-3-yl)-1-phenyl-1H-pyrazole-3-carboxamide | LCMS Rt = 1.63 minutes MS m/z 540.15 [M + H]⁺ |
| 572 | 5-{[2,4-dichloro-5-(3-fluoropyridin-2-yl)benzoyl]amino}-N-(3-hydroxypropyl)-1-phenyl-1H-pyrazole-3-carboxamide | LCMS Rt = 1.58 minutes MS m/z 528.12 [M + H]⁺ |
| 573 | 5-{[2,4-dichloro-5-(3-fluoropyridin-2-yl)benzoyl]amino}-N-(2-methoxyethyl)-1-phenyl-1H-pyrazole-3-carboxamide | LCMS Rt = 1.64 minutes MS m/z 528.21 [M + H]⁺ |
| 574 | 5-{[2,4-dichloro-5-(3-fluoropyridin-2-yl)benzoyl]amino}-N-(1,2-oxazol-5-ylmethyl)-1-phenyl-1H-pyrazole-3-carboxamide | LCMS Rt = 1.63 minutes MS m/z 551.17 [M + H]⁺ |
| 575 | 5-{[2,4-dichloro-5-(3-fluoropyridin-2-yl)benzoyl]amino}-1-phenyl-N-(pyridazin-3-ylmethyl)-1H-pyrazole-3-carboxamide | LCMS Rt = 1.62 minutes MS m/z 562.16 [M + H]⁺ |
| 576 | 5-{[2,4-dichloro-5-(3-fluoropyridin-2-yl)benzoyl]amino}-N-(1,3-oxazol-2-ylmethyl)-1-phenyl-1H-pyrazole-3-carboxamide | LCMS Rt = 1.63 minutes MS m/z 551.17 [M + H]⁺ |
| 577 | 5-{[2,4-dichloro-5-(3-fluoropyridin-2-yl)benzoyl]amino}-N-(oxetan-3-ylmethyl)-1-phenyl-1H-pyrazole-3-carboxamide | LCMS Rt = 1.62 minutes MS m/z 540.17 [M + H]⁺ |
| 578 | 5-{[2,4-dichloro-5-(3-fluoropyridin-2-yl)benzoyl]amino}-1-phenyl-N-(pyrazin-2-ylmethyl)-1H-pyrazole-3-carboxamide | LCMS Rt = 1.64 minutes MS m/z 562.13 [M + H]⁺ |
| 579 | 5-{[2,4-dichloro-5-(3-fluoropyridin-2-yl)benzoyl]amino}-N-(1,2-oxazol-3-ylmethyl)-1-phenyl-1H-pyrazole-3-carboxamide | LCMS Rt = 1.64 minutes MS m/z 551.16 [M + H]⁺ |
| 580 | 5-{[2,4-dichloro-5-(3-fluoropyridin-2-yl)benzoyl]amino}-N-[(1-hydroxycyclopropyl)methyl]-1-phenyl-1H-pyrazole-3-carboxamide | LCMS Rt = 1.6 minutes MS m/z 540.18 [M + H]⁺ |

-continued

| Example Number | Name | Data |
|---|---|---|
| 581 | 5-{[2,4-dichloro-5-(3-fluoropyridin-2-yl)benzoyl]amino}-N-(cis-3-hydroxycyclobutyl)-1-phenyl-1H-pyrazole-3-carboxamide | LCMS Rt = 1.57 minutes MS m/z 540.16 [M + H]+ |
| 582 | 5-{[2,4-dichloro-5-(pyridin-2-yl)benzoyl]amino}-1-phenyl-N-[2-(1H-1,2,4-triazol-1-yl)ethyl]-1H-pyrazole-3-carboxamide | LCMS Rt = 1.6 minutes MS m/z 547.17 [M + H]+ |
| 583 | 5-{[2,4-dichloro-5-(pyridin-2-yl)benzoyl]amino}-N-(1,3-oxazol-4-ylmethyl)-1-phenyl-1H-pyrazole-3-carboxamide | LCMS Rt = 1.62 minutes MS m/z 533.14 [M + H]+ |
| 584 | 5-{[2,4-dichloro-5-(pyridin-2-yl)benzoyl]amino}-N-(1-methylpyrrolidin-3-yl)-1-phenyl-1H-pyrazole-3-carboxamide | LCMS Rt = 1.43 minutes MS m/z 533.22 [M − H]− |
| 585 | 5-{[2,4-dichloro-5-(pyridin-2-yl)benzoyl]amino}-N-[2-(dimethylamino)-2-oxoethyl]-1-phenyl-1H-pyrazole-3-carboxamide | LCMS Rt = 1.62 minutes MS m/z 537.18 [M + H]+ |
| 586 | 5-{[2,4-dichloro-5-(pyridin-2-yl)benzoyl]amino}-1-phenyl-N-(pyrimidin-2-ylmethyl)-1H-pyrazole-3-carboxamide | LCMS Rt = 1.64 minutes MS m/z 544.16 [M + H]+ |
| 587 | 5-{[2,4-dichloro-5-(pyridin-2-yl)benzoyl]amino}-1-phenyl-N-[2-(2-hydroxyethoxy)ethyl]-1H-pyrazole-3-carboxamide | LCMS Rt = 1.56 minutes MS m/z 540.2 [M + H]+ |
| 588 | 5-{[2,4-dichloro-5-(pyridin-2-yl)benzoyl]amino}-1-phenyl-N-(tetrahydrofuran-3-ylmethyl)-1H-pyrazole-3-carboxamide | LCMS Rt = 1.65 minutes MS m/z 536.2 [M + H]+ |
| 589 | 5-{[2,4-dichloro-5-(pyridin-2-yl)benzoyl]amino}-1-phenyl-N-(pyridin-2-ylmethyl)-1H-pyrazole-3-carboxamide | LCMS Rt = 1.59 minutes MS m/z 543.17 [M + H]+ |
| 590 | 5-{[2,4-dichloro-5-(pyridin-2-yl)benzoyl]amino}-N-(trans-3-hydroxycyclobutyl)-1-phenyl-1H-pyrazole-3-carboxamide | LCMS Rt = 1.57 minutes MS m/z 522.22 [M + H]+ |
| 591 | 5-{[2,4-dichloro-5-(pyridin-2-yl)benzoyl]amino}-N-[(3S)-5-oxopyrrolidin-3-yl]-1-phenyl-1H-pyrazole-3-carboxamide | LCMS Rt = 1.55 minutes MS m/z 535.18 [M + H]+ |
| 592 | 5-{[2,4-dichloro-5-(pyridin-2-yl)benzoyl]amino}-N-[(2R)-2,3-dihydroxypropyl]-1-phenyl-1H-pyrazole-3-carboxamide | LCMS Rt = 1.51 minutes MS m/z 526.17 [M + H]+ |
| 593 | 5-{[2,4-dichloro-5-(pyridin-2-yl)benzoyl]amino}-N-(1,3-oxazol-2-ylmethyl)-1-phenyl-1H-pyrazole-3-carboxamide | LCMS Rt = 1.63 minutes MS m/z 533.16 [M + H]+ |
| 594 | 5-{[2,4-dichloro-5-(pyridin-2-yl)benzoyl]amino}-1-phenyl-N-[2-(1H-1,2,3-triazol-1-yl)ethyl]-1H-pyrazole-3-carboxamide | LCMS Rt = 1.59 minutes MS m/z 547.17 [M + H]+ |
| 595 | N-cyclopropyl-5-{[2,4-dichloro-5-(pyridin-2-yl)benzoyl]amino}-1-phenyl-1H-pyrazole-3-carboxamide | LCMS Rt = 1.66 minutes MS m/z 492.18 [M + H]+ |
| 596 | 5-{[2,4-dichloro-5-(pyridin-2-yl)benzoyl]amino}-N-[(3R,4S)-4-hydroxytetrahydrofuran-3-yl]-1-phenyl-1H-pyrazole-3-carboxamide | LCMS Rt = 1.55 minutes MS m/z 538.2 [M + H]+ |
| 597 | 5-{[2,4-dichloro-5-(pyridin-2-yl)benzoyl]amino}-1-phenyl-N-(pyrimidin-4-ylmethyl)-1H-pyrazole-3-carboxamide | LCMS Rt = 1.63 minutes MS m/z 544.2 [M + H]+ |
| 598 | 1-[(5-{[2,4-dichloro-5-(pyridin-2-yl)benzoyl]amino}-1-phenyl-1H-pyrazol-3-yl)carbonyl]pyrrolidine-3-carboxamide | LCMS Rt = 1.56 minutes MS m/z 549.19 [M + H]+ |
| 599 | 2,4-dichloro-N-{3-[(3-hydroxyazetidin-1-yl)carbonyl]-1-phenyl-1H-pyrazol-5-yl}-5-(pyridin-2-yl)benzamide | LCMS Rt = 1.57 minutes MS m/z 508.09 [M + H]+ |
| 600 | 5-{[2,4-dichloro-5-(pyridin-2-yl)benzoyl]amino}-N-methyl-1-phenyl-1H-pyrazole-3-carboxamide | LCMS Rt = 1.61 minutes MS m/z 466.17 [M + H]+ |
| 601 | 5-{[2,4-dichloro-5-(pyridin-2-yl)benzoyl]amino}-N-(2-methoxyethyl)-1-phenyl-1H-pyrazole-3-carboxamide | LCMS Rt = 1.64 minutes MS m/z 510.18 [M + H]+ |
| 602 | 5-{[2,4-dichloro-5-(pyridin-2-yl)benzoyl]amino}-N-[(5-methyl-1,3,4-oxadiazol-2-yl)methyl]-1-phenyl-1H-pyrazole-3-carboxamide | LCMS Rt = 1.6 minutes MS m/z 548.15 [M + H]+ |
| 603 | 5-{[2,4-dichloro-5-(pyridin-2-yl)benzoyl]amino}-1-phenyl-N-(tetrahydro-2H-pyran-4-yl)-1H-pyrazole-3-carboxamide | LCMS Rt = 1.65 minutes MS m/z 536.11 [M + H]+ |
| 604 | 5-{[2,4-dichloro-5-(pyridin-2-yl)benzoyl]amino}-N-ethyl-1-phenyl-1H-pyrazole-3-carboxamide | LCMS Rt = 1.65 minutes MS m/z 480.11 [M + H]+ |
| 605 | (3S)-1-[(5-{[2,4-dichloro-5-(pyridin-2-yl)benzoyl]amino}-1-phenyl-1H-pyrazol-3-yl)carbonyl]piperidine-3-carboxamide | LCMS Rt = 1.58 minutes MS m/z 563.2 [M + H]+ |

| Example Number | Name | Data |
| --- | --- | --- |
| 606 | 5-{[2,4-dichloro-5-(pyridin-2-yl)benzoyl]amino}-N-[1-(hydroxymethyl)cyclopropyl]-1-phenyl-1H-pyrazole-3-carboxamide | LCMS Rt = 1.59 minutes MS m/z 522.17 [M + H]+ |
| 607 | 5-{[2,4-dichloro-5-(pyridin-2-yl)benzoyl]amino}-N-[(1-methyl-1H-1,2,3-triazol-4-yl)methyl]-1-phenyl-1H-pyrazole-3-carboxamide | LCMS Rt = 1.63 minutes MS m/z 547.17 [M + H]+ |
| 608 | 2,4-dichloro-N-{3-[(3-oxopiperazin-1-yl)carbonyl]-1-phenyl-1H-pyrazol-5-yl}-5-(pyridin-2-yl)benzamide | LCMS Rt = 1.56 minutes MS m/z 535.18 [M + H]+ |
| 609 | 5-{[2,4-dichloro-5-(pyridin-2-yl)benzoyl]amino}-1-phenyl-N-(pyrazin-2-ylmethyl)-1H-pyrazole-3-carboxamide | LCMS Rt = 1.63 minutes MS m/z 544.21 [M + H]+ |
| 610 | 5-{[2,4-dichloro-5-(pyridin-2-yl)benzoyl]amino}-N-[(5-oxopyrrolidin-2-yl)methyl]-1-phenyl-1H-pyrazole-3-carboxamide | LCMS Rt = 1.58 minutes MS m/z 549.2 [M + H]+ |
| 611 | 5-{[2,4-dichloro-5-(pyridin-2-yl)benzoyl]amino}-1-phenyl-N-[(3S)-tetrahydrofuran-3-yl]-1H-pyrazole-3-carboxamide | LCMS Rt = 1.63 minutes MS m/z 522.17 [M + H]+ |
| 612 | 5-{[2,4-dichloro-5-(pyridin-2-yl)benzoyl]amino}-1-phenyl-N-[(3R)-tetrahydrofuran-3-yl]-1H-pyrazole-3-carboxamide | LCMS Rt = 1.63 minutes MS m/z 522.12 [M + H]+ |
| 613 | 5-{[2,4-dichloro-5-(pyridin-2-yl)benzoyl]amino}-N-(3-methyloxetan-3-yl)-1-phenyl-1H-pyrazole-3-carboxamide | LCMS Rt = 1.63 minutes MS m/z 522.17 [M + H]+ |
| 614 | 5-{[2,4-dichloro-5-(pyridin-2-yl)benzoyl]amino}-N-(cis-3-hydroxycyclobutyl)-1-phenyl-1H-pyrazole-3-carboxamide | LCMS Rt = 1.56 minutes MS m/z 522.2 [M + H]+ |
| 615 | 5-{[2,4-dichloro-5-(pyridin-2-yl)benzoyl]amino}-N-(cis-4-hydroxycyclohexyl)-1-phenyl-1H-pyrazole-3-carboxamide | LCMS Rt = 1.61 minutes MS m/z 550.19 [M + H]+ |
| 616 | 5-(2,4-dichloro-5-(pyridin-2-yl)benzamido)-N-((3S,4R)-3-hydroxytetrahydro-2H-pyran-4-yl)-1-phenyl-1H-pyrazole-3-carboxamide | LCMS Rt = 1.57 minutes MS m/z 552.19 [M + H]+ |
| 617 | N-[(2-aminopyridin-4-yl)methyl]-5-{[2,4-dichloro-5-(pyridin-2-yl)benzoyl]amino}-1-phenyl-1H-pyrazole-3-carboxamide | LCMS Rt = 1.44 minutes MS m/z 558.23 [M + H]+ |
| 618 | 5-{[2,4-dichloro-5-(pyridin-2-yl)benzoyl]amino}-N-[3-(2-hydroxyethyl)oxetan-3-yl]-1-phenyl-1H-pyrazole-3-carboxamide | LCMS Rt = 1.56 minutes MS m/z 552.19 [M + H]+ |
| 619 | 5-{[2,4-dichloro-5-(pyridin-2-yl)benzoyl]amino}-N-(1-methylazetidin-3-yl)-1-phenyl-1H-pyrazole-3-carboxamide | LCMS Rt = 1.42 minutes MS m/z 521.19 [M + H]+ |
| 620 | 5-{[2,4-dichloro-5-(pyridin-2-yl)benzoyl]amino}-N-[(2S)-1-hydroxy-3-methoxypropan-2-yl]-1-phenyl-1H-pyrazole-3-carboxamide | LCMS Rt = 1.58 minutes MS m/z 540.2 [M + H]+ |
| 621 | 5-{[2,4-dichloro-5-(pyridin-2-yl)benzoyl]amino}-N-[(2-methyl-1H-imidazol-5-yl)methyl]-1-phenyl-1H-pyrazole-3-carboxamide | LCMS Rt = 1.43 minutes MS m/z 546.15 [M + H]+ |
| 622 | 5-{[2,4-dichloro-5-(pyridin-2-yl)benzoyl]amino}-N-[(2R)-1-hydroxy-3-methoxypropan-2-yl]-1-phenyl-1H-pyrazole-3-carboxamide | LCMS Rt = 1.58 minutes MS m/z 540.2 [M + H]+ |
| 623 | 5-{[2,4-dichloro-5-(pyridin-2-yl)benzoyl]amino}-N-[(1-methyl-1H-pyrazol-4-yl)methyl]-1-phenyl-1H-pyrazole-3-carboxamide | LCMS Rt = 1.64 minutes MS m/z 546.19 [M + H]+ |
| 624 | 5-{[2,4-dichloro-5-(pyridin-2-yl)benzoyl]amino}-N-(1,2-oxazol-3-ylmethyl)-1-phenyl-1H-pyrazole-3-carboxamide | LCMS Rt = 1.63 minutes MS m/z 533.18 [M + H]+ |
| 625 | 5-{[2,4-dichloro-5-(pyridin-2-yl)benzoyl]amino}-N-[(3-methyl-1H-1,2,4-triazol-5-yl)methyl]-1-phenyl-1H-pyrazole-3-carboxamide | LCMS Rt = 1.56 minutes MS m/z 547.18 [M + H]+ |
| 626 | 5-{[2,4-dichloro-5-(pyridin-2-yl)benzoyl]amino}-N-(1,3-oxazol-5-ylmethyl)-1-phenyl-1H-pyrazole-3-carboxamide | LCMS Rt = 1.62 minutes MS m/z 533.17 [M + H]+ |
| 627 | 5-{[2,4-dichloro-5-(pyridin-2-yl)benzoyl]amino}-N-[(3S,4R)-4-hydroxytetrahydrofuran-3-yl]-1-phenyl-1H-pyrazole-3-carboxamide | LCMS Rt = 1.55 minutes MS m/z 538.18 [M + H]+ |
| 628 | 5-{[2-chloro-4-fluoro-5-(pyridin-2-yl)benzoyl]amino}-1-phenyl-N-(pyridin-2-ylmethyl)-1H-pyrazole-3-carboxamide | LCMS Rt = 1.58 minutes MS m/z 527.09 [M + H]+ |
| 629 | 5-{[2-chloro-4-fluoro-5-(pyridin-2-yl)benzoyl]amino}-N-[(3-methyl-1H-1,2,4-triazol-5-yl)methyl]-1-phenyl-1H-pyrazole-3-carboxamide | LCMS Rt = 1.54 minutes MS m/z 531.09 [M + H]+ |
| 630 | 2-chloro-4-fluoro-N-{3-[(3-hydroxy-3-methylazetidin-1-yl)carbonyl]-1-phenyl-1H-pyrazol-5-yl}-5-(pyridin-2-yl)benzamide | LCMS Rt = 1.58 minutes MS m/z 506.09 [M + H]+ |

-continued

| Example Number | Name | Data |
|---|---|---|
| 631 | 1-[(5-{[2-chloro-4-fluoro-5-(pyridin-2-yl)benzoyl]amino}-1-phenyl-1H-pyrazol-3-yl)carbonyl]pyrrolidine-3-carboxamide | LCMS Rt = 1.54 minutes MS m/z 533.23 [M + H]+ |
| 632 | 5-{[2-chloro-4-fluoro-5-(pyridin-2-yl)benzoyl]amino}-N-[(3S,4R)-4-hydroxytetrahydrofuran-3-yl]-1-phenyl-1H-pyrazole-3-carboxamide | LCMS Rt = 1.54 minutes MS m/z 522.22 [M + H]+ |
| 633 | 5-{[2-chloro-4-fluoro-5-(pyridin-2-yl)benzoyl]amino}-1-phenyl-N-(tetrahydro-2H-pyran-4-yl)-1H-pyrazole-3-carboxamide | LCMS Rt = 1.64 minutes MS m/z 520.22 [M + H]+ |
| 634 | 5-{[2-chloro-4-fluoro-5-(pyridin-2-yl)benzoyl]amino}-N-[(1-hydroxycyclopropyl)methyl]-1-phenyl-1H-pyrazole-3-carboxamide | LCMS Rt = 1.58 minutes MS m/z 506.09 [M + H]+ |
| 635 | 5-{[2-chloro-4-fluoro-5-(pyridin-2-yl)benzoyl]amino}-1-phenyl-N-(pyridazin-3-ylmethyl)-1H-pyrazole-3-carboxamide | LCMS Rt = 1.6 minutes MS m/z 528.21 [M + H]+ |
| 636 | 5-{[2-chloro-4-fluoro-5-(pyridin-2-yl)benzoyl]amino}-N-[(5-oxopyrrolidin-2-yl)methyl]-1-phenyl-1H-pyrazole-3-carboxamide | LCMS Rt = 1.56 minutes MS m/z 533.11 [M + H]+ |
| 637 | 5-{[2-chloro-4-fluoro-5-(pyridin-2-yl)benzoyl]amino}-N-[3-(hydroxymethyl)oxetan-3-yl]-1-phenyl-1H-pyrazole-3-carboxamide | LCMS Rt = 1.54 minutes MS m/z 522.22 [M + H]+ |
| 638 | 2-chloro-4-fluoro-N-{3-[(3-oxopiperazin-1-yl)carbonyl]-1-phenyl-1H-pyrazol-5-yl}-5-(pyridin-2-yl)benzamide | LCMS Rt = 1.54 minutes MS m/z 519.1 [M + H]+ |
| 639 | 5-{[2-chloro-4-fluoro-5-(pyridin-2-yl)benzoyl]amino}-N-(2-methoxyethyl)-1-phenyl-1H-pyrazole-3-carboxamide | LCMS Rt = 1.62 minutes MS m/z 494.13 [M + H]+ |
| 640 | 5-{[2-chloro-4-fluoro-5-(pyridin-2-yl)benzoyl]amino}-1-phenyl-N-(pyrimidin-4-ylmethyl)-1H-pyrazole-3-carboxamide | LCMS Rt = 1.61 minutes MS m/z 528.07 [M + H]+ |
| 641 | 5-{[2-chloro-4-fluoro-5-(pyridin-2-yl)benzoyl]amino}-1-phenyl-N-[2-(1H-1,2,3-triazol-1-yl)ethyl]-1H-pyrazole-3-carboxamide | LCMS Rt = 1.58 minutes MS m/z 531.23 [M + H]+ |
| 642 | (3S)-1-[(5-{[2-chloro-4-fluoro-5-(pyridin-2-yl)benzoyl]amino}-1-phenyl-1H-pyrazol-3-yl)carbonyl]piperidine-3-carboxamide | LCMS Rt = 1.56 minutes MS m/z 547.11 [M + H]+ |
| 643 | 5-{[2-chloro-4-fluoro-5-(pyridin-2-yl)benzoyl]amino}-N-(1-hydroxypropan-2-yl)-1-phenyl-1H-pyrazole-3-carboxamide | LCMS Rt = 1.56 minutes MS m/z 494.1 [M + H]+ |
| 644 | 5-{[2-chloro-4-fluoro-5-(pyridin-2-yl)benzoyl]amino}-N-(3-methyloxetan-3-yl)-1-phenyl-1H-pyrazole-3-carboxamide | LCMS Rt = 1.62 minutes MS m/z 506.09 [M + H]+ |
| 645 | 5-{[2-chloro-4-fluoro-5-(pyridin-2-yl)benzoyl]amino}-N-[(2S)-1-hydroxypropan-2-yl]-1-phenyl-1H-pyrazole-3-carboxamide | LCMS Rt = 1.57 minutes MS m/z 494.1 [M + H]+ |
| 646 | 5-{[2-chloro-4-fluoro-5-(pyridin-2-yl)benzoyl]amino}-1-phenyl-N-(pyrazin-2-ylmethyl)-1H-pyrazole-3-carboxamide | LCMS Rt = 1.62 minutes MS m/z 528.21 [M + H]+ |
| 647 | 5-{[2-chloro-4-fluoro-5-(pyridin-2-yl)benzoyl]amino}-1-phenyl-N-(1H-1,2,4-triazol-3-yl)-1H-pyrazole-3-carboxamide | LCMS Rt = 1.56 minutes MS m/z 503.19 [M + H]+ |
| 648 | 5-{[2-chloro-4-fluoro-5-(pyridin-2-yl)benzoyl]amino}-N-[3-(2-hydroxyethyl)oxetan-3-yl]-1-phenyl-1H-pyrazole-3-carboxamide | LCMS Rt = 1.54 minutes MS m/z 536.11 [M + H]+ |
| 649 | 5-{[2-chloro-4-fluoro-5-(pyridin-2-yl)benzoyl]amino}-N-[(2R)-1-hydroxy-3-methoxypropan-2-yl]-1-phenyl-1H-pyrazole-3-carboxamide | LCMS Rt = 1.57 minutes MS m/z 524.12 [M + H]+ |
| 650 | 5-(2-chloro-4-fluoro-5-(pyridin-2-yl)benzamido)-N-((3S,4R)-3-hydroxytetrahydro-2H-pyran-4-yl)-1-phenyl-1H-pyrazole-3-carboxamide | LCMS Rt = 1.55 minutes MS m/z 536.25 [M + H]+ |
| 651 | 2-chloro-4-fluoro-N-{3-[(3-hydroxyazetidin-1-yl)carbonyl]-1-phenyl-1H-pyrazol-5-yl}-5-(pyridin-2-yl)benzamide | LCMS Rt = 1.55 minutes MS m/z 492.2 [M + H]+ |
| 652 | 5-{[2-chloro-4-fluoro-5-(pyridin-2-yl)benzoyl]amino}-N-ethyl-1-phenyl-1H-pyrazole-3-carboxamide | LCMS Rt = 1.63 minutes MS m/z 464.22 [M + H]+ |
| 653 | 5-{[2-chloro-4-fluoro-5-(pyridin-2-yl)benzoyl]amino}-N-[(5-methyl-1,3,4-oxadiazol-2-yl)methyl]-1-phenyl-1H-pyrazole-3-carboxamide | LCMS Rt = 1.58 minutes MS m/z 532.21 [M + H]+ |
| 654 | 5-{[2-chloro-4-fluoro-5-(pyridin-2-yl)benzoyl]amino}-N-[1-(hydroxymethyl)cyclopropyl]-1-phenyl-1H-pyrazole-3-carboxamide | LCMS Rt = 1.57 minutes MS m/z 506.23 [M + H]+ |
| 655 | 5-{[2-chloro-4-fluoro-5-(pyridin-2-yl)benzoyl]amino}-N-[(2S)-1-hydroxy-3-methoxypropan-2-yl]-1-phenyl-1H-pyrazole-3-carboxamide | LCMS Rt = 1.57 minutes MS m/z 524.22 [M + H]+ |

-continued

| Example Number | Name | Data |
|---|---|---|
| 656 | 5-{[2-chloro-4-fluoro-5-(pyridin-2-yl)benzoyl]amino}-N-[(2R)-1-hydroxypropan-2-yl]-1-phenyl-1H-pyrazole-3-carboxamide | LCMS Rt = 1.56 minutes MS m/z 494.1 [M + H]+ |
| 657 | 5-{[2-chloro-4-fluoro-5-(pyridin-2-yl)benzoyl]amino}-N-(oxetan-3-ylmethyl)-1-phenyl-1H-pyrazole-3-carboxamide | LCMS Rt = 1.6 minutes MS m/z 506.22 [M + H]+ |
| 658 | 5-{[2-chloro-4-fluoro-5-(pyridin-2-yl)benzoyl]amino}-N-(3-hydroxy-3-methylbutyl)-1-phenyl-1H-pyrazole-3-carboxamide | LCMS Rt = 1.61 minutes MS m/z 522.12 [M + H]+ |
| 659 | 5-{[2,4-dichloro-5-(pyridin-2-yl)benzoyl]amino}-1-phenyl-N-[(3R)-pyrrolidin-3-yl]-1H-pyrazole-3-carboxamide | LCMS Rt = 1.41 minutes MS m/z 519.21 [M − H]− |
| 660 | N-[(2R)-1-aminopropan-2-yl]-5-{[2,4-dichloro-5-(pyridin-2-yl)benzoyl]amino}-1-phenyl-1H-pyrazole-3-carboxamide | LCMS Rt = 1.41 minutes MS m/z 507.17 [M − H]− |
| 661 | N-[(1R,3R)-3-aminocyclopentyl]-5-{[2,4-dichloro-5-(pyridin-2-yl)benzoyl]amino}-1-phenyl-1H-pyrazole-3-carboxamide | LCMS Rt = 1.42 minutes MS m/z 533.16 [M − H]− |
| 662 | N-(cis-3-aminocyclobutyl)-5-{[2,4-dichloro-5-(pyridin-2-yl)benzoyl]amino}-1-phenyl-1H-pyrazole-3-carboxamide | LCMS Rt = 1.41 minutes MS m/z 519.12 [M − H]− |
| 663 | N-[(2S)-2-aminopropyl]-5-{[2,4-dichloro-5-(pyridin-2-yl)benzoyl]amino}-1-phenyl-1H-pyrazole-3-carboxamide | LCMS Rt = 1.41 minutes MS m/z 507.17 [M − H]− |
| 664 | N-(trans-3-aminocyclobutyl)-5-{[2,4-dichloro-5-(pyridin-2-yl)benzoyl]amino}-1-phenyl-1H-pyrazole-3-carboxamide | LCMS Rt = 1.41 minutes MS m/z 519.14 [M − H]− |
| 665 | N-[(2R)-2-aminopropyl]-5-{[2,4-dichloro-5-(pyridin-2-yl)benzoyl]amino}-1-phenyl-1H-pyrazole-3-carboxamide | LCMS Rt = 1.41 minutes MS m/z 507.2 [M − H]− |
| 666 | 5-{[2,4-dichloro-5-(pyridin-2-yl)benzoyl]amino}-1-phenyl-N-[(3S)-pyrrolidin-3-yl]-1H-pyrazole-3-carboxamide | LCMS Rt = 1.41 minutes MS m/z 521.23 [M + H]+ |
| 667 | N-[(2S)-1-aminopropan-2-yl]-5-{[2,4-dichloro-5-(pyridin-2-yl)benzoyl]amino}-1-phenyl-1H-pyrazole-3-carboxamide | LCMS Rt = 1.41 minutes MS m/z 507.18 [M − H]− |
| 668 | N-(3-aminopropyl)-5-{[2,4-dichloro-5-(pyridin-2-yl)benzoyl]amino}-1-phenyl-1H-pyrazole-3-carboxamide | LCMS Rt = 1.41 minutes MS m/z 507.11 [M − H]− |
| 669 | 5-{[2,4-dichloro-5-(pyridin-2-yl)benzoyl]amino}-N-[2-(methylamino)ethyl]-1-phenyl-1H-pyrazole-3-carboxamide | LCMS Rt = 1.41 minutes MS m/z 507.16 [M − H]− |
| 670 | N-(2-aminoethyl)-5-{[2,4-dichloro-5-(pyridin-2-yl)benzoyl]amino}-N-methyl-1-phenyl-1H-pyrazole-3-carboxamide | LCMS Rt = 1.41 minutes MS m/z 507.16 [M − H]− |
| 671 | 5-{[2-chloro-4-fluoro-5-(pyridin-2-yl)benzoyl]amino}-N-[(3S)-5-oxopyrrolidin-3-yl]-1-phenyl-1H-pyrazole-3-carboxamide | LCMS Rt = 1.53 minutes MS m/z 519.19 [M + H]+ |
| 672 | 5-{[2-chloro-4-fluoro-5-(pyridin-2-yl)benzoyl]amino}-N-[(5-methoxypyridin-2-yl)methyl]-1-phenyl-1H-pyrazole-3-carboxamide | LCMS Rt = 1.63 minutes MS m/z 557.02 [M + H]+ |
| 673 | 5-{[2-chloro-4-fluoro-5-(pyridin-2-yl)benzoyl]amino}-N-[2-(2-oxo-1,3-oxazolidin-3-yl)ethyl]-1-phenyl-1H-pyrazole-3-carboxamide | LCMS Rt = 1.57 minutes MS m/z 549.17 [M + H]+ |
| 674 | 5-{[2-chloro-4-fluoro-5-(pyridin-2-yl)benzoyl]amino}-N-{[2-(methylamino)pyridin-3-yl]methyl}-1-phenyl-1H-pyrazole-3-carboxamide | LCMS Rt = 1.44 minutes MS m/z 556.18 [M + H]+ |
| 675 | 5-{[2-chloro-4-fluoro-5-(pyridin-2-yl)benzoyl]amino}-N-[2-(2-oxoimidazolidin-1-yl)ethyl]-1-phenyl-1H-pyrazole-3-carboxamide | LCMS Rt = 1.56 minutes MS m/z 548.24 [M + H]+ |
| 676 | 5-{[2-chloro-4-fluoro-5-(pyridin-2-yl)benzoyl]amino}-N-[(6-methoxypyridin-3-yl)methyl]-1-phenyl-1H-pyrazole-3-carboxamide | LCMS Rt = 1.68 minutes MS m/z 557.21 [M + H]+ |
| 677 | 5-{[2-chloro-4-fluoro-5-(pyridin-2-yl)benzoyl]amino}-N-[(5-hydroxy-4-methyl-4H-1,2,4-triazol-3-yl)methyl]-1-phenyl-1H-pyrazole-3-carboxamide | LCMS Rt = 1.52 minutes MS m/z 547.22 [M + H]+ |
| 678 | 5-{[2-chloro-4-fluoro-5-(pyridin-2-yl)benzoyl]amino}-N-[(3-hydroxy-1,2-oxazol-5-yl)methyl]-1-phenyl-1H-pyrazole-3-carboxamide | LCMS Rt = 1.56 minutes MS m/z 533.14 [M + H]+ |
| 679 | 5-{[2-chloro-4-fluoro-5-(pyridin-2-yl)benzoyl]amino}-N-{[5-(methoxymethyl)-1H-pyrazol-3-yl]methyl}-1-phenyl-1H-pyrazole-3-carboxamide | LCMS Rt = 1.58 minutes MS m/z 560.23 [M + H]+ |
| 680 | N-[(2-amino-6-methylpyridin-3-yl)methyl]-5-{[2-chloro-4-fluoro-5-(pyridin-2-yl)benzoyl]amino}-1-phenyl-1H-pyrazole-3-carboxamide | LCMS Rt = 1.44 minutes MS m/z 556.03 [M + H]+ |

| Example Number | Name | Data |
|---|---|---|
| 681 | N-(1-acetylpiperidin-4-yl)-5-{[2-chloro-4-fluoro-5-(pyridin-2-yl)benzoyl]amino}-1-phenyl-1H-pyrazole-3-carboxamide | LCMS Rt = 1.61 minutes MS m/z 561.2 [M + H]+ |
| 682 | 5-{[2-chloro-4-fluoro-5-(pyridin-2-yl)benzoyl]amino}-N-[(3-methoxypyridin-2-yl)methyl]-1-phenyl-1H-pyrazole-3-carboxamide | LCMS Rt = 1.64 minutes MS m/z 557.21 [M + H]+ |
| 683 | 2-chloro-4-fluoro-N-{3-[(5-methylhexahydropyrrolo[3,4-c]pyrrol-2(1H)-yl)carbonyl]-1-phenyl-1H-pyrazol-5-yl}-5-(pyridin-2-yl)benzamide | LCMS Rt = 1.4 minutes MS m/z 545.04 [M + H]+ |
| 684 | 2-chloro-N-{3-[(4-cyclopropyl-3-oxopiperazin-1-yl)carbonyl]-1-phenyl-1H-pyrazol-5-yl}-4-fluoro-5-(pyridin-2-yl)benzamide | LCMS Rt = 1.62 minutes MS m/z 559.21 [M + H]+ |
| 685 | 5-{[2-chloro-4-fluoro-5-(pyridin-2-yl)benzoyl]amino}-N,N-bis(2-hydroxypropyl)-1-phenyl-1H-pyrazole-3-carboxamide | LCMS Rt = 1.56 minutes MS m/z 552.23 [M + H]+ |
| 686 | 5-{[2-chloro-4-fluoro-5-(pyridin-2-yl)benzoyl]amino}-N-{[6-(methylamino)pyridin-3-yl]methyl}-1-phenyl-1H-pyrazole-3-carboxamide | LCMS Rt = 1.42 minutes MS m/z 556.05 [M + H]+ |
| 687 | 5-{[2-chloro-4-fluoro-5-(pyridin-2-yl)benzoyl]amino}-N-[(5-hydroxypyridin-2-yl)methyl]-1-phenyl-1H-pyrazole-3-carboxamide | LCMS Rt = 1.5 minutes MS m/z 542.99 [M + H]+ |
| 688 | 5-{[2-chloro-4-fluoro-5-(pyridin-2-yl)benzoyl]amino}-N-[(2-methoxypyridin-4-yl)methyl]-1-phenyl-1H-pyrazole-3-carboxamide | LCMS Rt = 1.67 minutes MS m/z 557.02 [M + H]+ |
| 689 | N-[3-({3-[acetyl(methyl)amino]pyrrolidin-1-yl}carbonyl)-1-phenyl-1H-pyrazol-5-yl]-2-chloro-4-fluoro-5-(pyridin-2-yl)benzamide | LCMS Rt = 1.63 minutes MS m/z 561.03 [M + H]+ |
| 690 | 5-{[2-chloro-4-fluoro-5-(pyridin-2-yl)benzoyl]amino}-N-[(3-hydroxypyridin-2-yl)methyl]-1-phenyl-1H-pyrazole-3-carboxamide | LCMS Rt = 1.5 minutes MS m/z 543.17 [M + H]+ |
| 691 | 1-[(5-{[2-chloro-4-fluoro-5-(pyridin-2-yl)benzoyl]amino}-1-phenyl-1H-pyrazol-3-yl)carbonyl]-N,N-dimethyl-L-prolinamide | LCMS Rt = 1.64 minutes MS m/z 559.19 [M − H]− |
| 692 | 5-{[2-chloro-4-fluoro-5-(pyridin-2-yl)benzoyl]amino}-N-[(4-methoxypyridin-2-yl)methyl]-1-phenyl-1H-pyrazole-3-carboxamide | LCMS Rt = 1.45 minutes MS m/z 557.21 [M + H]+ |
| 693 | N-[(3-aminopyridin-4-yl)methyl]-5-{[2-chloro-4-fluoro-5-(pyridin-2-yl)benzoyl]amino}-1-phenyl-1H-pyrazole-3-carboxamide | LCMS Rt = 1.41 minutes MS m/z 542.01 [M + H]+ |
| 694 | 5-{[2-chloro-4-fluoro-5-(pyridin-2-yl)benzoyl]amino}-N-{[6-(hydroxymethyl)pyridin-2-yl]methyl}-1-phenyl-1H-pyrazole-3-carboxamide | LCMS Rt = 1.53 minutes MS m/z 557.21 [M + H]+ |
| 695 | N-[(3-aminopyridin-2-yl)methyl]-5-{[2-chloro-4-fluoro-5-(pyridin-2-yl)benzoyl]amino}-1-phenyl-1H-pyrazole-3-carboxamide | LCMS Rt = 1.43 minutes MS m/z 542.2 [M + H]+ |
| 696 | 5-{[2-chloro-4-fluoro-5-(pyridin-2-yl)benzoyl]amino}-1-phenyl-N-[(3R)-pyrrolidin-3-yl]-1H-pyrazole-3-carboxamide | LCMS Rt = 1.39 minutes MS m/z 505.05 [M + H]+ |
| 697 | N-[(2R)-2-aminopropyl]-5-{[2-chloro-4-fluoro-5-(pyridin-2-yl)benzoyl]amino}-1-phenyl-1H-pyrazole-3-carboxamide | LCMS Rt = 1.38 minutes MS m/z 491.13 [M − H]− |
| 698 | N-(azetidin-3-yl)-5-{[2-chloro-4-fluoro-5-(pyridin-2-yl)benzoyl]amino}-1-phenyl-1H-pyrazole-3-carboxamide | LCMS Rt = 1.39 minutes MS m/z 491.03 [M + H]+ |
| 699 | N-[(1R,3R)-3-aminocyclopentyl]-5-{[2-chloro-4-fluoro-5-(pyridin-2-yl)benzoyl]amino}-1-phenyl-1H-pyrazole-3-carboxamide | LCMS Rt = 1.4 minutes MS m/z 517.15 [M − H]− |
| 700 | N-[(2S)-2-aminopropyl]-5-{[2-chloro-4-fluoro-5-(pyridin-2-yl)benzoyl]amino}-1-phenyl-1H-pyrazole-3-carboxamide | LCMS Rt = 1.39 minutes MS m/z 491.13 [M − H]− |
| 701 | N-[(2R)-1-aminopropan-2-yl]-5-{[2-chloro-4-fluoro-5-(pyridin-2-yl)benzoyl]amino}-1-phenyl-1H-pyrazole-3-carboxamide | LCMS Rt = 1.39 minutes MS m/z 493.08 [M + H]+ |
| 702 | N-[(2S)-1-aminopropan-2-yl]-5-{[2-chloro-4-fluoro-5-(pyridin-2-yl)benzoyl]amino}-1-phenyl-1H-pyrazole-3-carboxamide | LCMS Rt = 1.39 minutes MS m/z 493.08 [M + H]+ |
| 703 | N-(2-aminoethyl)-5-{[2-chloro-4-fluoro-5-(pyridin-2-yl)benzoyl]amino}-N-methyl-1-phenyl-1H-pyrazole-3-carboxamide | LCMS Rt = 1.38 minutes MS m/z 493.07 [M + H]+ |
| 704 | 5-{[2-chloro-4-fluoro-5-(3-fluoropyridin-2-yl)benzoyl]amino}-N-[2-(methylamino)ethyl]-1-phenyl-1H-pyrazole-3-carboxamide | LCMS Rt = 1.39 minutes MS m/z 511.04 [M + H]+ |
| 705 | N-(trans-3-aminocyclobutyl)-5-{[2-chloro-4-fluoro-5-(3-fluoropyridin-2-yl)benzoyl]amino}-1-phenyl-1H-pyrazole-3-carboxamide | LCMS Rt = 1.39 minutes MS m/z 521.23 [M − H]− |

-continued

| Example Number | Name | Data |
|---|---|---|
| 706 | N-[(1R,3R)-3-aminocyclopentyl]-5-{[2-chloro-4-fluoro-5-(3-fluoropyridin-2-yl)benzoyl]amino}-1-phenyl-1H-pyrazole-3-carboxamide | LCMS Rt = 1.4 minutes MS m/z 535.25 [M − H]⁻ |
| 707 | N-(azetidin-3-yl)-5-{[2-chloro-4-fluoro-5-(3-fluoropyridin-2-yl)benzoyl]amino}-1-phenyl-1H-pyrazole-3-carboxamide | LCMS Rt = 1.4 minutes MS m/z 509.03 [M + H]⁺ |
| 708 | 5-{[2-chloro-4-fluoro-5-(3-fluoropyridin-2-yl)benzoyl]amino}-1-phenyl-N-[(3S)-pyrrolidin-3-yl]-1H-pyrazole-3-carboxamide | LCMS Rt = 1.4 minutes MS m/z 521.21 [M − H]⁻ |
| 709 | 5-{[2-chloro-4-fluoro-5-(3-fluoropyridin-2-yl)benzoyl]amino}-1-phenyl-N-[(3R)-pyrrolidin-3-yl]-1H-pyrazole-3-carboxamide | LCMS Rt = 1.4 minutes MS m/z 521.2 [M − H]⁻ |
| 710 | N-(cis-3-aminocyclobutyl)-5-{[2-chloro-4-fluoro-5-(3-fluoropyridin-2-yl)benzoyl]amino}-1-phenyl-1H-pyrazole-3-carboxamide | LCMS Rt = 1.38 minutes MS m/z 521.21 [M − H]⁻ |
| 711 | N-(3-aminopropyl)-5-{[2-chloro-4-fluoro-5-(3-fluoropyridin-2-yl)benzoyl]amino}-1-phenyl-1H-pyrazole-3-carboxamide | LCMS Rt = 1.38 minutes MS m/z 509.2 [M − H]⁻ |
| 712 | N-[(2S)-2-aminopropyl]-5-{[2-chloro-4-fluoro-5-(3-fluoropyridin-2-yl)benzoyl]amino}-1-phenyl-1H-pyrazole-3-carboxamide | LCMS Rt = 1.39 minutes MS m/z 511.05 [M + H]⁺ |
| 713 | N-[(2S)-1-aminopropan-2-yl]-5-{[2-chloro-4-fluoro-5-(3-fluoropyridin-2-yl)benzoyl]amino}-1-phenyl-1H-pyrazole-3-carboxamide | LCMS Rt = 1.42 minutes MS m/z 511.06 [M + H]⁺ |
| 714 | N-[(2R)-1-aminopropan-2-yl]-5-{[2-chloro-4-fluoro-5-(3-fluoropyridin-2-yl)benzoyl]amino}-1-phenyl-1H-pyrazole-3-carboxamide | LCMS Rt = 1.4 minutes MS m/z 509.2 [M − H]⁻ |
| 715 | N-[(2R)-2-aminopropyl]-5-{[2-chloro-4-fluoro-5-(3-fluoropyridin-2-yl)benzoyl]amino}-1-phenyl-1H-pyrazole-3-carboxamide | LCMS Rt = 1.39 minutes MS m/z 511.06 [M + H]⁺ |
| 716 | N-(trans-3-aminocyclobutyl)-5-{[2,4-dichloro-5-(3-fluoropyridin-2-yl)benzoyl]amino}-1-phenyl-1H-pyrazole-3-carboxamide | LCMS Rt = 1.41 minutes MS m/z 539.01 [M + H]⁺ |
| 717 | N-[(1R,3R)-3-aminocyclopentyl]-5-{[2,4-dichloro-5-(3-fluoropyridin-2-yl)benzoyl]amino}-1-phenyl-1H-pyrazole-3-carboxamide | LCMS Rt = 1.42 minutes MS m/z 551.16 [M − H]⁻ |
| 718 | N-[(2S)-1-aminopropan-2-yl]-5-{[2,4-dichloro-5-(3-fluoropyridin-2-yl)benzoyl]amino}-1-phenyl-1H-pyrazole-3-carboxamide | LCMS Rt = 1.41 minutes MS m/z 527 [M + H]⁺ |
| 719 | 5-{[2,4-dichloro-5-(3-fluoropyridin-2-yl)benzoyl]amino}-1-phenyl-N-[(3R)-pyrrolidin-3-yl]-1H-pyrazole-3-carboxamide | LCMS Rt = 1.42 minutes MS m/z 539.03 [M + H]⁺ |
| 720 | N-(3-aminopropyl)-5-{[2,4-dichloro-5-(3-fluoropyridin-2-yl)benzoyl]amino}-1-phenyl-1H-pyrazole-3-carboxamide | LCMS Rt = 1.41 minutes MS m/z 525.2 [M − H]⁻ |
| 721 | N-(2-aminoethyl)-5-{[2,4-dichloro-5-(3-fluoropyridin-2-yl)benzoyl]amino}-N-methyl-1-phenyl-1H-pyrazole-3-carboxamide | LCMS Rt = 1.41 minutes MS m/z 525.18 [M − H]⁻ |
| 722 | N-(cis-3-aminocyclobutyl)-5-{[2,4-dichloro-5-(3-fluoropyridin-2-yl)benzoyl]amino}-1-phenyl-1H-pyrazole-3-carboxamide | LCMS Rt = 1.41 minutes MS m/z 539.04 [M + H]⁺ |
| 723 | N-[(2R)-2-aminopropyl]-5-{[2,4-dichloro-5-(3-fluoropyridin-2-yl)benzoyl]amino}-1-phenyl-1H-pyrazole-3-carboxamide | LCMS Rt = 1.42 minutes MS m/z 525.19 [M − H]⁻ |
| 724 | N-[(2S)-2-aminopropyl]-5-{[2,4-dichloro-5-(3-fluoropyridin-2-yl)benzoyl]amino}-1-phenyl-1H-pyrazole-3-carboxamide | LCMS Rt = 1.43 minutes MS m/z 527.05 [M + H]⁺ |
| 725 | N-[(2R)-1-aminopropan-2-yl]-5-{[2,4-dichloro-5-(3-fluoropyridin-2-yl)benzoyl]amino}-1-phenyl-1H-pyrazole-3-carboxamide | LCMS Rt = 1.41 minutes MS m/z 525.19 [M − H]⁻ |
| 726 | 5-{[2,4-dichloro-5-(3-fluoropyridin-2-yl)benzoyl]amino}-N-[2-(methylamino)ethyl]-1-phenyl-1H-pyrazole-3-carboxamide | LCMS Rt = 1.42 minutes MS m/z 527.04 [M + H]⁺ |
| 727 | 5-{[2,4-dichloro-5-(5-fluoropyridin-2-yl)benzoyl]amino}-N-[2-(methylamino)ethyl]-1-phenyl-1H-pyrazole-3-carboxamide | LCMS Rt = 1.42 minutes MS m/z 525.2 [M − H]⁻ |
| 728 | N-(azetidin-3-yl)-5-{[2,4-dichloro-5-(5-fluoropyridin-2-yl)benzoyl]amino}-1-phenyl-1H-pyrazole-3-carboxamide | LCMS Rt = 1.43 minutes MS m/z 525 [M + H]⁺ |
| 729 | N-(cis-3-aminocyclobutyl)-5-{[2,4-dichloro-5-(5-fluoropyridin-2-yl)benzoyl]amino}-1-phenyl-1H-pyrazole-3-carboxamide | LCMS Rt = 1.42 minutes MS m/z 537.18 [M − H]⁻ |
| 730 | N-[(2S)-2-aminopropyl]-5-{[2,4-dichloro-5-(5-fluoropyridin-2-yl)benzoyl]amino}-1-phenyl-1H-pyrazole-3-carboxamide | LCMS Rt = 1.42 minutes MS m/z 525.18 [M − H]⁻ |

| Example Number | Name | Data |
|---|---|---|
| 731 | 5-{[2,4-dichloro-5-(5-fluoropyridin-2-yl)benzoyl]amino}-1-phenyl-N-[(3R)-pyrrolidin-3-yl]-1H-pyrazole-3-carboxamide | LCMS Rt = 1.43 minutes MS m/z 537.2 [M − H]⁻ |
| 732 | N-[(2S)-1-aminopropan-2-yl]-5-{[2,4-dichloro-5-(5-fluoropyridin-2-yl)benzoyl]amino}-1-phenyl-1H-pyrazole-3-carboxamide | LCMS Rt = 1.43 minutes MS m/z 525.09 [M − H]⁻ |
| 733 | N-(2-aminoethyl)-5-{[2,4-dichloro-5-(5-fluoropyridin-2-yl)benzoyl]amino}-N-methyl-1-phenyl-1H-pyrazole-3-carboxamide | LCMS Rt = 1.43 minutes MS m/z 525.17 [M − H]⁻ |
| 734 | N-(3-aminopropyl)-5-{[2,4-dichloro-5-(5-fluoropyridin-2-yl)benzoyl]amino}-1-phenyl-1H-pyrazole-3-carboxamide | LCMS Rt = 1.42 minutes MS m/z 525.19 [M − H]⁻ |
| 735 | N-[(2R)-2-aminopropyl]-5-{[2,4-dichloro-5-(5-fluoropyridin-2-yl)benzoyl]amino}-1-phenyl-1H-pyrazole-3-carboxamide | LCMS Rt = 1.42 minutes MS m/z 525.15 [M − H]⁻ |
| 736 | N-[(1R,3R)-3-aminocyclopentyl]-5-{[2,4-dichloro-5-(5-fluoropyridin-2-yl)benzoyl]amino}-1-phenyl-1H-pyrazole-3-carboxamide | LCMS Rt = 1.44 minutes MS m/z 551.24 [M − H]⁻ |
| 737 | N-(trans-3-aminocyclobutyl)-5-{[2,4-dichloro-5-(5-fluoropyridin-2-yl)benzoyl]amino}-1-phenyl-1H-pyrazole-3-carboxamide | LCMS Rt = 1.43 minutes MS m/z 539.01 [M + H]⁺ |
| 738 | N-[(2R)-1-aminopropan-2-yl]-5-{[2,4-dichloro-5-(5-fluoropyridin-2-yl)benzoyl]amino}-1-phenyl-1H-pyrazole-3-carboxamide | LCMS Rt = 1.42 minutes MS m/z 525.09 [M − H]⁻ |
| 739 | 5-{[2,4-dichloro-5-(5-fluoropyridin-2-yl)benzoyl]amino}-1-phenyl-N-[(3S)-pyrrolidin-3-yl]-1H-pyrazole-3-carboxamide | LCMS Rt = 1.42 minutes MS m/z 537.19 [M − H]⁻ |
| 740 | 5-{[2,4-dichloro-5-(3-fluoropyridin-2-yl)benzoyl]amino}-1-phenyl-N-(pyrimidin-5-ylmethyl)-1H-pyrazole-3-carboxamide | LCMS Rt = 1.63 minutes MS m/z 561.99 [M + H]⁺ |
| 741 | 5-{[2,4-dichloro-5-(3-fluoropyridin-2-yl)benzoyl]amino}-N-[(4-methyl-4H-1,2,4-triazol-3-yl)methyl]-1-phenyl-1H-pyrazole-3-carboxamide | LCMS Rt = 1.59 minutes MS m/z 565.15 [M + H]⁺ |
| 742 | 5-{[2,4-dichloro-5-(3-fluoropyridin-2-yl)benzoyl]amino}-N-(3-hydroxy-2-methylpropyl)-1-phenyl-1H-pyrazole-3-carboxamide | LCMS Rt = 1.61 minutes MS m/z 542.06 [M + H]⁺ |
| 743 | 5-{[2,4-dichloro-5-(3-fluoropyridin-2-yl)benzoyl]amino}-N-[(1-hydroxycyclobutyl)methyl]-1-phenyl-1H-pyrazole-3-carboxamide | LCMS Rt = 1.64 minutes MS m/z 554.14 [M + H]⁺ |
| 744 | 5-{[2,4-dichloro-5-(3-fluoropyridin-2-yl)benzoyl]amino}-N-[3-(methylamino)-3-oxopropyl]-1-phenyl-1H-pyrazole-3-carboxamide | LCMS Rt = 1.58 minutes MS m/z 555.12 [M + H]⁺ |
| 745 | 5-{[2,4-dichloro-5-(3-fluoropyridin-2-yl)benzoyl]amino}-N-[3-(hydroxymethyl)oxetan-3-yl]-1-phenyl-1H-pyrazole-3-carboxamide | LCMS Rt = 1.56 minutes MS m/z 556.14 [M + H]⁺ |
| 746 | N-(2-cyanoethyl)-5-{[2,4-dichloro-5-(3-fluoropyridin-2-yl)benzoyl]amino}-1-phenyl-1H-pyrazole-3-carboxamide | LCMS Rt = 1.62 minutes MS m/z 523.01 [M + H]⁺ |
| 747 | N-[1-cyano-2-(methylamino)-2-oxoethyl]-5-{[2,4-dichloro-5-(3-fluoropyridin-2-yl)benzoyl]amino}-1-phenyl-1H-pyrazole-3-carboxamide | LCMS Rt = 1.6 minutes MS m/z 566.13 [M + H]⁺ |
| 748 | 5-{[2,4-dichloro-5-(3-fluoropyridin-2-yl)benzoyl]amino}-1-phenyl-N-[2-(1H-1,2,4-triazol-5-yl)ethyl]-1H-pyrazole-3-carboxamide | LCMS Rt = 1.56 minutes MS m/z 565.01 [M + H]⁺ |
| 749 | N-[2-(acetylamino)ethyl]-5-{[2,4-dichloro-5-(3-fluoropyridin-2-yl)benzoyl]amino}-1-phenyl-1H-pyrazole-3-carboxamide | LCMS Rt = 1.58 minutes MS m/z 555.12 [M + H]⁺ |
| 750 | 5-{[2,4-dichloro-5-(3-fluoropyridin-2-yl)benzoyl]amino}-N-[(1-methyl-1H-1,2,3-triazol-5-yl)methyl]-1-phenyl-1H-pyrazole-3-carboxamide | LCMS Rt = 1.6 minutes MS m/z 565.11 [M + H]⁺ |
| 751 | 2,4-dichloro-5-(3-fluoropyridin-2-yl)-N-(3-{[3-(methylamino)azetidin-1-yl]carbonyl}-1-phenyl-1H-pyrazol-5-yl)benzamide | LCMS Rt = 1.41 minutes MS m/z 539.22 [M + H]⁺ |
| 752 | 5-{[2,4-dichloro-5-(3-fluoropyridin-2-yl)benzoyl]amino}-N-[2-(2-oxopiperazin-1-yl)ethyl]-1-phenyl-1H-pyrazole-3-carboxamide | LCMS Rt = 1.4 minutes MS m/z 596.19 [M + H]⁺ |
| 753 | 5-{[2,4-dichloro-5-(3-fluoropyridin-2-yl)benzoyl]amino}-N-[(2S)-2-(glycylamino)propyl]-1-phenyl-1H-pyrazole-3-carboxamide | LCMS Rt = 1.41 minutes MS m/z 584.25 [M + H]⁺ |
| 754 | 2,4-dichloro-5-(3-fluoropyridin-2-yl)-N-(3-{[3-methyl-3-(methylamino)azetidin-1-yl]carbonyl}-1-phenyl-1H-pyrazol-5-yl)benzamide | LCMS Rt = 1.42 minutes MS m/z 553.26 [M + H]⁺ |
| 755 | N-{3-[(4-amino-4-methylpiperidin-1-yl)carbonyl]-1-phenyl-1H-pyrazol-5-yl}-2,4-dichloro-5-(3-fluoropyridin-2-yl)benzamide | LCMS Rt = 1.41 minutes MS m/z 567.24 [M + H]⁺ |

| Example Number | Name | Data |
| --- | --- | --- |
| 756 | N-(3-{[2-(2-aminoethyl)morpholin-4-yl]carbonyl}-1-phenyl-1H-pyrazol-5-yl)-2,4-dichloro-5-(3-fluoropyridin-2-yl)benzamide | LCMS Rt = 1.41 minutes MS m/z 583.23 [M + H]+ |
| 757 | 2,4-dichloro-N-[3-(3,6-diazabicyclo[3.2.0]hept-3-ylcarbonyl)-1-phenyl-1H-pyrazol-5-yl]-5-(3-fluoropyridin-2-yl)benzamide | LCMS Rt = 1.41 minutes MS m/z 551.21 [M + H]+ |
| 758 | N-{3-[(2-amino-7-azaspiro[3.5]non-7-yl)carbonyl]-1-phenyl-1H-pyrazol-5-yl}-2,4-dichloro-5-(3-fluoropyridin-2-yl)benzamide | LCMS Rt = 1.42 minutes MS m/z 593.22 [M + H]+ |
| 759 | N-(3-{[(3S)-3-aminopyrrolidin-1-yl]carbonyl}-1-phenyl-1H-pyrazol-5-yl)-2,4-dichloro-5-(3-fluoropyridin-2-yl)benzamide | LCMS Rt = 1.4 minutes MS m/z 539.18 [M + H]+ |
| 760 | 2,4-dichloro-5-(3-fluoropyridin-2-yl)-N-(3-{[(1R,4R)-7-hydroxy-2,5-diazabicyclo[2.2.1]hept-2-yl]carbonyl}-1-phenyl-1H-pyrazol-5-yl)benzamide | LCMS Rt = 1.4 minutes MS m/z 567.2 [M + H]+ |
| 761 | N-{3-[(3-amino-3-methylpyrrolidin-1-yl)carbonyl]-1-phenyl-1H-pyrazol-5-yl}-2,4-dichloro-5-(3-fluoropyridin-2-yl)benzamide | LCMS Rt = 1.41 minutes MS m/z 553.24 [M + H]+ |
| 762 | 2,4-dichloro-5-(3-fluoropyridin-2-yl)-N-(3-{[4-(methylamino)piperidin-1-yl]carbonyl}-1-phenyl-1H-pyrazol-5-yl)benzamide | LCMS Rt = 1.41 minutes MS m/z 567.24 [M + H]+ |
| 763 | N-{3-[(1-amino-3-azabicyclo[3.1.0]hex-3-yl)carbonyl]-1-phenyl-1H-pyrazol-5-yl}-2,4-dichloro-5-(3-fluoropyridin-2-yl)benzamide | LCMS Rt = 1.41 minutes MS m/z 551.17 [M + H]+ |
| 764 | N-{3-[(3-aminopyrrolidin-1-yl)carbonyl]-1-phenyl-1H-pyrazol-5-yl}-2,4-dichloro-5-(3-fluoropyridin-2-yl)benzamide | LCMS Rt = 1.4 minutes MS m/z 539.22 [M + H]+ |
| 765 | N-(3-{[4-(2-aminoethyl)piperazin-1-yl]carbonyl}-1-phenyl-1H-pyrazol-5-yl)-2,4-dichloro-5-(3-fluoropyridin-2-yl)benzamide | LCMS Rt = 1.37 minutes MS m/z 582.21 [M + H]+ |
| 766 | N-{3-[(4-aminopiperidin-1-yl)carbonyl]-1-phenyl-1H-pyrazol-5-yl}-2,4-dichloro-5-(3-fluoropyridin-2-yl)benzamide | LCMS Rt = 1.4 minutes MS m/z 553.22 [M + H]+ |
| 767 | N-{3-[(3-amino-3-methylazetidin-1-yl)carbonyl]-1-phenyl-1H-pyrazol-5-yl}-2,4-dichloro-5-(3-fluoropyridin-2-yl)benzamide | LCMS Rt = 1.41 minutes MS m/z 539.18 [M + H]+ |
| 768 | 2,4-dichloro-N-{3-[(1R,4R)-2,5-diazabicyclo[2.2.1]hept-2-ylcarbonyl]-1-phenyl-1H-pyrazol-5-yl}-5-(3-fluoropyridin-2-yl)benzamide | LCMS Rt = 1.41 minutes MS m/z 551.2 [M + H]+ |
| 769 | 2,4-dichloro-5-(3-fluoropyridin-2-yl)-N-(3-{[3-(methylamino)pyrrolidin-1-yl]carbonyl}-1-phenyl-1H-pyrazol-5-yl)benzamide | LCMS Rt = 1.41 minutes MS m/z 553.22 [M + H]+ |
| 770 | N-(3-{[(1R,5S,6s)-6-amino-3-azabicyclo[3.1.0]hex-3-yl]carbonyl}-1-phenyl-1H-pyrazol-5-yl)-2,4-dichloro-5-(3-fluoropyridin-2-yl)benzamide | LCMS Rt = 1.4 minutes MS m/z 551.21 [M + H]+ |
| 771 | N-(3-{[(3R)-3-aminopyrrolidin-1-yl]carbonyl}-1-phenyl-1H-pyrazol-5-yl)-2,4-dichloro-5-(3-fluoropyridin-2-yl)benzamide | LCMS Rt = 1.4 minutes MS m/z 539.21 [M + H]+ |
| 772 | N-(3-{[(3S,4S)-3-amino-4-fluoropyrrolidin-1-yl]carbonyl}-1-phenyl-1H-pyrazol-5-yl)-2,4-dichloro-5-(3-fluoropyridin-2-yl)benzamide | LCMS Rt = 1.42 minutes MS m/z 557.21 [M + H]+ |
| 773 | 5-{[2-chloro-4-fluoro-5-(3-fluoropyridin-2-yl)benzoyl]amino}-N-(3,3-difluoropiperidin-4-yl)-1-phenyl-1H-pyrazole-3-carboxamide | LCMS Rt = 1.42 minutes MS m/z 573.07 [M + H]+ |
| 774 | 5-{[2-chloro-4-fluoro-5-(3-fluoropyridin-2-yl)benzoyl]amino}-N-[(3-fluoropiperidin-3-yl)methyl]-1-phenyl-1H-pyrazole-3-carboxamide | LCMS Rt = 1.4 minutes MS m/z 569.24 [M + H]+ |
| 775 | 5-{[2-chloro-4-fluoro-5-(3-fluoropyridin-2-yl)benzoyl]amino}-N-[(3-fluoroazetidin-3-yl)methyl]-1-phenyl-1H-pyrazole-3-carboxamide | LCMS Rt = 1.41 minutes MS m/z 541.08 [M + H]+ |
| 776 | 5-{[2-chloro-4-fluoro-5-(3-fluoropyridin-2-yl)benzoyl]amino}-N-[(3R,4R)-3-fluoropiperidin-4-yl]-1-phenyl-1H-pyrazole-3-carboxamide | LCMS Rt = 1.39 minutes MS m/z 555.26 [M + H]+ |
| 777 | 5-{[2-chloro-4-fluoro-5-(3-fluoropyridin-2-yl)benzoyl]amino}-N-[(4,4-difluoropiperidin-3-yl)methyl]-1-phenyl-1H-pyrazole-3-carboxamide | LCMS Rt = 1.43 minutes MS m/z 587.11 [M + H]+ |
| 778 | N-{3-[(4-amino-3,3-difluoropiperidin-1-yl)carbonyl]-1-phenyl-1H-pyrazol-5-yl}-2-chloro-4-fluoro-5-(3-fluoropyridin-2-yl)benzamide | LCMS Rt = 1.4 minutes MS m/z 573.09 [M + H]+ |
| 779 | 5-{[2-chloro-4-fluoro-5-(3-fluoropyridin-2-yl)benzoyl]amino}-N-[(4-fluoropiperidin-3-yl)methyl]-1-phenyl-1H-pyrazole-3-carboxamide | LCMS Rt = 1.42 minutes MS m/z 569.1 [M + H]+ |
| 780 | 5-{[2-chloro-4-fluoro-5-(3-fluoropyridin-2-yl)benzoyl]amino}-N-[(3S,4S)-4-fluoropyrrolidin-3-yl]-1-phenyl-1H-pyrazole-3-carboxamide | LCMS Rt = 1.4 minutes MS m/z 541.08 [M + H]+ |

| Example Number | Name | Data |
|---|---|---|
| 781 | 5-{[2-chloro-4-fluoro-5-(3-fluoropyridin-2-yl)benzoyl]amino}-N-[(3-fluoropyrrolidin-3-yl)methyl]-1-phenyl-1H-pyrazole-3-carboxamide | LCMS Rt = 1.4 minutes MS m/z 555.11 [M + H]+ |
| 782 | 5-{[2-chloro-4-fluoro-5-(3-fluoropyridin-2-yl)benzoyl]amino}-N-(4,4-difluoropyrrolidin-3-yl)-1-phenyl-1H-pyrazole-3-carboxamide | LCMS Rt = 1.42 minutes MS m/z 559.1 [M + H]+ |
| 783 | 5-{[2-chloro-4-fluoro-5-(3-fluoropyridin-2-yl)benzoyl]amino}-N-(5,5-difluoropiperidin-3-yl)-1-phenyl-1H-pyrazole-3-carboxamide | LCMS Rt = 1.44 minutes MS m/z 573.1 [M + H]+ |
| 784 | 5-{[2-chloro-4-fluoro-5-(3-fluoropyridin-2-yl)benzoyl]amino}-N-[(3R,4S)-4-fluoropyrrolidin-3-yl]-1-phenyl-1H-pyrazole-3-carboxamide | LCMS Rt = 1.4 minutes MS m/z 541.12 [M + H]+ |
| 785 | 5-{[2-chloro-4-fluoro-5-(3-fluoropyridin-2-yl)benzoyl]amino}-N-[(3R,4S)-3-fluoropiperidin-4-yl]-1-phenyl-1H-pyrazole-3-carboxamide | LCMS Rt = 1.41 minutes MS m/z 555.11 [M + H]+ |
| 786 | 5-{[2-chloro-4-fluoro-5-(3-fluoropyridin-2-yl)benzoyl]amino}-N-{[(2S)-4,4-difluoropyrrolidin-2-yl]methyl}-1-phenyl-1H-pyrazole-3-carboxamide | LCMS Rt = 1.43 minutes MS m/z 573.09 [M + H]+ |
| 787 | 5-{[2-chloro-4-fluoro-5-(3-fluoropyridin-2-yl)benzoyl]amino}-N-(4-fluoropyrrolidin-3-yl)-1-phenyl-1H-pyrazole-3-carboxamide | LCMS Rt = 1.41 minutes MS m/z 541.11 [M + H]+ |
| 788 | N-(3-{[(3S,4R)-3-amino-4-fluoropiperidin-1-yl]carbonyl}-1-phenyl-1H-pyrazol-5-yl)-2-chloro-4-fluoro-5-(3-fluoropyridin-2-yl)benzamide | LCMS Rt = 1.4 minutes MS m/z 555.13 [M + H]+ |
| 789 | 5-{[2-chloro-4-fluoro-5-(3-fluoropyridin-2-yl)benzoyl]amino}-N-{[(2R)-4,4-difluoropyrrolidin-2-yl]methyl}-1-phenyl-1H-pyrazole-3-carboxamide | LCMS Rt = 1.43 minutes MS m/z 573.1 [M + H]+ |
| 790 | 2-chloro-4-fluoro-N-(3-{[(3S)-3-(fluoromethyl)piperazin-1-yl]carbonyl}-1-phenyl-1H-pyrazol-5-yl)-5-(3-fluoropyridin-2-yl)benzamide | LCMS Rt = 1.4 minutes MS m/z 555.12 [M + H]+ |
| 791 | N-(3-{[(3R,4R)-3-amino-4-fluoropiperidin-1-yl]carbonyl}-1-phenyl-1H-pyrazol-5-yl)-2-chloro-4-fluoro-5-(3-fluoropyridin-2-yl)benzamide | LCMS Rt = 1.39 minutes MS m/z 555.21 [M + H]+ |
| 792 | N-{3-[(3-amino-4-fluoropiperidin-1-yl)carbonyl]-1-phenyl-1H-pyrazol-5-yl}-2-chloro-4-fluoro-5-(3-fluoropyridin-2-yl)benzamide | LCMS Rt = 1.4 minutes MS m/z 555.09 [M + H]+ |
| 793 | 5-{[2-chloro-4-fluoro-5-(3-fluoropyridin-2-yl)benzoyl]amino}-N-{[(2S,4S)-4-fluoropyrrolidin-2-yl]methyl}-1-phenyl-1H-pyrazole-3-carboxamide | LCMS Rt = 1.41 minutes MS m/z 555.12 [M + H]+ |
| 794 | 5-{[2-chloro-4-fluoro-5-(3-fluoropyridin-2-yl)benzoyl]amino}-N-(3-fluoropiperidin-4-yl)-1-phenyl-1H-pyrazole-3-carboxamide | LCMS Rt = 1.41 minutes MS m/z 555.11 [M + H]+ |
| 795 | N-(3-amino-2,2-difluoropropyl)-5-{[2-chloro-4-fluoro-5-(3-fluoropyridin-2-yl)benzoyl]amino}-1-phenyl-1H-pyrazole-3-carboxamide | LCMS Rt = 1.4 minutes MS m/z 547.09 [M + H]+ |
| 796 | 5-{[2-chloro-5-(3-fluoropyridin-2-yl)benzoyl]amino}-N-[(1-methylpiperidin-3-yl)methyl]-1-phenyl-1H-pyrazole-3-carboxamide | LCMS Rt = 2.55 minutes MS m/z 547.12 [M + H]+ |
| 797 | 5-{[2-chloro-5-(3-fluoropyridin-2-yl)benzoyl]amino}-N-(1-methylazetidin-3-yl)-1-phenyl-1H-pyrazole-3-carboxamide | LCMS Rt = 2.53 minutes MS m/z 505.07 [M + H]+ |
| 798 | 5-{[2-chloro-5-(3-fluoropyridin-2-yl)benzoyl]amino}-N-[1-(dimethylamino)-3-methoxypropan-2-yl]-1-phenyl-1H-pyrazole-3-carboxamide | LCMS Rt = 2.66 minutes MS m/z 551.09 [M + H]+ |
| 799 | 5-{[2-chloro-5-(3-fluoropyridin-2-yl)benzoyl]amino}-N-[(3R)-1-methylpyrrolidin-3-yl]-1-phenyl-1H-pyrazole-3-carboxamide | LCMS Rt = 2.56 minutes MS m/z 519.24 [M + H]+ |
| 800 | 5-{[2-chloro-5-(3-fluoropyridin-2-yl)benzoyl]amino}-N-[(3-endo)-8-methyl-8-azabicyclo[3.2.1]oct-3-yl]-1-phenyl-1H-pyrazole-3-carboxamide | LCMS Rt = 2.58 minutes MS m/z 559.24 [M + H]+ |
| 801 | 5-{[2-chloro-5-(3-fluoropyridin-2-yl)benzoyl]amino}-N-[(1,3-dimethylpyrrolidin-3-yl)methyl]-1-phenyl-1H-pyrazole-3-carboxamide | LCMS Rt = 2.58 minutes MS m/z 547.12 [M + H]+ |
| 802 | 5-{[2-chloro-5-(3-fluoropyridin-2-yl)benzoyl]amino}-N-[4-(dimethylamino)-2-hydroxybutyl]-1-phenyl-1H-pyrazole-3-carboxamide | LCMS Rt = 2.5 minutes MS m/z 551.07 [M + H]+ |
| 803 | N-(1-azabicyclo[2.2.1]hept-3-yl)-5-{[2-chloro-5-(3-fluoropyridin-2-yl)benzoyl]amino}-1-phenyl-1H-pyrazole-3-carboxamide | LCMS Rt = 2.52 minutes MS m/z 531.09 [M + H]+ |
| 804 | 5-{[2-chloro-5-(3-fluoropyridin-2-yl)benzoyl]amino}-N-[(1-methylpyrrolidin-3-yl)methyl]-1-phenyl-1H-pyrazole-3-carboxamide | LCMS Rt = 2.76 minutes MS m/z 533.14 [M + H]+ |
| 805 | (R)-5-(2-chloro-5-(3-fluoropyridin-2-yl)benzamido)-1-phenyl-N-(quinuclidin-3-yl)-1H-pyrazole-3-carboxamide | LCMS Rt = 2.55 minutes MS m/z 545.08 [M + H]+ |

| Example Number | Name | Data |
|---|---|---|
| 806 | 5-{[2-chloro-5-(3-fluoropyridin-2-yl)benzoyl]amino}-N-[(1-methylazetidin-3-yl)methyl]-1-phenyl-1H-pyrazole-3-carboxamide | LCMS Rt = 2.54 minutes MS m/z 519.21 [M + H]+ |
| 807 | 5-{[2-chloro-5-(3-fluoropyridin-2-yl)benzoyl]amino}-N-[2-(morpholin-4-yl)ethyl]-1-phenyl-1H-pyrazole-3-carboxamide | LCMS Rt = 2.72 minutes MS m/z 549.07 [M + H]+ |
| 808 | 5-{[2-chloro-5-(3-fluoropyridin-2-yl)benzoyl]amino}-N-[(3S)-1-methylpyrrolidin-3-yl]-1-phenyl-1H-pyrazole-3-carboxamide | LCMS Rt = 2.55 minutes MS m/z 519.1 [M + H]+ |
| 809 | 5-{[2-chloro-5-(3-fluoropyridin-2-yl)benzoyl]amino}-N-[trans-4-(dimethylamino)cyclohexyl]-1-phenyl-1H-pyrazole-3-carboxamide | LCMS Rt = 2.56 minutes MS m/z 561.1 [M + H]+ |
| 810 | (S)-5-(2-chloro-5-(3-fluoropyridin-2-yl)benzamido)-1-phenyl-N-(quinuclidin-3-yl)-1H-pyrazole-3-carboxamide | LCMS Rt = 2.53 minutes MS m/z 545.08 [M + H]+ |
| 811 | 5-{[2-chloro-5-(3-fluoropyridin-2-yl)benzoyl]amino}-N-[1-(dimethylamino)propan-2-yl]-1-phenyl-1H-pyrazole-3-carboxamide | LCMS Rt = 2.63 minutes MS m/z 521.1 [M + H]+ |
| 812 | 5-{[2-chloro-5-(3-fluoropyridin-2-yl)benzoyl]amino}-N-[(1S,7aR)-hexahydro-1H-pyrrolizin-1-ylmethyl]-1-phenyl-1H-pyrazole-3-carboxamide | LCMS Rt = 2.56 minutes MS m/z 559.21 [M + H]+ |
| 813 | N-[(3R,4S)-1-azabicyclo[2.2.1]hept-3-yl]-5-{[2-chloro-5-(3-fluoropyridin-2-yl)benzoyl]amino}-1-phenyl-1H-pyrazole-3-carboxamide | LCMS Rt = 2.5 minutes MS m/z 531.09 [M + H]+ |
| 814 | 5-{[2-chloro-5-(3-fluoropyridin-2-yl)benzoyl]amino}-N-{[3-(dimethylamino)cyclobutyl]methyl}-1-phenyl-1H-pyrazole-3-carboxamide | LCMS Rt = 2.55 minutes MS m/z 547.12 [M + H]+ |
| 815 | 5-{[2-chloro-5-(3-fluoropyridin-2-yl)benzoyl]amino}-N-{cis-3-[(dimethylamino)methyl]cyclobutyl}-1-phenyl-1H-pyrazole-3-carboxamide | LCMS Rt = 2.55 minutes MS m/z 547.12 [M + H]+ |
| 816 | 5-(2-chloro-5-(3-fluoropyridin-2-yl)benzamido)-1-phenyl-N-(quinuclidin-4-ylmethyl)-1H-pyrazole-3-carboxamide | LCMS Rt = 2.55 minutes MS m/z 559.21 [M + H]+ |
| 817 | 5-{[2-chloro-5-(3-fluoropyridin-2-yl)benzoyl]amino}-N-[(1-methylpiperidin-4-yl)methyl]-1-phenyl-1H-pyrazole-3-carboxamide | LCMS Rt = 2.53 minutes MS m/z 547.25 [M + H]+ |
| 818 | 5-{[2-chloro-5-(3-fluoropyridin-2-yl)benzoyl]amino}-N-[(3S,4S)-4-(dimethylamino)tetrahydrofuran-3-yl]-1-phenyl-1H-pyrazole-3-carboxamide | LCMS Rt = 2.68 minutes MS m/z 549.11 [M + H]+ |
| 819 | 5-{[2-chloro-5-(3-fluoropyridin-2-yl)benzoyl]amino}-N-(cis-3-hydroxycyclobutyl)-1-phenyl-1H-pyrazole-3-carboxamide | LCMS Rt = 1.54 minutes MS m/z 506.29 [M + H]+ |
| 820 | 5-{[2-chloro-5-(3-fluoropyridin-2-yl)benzoyl]amino}-N-(2-hydroxy-2-methylpropyl)-1-phenyl-1H-pyrazole-3-carboxamide | LCMS Rt = 1.59 minutes MS m/z 506.25 [M − H]− |
| 821 | 5-{[2-chloro-5-(3-fluoropyridin-2-yl)benzoyl]amino}-N-(3-methyl-1H-pyrazol-5-yl)-1-phenyl-1H-pyrazole-3-carboxamide | LCMS Rt = 1.63 minutes MS m/z 516.27 [M + H]+ |
| 822 | 5-{[2-chloro-5-(3-fluoropyridin-2-yl)benzoyl]amino}-N-(trans-4-hydroxycyclohexyl)-1-phenyl-1H-pyrazole-3-carboxamide | LCMS Rt = 1.59 minutes MS m/z 534.34 [M + H]+ |
| 823 | 5-{[2-chloro-5-(3-fluoropyridin-2-yl)benzoyl]amino}-N-[(1S,3R)-3-hydroxycyclopentyl]-1-phenyl-1H-pyrazole-3-carboxamide | LCMS Rt = 1.58 minutes MS m/z 520.36 [M + H]+ |
| 824 | 5-{[2-chloro-5-(3-fluoropyridin-2-yl)benzoyl]amino}-N-(3-hydroxy-2-methylpropyl)-1-phenyl-1H-pyrazole-3-carboxamide | LCMS Rt = 1.59 minutes MS m/z 508.32 [M + H]+ |
| 825 | 5-{[2-chloro-5-(3-fluoropyridin-2-yl)benzoyl]amino}-N-[(1-hydroxycyclopropyl)methyl]-1-phenyl-1H-pyrazole-3-carboxamide | LCMS Rt = 1.58 minutes MS m/z 506.32 [M + H]+ |
| 826 | 5-{[2-chloro-5-(3-fluoropyridin-2-yl)benzoyl]amino}-N-(1H-imidazol-5-ylmethyl)-1-phenyl-1H-pyrazole-3-carboxamide | LCMS Rt = 1.4 minutes MS m/z 516.31 [M + H]+ |
| 827 | 5-{[2-chloro-5-(3-fluoropyridin-2-yl)benzoyl]amino}-N-(2,2-difluoropropyl)-1-phenyl-1H-pyrazole-3-carboxamide | LCMS Rt = 1.67 minutes MS m/z 514.27 [M + H]+ |
| 828 | 5-{[2-chloro-5-(3-fluoropyridin-2-yl)benzoyl]amino}-N-(cis-4-hydroxycyclohexyl)-1-phenyl-1H-pyrazole-3-carboxamide | LCMS Rt = 1.59 minutes MS m/z 534.3 [M + H]+ |
| 829 | 5-{[2-chloro-5-(3-fluoropyridin-2-yl)benzoyl]amino}-N-(3-hydroxycyclobutyl)-1-phenyl-1H-pyrazole-3-carboxamide | LCMS Rt = 1.55 minutes MS m/z 506.31 [M + H]+ |
| 830 | 5-{[2-chloro-5-(3-fluoropyridin-2-yl)benzoyl]amino}-N-[(3-hydroxyoxetan-3-yl)methyl]-1-phenyl-1H-pyrazole-3-carboxamide | LCMS Rt = 1.54 minutes MS m/z 522.35 [M + H]+ |

| Example Number | Name | Data |
|---|---|---|
| 831 | 5-{[2-chloro-5-(3-fluoropyridin-2-yl)benzoyl]amino}-N-(2-hydroxy-3-methoxypropyl)-1-phenyl-1H-pyrazole-3-carboxamide | LCMS Rt = 1.56 minutes MS m/z 524.17 [M + H]+ |
| 832 | 5-{[2-chloro-5-(3-fluoropyridin-2-yl)benzoyl]amino}-N-[cis-3-(hydroxymethyl)cyclobutyl]-1-phenyl-1H-pyrazole-3-carboxamide | LCMS Rt = 1.57 minutes MS m/z 520.31 [M + H]+ |
| 833 | 5-{[2-chloro-5-(3-fluoropyridin-2-yl)benzoyl]amino}-N-(oxetan-3-ylmethyl)-1-phenyl-1H-pyrazole-3-carboxamide | LCMS Rt = 1.59 minutes MS m/z 506.28 [M + H]+ |
| 834 | 5-{[2-chloro-4-fluoro-5-(3-fluoropyridin-2-yl)benzoyl]amino}-N-(cis-4-hydroxycyclohexyl)-1-phenyl-1H-pyrazole-3-carboxamide | LCMS Rt = 1.6 minutes MS m/z 552.23 [M + H]+ |
| 835 | 5-{[2-chloro-4-fluoro-5-(3-fluoropyridin-2-yl)benzoyl]amino}-N-[(3R,4S)-4-hydroxytetrahydrofuran-3-yl]-1-phenyl-1H-pyrazole-3-carboxamide | LCMS Rt = 1.55 minutes MS m/z 540.25 [M + H]+ |
| 836 | N-[(2-aminopyridin-4-yl)methyl]-5-{[2-chloro-4-fluoro-5-(3-fluoropyridin-2-yl)benzoyl]amino}-1-phenyl-1H-pyrazole-3-carboxamide | LCMS Rt = 1.43 minutes MS m/z 560.13 [M + H]+ |
| 837 | 5-{[2-chloro-4-fluoro-5-(3-fluoropyridin-2-yl)benzoyl]amino}-N-(2-methoxyethyl)-1-phenyl-1H-pyrazole-3-carboxamide | LCMS Rt = 1.62 minutes MS m/z 512.22 [M + H]+ |
| 838 | 5-{[2-chloro-4-fluoro-5-(3-fluoropyridin-2-yl)benzoyl]amino}-1-phenyl-N-(pyridazin-4-ylmethyl)-1H-pyrazole-3-carboxamide | LCMS Rt = 1.6 minutes MS m/z 546.19 [M + H]+ |
| 839 | 5-{[2,4-dichloro-5-(pyridin-2-yl)benzoyl]amino}-N-(1-hydroxypropan-2-yl)-1-phenyl-1H-pyrazole-3-carboxamide | LCMS Rt = 1.58 minutes MS m/z 510.18 [M + H]+ |
| 840 | N-(cis-3-aminocyclobutyl)-5-{[2-chloro-4-fluoro-5-(pyridin-2-yl)benzoyl]amino}-1-phenyl-1H-pyrazole-3-carboxamide | LCMS Rt = 1.38 minutes MS m/z 505.06 [M + H]+ |
| 841 | 5-{[2-chloro-4-fluoro-5-(pyridin-2-yl)benzoyl]amino}-N-(1,3,4-oxadiazol-2-ylmethyl)-1-phenyl-1H-pyrazole-3-carboxamide | MS m/z 518.0 [M + H]+ |

Preparation 1

5-(5-(6-amino-3-fluoropyridin-2-yl)-2-chlorobenzamido)-1-phenyl-1H-pyrazole-3-carboxamide

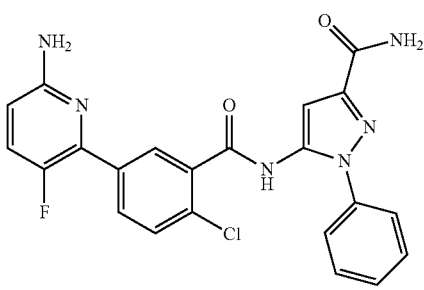 [SMILES: NC(=O)c1cc(NC(=O)c2cc(-c3nc(N)ccc3F)ccc2Cl)n(-c2ccccc2)n1]

A solution of 5-(2-chloro-5-(4,4,5,5-tetramethyl-1,3,2-dioxaborolan-2-yl)benzamido)-1-phenyl-1H-pyrazole-3-carboxamide (Preparation 3, 50 mg, 0.11 mmol), 6-chloro-5-fluoropyridin-2-amine (47 mg, 0.32 mmol), tetrakis(triphenylphosphine)palladium (12 mg, 0.01 mmol) and potassium carbonate (30 mg, 0.21 mmol) in dioxane (1.5 mL) and water (1.5 mL) was heated at 110° C. under microwave irradiation for 1 hour. The reaction was poured into water (25 mL) and extracted with EtOAc (2×25 mL). The organic layer was washed with brine (10 mL), dried over magnesium sulphate and concentrated in vacuo.

The residue was purified using silica gel column chromatography eluting with EtOAc followed by 10% MeOH in DCM. The resulting solid was triturated with EtOAc to afford the title compound (15 mg, 31%).

$^1$H NMR (400 MHz, DMSO-d$_6$): δ ppm 6.07 (s, 2H), 6.51 (m, 1H), 6.90 (s, 1H), 7.68-7.37 (m, 9H), 7.96 (s, 2H), 10.78 (s, 1H).

LCMS Rt=2.53 minutes MS m/z 451 [M+H]+

Preparation 2

Ethyl 5-(5-(6-aminopyridin-2-yl)-2-chlorobenzamido)-1-phenyl-1H-pyrazole-3-carboxylate

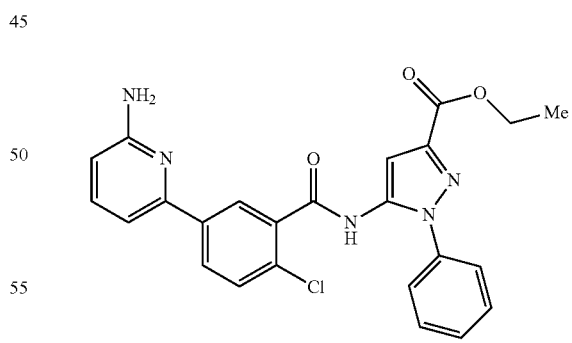

6-amino-2-bromopyridine (835.5 mg, 4.83 mmol), sodium carbonate (1.39 g, 13.2 mmol) and water (0.5 mL) were added to the solution of ethyl 5-(2-chloro-5-(4,4,5,5-tetramethyl-1,3,2-dioxaborolan-2-yl)benzamido)-1-phenyl-1H-pyrazole-3-carboxylate in dioxane obtained in Preparation 5. The reaction was degassed with nitrogen for 30 minutes before the addition of Pd(dppf)Cl$_2$ with further degassing for 10 minutes. The reaction was heated to 100° C. for 16 hours. The reaction was cooled and eluted through a pad of silica, eluting with EtOAc (50 mL). The organic solution was washed with water (50 mL) dried over magnesium sulfate and concentrated in vacuo. The residue was purified using silica gel column chromatography eluting with 30-50% EtOAc in heptanes to afford the title compound as a pale yellow solid (1.02 g, 51%).

$^1$H NMR (400 MHz, CDCl$_3$): δ ppm 1.42 (t, 3H), 4.44 (q, 2H), 4.92 (br s, 2H), 6.55 (d, 1H), 7.08 (d, 1H), 7.38-7.57 (m, 7H), 7.97 (d, 1H), 8.43 (s, 1H), 8.66 (br s, 1H).

LCMS Rt=2.33 minutes MS m/z 462 [M+H]$^+$

Preparation 3

5-(2-chloro-5-(4,4,5,5-tetramethyl-1,3,2-dioxaborolan-2-yl)benzamido)-1-phenyl-1H-pyrazole-3-carboxamide

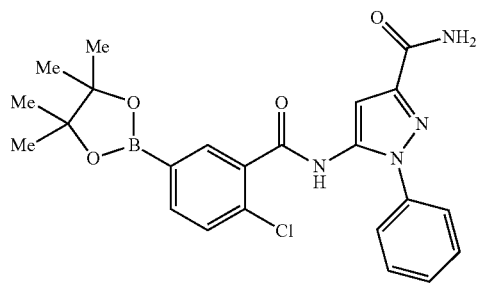 [SMILES: CC1(C)OB(c2ccc(Cl)c(C(=O)Nc3cc(C(N)=O)nn3-c3ccccc3)c2)OC1(C)C]

To solution of 5-(5-bromo-2-chlorobenzamido)-1-phenyl-1H-pyrazole-3-carboxamide (Preparation 14, 536 mg, 1.28 mmol) in dioxane (15 mL) was added 4,4,4',4',5,5,5',5'-octamethyl-2,2'-bi(1,3,2-dioxaborolane) (390 mg, 1.54 mmol) and potassium acetate (380 mg, 3.85 mmol). The reaction was degassed with nitrogen for 5 minutes before the addition of Pd(dppf)Cl$_2$ (52 mg, 0.06 mmol) and heated to 100° C. for 2.5 hours. The reaction was cooled, filtered and the filtrate purified using silica gel column chromatography eluting with 70% EtOAc in heptanes to afford the title compound (463 mg, 60%).

$^1$H NMR (400 MHz, DMSO-d$_6$): δ ppm 1.15 (s, 12H), 6.89 (s, 1H), 7.37 (br s, 1H), 7.48-7.61 (m, 7H), 7.67 (br s, 1H), 7.71 (s, 1H), 10.66 (br s, 1H).

Preparation 4

Ethyl 5-(2,4-dichloro-5-(4,4,5,5-tetramethyl-1,3,2-dioxaborolan-2-yl)benzamido)-1-phenyl-1H-pyrazole-3-carboxylate

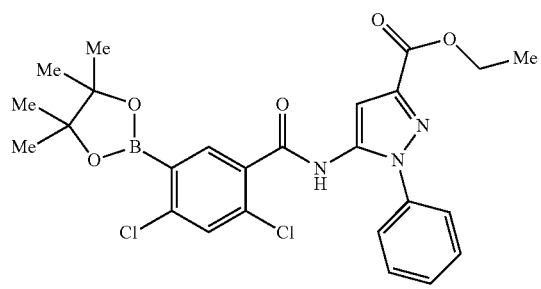 [SMILES: CCOC(=O)c1cc(NC(=O)c2cc(B3OC(C)(C)C(C)(C)O3)c(Cl)cc2Cl)n(-c2ccccc2)n1]

To a solution of ethyl 5-(5-bromo-2,4-dichlorobenzamido)-1-phenyl-1H-pyrazole-3-carboxylate (Preparation 16, 615 mg, 1.273 mmol) in dioxane (22 mL) was added 4,4,4',4',5,5,5',5'-octamethyl-2,2'-bi(1,3,2-dioxaborolane) (485 mg, 1.90 mmol), potassium acetate (250 mg, 2.54 mmol) and [1,1'-bis(diphenylphosphino)ferrocene]dichloropalladium(II) (47 mg, 0.064 mmol). The reaction was degassed and heated to reflux for 2 hours. Further [1,1'-bis(diphenylphosphino)ferrocene]dichloropalladium(II) (47 mg) was added and reflux continued for another 16 hours. The reaction was cooled and taken on directly to the next step as a solution of the title compound in dioxane.

Preparation 5

Ethyl 5-(2-chloro-5-(4,4,5,5-tetramethyl-1,3,2-dioxaborolan-2-yl)benzamido)-1-phenyl-1H-pyrazole-3-carboxylate

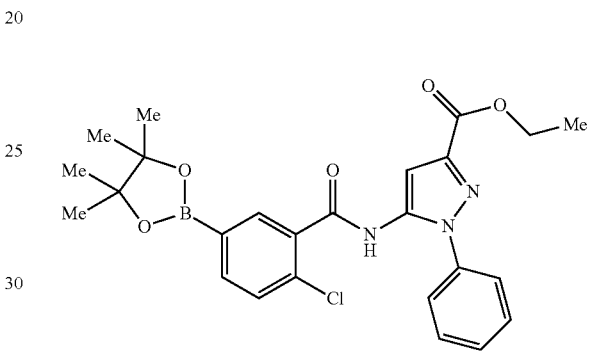

To a degassed solution of ethyl 5-(5-bromo-2-chlorobenzamido)-1-phenyl-1H-pyrazole-3-carboxylate (Preparation 13, 1.97 g, 4.39 mmol) and bis-pinacolatodiboron (1.23 g, 4.83 mmol) in dioxane (20 mL) was added potassium acetate (1.29 g, 13.7 mmol) and palladium(diphenylphosphineferrocenyl)dichloride (179 mg, 0.22 mmol). The reaction was degassed for a further 30 minutes before heating to 100° C. for 16 hours. The reaction was cooled to room temperature and used directly in the next step.

Preparation 6

Ethyl 1-(3-(benzyloxy)phenyl)-5-(2-chloro-5-(4,4,5,5-tetramethyl-1,3,2-dioxaborolan-2-yl)benzamido)-1H-pyrazole-3-carboxylate

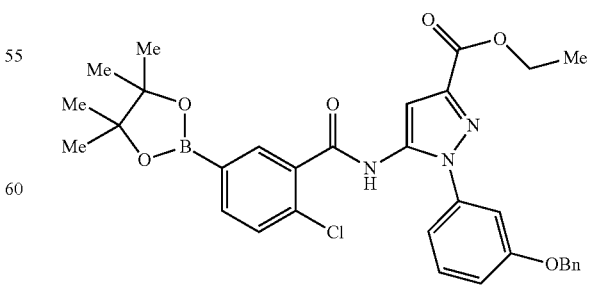

The title compound was prepared according to the method described for Preparation 5 using ethyl 1-(3-(benzyloxy)phenyl)-5-(5-bromo-2-chlorobenzamido)-1H-pyrazole-3-carboxylate (Preparation 17). Used as a solution in dioxane directly in the next step.

Preparation 7

2-chloro-N-(3-cyano-1-phenyl-1H-pyrazol-5-yl)-5-(4,4,5,5-tetramethyl-1,3,2-dioxaborolan-2-yl)benzamide

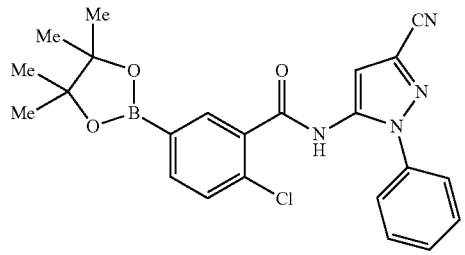 [SMILES: CC1(C)OB(c2ccc(Cl)c(C(=O)Nc3cc(C#N)nn3-c3ccccc3)c2)OC1(C)C]

To a degassed solution of 5-bromo-2-chloro-N-(3-cyano-1-phenyl-1H-pyrazol-5-yl)benzamide (Preparation 15, 500 mg, 1.25 mmol), bis(pinacolato)diboron (350 mg, 1.37 mmol) and potassium acetate (368 mg, 3.75 mmol) in 1,4-dioxane (10 mL) was added Pd(dppf)Cl$_2$ (99 mg, 0.13 mmol) and the reaction was heated to reflux for 2.5 hours. The reaction was cooled to room temperature and concentrated in vacuo. The residue was partitioned between EtOAc (20 mL) and water (15 mL). The aqueous layer was extracted with EtOAc (2×15 mL) and the organic extracts were combined, dried over sodium sulphate and concentrated in vacuo. The residue was purified using silica gel column chromatography eluting with 20-30% EtOAc in heptanes to afford the title compound (0.65 g, quant.).

$^1$H NMR (400 MHz, CDCl$_3$): δ ppm 1.35 (s, 12H), 7.30 (s, 1H), 7.40 (d, 1H), 7.45-7.62 (m, 5H), 7.82 (d, 1H), 8.26 (s, 1H), 8.40 (br s, 1H).

Preparation 8

2-chloro-N-(3-cyano-1-phenyl-1H-pyrazol-5-yl)-3-fluoro-5-(4,4,5,5-tetramethyl-1,3,2-dioxaborolan-2-yl)benzamide

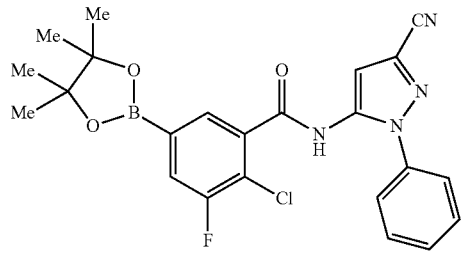 [SMILES: CC1(C)OB(c2cc(F)c(Cl)c(C(=O)Nc3cc(C#N)nn3-c3ccccc3)c2)OC1(C)C]

The title compound was prepared according to the method described for Preparation 7 using 5-bromo-2-chloro-N-(3-cyano-1-phenyl-1H-pyrazol-5-yl)-3-fluorobenzamide (Preparation 18).

$^1$H NMR (400 MHz, DMSO-d$_6$): δ ppm 1.29 (s, 12H), 7.30 (s, 1H), 7.49-7.62 (m, 7H), 10.98 (br s, 1H).

Preparation 9

6-chloro-N-(3-cyano-1-phenyl-1H-pyrazol-5-yl)-2-fluoro-3-(4,4,5,5-tetramethyl-1,3,2-dioxaborolan-2-yl)benzamide

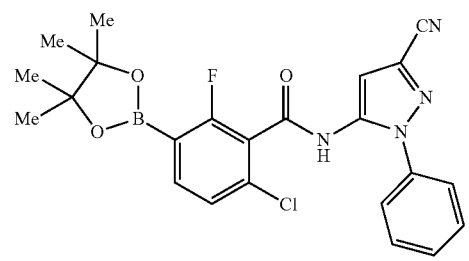 [SMILES: CC1(C)OB(c2ccc(Cl)c(C(=O)Nc3cc(C#N)nn3-c3ccccc3)c2F)OC1(C)C]

The title compound was prepared according to the method described for Preparation 7 using 3-bromo-6-chloro-N-(3-cyano-1-phenyl-1H-pyrazol-5-yl)-2-fluorobenzamide (Preparation 19).

$^1$H NMR (400 MHz, CDCl$_3$): δ ppm 1.27 (s, 12H), 7.17-7.22 (m, 1H), 7.43-7.52 (m, 7H).

Preparation 10

5-(2-chloro-5-(4,4,5,5-tetramethyl-1,3,2-dioxaborolan-2-yl)benzamido)-N-cyclopropyl-1-phenyl-1H-pyrazole-3-carboxamide

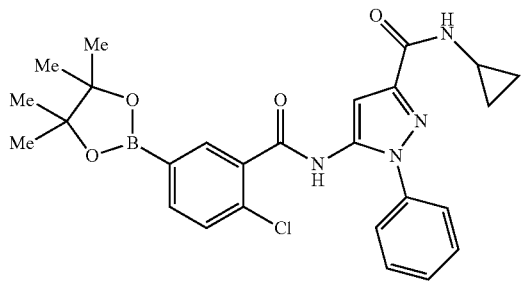 [SMILES: CC1(C)OB(c2ccc(Cl)c(C(=O)Nc3cc(C(=O)NC4CC4)nn3-c3ccccc3)c2)OC1(C)C]

5-(5-bromo-2-chlorobenzamido)-N-cyclopropyl-1-phenyl-1H-pyrazole-3-carboxamide (Preparation 11, 290 mg, 0.63 mmol), bis(pinacolato)diboron (168 mg, 0.66 mmol) and KOAc (155 mg, 1.58 mmol) in dioxane (15 mL) was degassed with nitrogen for 25 minutes. Pd(dppf)Cl$_2$ (26 mg, 0.03 mmol) was added and the reaction was degassed and heated at 110° C. for 4 hours. The reaction was cooled used directly in the next reaction without further purification.

Preparation 11

5-(5-bromo-2-chlorobenzamido)-N-cyclopropyl-1-phenyl-1H-pyrazole-3-carboxamide

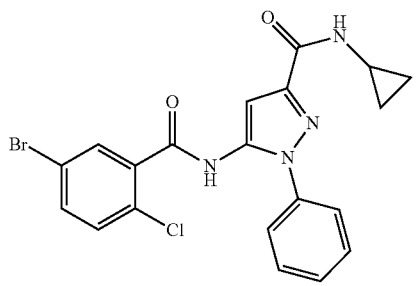 [SMILES: O=C(NC1CC1)c1cc(NC(=O)c2cc(Br)ccc2Cl)n(-c2ccccc2)n1]

To 5-(5-bromo-2-chlorobenzamido)-1-phenyl-1H-pyrazole-3-carboxylic acid (Preparation 12, 200 mg, 0.48 mmol), cyclopropylamine (137 mg, 2.40 mmol) and pyridine (114 mg, 1.44 mmol) in methyl THF (5 mL) was added 1-propylphosphonic acid cyclic anhydride (50% solution in EtOAc, 0.48 mL, 0.82 mmol) at room temperature. The reaction was stirred at room temperature for 17 hours. A 2M aqueous solution of potassium carbonate was added until the pH became basic and the solution was extracted with EtOAc (3×15 mL). The combined organic layers were concentrated in vacuo and the residue was purified by silica gel column chromatography eluting with EtOAc to afford the title compound (290 mg, 88%).

$^1$H NMR (400 MHz, CDCl$_3$): δ ppm 0.61-0.66 (m, 2H), 0.84-0.88 (m, 2H), 2.88-2.92 (m, 1H), 6.99 (s, 1H), 7.24-7.30 (m, 2H), 7.35 (s, 1H), 7.51-7.59 (m, 5H), 8.02 (d, 1H), 8.35 (s, 1H).

LCMS Rt=3.09 minutes MS m/z 459 [M]$^+$

Preparation 12

5-(5-bromo-2-chlorobenzamido)-1-phenyl-1H-pyrazole-3-carboxylic acid

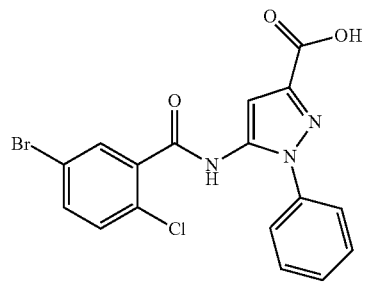 [SMILES: O=C(O)c1cc(NC(=O)c2cc(Br)ccc2Cl)n(-c2ccccc2)n1]

To a suspension of ethyl 5-(5-bromo-2-chlorobenzamido)-1-phenyl-1H-pyrazole-3-carboxylate (Preparation 13, 2.81 mmol, 1.26 g) in EtOH (14 mL) was added 0.5M aqueous LiOH solution (14.04 mmol, 336 mg in 28 mL of water). The reaction was stirred at 40° C. for 3 hours before acidifying to pH=5 with 1N HCl. The resulting precipitate was filtered and dried to afford the title compound (1.13 g, 97%).

$^1$H NMR (400 MHz, DMSO-d$_6$): δ ppm 6.95 (s, 1H), 7.46-7.50 (m, 1H), 7.53-7.59 (m, 4H), 7.67-7.70 (dd, 1H), 7.73 (d, 1H), 9.80 (s, 1H), 10.84 (s, 1H), 13.02 (br s, 1H). MS m/z 420 [M+H]$^+$

Preparation 13

Ethyl 5-(5-bromo-2-chlorobenzamido)-1-phenyl-1H-pyrazole-3-carboxylate

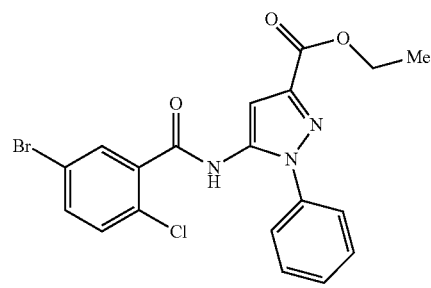 [SMILES: CCOC(=O)c1cc(NC(=O)c2cc(Br)ccc2Cl)n(-c2ccccc2)n1]

Pyridine (12.9 mL, 161 mmol) was added to a solution of ethyl 5-amino-1-phenyl-1H-pyrazole-3-carboxylate (9.32 g, 40.3 mmol) and 5-bromo-2-chlorobenzoic acid (10.4 g, 44.3 mmol) in 2-methyl-tetrahydrofuran (100 mL). The reaction was heated to 85° C. before the addition of propylphosphonic anhydride (38.5 mL, 60.4 mmol, 50% solution in EtOAc) drop-wise. The reaction was heated at 85° C. for 16 hours before cooling to room temperature. The organic solution was washed with saturated aqueous sodium hydrogen carbonate solution (3×25 mL), saturated brine (30 mL) and concentrated in vacuo. The resulting solid was triturated with TBME (5×50 mL) to afford the title compound (13.7 g, 76%).

$^1$H NMR (400 MHz, CDCl$_3$): δ ppm 1.42 (t, 3H), 4.44 (q, 2H), 7.25 (d, 1H), 7.39 (s, 1H), 7.51 (m, 5H), 8.02 (d, 1H), 8.43 (s, 1H).

LCMS Rt=3.13 minutes MS m/z 448 [M+H]$^+$

Preparation 14

5-(5-bromo-2-chlorobenzamido)-1-phenyl-1H-pyrazole-3-carboxamide

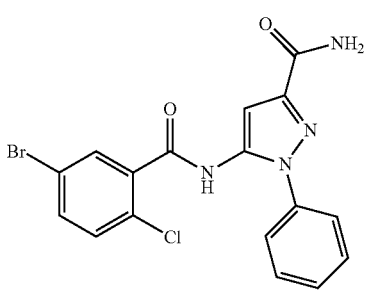 [SMILES: NC(=O)c1cc(NC(=O)c2cc(Br)ccc2Cl)n(-c2ccccc2)n1]

To a solution of 5-bromo-2-chloro-N-(3-cyano-1-phenyl-1H-pyrazol-5-yl)benzamide (Preparation 15, 500 mg, 1.24 mmol) in DMSO (5 mL) was added K$_2$CO$_3$ (340 mg, 2.48 mmol) followed by H$_2$O$_2$ (50% by weight, aqueous solution, 1.69 mL, 24.9 mmol). The reaction was stirred at room temperature for 3 hours. The reaction was quenched by the addition of saturated aqueous KHSO$_4$ solution (5 mL) followed by water (15 mL) and EtOAc (40 mL). The mixture was filtered and separated. The organic layer was washed with brine (40 mL), dried over MgSO$_4$, and concentrated in vacuo. The residue was slurried in water and filtered to afford the title compound (457 mg, 88%).

$^1$H NMR (400 MHz, DMSO-d$_6$): δ ppm 6.89 (s, 1H), 7.35 (br s, 1H), 7.44-7.72 (m, 9H), 10.77 (br s, 1H).

LCMS Rt=2.54 minutes MS m/z 419 [M+H]$^+$

Preparation 15

5-bromo-2-chloro-N-(3-cyano-1-phenyl-1H-pyrazol-5-yl)benzamide

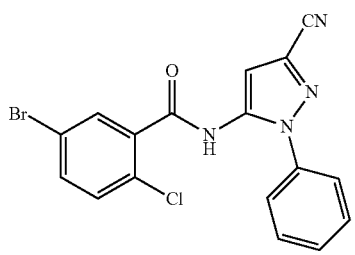 [SMILES: N#Cc1cc(NC(=O)c2cc(Br)ccc2Cl)n(-c2ccccc2)n1]

To a solution of 5-amino-1-phenyl-1H-pyrazole-3-carbonitrile (Preparation 53, 400 mg, 2.17 mmol) in 2-methyltetrahydrofuran (12 mL) was added pyridine (524 uL, 6.51 mmol) and 5-bromo-2-chlorobenzoic acid (768 mg, 3.26 mmol). The mixture was heated to 85° C. and propylphosphonic anhydride (50% w/w in EtOAc, 3.10 mL, 4.34 mmol), was added dropwise. The reaction was heated at 85° C. for 16 hours, then stirred for 48 hours at room temperature. The reaction was quenched by the addition of 10% aqueous potassium carbonate solution (24 mL, 17.4 mmol) with stirring at room temperature for 1 hour. The reaction was diluted to 150 mL with EtOAc and washed with 10% aqueous solution of potassium carbonate (100 mL) followed by 2M aqueous HCl (100 mL). The organic layer was dried over magnesium sulphate and concentrated in vacuo. The residue was purified using silica gel column chromatography eluting with 0-1% methanol in dichloromethane to afford the title compound (640 mg, 74%).

$^1$H NMR (400 MHz, DMSO-d$_6$): δ ppm 7.24 (s, 1H), 7.45-7.62 (m, 6H), 7.72 (m, 2H), 11.04 (s, 1H).

Preparation 16

Ethyl 5-(5-bromo-2,4-dichlorobenzamido)-1-phenyl-1H-pyrazole-3-carboxylate

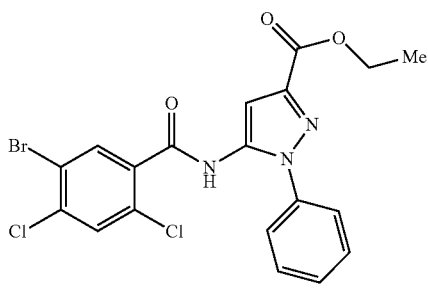 [SMILES: CCOC(=O)c1cc(NC(=O)c2cc(Br)c(Cl)cc2Cl)n(-c2ccccc2)n1]

To a solution of ethyl 5-amino-1-phenyl-1H-pyrazole-3-carboxylate (417 mg, 1.803 mmol) and 2,5-dibromo-4-chlorobenzoic acid (535 mg, 1.983 mmol) in 2-Methyl THF (20 mL) was added pyridine (583 μL, 7.212 mmol) and the reaction was heated to reflux. Propylphosphonic anhydride (50% solution in EtOAc, 1.72 mL, 2.705 mmol) was added and the reaction continued at reflux for 16 hours. The cooled reaction was washed with 1M HCl (25 mL), 2M aqueous Na$_2$CO$_3$ solution (25 mL) and brine (25 mL). The organic layer was dried over magnesium sulfate and concentrated in vacuo. The resulting solid was triturated with 1:1 TBME:heptane to afford the title compound as a yellow solid (615 mg, 75%).

$^1$H NMR (400 MHz, CDCl$_3$): δ ppm 1.42 (t, 3H), 4.44 (q, 2H), 7.38 (s, 1H), 7.48 (m, 1H), 7.51-7.55 (m, 5H), 8.19 (s, 1H), 8.45 (br s, 1H).

Preparation 17

Ethyl 1-(3-(benzyloxy)phenyl)-5-(5-bromo-2-chlorobenzamido)-1H-pyrazole-3-carboxylate

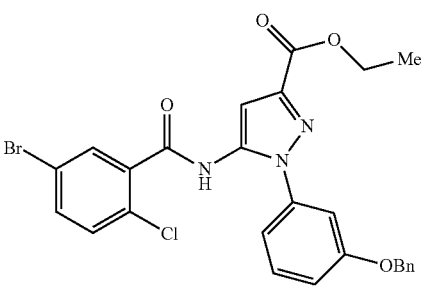 [SMILES: CCOC(=O)c1cc(NC(=O)c2cc(Br)ccc2Cl)n(-c2cccc(OCc3ccccc3)c2)n1]

The title compound was prepared according to the method described for Preparation 16 using ethyl 5-amino-1-(3-(benzyloxy)phenyl)-1H-pyrazole-3-carboxylate (Preparation 54) and 2-chloro-5-bromobenzoic acid. The residue was purified using silica gel column chromatography eluting with 30-40% EtOAc in heptanes.

$^1$H NMR (400 MHz, DMSO-d$_6$): δ ppm 1.31 (t, 3H), 4.31 (q, 2H), 5.14 (s, 2H), 7.02 (s, 1H), 7.12-7.18 (m, 2H), 7.25 (m, 1H), 7.30-7.50 (m, 7H), 7.69 (dd, 1H), 7.76 (d, 1H), 10.88 (br s, 1H).

Preparation 18

5-bromo-2-chloro-N-(3-cyano-1-phenyl-1H-pyrazol-5-yl)-3-fluorobenzamide

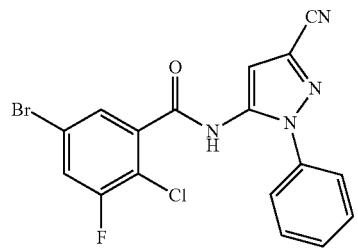 [SMILES: N#Cc1cc(NC(=O)c2cc(Br)cc(F)c2Cl)n(-c2ccccc2)n1]

The title compound was prepared according to the method described for Preparation 16 using 5-amino-1-phenyl-1H-pyrazole-3-carbonitrile (Preparation 53) and 5-bromo-2-chloro-3-fluorobenzoic acid.

$^1$H NMR (400 MHz, DMSO-d$_6$): δ ppm 7.26 (s, 1H), 7.51-7.60 (m, 5H), 7.63-7.64 (m, 1H), 7.94 (dd, 1H), 11.10 (br s, 1H).

LCMS Rt=3.44 minutes MS m/z 420 [M+H]$^+$

Preparation 19

3-bromo-6-chloro-N-(3-cyano-1-phenyl-1H-pyrazol-5-yl)-2-fluorobenzamide

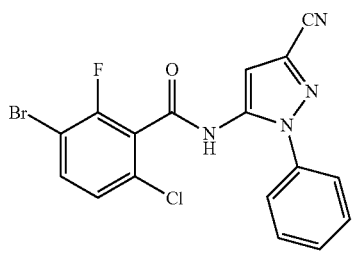 [SMILES: N#Cc1cc(NC(=O)c2c(Cl)ccc(Br)c2F)n(-c2ccccc2)n1]

To a solution of 3-bromo-6-chloro-2-fluorobenzoic acid (1 g, 3.95 mmol) in DCM (20 mL) was added DMF (1 drop) followed by oxalyl chloride (0.7 mL, 7.89 mmol) dropwise. The reaction was stirred at room temperature for 30 minutes before concentrating in vacuo and azeotroping with DCM. The residue was dissolved in MeCN (5 mL) and 5-amino-1-phenyl-1H-pyrazole-3-carbonitrile (655 mg, 3.56 mmol) and triethylamine (0.55 mL, 3.95 mmol) in MeCN (7 mL) were added. The reaction was heated at 120° C. for 1 hour under microwave irradiation. 2M NaOH (aq) (20 mL) was added with vigorous stirring at room temperature for 1.5 hours. The organic layer was separated, washed with 2M HCl (aq) (2×20 mL), dried over magnesium sulfate and concentrated in vacuo. The residue was purified using silica gel column chromatography eluting with 10-30% EtOAc in heptanes to afford the title compound (200 mg, 13%).

$^1$H NMR (400 MHz, CDCl$_3$): δ ppm 7.15 (s, 1H), 7.25 (d, 1H), 7.31-7.40 (m, 1H), 7.43-7.47 (m, 2H), 7.59-7.66 (m, 1H), 7.72-7.74 (m, 2H), 11.32 (br s, 1H).

Preparation 20

2,4-dichloro-5-(5-fluoropyridin-2-yl)benzoic acid hydrochloride

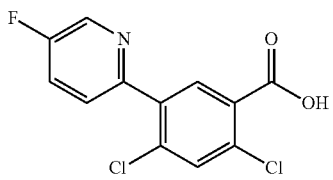 [SMILES: O=C(O)c1cc(-c2ccc(F)cn2)c(Cl)cc1Cl]

To a suspension of methyl 2,4-dichloro-5-(5-fluoropyridin-2-yl)benzoate (Preparation 34, 1 g, 3.33 mmol) in methanol (20 mL) was added 2M aqueous sodium hydroxide solution (3.3 mL, 6.66 mmol) and the reaction was heated at 50° C. for 1 hour. The reaction was concentrated in vacuo and the residue stirred with 2M aqueous hydrochloric acid (30 mL). The resulting precipitate was filtered, washed with water and dried in vacuo to afford the title compound as a white solid (900 mg, 84%).

$^1$H NMR (400 MHz, DMSO-d$_6$): δ ppm 7.79-7.84 (m, 1H), 7.84-7.91 (m, 1H), 7.87-7.89 (s, 1H), 7.97-8.00 (s, 1H), 8.69-8.72 (s, 1H), 13.63-13.71 (br s, 1H).

LCMS Rt=1.89 minutes MS m/z 284 [M−H]$^-$

Preparation 21

2-chloro-4-fluoro-5-(3-fluoropyridin-2-yl)benzoic acid

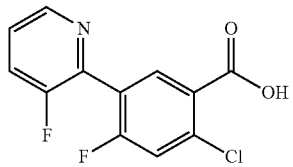 [SMILES: O=C(O)c1cc(-c2ncccc2F)c(F)cc1Cl]

To a mixture of methyl 2-chloro-4-fluoro-5-(3-fluoropyridin-2-yl)benzoate (Preparation 36, 240 mg, 0.85 mmol) in ethanol (5 mL) was added 2M LiOH in water (2.1 mL, 4.23 mmol). The reaction was stirred at room temperature for 1 hour before neutralising with 2M HCl (aq). The resulting precipitate was collected, washed with water and dried to afford the title compound as a white solid (160 mg, 70%).

$^1$H NMR (400 MHz, CDCl$_3$): δ ppm 7.59-7.63 (m, 1H), 7.75 (d, 1H), 7.88-7.92 (m, 1H), 8.08 (d, 1H), 8.58-8.59 (m, 1H), 13.60 (br s, 1H).

LCMS Rt=2.27 minutes MS m/z 270 [M+H]$^+$

The following Preparations were prepared according to the method described for Preparation 21 or 22 using the appropriate ester as described below.

| Prep Number | Name/Structure | Starting Material | Data |
|---|---|---|---|
| 22 | 2-chloro-4-fluoro-5-(pyridin-2-yl)benzoic acid | Methyl 2-chloro-4-fluoro-5-(pyridine-2-yl)benzoate (Preparation 40). | $^1$H NMR (400 MHz, DMSO-d$_6$): δ ppm 7.43 (m, 1H), 7.70 (d, 1H), 7.80 (d, 1H), 7.91 (m, 1H), 8.45 (d, 1H), 8.72 (d, 1H), 13.57 (br s, 1H). |

| Prep Number | Name/Structure | Starting Material | Data |
|---|---|---|---|
| 23 | 2-chloro-5-(6-(1,1-difluoroethyl)pyridin-2-yl)benzoic acid 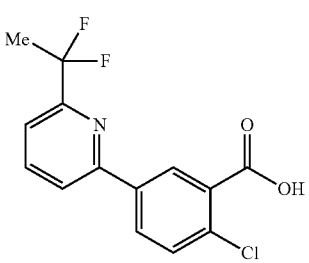 [SMILES: CC(F)(F)c1cccc(-c2ccc(Cl)c(C(=O)O)c2)n1] | Methyl 2-chloro-5-(6-(1,1-difluoroethyl)pyridin-2-yl)benzoate (Preparation 31). | $^1$H NMR (400 MHz, CDCl$_3$): δ ppm 2.10 (t, 3H), 7.60-7.70 (m, 2H), 7.85-7.95 (m, 2H), 8.23 (m, 1H), 8.70 (s, 1H). |
| 24 | 2-chloro-4-fluoro-5-(5-fluoropyridin-2-yl)benzoic acid 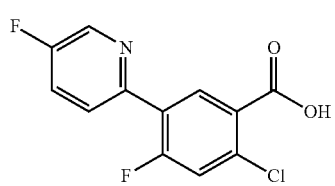 | Methyl 2-chloro-4-fluoro-5-(5-fluoropyridin-2-yl)benzoate (Preparation 41). | $^1$H NMR (400 MHz, DMSO-d$_6$): δ ppm 7.72 (d, 1H), 7.76-7.96 (m, 3H), 8.42 (d, 1H), 8.75 (d, 1H). |
| 25 | 2-chloro-4-methyl-5-(pyridin-2-yl)benzoic acid 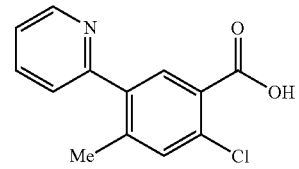 [SMILES: Cc1cc(Cl)c(C(=O)O)cc1-c1ccccn1] | Methyl 2-chloro-4-methyl-5-(pyridin-2-yl)benzoate (Preparation 42). | $^1$H NMR (400 MHz, MeOH-d$_4$): δ ppm 2.32 (s, 3H), 7.40-7.45 (m, 1H), 7.47 (s, 1H), 7.55 (d, 1H), 7.84 (s, 1H), 7.94 (m, 1H), 8.61 (d, 1H). |
| 26 | 2-chloro-4-methoxy-5-(pyridin-2-yl)benzoic acid 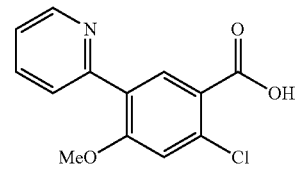 [SMILES: COc1cc(Cl)c(C(=O)O)cc1-c1ccccn1] | Methyl 2-chloro-4-methoxy-5-(pyridin-2-yl)benzoate (Preparation 35). | $^1$H NMR (400 MHz, DMSO-d$_6$): δ ppm 3.93 (s, 3H), 7.30 (s, 1H), 7.33-7.36 (m, 1H), 7.81-7.89 (m, 2H), 8.34 (s, 1H), 8.67 (d, 1H), 13.10 (br s, 1H). LCMS Rt = 1.84 minutes MS m/z 264 [M + H]$^+$ |
| 27 | 2,4-dichloro-5-(3-fluoropyridin-2-yl)benzoic acid 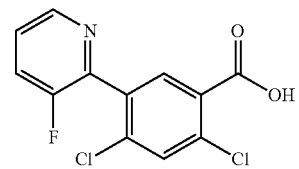 [SMILES: O=C(O)c1cc(-c2ccccn2)c(Cl)cc1Cl] | Methyl 2,4-dichloro-5-(3-fluoropyridin-2-yl)benzoate (Preparation 43). | $^1$H NMR (400 MHz, DMSO-d$_6$): δ ppm 7.58-7.65 (m, 1H), 7.86-7.94 (m, 3H), 8.53-8.58 (m, 1H), 13.66-13.77 (br s, 1H). |

-continued

| Prep Number | Name/Structure | Starting Material | Data |
|---|---|---|---|
| 28 | 2-chloro-5-(6-(2,2-difluoroethyl)pyridin-2-yl)benzoic acid | Methyl 2-chloro-5-(6-(2,2-difluoroethyl)pyridin-2-yl)benzoate (Preparation 32) | $^1$H NMR (400 MHz, CDCl$_3$): δ ppm 3.40 (m, 1H), 6.20-6.40 (t, 1H), 7.15 (m, 1H), 7.60-7.80 (m, 4H), 8.20 (m, 1H), 8.40 (s, 1H). MS m/z 298 [M + H]$^+$ |
| 29 | 2,4-dichloro-5-(6-(methoxymethyl)pyridin-2-yl)benzoic acid | Methyl 2,4-dichloro-5-(6-(methoxymethyl)pyridin-2-yl)benzoate (Preparation 37). | $^1$H NMR (400 MHz, CDCl$_3$): δ ppm 3.54 (s, 3H), 4.76 (s, 2H), 7.54 (d, 1H), 7.58-7.62 (m, 2H), 7.86 (t, 1H), 8.24 (s, 1H). |

Preparation 22A

Alternative Method for Synthesis of Preparation 22

2-chloro-4-fluoro-5-(pyridin-2-yl)benzoic acid

To a suspension of methyl 2-chloro-4-fluoro-5-(pyridin-2-yl)benzoate (Preparation 40A, 37.6 g, 142 mmol) in methanol (300 mL) was added aqueous sodium hydroxide solution (300 mL, 2 M). The reaction mixture was stirred at 40° C. for 2 hours. The mixture was filtered and the filtrate acidified to pH 6-7 with aqueous HCl solution (300 mL, 2 M). The resulting solid was collected by filtration, washed with water (20 mL) and dried under vacuum over potassium hydroxide at 50° C. for 48 h to afford the title compound as a white solid (36.2 g, 100%).

$^1$H NMR (300 MHz, DMSO-d$_6$): δ ppm 7.43 (m, 1H), 7.65-7.69 (d, 1H), 7.78-7.82 (d, 1H), 7.88-7.92 (m, 1H), 8.43-8.46 (d, 1H), 8.70-8.72 (d, 1H).

LCMS Rt=1.55 minutes, MS m/z 249.9 [M–H]$^-$, 251.9 [M+H]$^+$

LCMS acidic analytical conditions:

Column: XBridge C18 2.5 μm 2.1×20 mm IS

Mobile phase A: Water

Mobile phase B: Acetonitrile

Mobile phase D: 2% formic acid

Run time=3.0 minutes; Initial: 0% to 95% B with D over 2.1 minutes, hold to 2.4 minutes.

Detectors: UV and mass spectrometer

Preparation 27A

Alternative Method for Synthesis of Preparation 27

2,4-dichloro-5-(3-fluoropyridin-2-yl)benzoic acid

To the organic solution of methyl 2,4-dichloro-5-(3-fluoropyridin-2-yl)benzoate (from Preparation 43A, 1.95 mol) was added a solution of sodium hydroxide (234 g, 5.85 mol) in water (2.8 L) and the reaction stirred at room temperature for 1 hour. The mixture was concentrated in vacuo to remove organic solvents to a volume of approximately 5 L. The remaining aqueous phase was washed with ethyl acetate (3×2 L) and then acidified to pH2 with aqueous HCl (2 M). The resulting precipitate was collected by filtration and washed with water (2 L). The solid was ground to a fine powder and slurried with diethyl ether (2.5 L) and filtered to afford the title compound as an off-white solid (181 g).

$^1$H NMR (300 MHz, DMSO-d$_6$): δ ppm 7.59-7.61 (m, 1H), 7.87-7.90 (m, 3H), 8.53-8.55 (m, 1H).

UPLC Rt=0.49 minutes, MS m/z 284.12 [M–H]$^-$, 286.09 [M+H]$^+$

UPLC basic analytical conditions:

Column: XBridge BEH C18 2.5 μm 2.1×50 mm

Mobile phase A: 10 mM NH$_4$HCO$_3$ in water (pH 10)

Mobile phase B: Acetonitrile

Run time=1.2 minutes; Initial: 98%A, 2% B to 2% A and 98% B at 1.0 minutes, hold to 1.2 minutes.

Detectors: UV and mass spectrometer

Preparation 30

2,4-dichloro-5-(pyridin-2-yl)benzoic acid

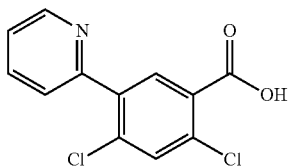

To a solution of methyl 2,4-dichloro-5-(pyridin-2-yl)benzoate (Preparation 44, 3.96 g, 14 mmol) in industrial methylated spirit (60 mL) was added a 2M solution of LiOH in water (35 mL, 70 mmol) and the reaction was stirred at room temperature for 3 hours. The reaction was acidified with 2M HCl (aq) (35 mL) to afford a white precipitate that was filtered and washed with industrial methylated spirit to afford the title compound (3.76 g, quant.).

$^1$H NMR (400 MHz, DMSO-$d_6$): δ ppm 7.40 (m, 1H), 7.75 (m, 1H), 7.80 (s, 1H), 7.85 (m, 1H), 7.95 (m, 1H), 8.70 (d, 1H).

LCMS Rt=2.40 minutes MS m/z 268 [M+H]$^+$

Preparation 31

Methyl 2-chloro-5-(6-(1,1-difluoroethyl)pyridin-2-yl)benzoate

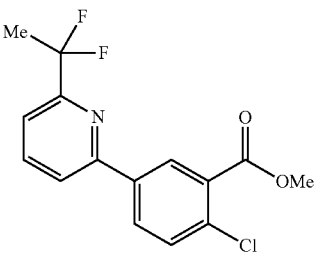 [SMILES: COC(=O)c1cc(-c2cccc(C(C)(F)F)n2)ccc1Cl]

To a solution of methyl 5-(6-acetylpyridin-2-yl)-2-chlorobenzoate (Preparation 38, 104 mg, 0.36 mmol) in DCM (1.8 mL) was added Deoxo-Fluor (264 uL, 1.43 mmol) dropwise. The reaction was stirred at room temperature for 18 hours. The reaction was quenched by the addition of saturated aqueous sodium bicarbonate solution (10 mL) and stirred for 15 minutes. The organic layer was collected and the aqueous layer extracted into DCM (2×5 mL). The organic extracts were combined, dried over sodium sulphate and concentrated in vacuo. The residue was purified using silica gel column chromatography eluting with 0-25% EtOAc in heptanes to afford the title compound.

$^1$H NMR (400 MHz, CDCl$_3$): δ ppm 2.10 (t, 3H), 4.00 (s, 3H), 7.58 (m, 1H), 7.62 (m, 1H), 7.82 (m, 1H), 7.90 (m, 1H), 8.15 (m, 1H), 8.45 (s, 1H).

Preparation 32

Methyl 2-chloro-5-(6-(2,2-difluoroethyl)pyridin-2-yl)benzoate

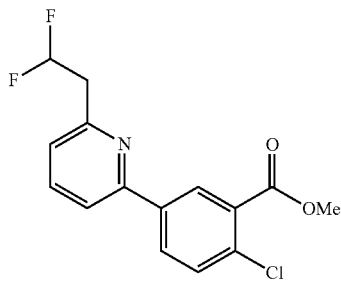 [SMILES: COC(=O)c1cc(-c2cccc(CC(F)F)n2)ccc1Cl]

To a solution of methyl 2-chloro-5-(6-(2,2-difluorovinyl)pyridin-2-yl)benzoate (Preparation 33, 105 mg, 0.34 mmol) in EtOAc (1 mL) was added 10% palladium on alumina (36 mg, 0.03 mmol) and stirred at room temperature under 15 psi of hydrogen for 2 hours. The reaction was filtered and concentrated in vacuo. The residue was purified using silica gel column chromatography eluting with 0-20% EtOAc in heptanes to afford the title compound.

$^1$H NMR (400 MHz, CDCl$_3$): δ ppm 3.40 (m, 1H), 4.00 (s, 3H), 6.20-6.40 (t, 1H), 7.10 (m, 1H), 7.60-7.80 (m, 4H), 8.10 (m, 1H), 8.50 (m, 1H).

Preparation 33

Methyl 2-chloro-5-(6-(2,2-difluorovinyl)pyridin-2-yl)benzoate

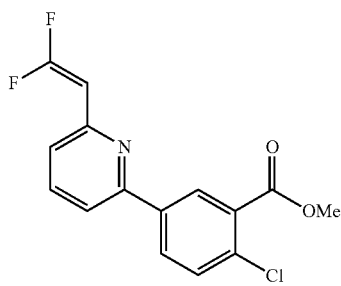 [SMILES: COC(=O)c1cc(-c2cccc(C=C(F)F)n2)ccc1Cl]

To a solution of methyl 2-chloro-5-(6-formylpyridin-2-yl)benzoate (Preparation 39, 302 mg, 1.10 mmol) in DMF (5.5 mL) was added sodium chlorodifluoroacetate (250 mg, 1.64 mmol) and triphenylphosphine (435 mg, 1.64 mmol) and heated to 120° C. for 40 minutes followed by cooling to room temperature for 2 hours. The reaction was concentrated in vacuo and partitioned between water and EtOAc. The aqueous layer was washed with EtOAc (2×10 mL) and the organic layers combined, washed with brine, dried over sodium sulphate and concentrated in vacuo. The residue was purified using silica gel column chromatography eluting with 0-20% EtOAc in heptanes to afford the title compound.

$^1$H NMR (400 MHz, CDCl$_3$): δ ppm 4.00 (s, 3H), 5.20-5.40 (m, 1H), 7.40 (m, 1H), 7.50-7.70 (m, 2H), 7.70 (m, 1H), 8.30 (m, 1H), 8.50 (s, 1H).

Preparation 34

Methyl 2,4-dichloro-5-(5-fluoropyridin-2-yl)benzoate

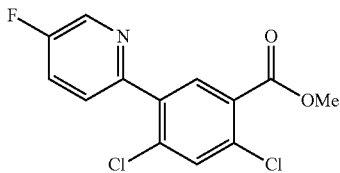

To the solution of methyl 2,4-dichloro-5-(4,4,5,5-tetramethyl-1,3,2-dioxaborolan-2-yl)benzoate in anhydrous THF (Preparation 45, 10 mL, 1.61 g, 4.88 mmol) was added 2-bromo-5-fluoropyridine (856 mg, 4.88 mmol), sodium carbonate (1.55 g, 14.59 mmol) and water (2 mL). The reaction was degassed with nitrogen for 15 minutes followed by the addition of Pd(PPh$_3$)$_4$ (280 mg, 0.244 mmol) with further degassing for 5 minutes. The reaction was heated to reflux under a nitrogen atmosphere for 2 hours. The reaction was concentrated in vacuo and the residue partitioned between EtOAc (35 mL) and water (35 mL). The organic layer was dried over magnesium sulphate and concentrated in vacuo. The residue was purified by silica gel column chromatography eluting with 5-20% EtOAc in heptanes to afford the title compound as a white solid (1 g, 67%).

$^1$H NMR (400 MHz, CDCl$_3$): δ ppm 3.91-3.94 (s, 3H), 7.47-7.54 (m, 1H), 7.61-7.63 (s, 1H), 7.66-7.71 (m, 1H), 8.13-8.15 (s, 1H), 8.57-8.60 (d, 1H).

Preparation 35

Methyl 2-chloro-4-methoxy-5-(pyridin-2-yl)benzoate

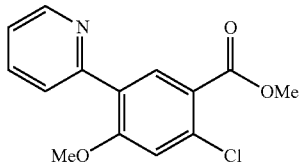 [SMILES: COC(=O)c1cc(-c2ccccn2)c(OC)cc1Cl]

To a solution of methyl 2-chloro-4-methoxy-5-(4,4,5,5-tetramethyl-1,3,2-dioxaborolan-2-yl)benzoate in dioxane (Preparation 47, 935 mg, 2.86 mmol) was added 2M Na$_2$CO$_3$ (4.30 mL, 8.58 mmol) and stirred for 15 minutes at room temperature. 2-bromopyridine (542 mg, 3.43 mmol) was added and the reaction was purged with nitrogen for 15 minutes. Pd(dppf)Cl$_2$ (117 mg, 0.14 mmol) was added and the reaction heated at 110° C. for 2 hours. The reaction was cooled to room temperature, filtered through arbocel and washed with EtOAc (50 mL). The filtrate was washed with brine (50 mL) and the aqueous layer was re-extracted with EtOAc (50 mL). The combined organic layers were dried over magnesium sulphate and concentrated in vacuo. The residue was purified using silica gel column chromatography eluting with 10-20% EtOAc in heptanes to afford the title compound (282 mg, 35% over 2 steps).

$^1$H NMR (400 MHz, CDCl$_3$): δ ppm 3.90 (s, 3H), 3.92 (s, 3H), 7.06 (s, 1H), 7.23-7.26 (m, 1H), 7.71 (m, 1H), 7.79 (m, 1H), 8.42 (s, 1H), 8.70-8.72 (m, 1H).

LCMS Rt=2.70 minutes MS m/z 278 [M+H]$^+$

Preparation 36

Methyl 2-chloro-4-fluoro-5-(3-fluoropyridin-2-yl)benzoate

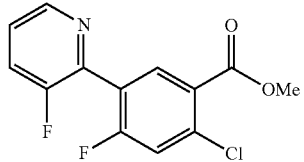 [SMILES: COC(=O)c1cc(-c2ncccc2F)c(F)cc1Cl]

To a solution of methyl 2-chloro-4-fluoro-5-(4,4,5,5-tetramethyl-1,3,2-dioxaborolan-2-yl)benzoate (1.67 g, 5.30 mmol) in THF (10 mL) was added 2-bromo-3-fluoropyridine (933 mg, 5.30 mmol), tri(o-tolyl)phosphine (67 mg, 0.22 mmol), Na$_2$CO$_3$ (2.25 g, 21.2 mmol) and water (1.6 mL) and the reaction was purged with nitrogen for 15 minutes. Bis (dibenzylidene acetone)palladium (63 mg, 0.11 mmol) was added with further purging with nitrogen for 10 minutes before heating at 80° C. for 1 hour. The reaction was cooled to room temperature and filtered through a pad of arbocel, washing through with EtOAc (50 mL). The filtrate was washed with water (50 mL), dried over magnesium sulfate and concentrated in vacuo. The residue was purified using silica gel column chromatography eluting with 10-20% EtOAc in heptanes to afford the title compound (240 mg, 21%).

$^1$H NMR (400 MHz, CDCl$_3$): δ ppm 3.93 (s, 3H), 7.33 (d, 1H), 7.38-7.42 (m, 1H), 7.51-7.56 (m, 1H), 8.23 (d, 1H), 8.56 (m, 1H).

The following Preparations were prepared according to the method described for Preparation 34 or 35 or 36 using the appropriate boronic ester and halopyridine as described below.

| Prep Number | Name/Structure | Starting Materials | Data |
|---|---|---|---|
| 37 | Methyl 2,4-dichloro-5-(6-(methoxymethyl)pyridin-2-yl)benzoate | Methyl 2,4-dichloro-5-(4,4,5,5-tetramethyl-1,3,2-dioxaborolan-2-yl)benzoate in anhydrous THF (Preparation 45) and 2-bromo-6-(methoxymethyl)pyridine. | $^1$H NMR (400 MHz, CDCl$_3$): δ ppm 3.52 (s, 3H), 3.94 (s, 3H), 4.68 (s, 2H), 7.48 (d, 1H), 7.54 (d, 1H), 7.60 (s, 1H), 7.82 (t, 1H), 8.14 (s, 1H). |

| Prep Number | Name/Structure | Starting Materials | Data |
|---|---|---|---|
| 38 | Methyl 5-(6-acetylpyridin-2-yl)-2-chlorobenzoate | Methyl 2-chloro-5-(4,4,5,5-tetramethyl-1,3,2-dioxaborolan-2-yl)benzoate and 1-(6-bromopyridin-2-yl)ethan-1-one. | $^1$H NMR (400 MHz, CDCl$_3$): δ ppm 2.80 (s, 3H), 4.00 (s, 3H), 7.60 (m, 1H), 7.95 (m, 2H), 8.05 (m, 1H), 8.20 (m, 1H), 8.50 (s, 1H). |
| 39 | Methyl 2-chloro-5-(6-formylpyridin-2-yl)benzoate | Methyl 2-chloro-5-(4,4,5,5-tetramethyl-1,3,2-dioxaborolan-2-yl)benzoate and 6-bromopicolinaldehyde. | $^1$H NMR (400 MHz, CDCl$_3$): δ ppm 4.00 (s, 3H), 7.90-8.00 (m, 3H), 8.20 (m, 1H), 8.60 (s, 1H), 10.20 (s, 1H). |
| 40 | Methyl 2-chloro-4-fluoro-5-(pyridin-2-yl)benzoate | Methyl 2-chloro-4-fluoro-5-(4,4,5,5-tetramethyl-1,3,2-dioxaborolan-2-yl)benzoate. | $^1$H NMR (400 MHz, CDCl$_3$): δ ppm 3.94 (s, 3H), 7.33 (t, 1H), 7.79 (d, 2H), 8.62 (d, 1H), 8.74 (d, 1H). |
| 41 | Methyl 2-chloro-4-fluoro-5-(5-fluoropyridin-2-yl)benzoate | Methyl 2-chloro-4-fluoro-5-(4,4,5,5-tetramethyl-1,3,2-dioxaborolan-2-yl)benzoate and 2-bromo-5-fluoropyridine. | $^1$H NMR (400 MHz, CDCl$_3$): δ ppm 3.95 (s, 3H), 7.31 (d, 1H), 7.50 (m, 1H), 7.79-7.84 (m, 1H), 8.57-8.61 (m, 2H). |
| 42 | Methyl 2-chloro-4-methyl-5-(pyridin-2-yl)benzoate | 2-chloro-4-methyl-5-(4,4,5,5-tetramethyl-1,3,2-dioxaborolan-2-yl)benzoate (Preparation 46). | $^1$H NMR (400 MHz, MeOH-d$_4$): δ ppm 2.32 (s, 3H), 3.88 (s, 3H), 7.49 (dd, 1H), 7.52 (s, 1H), 7.54 (d, 1H), 7.83 (s, 1H), 7.94 (m, 1H), 8.61 (d, 1H). |

-continued

| Prep Number | Name/Structure | Starting Materials | Data |
|---|---|---|---|
| 43 | Methyl 2,4-dichloro-5-(3-fluoropyridin-2-yl)benzoate | Methyl 2,4-dichloro-5-(4,4,5,5-tetramethyl-1,3,2-dioxaborolan-2-yl)benzoate and 2-bromo-3-fluoropyridine. | $^1$H NMR (400 MHz, CDCl$_3$): δ ppm 3.90-3.93 (s, 3H), 7.38-7.45 (m, 1H), 7.50-7.53 (m, 1H), 7.62-7.65 (s, 1H), 8.01-8.04 (s, 1H), 8.53-8.57 (m, 1H). |

Preparation 40A

Alternative Method for Synthesis of Preparation 40

Methyl 2-chloro-4-fluoro-5-(pyridin-2-yl)benzoate

To a solution of methyl 2-chloro-4-fluoro-5-(4,4,5,5-tetramethyl-1,3,2-dioxaborolan-2-yl)benzoate (212 mmol) in THF (400 mL), was added 2-bromopyridine (33.4 g, 211 mmol), potassium carbonate (117 g, 848 mmol) and water (64 mL). The mixture was degassed with argon for 30 minutes. To this mixture was added tetrakis(triphenylphosphine)palladium (12.2 g, 10.6 mmol) and the mixture heated at reflux for 1.5 h. The mixture was cooled to room temperature and filtered through Celite, washing with EtOAc (1.2 L) and water (800 mL). The filtrate was diluted with saturated aqueous brine solution (200 mL) and the aqueous layer separated and extracted with EtOAc (600 mL). The combined organic layers were dried (MgSO$_4$) and concentrated in vacuo. The residue was purified by column chromatography over silica gel, eluting with EtOAc:hexane (3:17 to 1:4) and concentrated in vacuo to a slurry, which was diluted with heptane (100 mL) and cooled to 0° C. The solid was collected by filtration to afford the title compound (37.6 g, 67%).

$^1$H NMR (300 MHz, CDCl$_3$): δ ppm 3.94 (s, 3H), 7.29-7.33 (m, 2H), 7.78-7.79 (m, 2H), 8.61-8.63 (d, 1H), 8.73-8.75 (m, 1H).

UPLC Rt=0.83 minutes, MS m/z 266.1 [M+H]$^+$

Preparation 43A

Alternative Method for Synthesis of Preparation 43

Methyl 2,4-dichloro-5-(3-fluoropyridin-2-yl)benzoate

To a solution of methyl 2,4-dichloro-5-(4,4,5,5-tetramethyl-1,3,2-dioxaborolan-2-yl)benzoate (1.95 mol) in THF (4 L), was added portionwise a solution of potassium carbonate (807 g, 5.85 mol) in water (1.6 L), followed by 2-bromo-3-fluoropyridine (361 g, 2.05 mol) and the mixture degassed with argon. To this mixture was added tetrakis(triphenylphosphine)palladium (56.4 g, 48.8 mmol) and the mixture heated at reflux for 5 h. The mixture was cooled to room temperature and the organic layer separated and washed with brine (1 L). This organic solution containing the title compound was used directly in the next reaction (Preparation 27A).

Preparation 44

Methyl 2,4-dichloro-5-(pyridin-2-yl)benzoate

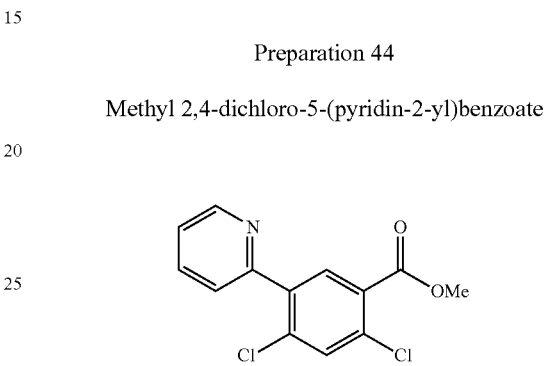

To a solution of methyl 2,4-dichloro-5-(4,4,5,5-tetramethyl-1,3,2-dioxaborolan-2-yl)benzoate (Preparation 45, 5 g, 15 mmol) in dioxane (30 mL) and water (10 mL) was added 2-bromopyridine (1.73 mL, 18 mmol), tetrakis(triphenylphosphine)palladium (0) (1.75 g, 1.51 mmol) and potassium carbonate (4.18 g, 30 mmol). The reaction was heated to 110° C. The reaction was cooled, extracted into EtOAc and separated. The organic layer was washed with brine, dried over magnesium sulphate and concentrated in vacuo. The residue was purified using silica gel column chromatography eluting with 10-50% EtOAc in heptanes followed by trituration with TBME to afford the title compound (3.96 g, 93%).

$^1$H NMR (400 MHz, CDCl$_3$): δ ppm 3.90 (s, 3H), 7.29-7.33 (m, 1H), 7.60 (s, 1H), 7.66 (d, 1H), 7.75-7.79 (m, 1H), 8.15 (s, 1H), 8.71-8.73 (m, 1H).

LCMS Rt=3.17 minutes MS m/z 282 [M+H]$^+$

Preparation 45

Methyl 2,4-dichloro-5-(4,4,5,5-tetramethyl-1,3,2-dioxaborolan-2-yl)benzoate

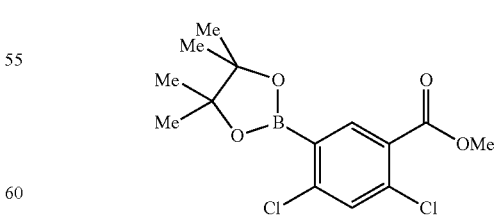

Methyl 2,4-dichlorobenzoate (2 g, 9.75 mmol), bis(pinacolato)diboron (1.89 g, 7.3 mmol) and 4,4'-di-tert-butyl-2,2'-bipyridine (105 mg, 0.39 mmol) were dissolved in anhydrous tetrahydrofuran (20 mL) and degassed with nitrogen for 15 minutes. [Ir(COD)OMe]$_2$ (129 mg, 0.2 mmol) was added, the reaction degassed for a further 5 minutes and then heated to reflux under an atmosphere of nitrogen for 3 hours. The solution was used crude with an assumed quantitative yield in the next step.

Preparation 46

Methyl 2-chloro-4-methyl-5-(4,4,5,5-tetramethyl-1,3,2-dioxaborolan-2-yl)benzoate

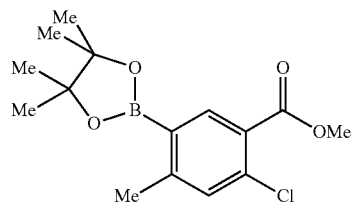 [SMILES: COC(=O)c1cc(B2OC(C)(C)C(C)(C)O2)c(C)cc1Cl]

A suspension of methyl 2-chloro-5-iodo-4-methylbenzoate (Preparation 48, 1.70 g, 5.47 mmol), bis(pinacolato)diboron (2.80 g, 11.0 mmol), potassium acetate (1.60 g, 16.4 mmol) and [1,1'-bis(diphenylphosphino)ferrocene]dichloropalladium (II) (0.40 g, 0.55 mmol) in 1,4 dioxane (30 mL) was heated at 110° C. for 18 hours. The reaction was concentrated in vacuo, slurried in EtOAc (200 mL) and filtered. The filtrate was washed with water (200 mL), dried over magnesium sulfate and concentrated in vacuo. The residue was purified using silica gel column chromatography eluting with 0-10% EtOAc in heptanes to afford the title compound (1.7 g, quantitative).

$^1$H NMR (400 MHz, CDCl$_3$): δ ppm 1.25 (s, 12H), 1.57 (s, 3H), 3.90 (s, 3H), 7.25 (s, 1H), 8.21 (s, 1H).

Preparation 47

Methyl 2-chloro-4-methoxy-5-(4,4,5,5-tetramethyl-1,3,2-dioxaborolan-2-yl)benzoate

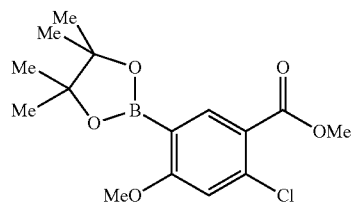 [SMILES: COC(=O)c1cc(B2OC(C)(C)C(C)(C)O2)c(OC)cc1Cl]

The title compound was prepared according to the method described for Preparation 46 using methyl 5-bromo-2-chloro-4-methoxybenzoate (Preparation 50). The crude product was used directly in the next step as a solution in dioxane.

Preparation 48

Methyl 2-chloro-5-iodo-4-methylbenzoate

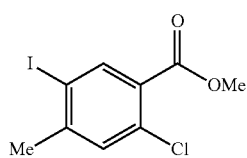 [SMILES: COC(=O)c1cc(I)c(C)cc1Cl]

To a solution of 2-chloro-5-iodo-4-methylbenzoic acid (Preparation 49, 2.50 g, 8.43 mmol) in methanol (50 mL) was added concentrated sulfuric acid (1.2 mL) and the reaction was heated at 60° C. for 18 hours. The reaction was cooled, concentrated in vacuo, diluted with water and basified with potassium carbonate until pH=9. The aqueous solution was extracted with EtOAc (3×100 mL), the organic layers combined, washed with water (100 mL), brine (100 mL), dried over magnesium sulphate and concentrated in vacuo to afford the title compound (2.3 g, 88%).

$^1$H NMR (400 MHz, CDCl$_3$): δ ppm 2.47 (s, 3H), 3.91 (s, 3H), 7.31 (s, 1H), 8.27 (s, 1H).

Preparation 49

2-chloro-5-iodo-4-methylbenzoic acid

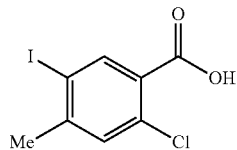 [SMILES: Cc1cc(Cl)c(C(=O)O)cc1I]

To a solution of 4-methyl-2-chlorobenzoic acid 1 (2.50 g, 14.7 mmol) and (trifluoromethyl) sulfonic acid (65.0 mL, 73.3 mmol) in dichloromethane (20 mL) at 0° C. was added N-iodosuccinimide (3.50 g, 15.4 mmol) portion wise over a period of 10 minutes. The mixture was stirred at room temperature for 30 minutes, quenched with ice, then water (60 mL) and extracted into EtOAc (100 mL). The layers were separated and the aqueous layer was washed with EtOAc (2×50 mL). The combined organic layers were washed with 10% aqueous sodium sulfite solution (60 mL), dried over magnesium sulphate and concentrated in vacuo to afford the title compound (2.5 g, 57%).

$^1$H NMR (400 MHz, MeOH-d$_4$): δ ppm 2.42 (s, 3H), 7.41 (s, 1H), 8.24 (s, 1H).

Preparation 50

Methyl 5-bromo-2-chloro-4-methoxybenzoate

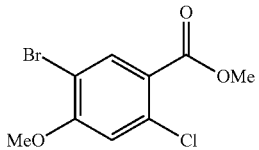 [SMILES: COC(=O)c1cc(Br)c(OC)cc1Cl]

A solution of methyl 5-bromo-2-chloro-4-hydroxybenzoate (Preparation 51, 2.5 g, 9.42 mmol) and lithium hydroxide monohydrate (395 mg, 9.42 mmol) in THF (10 mL) was stirred at room temperature for 10 minutes. Dimethyl sulphate (0.45 mL, 4.71 mmol) was added dropwise and left to stir at room temperature for 45 minutes before heating to 75° C. for 3 hours. Additional dimethyl sulphate (0.45 mL, 4.71 mmol) was added dropwise and the reaction stirred at 75° C. for 16 hours. The reaction was cooled to room temperature, diluted with EtOAc (20 mL), washed with brine (30 mL), dried over magnesium sulphate and concentrated in vacuo. The residue was purified by silica gel column chromatography eluting from 5-10% EtOAc in heptanes to afford the title compound as a white solid (1.70 g, 65%).

¹H NMR (400 MHz, DMSO-d₆): δ ppm 3.81 (s, 3H), 3.94 (s, 3H), 7.29 (s, 1H), 8.04 (s, 1H).

Preparation 51

Methyl 5-bromo-2-chloro-4-hydroxybenzoate

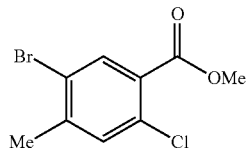 [SMILES: COC(=O)c1cc(Br)c(C)cc1Cl]

A solution of methyl 2-chloro-4-hydroxybenzoate (5.0 g, 26.8 mmol) in MeCN (100 mL) was cooled to –30° C. Triflic acid (2.60 mL, 29.48 mmol) was added followed by N-bromosuccinimide (5.25 g, 29.48 mmol) and the reaction was warmed to room temperature and stirred for 1.5 hours. The reaction was quenched by the addition of saturated aqueous Na₂CO₃ solution (50 mL). The solution was extracted with EtOAc (2×100 mL), the combined organic layers were combined, dried over magnesium sulphate and concentrated in vacuo. The residue was purified by silica gel column chromatography eluting with 20-40% EtOAc in heptanes to afford the title compound as a white solid (2.60 g, 37%).

¹H NMR (400 MHz, DMSO-d₆): δ ppm 3.78 (s, 3H), 7.03 (s, 1H), 8.00 (s, 1H), 11.60 (br s, 1H).

MS m/z 264 [M–H]⁻

Preparation 52

2-chloro-3-fluoro-6-(methoxymethyl)pyridine

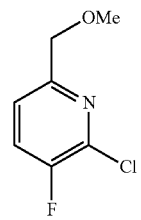

To a suspension of sodium hydride (0.48 g, 12 mmol, 60% dispersion in mineral oil) in THF (15 mL) at 5° C. under nitrogen was added (6-chloro-5-fluoropyridin-2-yl)methanol (1.57 g, 9.28 mmol) suspended in THF (20 mL). The resulting suspension was stirred at this temperature for 30 minutes and then iodomethane (0.75 mL, 12 mmol) was added slowly. The reaction was warmed to room temperature over 48 hours. Further iodomethane was added (173 µL, 2.8 mmol) and stirring at room temperature was continued for 4 hours followed by the addition of further sodium hydride (110 mg, 2.75 mmol) at 5° C. The reaction was continued stirring for 24 hours before quenching with water (10 mL) and saturated aqueous ammonium chloride solution (20 mL) until pH=7. The solution was extracted with diethyl ether (3×50 mL). The organic layers were dried over sodium sulphate, and concentrated in vacuo. The residue was purified using silica gel column chromatography eluting with 20-50% DCM in pentane to afford the title compound (600 mg, 37% yield).

¹H NMR (400 MHz, CDCl₃): δ ppm 3.45 (s, 3H), 4.50 (s, 2H), 7.38-7.41 (m, 1H), 7.42-7.50 (m, 1H).

Preparation 53

5-amino-1-phenyl-1H-pyrazole-3-carbonitrile

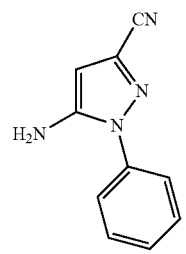 [SMILES: N#Cc1cc(N)n(-c2ccccc2)n1]

To a solution of ethyl 2-(phenyldiazenyl)succinonitrile (Preparation 55, 2.84 g, 15.43 mmol) in dichloromethane (103 mL) was added a 10% aqueous solution of potassium carbonate (77 mL, 55.71 mmol). The reaction was stirred at room temperature for 18 hours. The organic layer was separated dried over magnesium sulphate and concentrated in vacuo. The residue was purified using silica gel column chromatography eluting with 0-3% MeOH in DCM to afford the title compound (1.24 g, 44%).

¹H NMR (400 MHz, CDCl₃): δ ppm 3.96 (br s, 2H), 6.00 (s, 1H), 7.45 (m, 1H), 7.56 (m, 4H).

MS m/z 185 [M+H]⁺

Preparation 54

Ethyl 5-amino-1-(3-(benzyloxy)phenyl)-1H-pyrazole-3-carboxylate

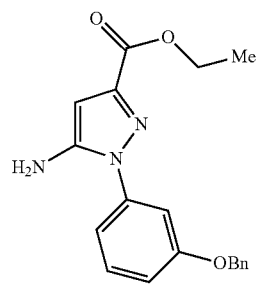 [SMILES: CCOC(=O)c1cc(N)n(-c2cccc(OCc3ccccc3)c2)n1]

To a suspension of potassium (Z)-1-cyano-3-ethoxy-3-oxoprop-1-en-2-olate (3.73 g, 20.82 mmol) in ethanol (100 mL) was added (3-(benzyloxy)phenyl)hydrazine hydrochloride (Preparation 61, 5.22 g, 20.82 mmol) and the reaction was heated at reflux for 24 hours. The reaction was cooled to room temperature, the solid was filtered and the filtrate was concentrated in vacuo. The residue was purified using silica gel column chromatography eluting with 20-40% EtOAc in heptanes to afford the title compound (4.76 g, 68%).

¹H NMR (400 MHz, DMSO-d₆): δ ppm 1.26 (t, 3H), 4.22 (d, 2H), 5.16 (s, 2H), 5.55 (br s, 2H), 5.87 (s, 1H), 7.03-7.06 (m, 1H), 7.15-7.17 (m, 1H), 7.20-7.21 (m, 1H), 7.30-7.46 (m, 6H).

Preparation 55

2-(phenyldiazenyl)succinonitrile

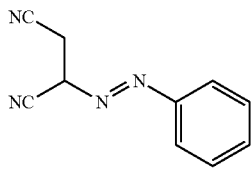 [SMILES: N#CCC(C#N)/N=N/c1ccccc1]

A solution of ethyl 2,3-dicyanopropanoate (1.58 g, 10.38 mmol) in methanol (52 mL) and pyridine (2.52 mL, 31.14 mmol) was cooled to 10° C. in an ice bath. Benzenediazonium tetrafluoroborate was added portion-wise over 20 minutes at 10° C. and the reaction stirred at room temperature for 18 hours. The reaction was concentrated in vacuo and partitioned between DCM and water. The organic layer was dried over magnesium sulphate and concentrated in vacuo to afford the title compound (2.8 g, 28%). The crude product was taken on directly to the next step.

Preparation 56

2,3-dichloro-6-(methoxymethyl)pyridine

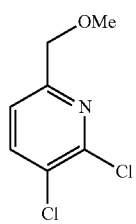

3-chloroperbenzoic acid (80%, 4.83 g, 13.96 mmol) was added portion-wise to a solution of 5-chloro-2-(methoxymethyl)pyridine (Preparation 57, 2 g, 12.69 mmol) in DCM (50 mL) at 0° C. The reaction was stirred for 18 hours at room temperature. The reaction mixture was quenched with 2M aqueous sodium hydroxide (25 mL) and brine (25 mL) and stirred vigorously. The organic layer was collected, washed with 2M aqueous sodium hydroxide (2×10 mL), water (10 mL), dried over sodium sulfate and concentrated in vacuo. A portion of the residue (100 mg, 0.576 mmol) was stirred in phosphoryl chloride (2 mL) at 80° C. for 2 hours. The reaction was concentrated in vacuo and vigorously stirred in DCM (10 mL) and saturated aqueous sodium bicarbonate solution (10 mL) for 5 hours. The organic layer was collected dried over sodium sulphate and concentrated in vacuo. The residue was purified using silica gel column chromatography eluting with DCM to afford the title compound (38 mg, 34%).

$^1$H NMR (400 MHz, CDCl$_3$): δ ppm 3.47 (s, 3H), 4.53 (s, 2H), 7.35 (d, 1H), 7.77 (d, 1H).

Preparation 57

5-chloro-2-(methoxymethyl)pyridine

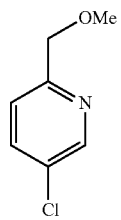

Sodium hydride (0.61 g, 60% in mineral oil, 15.32 mmol) was added to a solution of (5-chloropyridin-2-yl)methanol (2 g, 13.93 mmol) in THF (50 mL) and stirred at room temperature until no further gas evolution was observed. Iodomethane (0.95 mL, 15.32 mmol) was injected slowly and the reaction was allowed to stir at room temperature for 18 hours. The reaction was concentrated in vacuo, acidified with 2N HCl in water (25 mL) and extracted with EtOAc (2×20 mL). The aqueous layer was collected, basified with potassium hydroxide and extracted with DCM (3×20 mL). The organic layers were combined, washed with water, dried over sodium sulfate and concentrated in vacuo to afford the title compound (2 g, 91%).

$^1$H NMR (400 MHz, CDCl$_3$): δ ppm 3.47 (s, 3H), 4.55 (s, 2H), 7.38 (d, 1H), 7.67 (dd, 1H), 8.51 (d, 1H).

Preparation 58

2-bromo-6-(difluoromethoxy)pyridine

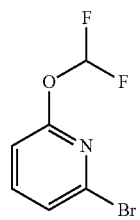 [SMILES: FC(F)Oc1cccc(Br)n1]

To a solution of 2-bromo-6-hydroxypyridine (535 mg, 3.07 mmol) in anhydrous acetonitrile (10 mL) was added sodium sulphate (44 mg, 0.31 mmol) and a solution of 2,2-difluoro-2-(fluorosulfonyl)acetic acid (0.35 mL, 3.38 mmol) in acetonitrile (2 mL). The reaction was stirred at room temperature for 18 hours. Saturated aqueous NaHCO$_3$ solution (10 mL) was added and the solution was concentrated in vacuo. The residue was dissolved in diethyl ether (30 mL), washed with water (20 mL), brine (20 mL), saturated aqueous NaHCO$_3$ solution (20 mL), dried over MgSO$_4$ and concentrated in vacuo. The residue was purified using silica gel column chromatography eluting with 70-100% DCM in heptanes to afford the title compound (347 mg, 50%).

$^1$H NMR (400 MHz, CDCl$_3$): δ ppm 6.87 (dd, 1H), 7.29 (dd, 1H), 7.44 (t, 1H), 7.58 (t, 1H).

Preparation 59

2-(5,6-dichloropyridin-2-yl)acetonitrile

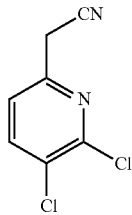 [SMILES: N#CCc1ccc(Cl)c(Cl)n1]

To a solution of 6-(bromomethyl)-2,3-dichloropyridine (Preparation 60, 2.90 g, 3.13 mmol) in IMS (20 mL) and water (15 mL) was added NaCN (552 mg, 11.3 mmol). The reaction was heated to 100° C. for 1 hour before cooling to room temperature and quenching with saturated aqueous NaHCO$_3$ solution (50 mL). The mixture was extracted with DCM (3×50 mL) and the organic layers combined, dried over MgSO$_4$ and concentrated in vacuo. The residue was purified using reverse phase column chromatography eluting with 0-100% MeCN in water with 0.1% formic acid to afford the title compound (341 mg, 15% over two steps).

$^1$H NMR (400 MHz, CDCl$_3$): δ ppm 3.80 (s, 2H), 7.30 (d, 1H), 7.70 (d, 1H).

Preparation 60

6-(bromomethyl)-2,3-dichloropyridine

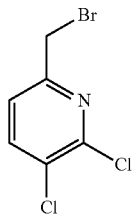

To a solution of 2,3-dichloro-6-methylpyridine (2 g, 12.3 mmol) in carbon tetrachloride (40 mL) was added NBS (2.64 g, 14.8 mmol) followed by AIBN (40 mg, 0.24 mmol). The reaction heated to 80° C. under nitrogen for 3.5 hours. The reaction was cooled and concentrated in vacuo. The residue was sonicated in heptanes and filtered. The filtrate was eluted through a pad of silica using 10% TBME in heptanes to afford the title compound (2.90 g). The crude material was taken on directly to the next step.

Preparation 61

(3-(benzyloxy)phenyl)hydrazine hydrochloride

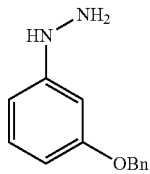 [SMILES: NNc1cccc(OCc2ccccc2)c1]

3-(benzyloxy)aniline (5 g, 25.09 mmol) was added dropwise to 6M HCl (100 mL) at 4° C. A solution of sodium nitrite (3.46 g, 50.19 mmol) in water (50 mL) was added dropwise over 10 minutes and the reaction was stirred for 1 hour. A solution of tin (II) chloride (17.53 g, 77.7 mmol) in 6M HCl (150 mL) was added dropwise over 20 minutes, maintaining the internal temperature below 7° C. The suspension was stirred for 2 hours before neutralising then basifying the reaction to pH>12 using sodium hydroxide. The aqueous layer was extracted with diethyl ether (3×150 mL), the combined organic layers were dried over sodium sulfate and concentrated in vacuo. The yellow oil was dissolved in HCl in methanol and concentrated in vacuo. The resulting solid was triturated with diethylether, filtered and dried in vacuo to afford the title compound as purple solid (5.22 g, 83%).

$^1$H NMR (400 MHz, DMSO-d$_6$): δ ppm 5.05 (s, 2H), 6.53-6.60 (m, 2H), 6.65-6.66 (m, 1H), 7.16 (t, 1H), 7.30-7.43 (m, 5H), 10.15 (br s, 3H).

Preparation 62

Racemic-1-(1H-1,2,3-triazol-4-yl)ethanamine hydrochloride

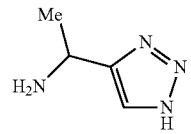

Racemic-N-(1-(1H-1,2,3-triazol-4-yl)ethyl)-2-methylpropane-2-sulfinamide (Preparation 63, 1.09 g, 5.04 mmol) was dissolved in methanol (10 mL). 4M HCl in MeOH (10 mL) was added and the mixture was stirred at room temperature for 5 hours. The reaction was concentrated in vacuo and triturated with TBME (50 mL), diethyl ether (20 mL) and finally with acetonitrile (20 mL). The remaining gum was azeotroped with methanol (10 mL) followed by toluene (10 mL) to afford the title compound as a pale yellow gum (780 mg, 100%).

$^1$H NMR (400 MHz, MeOH-d$_4$): δ ppm 1.68-1.70 (d, 3H), 4.67-4.72 (q, 1H), 4.95 (br s, 3H), 7.91 (s, 1H).

Preparation 63

Racemic-N-(1-(1H-1,2,3-triazol-4-yl)ethyl)-2-methylpropane-2-sulfinamide

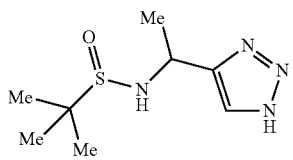 [SMILES: CC(NS(=O)C(C)(C)C)c1c[nH]nn1]

N-((1H-1,2,3-triazol-4-yl)methylene)-2-methylpropane-2-sulfinamide (Preparation 64, 2 g, 10 mmol) was dissolved in THF (80 mL) under nitrogen and cooled to −70° C. A solution of methylmagnesium bromide in diethyl ether (3.5M, 7.5 mL, 22.5 mmol) was added dropwise over a period of 15 minutes, keeping the reaction temperature below −60° C. The reaction was stirred with cooling for a further 40 minutes then the cooling bath was removed and the mixture was stirred at room temperature for 18 hours. The reaction was quenched by the addition of saturated aqueous sodium chloride solution (0.5 mL) followed by 2M (aq) HCl (12 mL).

The THF was removed in vacuo and the residue acidifed to pH=4 with 2M (aq) HCl. The solution was extracted with EtOAc (110 mL). The organic layer was dried over anhydrous sodium sulphate and concentrated in vacuo. The residue was purified by silica gel column chromatography eluting with 40-100% EtOAc in heptanes to afford the title compound as a 4:1 mixture of diastereomers (1.09 g, 50%).

Major isomer: $^1$H NMR (400 MHz, CDCl$_3$): δ ppm 1.27 (s, 9H), 1.59-1.60 (d, 3H), 4.23 (br s, 1H), 4.64-4.71 (m, 1H), 7.51 (s, 1H).

Minor isomer: $^1$H NMR (400 MHz, CDCl$_3$): δ ppm 1.23 (s, 9H), 1.62-1.64 (d, 3H), 3.75 (br s, 1H), 4.73-4.79 (m, 1H), 7.56 (s, 1H).

Preparation 64

N-((1H-1,2,3-triazol-4-yl)methylene)-2-methylpropane-2-sulfinamide

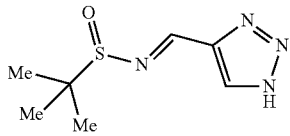 [SMILES: CC(C)(C)S(=O)/N=C/c1c[nH]nn1]

1H-1,2,3-triazole-4-carbaldehyde (1 g, 10.3 mmol) and 2-methylpropane-2-sulfinamide (1.25 g, 10.3 mmol) were dissolved in tetrahydrofuran (20 mL). Titanium tetraisopropoxide (3.1 mL, 10.5 mmol) was added and the reaction heated at reflux for 8 hours. After cooling to room temperature, the reaction was quenched by adding saturated aqueous sodium chloride solution (5 mL) followed by dilution with tetrahydrofuran (80 mL) and stirred for 30 minutes. The mixture was filtered through a pad of Arbocel and the filtrate concentrated in vacuo, azeotroping with THF to afford the title compound (2.02 g, 98%).

$^1$H NMR (400 MHz, MeOH-d$_4$): δ ppm 1.26 (s, 9H), 8.38 (s, 1H), 8.70 (s, 1H).

Preparation 65

2-(1-((2-(trimethylsilyl)ethoxy)methyl)-1H-1,2,3-triazol-4-yl)ethanamine and 2-(2-((2-(trimethylsilyl)ethoxy)methyl)-2H-1,2,3-triazol-4-yl)ethanamine and 2-(1-((2-(trimethylsilyl)ethoxy)methyl)-1H-1,2,3-triazol-5-yl)ethanamine

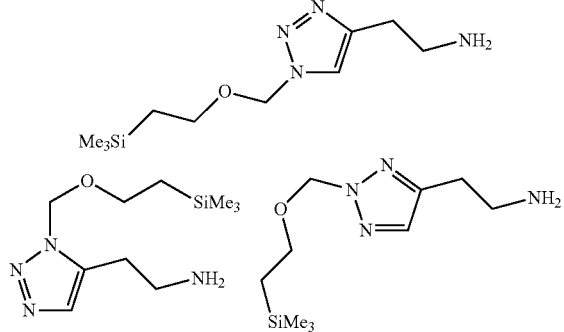

A mixture of 2-(1-((2-(trimethylsilyl)ethoxy)methyl)-1H-1,2,3-triazol-4-yl)acetonitrile and 2-(2-((2-(trimethylsilyl)ethoxy)methyl)-2H-1,2,3-triazol-4-yl)acetonitrile and 2-(1-((2-(trimethylsilyl)ethoxy)methyl)-1H-1,2,3-triazol-5-yl)acetonitrile (Preparation 66, 200 mg, 0.84 mmol) was dissolved in 7M methanolic ammonia (20 mL) and hydrogenated over Raney nickel (50 mg) at room temperature at 50 psi of hydrogen for 2 days. The catalyst was removed by filtration and the reaction was concentrated in vacuo. The residue was dissolved in a mixture of dichloromethane (20 mL) and methanol (5 mL) and slurried with a small amount of Arbocel filter agent. The suspension was filtered and the solvents were concentrated in vacuo to afford the title compounds as a mixture of three isomers (210 mg, 100%).

$^1$H NMR (400 MHz, MeOH-d$_4$): δ ppm 0.00 (s, 9H), 0.85-0.95 (m, 2H), 2.85-3.00 (m, 2H), 3.25-3.35 (m, 2H), 3.63-3.73 (m, 2H), 5.60-5.75 (m, 2H), 7.50-7.95 (m, 1H).

Preparation 66

2-(1((2-(trimethylsilyl)ethoxy)methyl)-1H-1,2,3-triazol-4-yl)acetonitrile and 2-(2-((2-(trimethylsilyl)ethoxy)methyl)-2H-1,2,3-triazol-4-yl)acetonitrile and 2-(1-((2-(trimethylsilyl)ethoxy)methyl)-1H-1,2,3-triazol-5-yl)acetonitrile

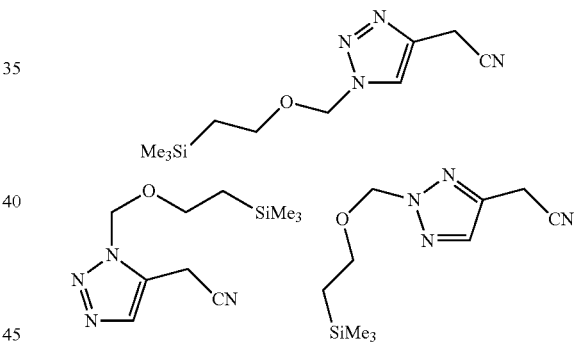

To a solution of a mixture of (1-((2-(trimethylsilyl)ethoxy)methyl)-1H-1,2,3-triazol-4-yl)methyl methanesulfonate and (2-((2-(trimethylsilyl)ethoxy)methyl)-2H-1,2,3-triazol-4-yl)methyl methanesulfonate and (1-((2-(trimethylsilyl)ethoxy)methyl)-1H-1,2,3-triazol-5-yl)methyl methanesulfonate (Preparation 67, 2.23 g, 7.26 mmol) in dimethylformamide (20 mL) was added sodium cyanide (400 mg, 8.16 mmol) and the reaction was stirred at room temperature for 18 hours. The reaction was partitioned between tert-butyl methyl ether (100 mL) and water (50 mL) with saturated aqueous sodium chloride solution (25 mL). The organic layer was washed with saturated aqueous sodium chloride solution (20 mL), dried over anhydrous sodium sulphate and concentrated in vacuo to afford the title compounds as a mixture of three isomers (1.92 g, 100%).

$^1$H NMR (400 MHz, CDCl$_3$): δ ppm 0.00-0.01 (s, 9H), 0.92-0.97 (m, 2H), 3.58-3.68 (m, 2H), 3.87-3.93 (m, 2H), 5.66-5.69 (m, 2H), 7.70-7.78 (m, 1H).

Preparation 67

(1-((2-(trimethylsilyl)ethoxy)methyl)-1H-1,2,3-triazol-4-yl)methyl methanesulfonate and (2-((2-(trimethylsilyl)ethoxy)methyl)-2H-1,2,3-triazol-4-yl)methyl methanesulfonate and (1-((2-(trimethylsilyl)ethoxy)methyl)-1H-1,2,3-triazol-5-yl)methyl methanesulfonate

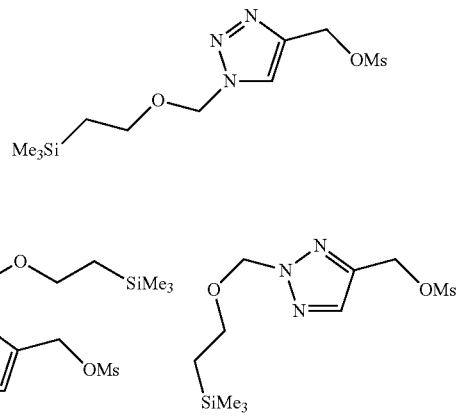

To a cooled solution of (1-((2-(trimethylsilyl)ethoxy)methyl)-1H-1,2,3-triazol-4-yl)methanol and (2-((2-(trimethylsilyl)ethoxy)methyl)-2H-1,2,3-triazol-4-yl)methanol and (1-((2-(trimethylsilyl)ethoxy)methyl)-1H-1,2,3-triazol-5-yl)methanol (Preparation 68, 1.99 g, 8.76 mmol) in dichloromethane (50 mL) was added triethylamine (1.5 mL, 10.78 mmol) followed by methanesulfonylchloride (750 µL, 9.68 mmol). The reaction was stirred at room temperature for 2.5 hours. The reaction was diluted to 100 mL with dichloromethane and was washed with a solution of citric acid (1 g) in water (80 mL). The organic layer was washed with water (40 mL), dried over anhydrous sodium sulphate and concentrated in vacuo to afford the title compounds as a mixture of three isomers (2.23 g, 83%).

$^1$H NMR (400 MHz, CDCl$_3$): δ ppm 0.00 (s, 9H), 0.92-0.97 (m, 2H), 3.05-3.07 (m, 3H), 3.59-3.69 (m, 2H), 5.38-5.43 (m, 2H), 5.67-5.72 (m, 2H), 7.72-7.90 (m, 1H).

Preparation 68

1-((2-(trimethylsilyl)ethoxy)methyl)-1H-1,2,3-triazole-4-carbaldehyde and 2-((2-(trimethylsilyl)ethoxy)methyl)-2H-1,2,3-triazole-4-carbaldehyde and 1-((2-(trimethylsilyl)ethoxy)methyl)-1H-1,2,3-triazole-5-carbaldehyde

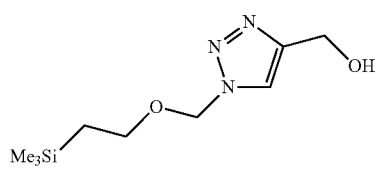

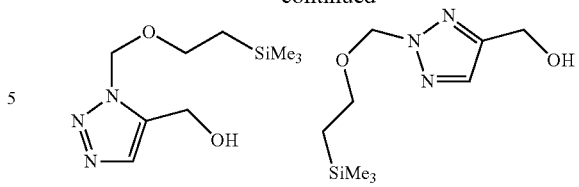

To a solution of 1H-1,2,3-triazole-4-carbaldehyde (850 mg, 8.76 mmol) and diisopropylethylamine (1.60 mL, 9.20 mmol) in dichloromethane (15 mL) was added 4-dimethylaminopyridine (50 mg, 0.41 mmol) followed by (2-(chloromethoxy)ethyl)trimethylsilane. The reaction was stirred at room temperature for 18 hours. The reaction was diluted with dichloromethane (70 mL) and washed with water (70 mL), saturated aqueous sodium chloride solution (30 mL), dried over anhydrous sodium sulphate and concentrated in vacuo to afford the title compounds as a mixture of three isomers (2.05 g, 100%).

$^1$H NMR (400 MHz, CDCl$_3$): δ ppm 0.02 (s, 9H), 0.94-1.00 (m, 2H), 3.64-3.75 (m, 2H), 5.79 (s, 2H), 6.05 (s, 2H), 8.17 (s, 1H), 8.30 (s, 1H), 8.32 (s, 1H), 10.12 (s, 1H), 10.19 (s, 1H), 10.23 (s, 1H).

Biological Activity

Isolated TRK Enzyme assays use the HTRF KinEASE-TK kit (Cisbio Cat#62TK0PEJ) with recombinant His-tagged cytoplasmic domains of each TRK receptor sourced from Invitrogen (see table below). This activity-assay measures the phosphorylation of tyrosine residues within a substrate from the HTRF kit which has been validated by Cisbio for a variety of tyrosine kinases including the TRK receptors.

Assay Details:

| Target | Invitrogen Cat# | Amino acids | FAC enzyme | FAC ATP | Assay Reaction Time |
|---|---|---|---|---|---|
| TRKA | PV3144 (NTRK1) | aa 441-796 | 4 nM | 40 uM | 35 min |
| TRKB | PV3616 (NTRK2) | aa 526-838 | 1 nM | 1.4 uM | 40 min |
| TRKC | PV3617 (NTRK3) | aa 510-825 | 10 nM | 15 uM | 30 min |

0.5 mM stock solutions of test compounds are prepared and serially diluted in 100% DMSO. A standard curve using the compound of Example 135 disclosed in WO2005/116035 of 150 uM is also prepared on each test plate. High percentage effect (HPE) is defined by 150 uM (using the compound of Example 135 as disclosed in WO2005/116035) and 0% effect (ZPE) is defined by 100% DMSO. Greiner low volume black plates containing 0.2 ul of serially diluted compound, standard and HPE/ZPE are created using the Bravo nanoliter dispenser.

1+ enzyme buffer is prepared from 5× Enzymatic Buffer from the Cisbio KinEASE TK kit using MilliQ water. The buffer is then supplemented with 10 mM MgCl and 2 mM DTT (both from Sigma). In the case of TRKB, the buffer is also supplemented with 125 nM Supplement Enzymatic Buffer (SEB) from the Cisbio kit.

2×FAC of enzyme and 2×FAC ATP diluted in 1× complete enzyme buffer is incubated at room temperature for 20 minutes to preactivate the enzyme. Following this preactivation step, 5 ul/well of enzyme+ATP mix is added using a Multidrop Micro to the assay plate, spotted with 0.2 ul 100%

DMSO compound. This is left for 20 mins at room temperature before adding 5 ul of 2 uM TK-substrate-Biotin (from the Cisbio kit) diluted in 1× enzyme buffer (1 uM FAC) using the Multidrop Micro. The reaction is incubated at room temperature for the optimized assay reaction time (see table). The reaction is stopped by adding 10 ul/well HTRF Detection Buffer containing 0.25 uM Streptavidin-XL665 (0.125 uM FAC) and 1:200 TK Antibody-Cryptate using a Multidrop.

After the Detection Reagent addition, plates are covered and incubated at room temperature for 60 minutes. HTRF signal is read using an Envision reader, measured as a ratio of emissions at two different wavelengths, 620 nm and 665 nm. Any compound that inhibits the action of the TRK kinase will have a lower fluorescence ratio value 665/620 nM than compounds which do not inhibit the TRK kinase. Test compound data are expressed as percentage inhibition defined by HPE and ZPE values for each plate. Percentage inhibition in the presence of test compound is plotted against compound concentration on a log scale to determine an $IC_{50}$ from the resultant sigmoid curve.

Cell Based Assays were carried out using Cell lines from DiscoveRx utilising their PathHunter technology and reagents in an antagonist assay:

| Target | DiscoveRx cell line Cat# | Cognate Neurotrophin |
|---|---|---|
| TRKA | 93-0462C3 | NGF |
| TRKA co expressed with p75 | 93-0529C3 | NGF |
| TRKB | 93-0463C3 | BDNF |
| TRKB co expressed with p75 | 93-0530C3 | BDNF |
| TRKC | 93-0464C3 | NT3 |
| TRKC co expressed with p75 | 93-0531C3 | NT3 |

The assays are based upon DiscoveRx's proprietary Enzyme Fragment Complementation (EFC) technology. In the case of the TRK cell lines, the enzyme acceptor (EA) protein is fused to a SH2 protein and the TRK receptor of interest has been tagged with a Prolink tag.

Upon neurotrophin binding, the TRK receptor becomes phosphorylated, and the tagged SH2 protein binds. This results in functional complementation and restored β-Galactosidase activity which is can be measured using the luminescent Galacton Star substrate within the PathHunter reagent kits.

Generally, small molecule inhibitors bind to the kinase domain so are not competing with the neurotrophin (agonist) which binds to an extracellular site. This means that the $IC_{50}$ is a good measure of affinity and should be unaffected by concentration neurotrophin stimulant.

Cryopreserved PathHunter cells are used from either in-house produced batches or bulk batches bought directly from DiscoveRx. Cryopreserved cells are resuscitated, spun 1000 rpm for 4 min to remove freezing media, and resuspended in MEM+0.5% horse serum (both Invitrogen) to $5e^5$ cells/ml. The cells are then plated using a Multidrop into Greiner white tissue culture treated plates at 20 ul/well and incubated for 24 h at 37° C., 5% $CO_2$, high humidity. On the day of the assay, the cell plates are allowed to cool to room temperature for 30 min prior to the assay.

4 mM stock solutions of test compounds are prepared and serially diluted in 100% DMSO. A standard curve using the compound of Example 135, WO2005/116035 at a top concentration of 150 uM is also prepared on each test plate. High percentage effect (HPE) is defined by 150 uM of the compound of Example 135, WO2005/116035 and 0% effect (ZPE) is defined by 100% DMSO. Plates containing 1 ul of serially diluted compound, standard and HPE/ZPE are diluted 1/66 in assay buffer (PBS minus $Ca^{2+}$, minus $Mg^{2+}$ with 0.05% pluronic F127) using a Wellmate. Using a Platemate Plus, 5 ul of 1/66 diluted test compounds is then transferred to the cell plate and allowed to reach equilibrium by incubating for 30 min at room temperature before addition of agonist stimulus: 10 ul/well of 2 nM (0.571 nM FAC) of the cognate neurotrophin (Peprotech) diluted in agonist buffer (HBSS with 0.25% BSA). Final assay concentration of the test compounds is 8.66 µM, (the compound of Example 135, WO2005/116035 FAC is 0.325 uM). The plates are left at room temperature for a further 2 hours before addition of 10 ul of the DiscoveRx PathHunter detection reagent (made up by adding 1 part Galacton Star, 5 parts Emerald II and 19 parts Cell Assay Buffer as per the manufacturer's instructions).

After reagent addition, plates are covered and incubated at room temperature for 60 minutes. Luminescence signal is read using an Envision. Test compound data are expressed as percentage inhibition defined by HPE and ZPE values for each plate. Percentage inhibition in the presence of test compound is plotted against compound concentration on a log scale to determine an $IC_{50}$ from the resultant sigmoid curve.

Brain Penetration Assays

In Vitro

MDCK-BCRP: MDCK-BCRP data may be collected according to the method described in "A 96-Well Efflux Assay To Identify ABCG2 Substrates Using a Stably Transfected MDCK II Cell Line" http://pubs.acs.org/doi/full/10.1021/mp050088t Yongling Xiao, Ralph Davidson, Arthur Smith, Dennis Pereira, Sabrina Zhao, John Soglia, David Gebhard, Sonia de Morais, and David B. Duignan, Mol. Pharm., 2006, 3 (1), pp 45-54.

MDCK-MDR1: MDCK-MDR1 data may be collected according to the method described in "Are MDCK Cells Transfected with the Human MDR1 Gene a Good Model of the Human Intestinal Mucosa?"http://www.springerlink-.com/content/qffhqlqbr4fnp3khf/fulltext.pdf Fuxing Tang, Kazutoshi Horie, and Ronald T. Borchardt, Pharmaceutical Research, Vol. 19, No. 6, June 2002.

In Vivo

Brain penetration may be measured according to the method described in "Assessing brain free fraction in early drug discovery". Read, K; Braggio, S., Expert Opinion Drug Metab Toxicol. (2010) 6 (3) 337-344.

TrkA $IC_{50}$ data (nM) are illustrated below. Where more than one reading was taken, the arithmetic mean is presented.

| Example Number | TrkA + p75 cell |
|---|---|
| 1 | 7.3 |
| 2 | 25.9 |
| 3 | 11.14 |
| 4 | 16.87 |
| 5 | 17.76 |
| 7 | 147.62 |
| 8 | 31.96 |
| 9 | 65.84 |
| 10 | 115.63 |
| 11 | 8.74 |
| 12 | 84.18 |
| 13 | 80.64 |
| 14 | 71.23 |
| 15 | 63.95 |
| 16 | 222.43 |
| 17 | 61.7 |

| Example Number | TrkA + p75 cell |
|---|---|
| 18 | 62.17 |
| 19 | 45.65 |
| 20 | 180.03 |
| 21 | 62.45 |
| 22 | 50.31 |
| 23 | 25.75 |
| 24 | 50.71 |
| 25 | 43.92 |
| 26 | 23.14 |
| 27 | 24.03 |
| 28 | 4.88 |
| 29 | 8.09 |
| 30 | 7.268 |
| 31 | 18.95 |
| 32 | 118.2 |
| 33 | 132.2 |
| 34 | 10.72 |
| 35 | 10.69 |
| 36 | 7.24 |
| 37 | 25.25 |
| 38 | 114.7 |
| 39 | 1.936 |
| 40 | 3.174 |
| 41 | 23.92 |
| 42 | 5.117 |
| 43 | 5.187 |
| 44 | 47.96 |
| 45 | 3.925 |
| 46 | 1.806 |
| 47 | 12.36 |
| 48 | 68.63 |
| 49 | 142.2 |
| 50 | 112.5 |
| 51 | 31.92 |
| 52 | 294.4 |
| 53 | 272.7 |
| 54 | 67.39 |
| 55 | 12.91 |
| 56 | 1065.83 |
| 57 | 9239.97 |
| 58 | 598.89 |
| 59 | 14.63 |
| 60 | 7.195 |
| 61 | 10.46 |
| 62 | 5250 |
| 63 | 145.93 |
| 64 | 2578.12 |
| 65 | 14329.54 |
| 66 | 8658.01 |
| 67 | 114.87 |
| 68 | 12.87 |
| 69 | 44.35 |
| 70 | 74.27 |
| 71 | 6.13 |
| 72 | 20.83 |
| 73 | 105.38 |
| 74 | 341.92 |
| 75 | 171.84 |
| 76 | 50000 |
| 77 | 136.65 |
| 78 | 67.65 |
| 79 | 1975.64 |
| 80 | 42.96 |
| 81 | 41.62 |
| 82 | 141.3 |
| 83 | 40.64 |
| 84 | 440.2 |
| 85 | 24.4 |
| 86 | 89.12 |
| 87 | 8.09 |
| 105 | 8036 |
| 134 | 4.61 |
| 135 | 25.3 |
| 136 | 1,570 |
| 137 | 9.30 |
| 138 | 3.41 |
| 139 | 667 |
| 140 | 29.5 |
| 141 | 10.6 |
| 142 | 18.4 |
| 143 | 15.7 |
| 144 | 7.10 |
| 145 | 42.6 |
| 146 | 26.4 |
| 147 | 12.3 |
| 148 | 9.67 |
| 149 | 20.2 |
| 150 | 10.3 |
| 151 | 2.98 |
| 152 | 6.16 |
| 153 | 4.72 |
| 154 | 13.7 |
| 155 | 7.91 |
| 156 | 18.6 |
| 157 | 45.3 |
| 158 | 4.71 |
| 159 | 189 |
| 160 | 8.70 |
| 161 | 9.58 |
| 162 | 5.45 |
| 163 | 196 |
| 164 | 177 |
| 165 | 2.45 |
| 166 | 13.7 |
| 167 | 12.9 |
| 168 | 6.93 |
| 169 | 4.22 |
| 170 | 4.03 |
| 171 | 15.9 |
| 172 | 18.8 |
| 173 | 582 |
| 174 | 2.53 |
| 175 | 12.9 |
| 176 | 2.60 |
| 177 | 4.91 |
| 178 | 3.05 |
| 179 | 1.74 |
| 180 | 2.80 |
| 181 | 8.71 |
| 182 | 18.1 |
| 183 | 12.6 |
| 184 | 24.9 |
| 185 | 340 |
| 186 | 93.3 |
| 187 | 4.67 |
| 188 | 10.1 |
| 189 | 12.1 |
| 190 | 22.6 |
| 191 | 10.6 |
| 192 | 19.7 |
| 193 | 13.0 |
| 194 | 12.1 |
| 195 | 9.90 |
| 196 | 12.0 |
| 197 | 12.7 |
| 198 | 10.9 |
| 199 | 13.0 |
| 200 | 13.4 |
| 201 | 12.0 |
| 202 | 20.7 |
| 203 | 25.0 |
| 204 | 15.0 |
| 205 | 11.0 |
| 206 | 29.8 |
| 207 | 2.06 |
| 208 | 5.55 |
| 209 | 48.2 |
| 210 | 37.9 |
| 211 | 14.2 |
| 212 | 20.7 |
| 213 | 6.72 |
| 214 | 3.63 |
| 215 | 13.0 |
| 216 | 7.21 |

| Example Number | TrkA + p75 cell |
|---|---|
| 217 | 54.1 |
| 218 | 82.0 |
| 219 | 7.35 |
| 220 | 1.71 |
| 221 | 126 |
| 222 | 3.37 |
| 223 | 38.0 |
| 224 | 9.42 |
| 225 | 101 |
| 226 | 61.4 |
| 227 | 75.8 |
| 228 | 58.1 |
| 229 | 61.8 |
| 230 | 70.7 |
| 231 | 95.4 |
| 232 | 267 |
| 233 | 56.8 |
| 234 | 61.0 |
| 235 | 67.6 |
| 236 | 86.2 |
| 237 | 102 |
| 238 | 151 |
| 239 | 55.0 |
| 240 | 89.7 |
| 241 | 65.6 |
| 242 | 163 |
| 243 | 290 |
| 244 | 374 |
| 245 | 179 |
| 246 | 86.2 |
| 247 | 99.4 |
| 248 | 67.4 |
| 249 | 107 |
| 250 | 113 |
| 251 | 115 |
| 252 | 39.8 |
| 253 | 199 |
| 254 | 171 |
| 255 | 182 |
| 256 | 8,130 |
| 257 | 213 |
| 258 | 803 |
| 259 | 236 |
| 260 | 541 |
| 261 | 18.2 |
| 262 | 19.8 |
| 263 | 43.9 |
| 264 | 44.3 |
| 265 | 28.4 |
| 266 | 30.8 |
| 267 | 86.6 |
| 268 | 26.0 |
| 269 | 41.7 |
| 270 | 69.8 |
| 271 | 19.8 |
| 272 | 35.0 |
| 273 | 68.0 |
| 274 | 14.2 |
| 275 | 18.2 |
| 276 | 22.4 |
| 277 | 25.9 |
| 278 | 92.5 |
| 279 | 47.7 |
| 280 | 76.1 |
| 281 | 22.4 |
| 282 | 24.4 |
| 283 | 25.9 |
| 284 | 26.3 |
| 285 | 28.7 |
| 286 | 53.5 |
| 287 | 27.2 |
| 288 | 45.5 |
| 289 | 20.1 |
| 290 | 37.4 |
| 291 | 41.9 |
| 292 | 12.4 |
| 293 | 50.4 |
| 294 | 19.5 |
| 295 | 31.9 |
| 296 | 15.0 |
| 297 | 21.4 |
| 298 | 32.1 |
| 299 | 53.1 |
| 300 | 20.9 |
| 301 | 22.0 |
| 302 | 24.1 |
| 303 | 9.77 |
| 304 | 1.71 |
| 305 | 6.14 |
| 306 | 79.8 |
| 307 | 85.5 |
| 308 | 190 |
| 309 | 331 |
| 310 | 475 |
| 311 | 480 |
| 312 | 743 |
| 313 | 196 |
| 314 | 234 |
| 315 | 294 |
| 316 | 301 |
| 317 | 345 |
| 318 | 8,660 |
| 319 | 215 |
| 320 | 320 |
| 321 | 375 |
| 322 | 471 |
| 323 | 573 |
| 324 | 610 |
| 325 | 659 |
| 326 | 859 |
| 327 | 130 |
| 328 | 223 |
| 329 | 241 |
| 330 | 328 |
| 331 | 159 |
| 332 | 211 |
| 333 | 270 |
| 334 | 296 |
| 335 | 297 |
| 336 | 636 |
| 337 | 657 |
| 338 | 968 |
| 339 | 1,180 |
| 340 | 1,290 |
| 341 | 1,360 |
| 342 | 1,470 |
| 343 | 1,010 |
| 344 | 1,060 |
| 345 | 1,090 |
| 346 | 1,730 |
| 347 | 1,920 |
| 348 | 493 |
| 349 | 1,110 |
| 350 | 82.9 |
| 351 | 67.9 |
| 352 | 114 |
| 353 | 164 |
| 354 | 834 |
| 355 | 882 |
| 356 | 79.8 |
| 357 | 131 |
| 358 | 39.3 |
| 359 | 46.2 |
| 360 | 47.2 |
| 361 | 53.3 |
| 362 | 150 |
| 363 | 57.6 |
| 364 | 74.3 |
| 365 | 61.8 |
| 366 | 66.7 |
| 367 | 223 |
| 368 | 228 |
| 369 | 26.3 |
| 370 | 61.0 |

-continued

| Example Number | TrkA + p75 cell |
|---|---|
| 371 | 72.9 |
| 372 | 134 |
| 373 | 741 |
| 374 | 236 |
| 375 | 85.8 |
| 376 | 42.1 |
| 377 | 198 |
| 378 | 21.1 |
| 379 | 81.9 |
| 380 | 93.6 |
| 381 | 105 |
| 382 | 50.6 |
| 383 | 23.8 |
| 384 | 24.7 |
| 385 | 28.5 |
| 386 | 59.4 |
| 387 | 119 |
| 388 | 133 |
| 389 | 102 |
| 390 | 62.8 |
| 391 | 340 |
| 392 | 7.46 |
| 393 | 32.9 |
| 394 | 48.2 |
| 395 | 54.6 |
| 396 | 74.9 |
| 397 | 88.0 |
| 398 | 18.8 |
| 399 | 298 |
| 400 | 613 |
| 401 | 26.1 |
| 402 | 38.0 |
| 403 | 130 |
| 404 | 254 |
| 405 | 36.2 |
| 406 | 93.2 |
| 407 | 127 |
| 408 | 296 |
| 409 | 132 |
| 410 | 366 |
| 411 | 1,460 |
| 412 | 101 |
| 413 | 147 |
| 414 | 16.2 |
| 415 | 12.8 |
| 416 | 26.0 |
| 417 | 27.4 |
| 418 | 34.6 |
| 419 | 34.2 |
| 420 | 253 |
| 421 | 21.3 |
| 422 | 2.96 |
| 423 | 101 |
| 424 | 25.9 |
| 425 | 22.8 |
| 426 | 19.3 |
| 427 | 47.1 |
| 428 | 49.0 |
| 429 | 73.4 |
| 430 | 32.8 |
| 431 | 42.0 |
| 432 | 30.4 |
| 433 | 28.3 |
| 434 | 21.4 |
| 435 | 80.3 |
| 436 | 37.0 |
| 437 | 28.3 |
| 438 | 13.4 |
| 439 | 37.1 |
| 440 | 26.2 |
| 441 | 56.6 |
| 442 | 50.4 |
| 443 | 31.3 |
| 444 | 4.75 |
| 445 | 27.8 |
| 446 | 4.81 |
| 447 | 36.5 |

-continued

| Example Number | TrkA + p75 cell |
|---|---|
| 448 | 74.9 |
| 449 | 64.1 |
| 450 | 46.7 |
| 451 | 17.2 |
| 452 | 1.43 |
| 453 | 22.0 |
| 454 | 116 |
| 455 | 38.2 |
| 456 | 38.6 |
| 457 | 51.3 |
| 458 | 59.9 |
| 459 | 98.3 |
| 460 | 25.2 |
| 461 | 20.7 |
| 462 | 55.5 |
| 463 | 31.8 |
| 464 | 13.2 |
| 465 | 178 |
| 466 | 30.8 |
| 467 | 17.4 |
| 468 | 28.5 |
| 469 | 30.9 |
| 470 | 32.7 |
| 471 | 17.9 |
| 472 | 189 |
| 473 | 24.7 |
| 474 | 24.2 |
| 475 | 34.6 |
| 476 | 13.7 |
| 477 | 41.7 |
| 478 | 28.6 |
| 479 | 24.2 |
| 480 | 32.5 |
| 481 | 17.0 |
| 482 | 44.0 |
| 483 | 34.9 |
| 484 | 23.1 |
| 485 | 10.2 |
| 486 | 11.8 |
| 487 | 98.8 |
| 488 | 33.1 |
| 489 | 7.26 |
| 490 | 44.9 |
| 491 | 41.2 |
| 492 | 24.6 |
| 493 | 14.5 |
| 494 | 15.1 |
| 495 | 12.4 |
| 496 | 18.1 |
| 497 | 23.7 |
| 498 | 46.6 |
| 499 | 15.8 |
| 500 | 2.84 |
| 501 | 15.7 |
| 502 | 8.87 |
| 503 | 26.7 |
| 504 | 20.9 |
| 505 | 12.0 |
| 506 | 14.2 |
| 507 | 25.6 |
| 508 | 21.1 |
| 509 | 8.88 |
| 510 | 7.01 |
| 511 | 25.0 |
| 512 | 17.1 |
| 513 | 14.2 |
| 514 | 13.7 |
| 515 | 32.0 |
| 516 | 21.4 |
| 517 | 14.8 |
| 518 | 11.3 |
| 519 | 16.4 |
| 520 | 25.5 |
| 521 | 8.14 |
| 522 | 20.3 |
| 523 | 16.2 |
| 524 | 75.5 |

| Example Number | TrkA + p75 cell |
|---|---|
| 525 | 14.2 |
| 526 | 12.7 |
| 527 | 11.7 |
| 528 | 42.2 |
| 529 | 12.2 |
| 530 | 9.37 |
| 531 | 3.41 |
| 532 | 6.10 |
| 533 | 5.97 |
| 534 | 17.3 |
| 535 | 5.46 |
| 536 | 6.13 |
| 537 | 6.61 |
| 538 | 4.46 |
| 539 | 15.9 |
| 540 | 1.51 |
| 541 | 7.09 |
| 542 | 35.7 |
| 543 | 4.69 |
| 544 | 8.12 |
| 545 | 9.46 |
| 546 | 4.14 |
| 547 | 15.1 |
| 548 | 9.51 |
| 549 | 4.66 |
| 550 | 5.01 |
| 551 | 6.96 |
| 552 | 10.2 |
| 553 | 5.78 |
| 554 | 33.4 |
| 555 | 4.41 |
| 556 | 8.96 |
| 557 | 1.02 |
| 558 | 4.02 |
| 559 | 4.68 |
| 560 | 7.59 |
| 561 | 8.36 |
| 562 | 7.22 |
| 563 | 5.12 |
| 564 | 4.97 |
| 565 | 8.90 |
| 566 | 6.32 |
| 567 | 3.22 |
| 568 | 17.6 |
| 569 | 8.51 |
| 570 | 4.73 |
| 571 | 5.95 |
| 572 | 4.36 |
| 573 | 9.00 |
| 574 | 2.46 |
| 575 | 3.21 |
| 576 | 20.2 |
| 577 | 10.3 |
| 578 | 5.97 |
| 579 | 5.15 |
| 580 | 6.37 |
| 581 | 5.83 |
| 582 | 9.94 |
| 583 | 7.64 |
| 579 | 5.15 |
| 580 | 6.37 |
| 581 | 5.83 |
| 582 | 9.94 |
| 583 | 7.64 |
| 584 | 29.1 |
| 585 | 21.9 |
| 586 | 13.6 |
| 587 | 14.5 |
| 588 | 8.60 |
| 589 | 6.67 |
| 590 | 7.46 |
| 591 | 118 |
| 592 | 26.5 |
| 593 | 18.7 |
| 594 | 11.9 |
| 595 | 6.33 |
| 596 | 16.7 |
| 597 | 9.10 |
| 598 | 75.1 |
| 599 | 20.4 |
| 600 | 7.06 |
| 601 | 9.67 |
| 602 | 11.7 |
| 603 | 28.0 |
| 604 | 9.17 |
| 605 | 31.4 |
| 606 | 6.49 |
| 607 | 4.92 |
| 608 | 34.8 |
| 609 | 4.98 |
| 610 | 52.1 |
| 611 | 13.1 |
| 612 | 11.4 |
| 613 | 9.09 |
| 614 | 13.1 |
| 615 | 7.23 |
| 616 | 16.0 |
| 617 | 1.17 |
| 618 | 13.7 |
| 619 | 44.4 |
| 620 | 20.4 |
| 621 | 9.36 |
| 622 | 13.2 |
| 623 | 8.23 |
| 624 | 8.34 |
| 625 | 14.6 |
| 626 | 6.82 |
| 627 | 11.4 |
| 628 | 19.4 |
| 629 | 34.5 |
| 630 | 62.5 |
| 631 | 114 |
| 632 | 27.6 |
| 633 | 33.9 |
| 634 | 25.5 |
| 635 | 17.7 |
| 636 | 95.4 |
| 637 | 52.3 |
| 638 | 67.2 |
| 639 | 38.8 |
| 640 | 21.2 |
| 641 | 36.3 |
| 642 | 55.6 |
| 643 | 28.7 |
| 644 | 31.0 |
| 645 | 24.7 |
| 646 | 11.9 |
| 647 | 19.4 |
| 648 | 31.4 |
| 649 | 41.1 |
| 650 | 40.6 |
| 651 | 43.7 |
| 652 | 19.1 |
| 653 | 28.0 |
| 654 | 22.0 |
| 655 | 46.2 |
| 656 | 31.1 |
| 657 | 32.3 |
| 658 | 34.8 |
| 659 | 50.3 |
| 660 | 22.9 |
| 661 | 102 |
| 662 | 46.9 |
| 663 | 147 |
| 664 | 38.1 |
| 665 | 134 |
| 666 | 96.1 |
| 667 | 172 |
| 668 | 21.6 |
| 669 | 120 |
| 670 | 130 |
| 671 | 164 |
| 672 | 32.7 |
| 673 | 56.5 |

| Example Number | TrkA + p75 cell |
| --- | --- |
| 674 | 9.98 |
| 675 | 179 |
| 676 | 27.5 |
| 677 | 156 |
| 678 | 125 |
| 679 | 21.1 |
| 680 | 2.65 |
| 681 | 61.3 |
| 682 | 95.8 |
| 683 | 202 |
| 684 | 104 |
| 685 | 710 |
| 686 | 1.77 |
| 687 | 2.27 |
| 688 | 4.56 |
| 689 | 85.0 |
| 690 | 14.1 |
| 691 | 327 |
| 692 | 54.1 |
| 693 | 11.8 |
| 694 | 13.8 |
| 695 | 45.6 |
| 696 | 666 |
| 697 | 276 |
| 698 | 2,390 |
| 699 | 277 |
| 700 | 364 |
| 701 | 97.4 |
| 702 | 326 |
| 703 | 546 |
| 704 | 218 |
| 705 | 81.3 |
| 706 | 166 |
| 707 | 891 |
| 708 | 310 |
| 709 | 158 |
| 710 | 53.1 |
| 711 | 34.2 |
| 712 | 131 |
| 713 | 185 |
| 714 | 37.5 |
| 715 | 113 |
| 716 | 27.2 |
| 717 | 75.7 |
| 718 | 100 |
| 719 | 26.3 |
| 720 | 14.4 |
| 721 | 79.4 |
| 722 | 31.5 |
| 723 | 69.0 |
| 724 | 92.8 |
| 725 | 12.2 |
| 726 | 66.8 |
| 727 | 241 |
| 728 | 865 |
| 729 | 142 |
| 730 | 429 |
| 731 | 98.7 |
| 732 | 491 |
| 733 | 413 |
| 734 | 73.0 |
| 735 | 263 |
| 736 | 358 |
| 737 | 116 |
| 738 | 77.3 |
| 739 | 261 |
| 740 | 2.02 |
| 741 | 36.9 |
| 742 | 4.50 |
| 743 | 10.4 |
| 744 | 10.3 |
| 745 | 11.3 |
| 746 | 3.25 |
| 747 | 9.13 |
| 748 | 14.9 |
| 749 | 15.4 |
| 750 | 5.96 |
| 751 | 16.8 |
| 752 | 126 |
| 753 | 471 |
| 754 | 22.7 |
| 755 | 91.8 |
| 756 | 214 |
| 757 | 116 |
| 758 | 55.2 |
| 759 | 20.7 |
| 760 | 352 |
| 761 | 38.5 |
| 762 | 140 |
| 763 | 20.1 |
| 764 | 32.1 |
| 765 | 211 |
| 766 | 105 |
| 767 | 17.0 |
| 768 | 35.0 |
| 769 | 34.0 |
| 770 | 22.3 |
| 771 | 35.7 |
| 772 | 10.8 |
| 773 | 7.66 |
| 774 | 45.1 |
| 775 | 58.3 |
| 776 | 18.9 |
| 777 | 57.4 |
| 778 | 66.0 |
| 779 | 49.1 |
| 780 | 49.9 |
| 781 | 40.6 |
| 782 | 30.8 |
| 783 | 24.8 |
| 784 | 29.7 |
| 785 | 19.4 |
| 786 | 36.5 |
| 787 | 28.9 |
| 788 | 82.2 |
| 789 | 171 |
| 790 | 87.6 |
| 791 | 54.7 |
| 792 | 36.9 |
| 793 | 61.9 |
| 794 | 25.7 |
| 795 | 14.6 |
| 796 | 334 |
| 797 | 144 |
| 798 | 868 |
| 799 | 132 |
| 800 | 221 |
| 801 | 239 |
| 802 | 299 |
| 803 | 124 |
| 804 | 483 |
| 805 | 101 |
| 806 | 492 |
| 807 | 201 |
| 808 | 149 |
| 809 | 76.0 |
| 810 | 123 |
| 811 | 608 |
| 812 | 1,280 |
| 813 | 149 |
| 814 | 359 |
| 815 | 116 |
| 816 | 429 |
| 817 | 269 |
| 818 | 138 |
| 819 | 75.8 |
| 820 | 101 |
| 821 | 290 |
| 822 | 57.1 |
| 823 | 45.8 |
| 824 | 58.5 |
| 825 | 89.5 |
| 826 | 34.3 |
| 827 | 67.9 |

-continued

| Example Number | TrkA + p75 cell |
| --- | --- |
| 828 | 67.1 |
| 829 | 82.2 |
| 830 | 73.7 |
| 831 | 128 |
| 832 | 82.6 |
| 833 | 79.3 |
| 834 | 9.71 |
| 835 | 19.8 |
| 836 | 1.04 |
| 837 | 21.4 |
| 838 | 7.49 |
| 839 | 10.2 |
| 840 | 104 |
| 841 | 176 |

All publications cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. 5-(2,4-dichloro-5-(pyridin-2-yl)benzamido)-N-(2-hydroxy-2-methylpropyl)-1-phenyl-1H-pyrazole-3-carboxamide, or a pharmaceutically acceptable salt thereof.

2. 5-{[2,4-dichloro-5-(3-fluoropyridin-2-yl)benzoyl]amino}-N-(2-hydroxy-2-methylpropyl)-1-phenyl-1H-pyrazole-3-carboxamide, or a pharmaceutically acceptable salt thereof.

3. A pharmaceutical composition comprising a compound or a pharmaceutically acceptable salt thereof, as defined in claim 1, and a pharmaceutically acceptable carrier.

4. A method of treatment of pain in a mammal, comprising treating said mammal with an effective amount of a compound or a pharmaceutically acceptable salt thereof, as defined in claim 1.

5. N-((1H-1,2,3-triazol-4-yl)methyl)-5-(2-chloro-4-fluoro-5-(pyridin-2-yl)benzamido)-1-phenyl-1H-pyrazole-3-carboxamide, or a pharmaceutically acceptable salt thereof.

6. 2,4-dichloro-5-(3-fluoropyridin-2-yl)-N-{3-[(3-oxopiperazin-1-yl)carbonyl]-1-phenyl-1H-pyrazol-5-yl}benzamide, or a pharmaceutically acceptable salt thereof.

7. 5-{[2,4-dichloro-5-(pyridin-2-yl)benzoyl]amino}-N-(trans-4-hydroxycyclohexyl)-1-phenyl-1H-pyrazole-3-carboxamide, or a pharmaceutically acceptable salt thereof.

8. N-(3-{[(3S,4S)-3-amino-4-fluoropyrrolidin-1-yl]carbonyl}-1-phenyl-1H-pyrazol-5-yl)-2,4-dichloro-5-(3-fluoropyridin-2-yl)benzamide, or a pharmaceutically acceptable salt thereof.

9. N-(3-amino-2,2-difluoropropyl)-5-{[2-chloro-4-fluoro-5-(3-fluoropyridin-2-yl)benzoyl]amino}-1-phenyl-1H-pyrazole-3-carboxamide, or a pharmaceutically acceptable salt thereof.

10. A pharmaceutical composition comprising a compound or a pharmaceutically acceptable salt thereof, as defined in claim 2, and a pharmaceutically acceptable carrier.

11. A pharmaceutical composition comprising a compound or a pharmaceutically acceptable salt thereof, as defined in claim 5, and a pharmaceutically acceptable carrier.

12. A pharmaceutical composition comprising a compound or a pharmaceutically acceptable salt thereof, as defined in claim 6, and a pharmaceutically acceptable carrier.

13. A pharmaceutical composition comprising a compound or a pharmaceutically acceptable salt thereof, as defined in claim 7, and a pharmaceutically acceptable carrier.

14. A pharmaceutical composition comprising a compound or a pharmaceutically acceptable salt thereof, as defined in claim 8, and a pharmaceutically acceptable carrier.

15. A pharmaceutical composition comprising a compound or a pharmaceutically acceptable salt thereof, as defined in claim 9, and a pharmaceutically acceptable carrier.

16. A method of treatment of pain in a mammal, comprising treating said mammal with an effective amount of a compound or a pharmaceutically acceptable salt thereof, as defined in of claim 2.

17. A method of treatment of pain in a mammal, comprising treating said mammal with an effective amount of a compound or a pharmaceutically acceptable salt thereof, as defined in of claim 5.

18. A method of treatment of pain in a mammal, comprising treating said mammal with an effective amount of a compound or a pharmaceutically acceptable salt thereof, as defined in of claim 6.

19. A method of treatment of pain in a mammal, comprising treating said mammal with an effective amount of a compound or a pharmaceutically acceptable salt thereof, as defined in of claim 7.

20. A method of treatment of pain in a mammal, comprising treating said mammal with an effective amount of a compound or a pharmaceutically acceptable salt thereof, as defined in of claim 8.

21. A method of treatment of pain in a mammal, comprising treating said mammal with an effective amount of a compound or a pharmaceutically acceptable salt thereof, as defined in of claim 9.

* * * * *